(12) United States Patent
Kotkow et al.

(10) Patent No.: US 7,498,304 B2
(45) Date of Patent: Mar. 3, 2009

(54) ANGIOGENESIS-MODULATING COMPOSITIONS AND USES

(75) Inventors: Karen Kotkow, Jamaica Plain, MA (US); Lee L. Rubin, Wellesley, MA (US)

(73) Assignee: Curis, Inc., Cambridge, MA (US)

( * ) Notice: Subject to any disclaimer, the term of this patent is extended or adjusted under 35 U.S.C. 154(b) by 611 days.

(21) Appl. No.: 10/652,686

(22) Filed: Aug. 29, 2003

(65) Prior Publication Data

US 2005/0054568 A1 Mar. 10, 2005

Related U.S. Application Data

(60) Provisional application No. 60/407,445, filed on Aug. 29, 2002.

(51) Int. Cl.
*A61K 39/395* (2006.01)

(52) U.S. Cl. ........... 514/12; 424/130.1; 424/155.1; 424/156.1

(58) Field of Classification Search ......... 424/130.1, 424/138.1, 155.1, 156.1
See application file for complete search history.

(56) References Cited

U.S. PATENT DOCUMENTS

| | | | |
|---|---|---|---|
| 5,681,278 A | 10/1997 | Igo et al. | |
| 5,789,543 A | 8/1998 | Ingham et al. | |
| 5,837,538 A | 11/1998 | Scott et al. | |
| 5,844,079 A * | 12/1998 | Ingham et al. | 530/350 |
| 6,027,882 A | 2/2000 | Scott et al. | |
| 6,165,747 A | 12/2000 | Ingham et al. | |
| 6,172,200 B1 | 1/2001 | Scott et al. | |
| 6,261,786 B1 | 7/2001 | Marigo et al. | |
| 6,271,363 B1 | 8/2001 | Ingham et al. | |
| 6,384,192 B1 | 5/2002 | Ingham et al. | |
| 6,429,354 B1 | 8/2002 | Scott et al. | |
| 6,432,970 B2 * | 8/2002 | Beachy et al. | 514/278 |
| 6,551,782 B1 | 4/2003 | Scott et al. | |
| 6,576,237 B1 | 6/2003 | Ingham et al. | |
| 6,607,913 B1 | 8/2003 | Ingham et al. | |
| 6,610,507 B2 | 8/2003 | Scott et al. | |
| 6,610,656 B1 | 8/2003 | Ingham et al. | |
| 6,613,798 B1 | 9/2003 | Porter | |
| 6,630,148 B1 | 10/2003 | Ingham et al. | |
| 6,664,075 B2 | 12/2003 | Ingham et al. | |
| 6,884,775 B1 | 4/2005 | Tabin et al. | |
| 6,921,646 B2 | 7/2005 | Scott et al. | |
| 6,946,257 B1 | 9/2005 | Scott et al. | |
| 7,060,450 B1 | 6/2006 | Tabin et al. | |
| 7,144,732 B2 | 12/2006 | Ingham et al. | |
| 2002/0015702 A1 | 2/2002 | Burkly et al. | |
| 2003/0022819 A1 | 1/2003 | Ling et al. | |
| 2004/0060568 A1 | 4/2004 | Dudek et al. | |
| 2004/0110663 A1 | 6/2004 | Dudek et al. | |
| 2005/0002933 A1 | 1/2005 | Baron et al. | |
| 2005/0054568 A1 | 3/2005 | Ling et al. | |

FOREIGN PATENT DOCUMENTS

| | | |
|---|---|---|
| WO | WO 95/18856 | 7/1995 |
| WO | WO-95/23223 | 8/1995 |
| WO | WO 9821227 A1 * | 5/1998 |
| WO | WO-98/35020 | 8/1998 |
| WO | WO 98/35020 | 8/1998 |
| WO | WO-99/10004 A2 | 3/1999 |
| WO | WO-00/15246 | 3/2000 |
| WO | WO 00/18428 | 4/2000 |
| WO | WO 00/25725 | 5/2000 |
| WO | WO 00/41545 | 7/2000 |
| WO | WO 00/74706 | 12/2000 |
| WO | WO 0074706 A1 * | 12/2000 |
| WO | WO 01/19800 A2 | 3/2001 |
| WO | WO 01/26644 A2 | 4/2001 |
| WO | WO 01/74344 A2 | 10/2001 |
| WO | WO-02/30462 | 4/2002 |
| WO | WO 02080952 A2 * | 10/2002 |

OTHER PUBLICATIONS

Stecca et al. (Journal of Biology 2002; 1: 9).*
Fujita et al. (Biochem. Biophys. Res. Comm. 1997; 238: 658-664).*
Jain (Scientific American Jul. 1994).*
Dillman (Annals of Internal Medicine, vol. 111, pp. 592-603, 1989).*
Weiner (Seminars Oncology, vol. 26, No. 4, 1999, pp. 41-50).*
Nelson et al. (J. Clin. Pathol: Mol. Pathol. 2000; 53: 111-117).*
Stedman's Online Medical Dictionary, 27th Edition.*
Greenspan et al. (Nature Biotechnology. 1999; 7: 936-937).*
Stancoviski et al. (Proceedings of the National Academy of Science USA. 1991; 88: 8691-8695).*
Jiang et al. (J. Biol. Chem. Feb. 11, 2005; 280 (6): 4656-4662).*
Ericson et al. (Cell 1996; 87: 661-673).*
Feng et al. (Clinical Cancer Research 2007; 13: 1389-1398).*
Huang et al. (Carcinogenesis 2006; 27: 1334-1340).*
Freshney (Culture of Animal Cells, A Manual of Basic Technique, Alan R. Liss, Inc., 1983, New York, p. 4).*
Dermer (Bio/Technology, 1994, 12:320).*
Apelqvist, A. et al. Sonic hedgehog directs specialized mesoderm differentiation in the intestine and pancreas. Current Biology 7, 801-804 (Oct. 1, 1997).
Asahara, T. et al. Tie2 receptor ligands, angiopoietin-1 and angiopoietin-2, modulate VEGF-Induced postnatal neovascularization. Circ. Res. 83, 233-240 (1997).
Ballara, S. C. et al. New vessels, new approaches: angiogenesis as a therapeutic target in musculoskeletal disorders. Int. J. Exp. Path. 80, 235-250 (1999).

(Continued)

*Primary Examiner*—Brandon J Fetterolf
(74) *Attorney, Agent, or Firm*—Ropes & Gray LLP

(57) ABSTRACT

Hedgehog agonists and antagonists can be used to regulate angiogenesis, and to prevent angiogenesis driven pathologies. Furthermore, hedgehog agonists and antagonists have utility in modulating tissue repair and in the treatment of many forms of cancer.

69 Claims, 45 Drawing Sheets

OTHER PUBLICATIONS

Banai, S. et al. Angiogenic-induced enhancement of collateral blood flow to ischemic myocardium by vascular endothelial growth factor in dogs. Circulation 89, 2183-2189 (May 1994).

Battler, A. et al. Intracoronary injection of basic fibroblast growth factor enhances angiogenesis in infracted swine myocardium. J. Am. Coll Cardiol. 22, 2001-2006 (Dec. 1993).

Beck, L. Jr. & D'Amore, P. A. Vascular development: cellular and molecular regulation. FASEB J. 11, 365-373 (Apr. 1997).

Bitgood, M. J. & McMahon, A. P. Hedgehog and Bmp genes are coexpressed at many diverse sites of cell-cell interaction in the mouse embryo. Dev. Biol. 172, 126-138 (Nov. 1995).

Bitgood, M. J. et al. Sertoli cell signaling by Desert hedgehog regulates the male germline. Curr. Biol. 6, 298-304 (1996).

Bhusham, M. et al. Levels of endothelial cell stimulating angiogenesis factor and vascular endothelial growth factor are elevated in psoriasis. Br. J. Dermatol. 141, 1054-1060 (Dec. 1994).

Buschmann & Schaper, W. The pathophysiology of the collateral circulation (arteriogenesis). J. Pathol. 190, 338-342 (Feb. 2000).

Carpenter, D. et al. Characterization of two patched receptors for the vertebrate hedgehog protein family. PNAS 95, 13630-13634 (Nov. 10, 1998).

Chiang, C. et al. Cyclopia and defective axial patterning in mice lacking sonic hedgehog gene function. Nature 383, 407-413 (1996).

Cherrington, J. M. et al. New paradigms for the treatment of cancer: the role of anti-angiogenesis agents. Adv. Cancer Res. 79, 1-38 (2000).

Couffinhal, T. et al. Impaired collateral vessel development associated with reduced expression of vascular endothelial growth factor in ApoE-/- mice. Circulation 99, 3188-3198 (1999).

D'Amato. Angiogenesis Inhibition in Age-related Macular Degeneration. Opthamology 102, 1261-1262 (Sep. 1995).

Ding, Q. et al. Mouse suppressor of fused is a negative regulator of sonic hedgehog signaling and alters the subcellular distribution of Gli 1. Curr. Biol. 7, 1119-1122 (Oct. 1999).

Dockter, J. L. Sclertome induction and differentiation. Curr. Top Dev Biol. 48, 77-127 (2000).

Dodd, J. et al. The when and where of floor plate induction. Science 282, 1654-1657 (1998).

Ericson, J. et al. Graded sonic hedgehog signaling and the specification of cell fate in the ventral neural tube. Cold Spring Harbor Symp. Quant. Biol. 62, 451-466 (1997).

Ericson, J. et al. Sonic hedgehog: a common signal for ventral patterning along the rostrocaudal axis of the neural tube. Int. J. Dev. Biol. 39, 809-816 (1995).

Engler, D. A. Use of vascular endothelial growth factor for therapeutic angiogenesis. Circulation 94, 1496-1498 (Oct. 1, 1996).

Fan, H. et al. Myc-epitope tagged proteins detected with the 9E10 antibody in immunofluorescence and immunoprecipitation assays but not in western blot analysis. Biochem. Cell Biol. 76, 125-128 (1998).

Folkman, J. & Shing, Y. Angiogenesis. J. Biol. Chem. 267, 10931-10934 (Jun. 5, 1992).

Fong, T. A. T. et al. SU5416 is a potent and selective inhibitor of the vascular endothelial growth factor receptor (Flk-1/KDR) that inhibits tyrosine kinase catalysis, tumor vascularization, and growth of multiple tumor types. Cancer Res. 59, 99-106 (Jan. 1999).

Goodrich, L. V. et al. Altered neural cell fate and medulloblastoma in mouse patched mutants. Science 277, 1109-1113 (1997).

Hammerschmidt, M. et al. The world according to hedgehog. TIG. 13, 14-21 (Jan. 1997).

Harada, K. et al. Basic fibroblast growth factor improves myocardial function in chronically ischemic porcine hearts. J. Clin. Invest. 94, 623-630 (Aug. 1994).

Hynes, M. et al. The seven-transmembrane receptor Smoothened cell-autonomously induces multiple ventral cell types. Nat. Neurosci. 3, 41-46 (Jan. 2000).

Ingham, P.W. Signaling by hedgehog family proteins in Drosophila and vertebrate development. Curr. Opin. Genet. Dev. 5, 492-498 (1995).

Isner, J. M. et al. Arterial gene transfer for therapeutic angiogenesis in patients with peripheral artery disease. Hum. Gene Ther. 7, 959-988 (May 20, 1996).

Iwamoto, M. et al. Actions of hedgehog proteins on skeletal cells. Crit. Rev. Oral Biol. Med. 10, 477-486 (1999).

Jensen, A. M. & Wallace, V. A. Expression of Sonic hedgehog and its putative role as a precursor cell mitogen in the developing mouse retina. Develop. 124, 363-371 (Jan. 1997).

Johnson, R. L. & Tabin, C. J. Molecular models for vertebrate limb development. Cell 90, 979-990 (1997).

Karasek, M. A. Progress in our understanding of the biology of psoriasis. Cutis. 64, 319-322 (Nov. 1999).

Karp, S. J. et al. Indian hedgehog coordinates endochondral bone growth and morphogenesis via parathyroid hormone related-protein-dependent and -independent pathways. Devel. 127, 543-548 (2000).

Kenyon, B. M. et al. A model of angiogenesis in the mouse cornea. Invest. Opthamol. Vis. Sci. 37, 1625-1632 (1996).

Klagsbrun, M. & D'Amore, P. A. Regulators of angiogenesis. Annu. Rev. Physiol. 53, 217-239 (1991).

Klohs, W. D. & Hamby, J. M. Antiangiogenic agents. Curr. Opin. Biotechnol. 10, 544-549 (Dec. 1999).

Kornowski, R. et al. Comparison between left ventricular electromechanical mapping and radionuclide perfusion imaging for detection of mycardial viability. Circulation 98, 1837-1841 (Nov. 1998).

Kornowski, R. et al. Delivery strategies to achieve therapeutic myocardial angiogenesis. Circulation 101, 454-458 (Feb. 2000).

Laham, R. J. et al. Intrapericardial delivery of fibroblast growth factor-2 induces neovascularization in a porcine model of chronic myocardial ischemia. J. Pharmacol. Exp. Ther. 292, 795-802 (Feb. 2000).

Landau, C. et al. Intrapericardial basic fibroblast growth factor induces myocardial angiogenesis in a rabbit model of chronic ischemia. Am. Heart J. 129, 924-931 (May 1995).

Lazarous, D. F. et al. Comparative Effects of Basic Fibroblast Growth Factor and Vascular Endothelial Growth Factor on Coronary Collateral Development and the Arterial Response to Injury. Circulation 94, 1074-1082 (Sep. 1996).

Lemire, J. M. et al. Characterization of cloned aortic smooth muscle cells from young rats. Am. J. Pathol. 144, 1068-1081 (1994).

Litingtung, Y. et al. Sonic hedgehog is essential to foregut development. Nat. Genet. 20, 58-61 (1998).

MaGovern C. J. et al. Regional angiogenesis induced in nonischemic tissue by an adenoviral vector expressing vascular endothelial growth factor. Hum. Gene. Ther. 8, 215-227 (Jan. 20, 1997).

Majesky, M. W. A little VEGF goes a long way: Therapeutic angiogenesis by direct injection of vascular endothelial growth factor-encoding plasmid DNA. Circulation 94, 3062-3064 (Dec. 15, 1996).

Mesri, E. A. et al. Expression of vascular endothelial growth factor from a defective herpes simplex virus type 1 amplicon vector induces angiogenesis in mice. Circ. Res. 76, 161-167 (Feb. 1995).

Motoyama, J. et al. Overlapping and non-overlapping Ptch2 expression with Shh during mouse embryogenesis. Mech. Dev. 78, 81-84 (Nov. 1998).

Murone, M. et al. Hedgehog signal transduction: from flies to vertebrates. Exp. Cell Res. 253, 25-33 (Nov. 25, 1999).

Murone, M. et al. Sonic hedgehog signaling by the patched smoothened receptor complex. Curr. Biol. 9, 76-84 (Jan. 28, 1996).

Ozaki, H. et al. Blockade of vascular endothelial cell growth factor receptor signaling is sufficient to completely prevent retinal neovascularization. Am. J. Pathol. 156, 697-707 (Feb. 2000).

Parmantier, E. et al. Schwann cell-derived Desert hedgehog controls the development of perpheral nerve sheaths. Neuron 23, 713-724 (1999).

Passaniti, A. et al. Methods in Laboratory Investigation: A Simple, Quantitative Method for Assessing Angiogenesis and Antiangiogenic Agents Using Reconstituted Basement Membrane, Heparin, and Fibroblast Growth Factor. Lab. Invest. 67, 519-528 (1992).

Peacock, D. J. et al. A Novel Angiogenesis Inhibitor Suppresses Rat Adjuvant Arthritis. Cell Immunol. 160, 178-184 (Feb. 1995).

Pearlman, J. D. Magnetic resonance mapping demonstrates benefits of VEGF-induced myocardial angiogenesis. Nat. Med. 1, 1085-1089 (Oct. 1995).

Pearse, R. V. II et al. Vertebrate homologs of Drosophila suppressor of fused interact with the gli family of transcriptional regulators. Dev. Biol. 212, 323-336 (Aug. 15, 1999).

Pepinsky, R. B. et al. Identification of a palmitic acid-modified form of human Sonic hedgehog. J. Biol. Chem. 273, 14037-14045 (1998).

Pepinsky, R. B. et al. Mapping sonic hedgehog-receptor interactions by steric interference. J. Biol. Chem. 275, 10995-11001 (2000).

Perrimon, N. Hedgehog and beyond. Cell 80, 517-520 (1995).

Pola et al. The morphogen Sonic hedgehog is an indirect angiogenic agent upregulating two families of angiogenic growth factors. Nat. Med. 7, 706-711 (2001).

Rivard, A. & Isner, J. M. Angiogenesis and vasculogenesis in treatment of cardiovascular disease. Mol. Med. 4, 429-440 (Jul. 1998).

Rivard, A. et al. Age-dependent impairment of angiogenesis. Circulation 99, 111-120 (Jan. 1999).

Rothman, A. et al. Development and characterization of a cloned rat pulmonary arterial smooth muscle cell line that maintains differentiated properties through multiple subcultures. Circulation 86, 1977-1986 (1992).

Sato, N. et al. Induction of the hair growth phase in postnatal mice by localized transient expression of Sonic hedgehog. J. Clin. Invest. 104, 855-864 (Oct. 1999).

Schratzberger, P. et al. Favorable effect of VEGF gene transfer on ischemic peripheral neuropathy. Nat. Med. 6, 405-413 (Apr. 2000).

Shou, M. et al. Effect of basic fibroblast growth factor on myocardial angiogenesis in dogs with mature collateral vessels. J. Am. Coll. Cardiol. 29, 1102-1106 (Apr. 1997).

St.-Jacques, B. et al. Sonic hedgehog signaling is essential for hair development. Curr. Biol. 8, 1058-1068 (1998).

St.-Jacques, B. et al. Indian hedgehog signaling regulates proliferation and differentiation of chondrocytes and is essential for bone formation. Genes Dev. 13, 2072-2086 (1999).

Stone, D. M. et al. Characterization of the human suppressor of fused, a negative regulator of the zinc-finger transcription factor Gli. J. Cell. Sci. 112, 4437-4448 (Dec. 1999).

Storgard, C. M. et al. Decreased angiogenesis and arthritic disease in rabbits treated with an alphavbeta3 antagonist. J. Clin. Invest. 103, 47-54 (Jan. 1999).

Takeshita, S. et al. Intramuscular administration of vascular endothelial growth factor induces dose-dependent collateral artery augmentation in a rabbit model of chronic limb ischemia. Circulation 90, 228-234 (Nov. 1994).

Takeshita, S. et al. Therapeutic angiogenesis following arterial gene transfer of vascular endothelial growth factor in a rabbit model of hindlimb ischemia. Biochem. Biophys. Res. Comm. 227, 628-635 (Oct. 14, 1996).

Taylor, F. R. et al. Enhanced potency of human sonic hedgehog by hydrophobic modification. Biochemistry 10, 4359-4371 (Apr. 2001).

Traiffort, E. et al. Discrete localizations of hedgehog signaling components in the developing and adult rat nervous system. Eur. J. Neurosci. 11, 3199-3214 (Sep. 1999).

Traiffort, E. et al. Regional Distribution of Sonic Hedgehog, patched, and smoothened mRNA in the adult rat brain. J. Neurochem. 70, 1327-1330 (Mar. 1998).

Unger, E. F. Basic fibroblast growth factor enhances myocardial collateral flow in a canine model. Am. J. Physiol. 266, 1588-1595 (Apr. 1994).

Vale, P.R. et al. Catheter-based myocardial gene transfer utilizing nonfluoroscopic electromechanical left ventricular mapping. J. Am. Coll. Cardiol. 34, 246-254 (Jul. 1999).

Valentini, R. P. et al. Post-translational Processing and Renal Expression of Mouse Indian Hedgehog. J. Biol. Chem. 272, 8466-8473 (Mar. 28, 1996).

Walsh, D. A. Angiogenesis and arthritis. Rheumatology 38, 103-112 (Feb. 1999).

Wang, L. C. et al. Conditional disruption of hedgehog signaling pathway defines its critical role in hair development and regeneration. J. Invest. Dermatol. 114, 901-908 (May 2000).

Wood, J. M. et al. PTL787/ZK 222584, a novel and potent inhibitor of vascular endothelial growth factor receptor tyrosine kinases, impairs vascular endothelial growth factor-induced responses and tumor growth after oral administration. Cancer Res. 60, 2178-2189 (Apr. 2000).

Yancopoulos, G. D. et al. Vasculogenesis, angiogenesis, and growth factors: ephrins enter the fray at the border. Cell 93, 661-664 (May 29, 1998).

Yanagisawa-Miwa, A. et al. Salvage of infracted myocardium by angiogenic action of basic fibroblast growth factor. Science 257, 1401-1403 (Sep. 4, 1992).

Zhu, Z. & Witte, L. Inhibition of tumor growth and metastasis by targeting tumor-associated angiogenesis with antagonists to the receptors of vascular endothelial growth factor. Invest. New Drugs 17, 195-212 (1999).

Carter et al. Allelic loss of chromosomes 16q and 10q in human prostate cancer. PNAS 87: 8751-8755 (1990).

Li et al. PTEN, a Putative Protein Tyrosine Phosphatase Gene Mutated in Human Brain, Breast, and Postate Cancer. Science 275:1943-1947 (1997).

Podlasek et al. Prostate Development Requires Sonic Hedgehog Expressed by the Urogenital Sinus Epithelium. Developmental Biology 209: 28-39 (1999).

McGarvey et al. PTCH gene mutations in invasive transitional cell carcinoma of the bladder. Oncogene 17: 1167-1172 (1998).

Smeets et al. Chromosomal Analysis of Bladder Cancer. Cancer Genetics and Cytogenetics 29: 29-41 (1987).

Berger et al. Chromosomes in Kidney, Ureter, and Bladder Cancer. Cancer Genetics and Cytogenetics 23: 1-24 (1986).

Cairns et al. Initiation of bladder cancer may involve deletion of a tumour-suppressor gene on chromosome 9. Oncogene 8: 1083-1085 (1992).

Gibas et al. Nonrandom Chromosomal Changes in Transitional Cell Carcinoma of the Bladder. Cancer Research 44:1257-1264 (1984).

Dalbagni et al. Genetic alternations in bladder cancer. Lancet 342: 469-471 (1993).

Pettet et al., "On the role of angiogenesis in wound healing," *Proc. R. Soc. Lond.*, B 263:1487-1493 (1996).

Ferrari, "Commentary on hibernating myocardium and its clinical relevance," *Basic Res. Cardiol.*, 90:52-54 (1995).

Dahmane, et al., "Activation of the transcription factor Gli 1 and the Sonic hedgehog signalling pathways in skin tumours", Nature, vol. 389, pp. 876-881 (1997).

Green, et al., "Basal cell carcinoma development is associated with induction of the expression of the transcription factor Gli-1", British Journal of Dermatology, vol. 139, pp. 911-915, (1998).

Roberts, et al., "Amplification of the gli Gene in Childhood Sarcomas", Cancer Research, vol. 49, pp. 5407-5413 (1989).

Thievessen et al., "Hedgehog Signaling in Normal Urothelial Cells and in Urothelial Carcinoma Cell Lines", Journal of Cellular Physiology, vol. 230, pp. 372-377 (2005).

Wang et al., "Shifting paradigms in Hedgehog Signaling", Current Opinion in Cell Biology, vol. 19, pp. 159-165 (2007).

Dahmane, et al., "Sonic hedgehog regulates the growth and patterning of the cerebellum", Development, vol. 126, pp. 3089-3100 (1999).

Ericson et al., "Two Critical Periods of Sonic Hedgehog Signaling Required for the Specification of Motor Neuron Identity", Cell, vol. 87, pp. 661-673 (1996).

Merseburger et al., "Tissue microarrays: applications in urological cancer research", World J. Urol., vol. 24, pp. 579-584 (2006).

Unwin et al., "Urological malignancies and the proteomic-genomic interface", Electrophoresis, vol. 20. pp. 3629-3637 (1999).

Wallace, Valerie A., "Purkinje-cell-derived Sonic hedgehog regulates granule neuron precursor cell proliferation in the developing mouse cerebellum", Current Biology, vol. 9, p. 445-448 (1999).

Yauch et al., "A paracrine requirement for hedgehog signalling in cancer"; available online Aug. 27, 2008 in advance of publication; doi:10.1038/nature07275 (2008).

* cited by examiner

```
                1
Indian   CGPGRVVGSR  RRPPRK-LVP  LAYKQFSPNV  PEKTLGASGR  YEGKIARSSE
Sonic    CGPGRGFG-K  RRHPKK-LTP  LAYKQFIPNV  AEKTLGASGR  YEGKISRNSE
Desert   CGPGRGPVGR  RRYARKQLVP  LLYKQFVPGV  PERTLGASGP  AEGRVARGSE 51
Indian   RFKELTPNYN  PDIIFKDEEN  TGADRLMTQR  CKDRLNSLAI  SVMNQWPGVK
Sonic    RFKELTPNYN  PDIIFKDEEN  TGADRLMTQR  CKDKLNALAI  SVMNQWPGVK
Desert   RFRDLVPNYN  PDIIFKDEEN  SGADRLMTER  CKERVNALAI  AVMNMWPGVR 101
Indian   LRVTEGWDED  GHHSEESLHY  EGRAVDITTS  DRDRNKYGLL  ARLAVEAGFD
Sonic    LRVTEGWDED  GHHSEESLHY  EGRAVDITTS  DRDRSKYGML  ARLAVEAGFD
Desert   LRVTEGWDED  GHHAQDSLHY  EGRALDITTS  DRDRNKYGLL  ARLAVEAGFD 151
Indian   WVYYESKAHV  HCSVKSEHSA  AAKTGG      SEQ ID NO: 23
Sonic    WVYYESKAHI  HCSVKAENSV  AAKSGG      SEQ ID NO. 24
Desert   WVYYESRNHV  HVSVKADNSL  AVRAGG      SEQ ID NO. 25
```

Gap(s), indicated by -, added to facilitate alignment

Fig. 1

```
C* G P G R  Xaa1 Xaa2 Xaa3 Xaa4 Xaa5      R R Xaa6 Xaa7 Xaa8 K Xaa9 L Xaa10 P

L Xaa11 Y K Q F Xaa12 P Xaa13 V           Xaa14 E K T L G A S G R

Xaa15 E G K Xaa16  Xaa17 R Xaa18 S E      R F K Xaa19 L Xaa20 P N Y N

P D I I F K D E E N                         Xaa21 G A D R L M T Xaa22 R

C K Xaa23 Xaa24 Xaa25 N S L A I           Xaa26 V M N Xaa27 W PG V K

L R V T E G W D E D                       G H H X2aa8 Xaa29 Xaa30 S L H Y
E G R A V D I T T S                       D R D R Xaa31 K Y G Xaa32 L

A R L A V E A G F D                         W V Y Y E S Xaa33 Xaa34 HXaa35

H Xaa36 S V K Xaa37 Xaa38                  Xaa39 S Xaa40 A A Xaa41 Xaa42 G G
```

Fig. 2

Hedgehog Protein is Expressed in Pancreatic Cancer

ANGIOGENESIS-MODULATING COMPOSITIONS AND USES

RELATED APPLICATIONS

This application claims priority to U.S. provisional application 60/407,445, filed Aug. 29, 2002, the disclosure of which is hereby incorporated by reference in its entirety.

BACKGROUND OF THE INVENTION

Hedgehog proteins act as morphogens in a wide variety of tissues during embryonic development (Ingham, 1995; Perrimon, 1995; Johnson and Tabin, 1997; Hammerschmidt et al., 1997). Vertebrate hedgehogs are crucial to a number of epithelial-mesenchymal inductive interactions during neuronal development, limb development, lung, bone, hair follicle and gut formation (Ericson et al., 1995; Roberts et al., 1995; Apelqvist et al., 1997; Ericson et al., 1997; Hammerschmidt et al., 1997; Johnson and Tabin, 1995; Pepicelli et al., 1998; Litingtung et al., 1998; Roberts et al., 1998; Dodd et al., 1998; Dockter, 2000). Mammalian hedgehog genes consist of sonic, indian and desert which are highly conserved between species (Zardoya, 1996). Sonic hedgehog (shh) is expressed widely during development and sonic null mice are embryonic lethal with multiple defects beginning early to midgestation (Bitgood and McMahon, 1995; Chiang et al., 1996; Litingtung et al., 1998; St-Jacques et al., 1998). Indian hedgehog (ihh) is expressed less widely and indian null mice survive till late gestation. However, Ihh null mice exhibit severe stunting of skeletal growth which correlates to the role of Ihh in regulating bone growth plate (St-Jacques et al., 1999; Karp et al., 2000). Desert hedgehog (dhh) is the most restricted in expression and Dhh null mice are viable, but as expected from the expression pattern, male gonads do not develop completely and the peripheral nerves develop in a disorganized fashion (Bitgood et al., 1996; Parmantier et al., 1999).

Hedgehog signalling occurs through the interaction of hedgehog protein with the hedgehog receptor, patched (Ptc) and this interaction's modulation of the co-receptor smoothened (Smo). The mammalian genome contains 2 patched genes, ptc1 and ptc2, both of which encode 12 transmembrane proteins containing a sterol sensing domain (Motoyama et al, 1998; Carpenter et al, 1998). The interaction of Hh and Ptc inactivates the repression of smoothened (Smo), a 7 transmembrane protein which then leads to activation of fused (Fu), a serine-threonine kinase, and the disassociation of a transcription factor, Gli, from the microtuble-associated Fu-Gli-Su(fu) complex. The uncomplexed Gli protein is transported to the nucleus where it activates downstream target genes of the hedgehog pathway including the ptc1 and gli1 genes (Ding et al., 1999; Murone et al, 1999a; Murone et al, 1999b; Pearse et al., 1999; Stone et al., 1999; Hynes et al, 2000).

Hedgehog genes have so far not been implicated directly in embryonic or adult angiogenesis. No vascular defects have been reported in shh, ihh or dhh knockout mice. However, we show here that cells in the adult vasculature both express ptc1 and can respond to exogenous hedgehog and, more importantly, hedgehog is able to induce robust neovascularization in the corneal pocket model of angiogenesis. The angiogenic response to hedgehog appears to occur through the activation of mesenchymal cells to produce VEGFs and Angiopoietins.

Angiogenesis, the process of sprouting new blood vessels from existing vasculature and arteriogenesis, the remodeling of small vessels into larger conduit vessels are both physiologically important aspects of vascular growth in adult tissues (Klagsbrun and D'Amore, 1991; Folkman and Shing, 1992; Beck and D'Amore, 1997; Yancopoulos et al., 1998; Buschman and Schaper, 2000). These processes of vascular growth are required for beneficial processes such as tissue repair, wound healing, recovery from tissue ischemia and menstrual cycling. They are also required for the development of pathological conditions such as the growth of neoplasias, diabetic retinopathy, rheumatoid arthritis, psoriasis, certain forms of macular degeneration, and certain inflammatory pathologies (Cherrington et al., 2000).

The ability to stimulate vascular growth has potential utility for treatment of ischemia-induced pathologies such as myocardial infarction, coronary artery disease, peripheral vascular disease, and stroke. The sprouting of new vessels and/or the expansion of small vessels in ischemic tissues prevents ischemic tissue death and induces tissue repair. Certain growth factors such as those in the vascular endothelial growth factor (VEGF) and fibroblast growth factor (FGF) families are able to stimulate vascular growth by acting on endothelial cells to induce angiogenesis. Other factors have also been shown to have angiogenic and arteriogenic activities such as MCPI (Buschman and Schaper, 2000) and angiopoietins. In preclinical models of myocardial infarction, both FGFs and VEGFs have been able to improve myocardial revascularization and function (Yanagisawa-Miwa et al, 1992; Battler et al., 1993; Harada et al., 1994; Banai et al., 1994; Unger et al., 1994; Mesri et al., 1995; Pearlman et al., 1995; Landau et al, 1995; Lazarous et al., 1996; Engler, 1996; Magovern et al., 1997; Shou et al., 1997). Also in models of peripheral vascular disease, VEGF and other angiogenic factors are able to induce angiogenesis and improve vascular perfusion of the ischemic limb (Majesky, 2000; Takeshita et al, 1996 and 1994; Rivard et al., 1998 and 1999, Isner et al, 1996).

A number of these factors are also implicated in vascular growth in pathological conditions such as tumor expansion, diabetic retinopathy and rheumatoid arthritis. The inhibition of vascular growth in these contexts has also shown beneficial effects in preclinical animal models (Klohs and Hamby, 1999; Zhu and Witte, 1999; Cherrington et al., 2000). For example, inhibition of angiogenesis by blocking vascular endothelial growth factor or its receptor has resulted in inhibition of tumor growth and in retinopathy (Fong et al., 1999; Wood et al., 2000; Ozaki et al., 2000). Also, the development of pathological pannus tissue in rheumatoid arthritis involves angiogenesis and can be blocked by inhibitors of angiogenesis (Peacock et al., 1995; Storgard et al., 1999).

Thus, the induction of angiogenesis and vascular growth is beneficial for tissue repair and would healing whereas inhibition of angiogenic growth factors can prevent angiogenesis driven pathologies. It would be useful to develop novel therapeutics that modulate angiogenesis.

Furthermore, the present invention demonstrates that the inhibition of hedgehog signaling decreases unwanted cellular proliferation, growth, differentiation and/or survival. Such unwanted cellular behavior is often observed in tumor cells (e.g., in cancer). Accordingly, the present invention provides methods and compositions of decreasing unwanted cellular behavior, such as occurs in cancer, by administering hedgehog antagonists.

SUMMARY OF THE INVENTION

Hedgehog proteins are angiogenic growth factors which can have utility in treating tissue repair and ischemia and inhibition of hedgehog proteins and the hedgehog pathway can prevent angiogenesis driven pathologies.

Furthermore, hedgehog signal transduction is involved in a wide array of proliferative events throughout embryonic and adult development. Inhibition of hedgehog signaling using a hedgehog antagonist can decrease or inhibit unwanted cellular proliferation, differentiation, migration and/or survival. Such unwanted cell behavior is a common hallmark of many cancers. Accordingly, the present invention provides methods and compositions for inhibiting unwanted cell behavior, as in cancers of any cell type. Without wishing to be bound by theory, it is appreciated that the inhibition of unwanted cellular behavior by administration of a hedgehog antagonist may be in part due to an inhibition of angiogenesis.

The present invention contemplates methods and reagents for antagonizing hedgehog signaling. Antagonism of hedgehog signaling can be used to decrease or inhibit at least one of undesirable proliferation, growth, differentiation, or survival of cells. Such undesirable proliferation, growth, differentiation, or survival of cells may be observed in conditions including many forms of cancer. It is contemplated that an agent which antagonizes hedgehog signaling, and thus inhibits the undesirable proliferation, growth, differentiation, or survival of cells, may be an agent which antagonizes hedgehog signaling by interacting with components of the hedgehog signaling pathway either extracellularly, at the cell surface, or intracellularly.

In certain aspects, the present invention makes available methods and reagents for inhibiting undesirable growth states that occur in cells with an active hedgehog signaling pathway. In one embodiment, the subject methods may be used to inhibit unwanted cell proliferation by determining whether cells overexpress a gli gene, and contacting cells that overexpress a gli gene with an effective amount of a hedgehog antagonist. In preferred embodiments, the unwanted cell proliferation is cancer or benign prostatic hyperplasia.

Another aspect of the present invention makes available methods for determining a treatment protocol comprising obtaining a tissue sample from a patient, and determining levels of gli gene expression in said sample, wherein overexpression of a gli gene indicates that treatment with a hedgehog antagonist is appropriate.

In other preferred embodiments, hedgehog antagonists of the invention are selected from a small molecule of less than 2000 daltons, a hedgehog antibody, a patched antibody, a smoothened antibody, a mutant hedgehog protein, an antisense nucleic acid, an RNAi construct, and a ribozyme. In yet another preferred embodiment, the hedgehog antagonist is a hedgehog antibody selected from a polyclonal antibody or a monoclonal antibody. Exemplary monoclonal antibodies are specifically immunoreactive with a vertebrate hedgehog polypeptide. In a preferred embodiment, such specifically immunoreactive monoclonal antibodies do not substantially cross react with either an invertebrate hedgehog polypeptide, or with other non-hedgehog polypeptides. Exemplary hedgehog monoclonal antibodies for use as hedgehog antagonists in the subject methods include 5E1, and antibodies which recognize the same epitope as 5E1. We note that 5E1 was deposited with the ATCC on Aug. 13, 2002.

In yet another aspect, the invention provides therapeutic compositions of hedgehog antagonists for use in the subject methods. Exemplary therapeutic compositions include, but are not limited to, hedgehog monoclonal antibodies and hedgehog polyclonal antibodies. Exemplary therapeutic compositions of hedgehog monoclonal antibodies comprise a therapeutically effective amount of 5E 1, or an antibody which recognizes the same epitope as 5E1, combined with a pharmaceutically acceptable excipient or carrier. Further exemplary compositions of hedgehog monoclonal antibodies comprise a therapeutically effective amount of an antibody which specifically recognizes a hedgehog epitope and blocks/antagonizes hedgehog signal transduction. The effective amount of said hedgehog antibody is sufficient to antagonize hedgehog signaling. The present invention further contemplates therapeutic compositions comprising combinations of more than one hedgehog antagonist formulated with a pharmaceutically acceptable excipient or carrier. Exemplary therapeutic compositions comprise combinations of two or more hedgehog antibodies formulated with a pharmaceutically acceptable excipient or carrier. Further exemplary compositions comprise combinations of one or more hedgehog antibodies, one or more hedgehog non-antibody antagonists (e.g., small organic molecules), and a pharmaceutically acceptable excipient or carrier.

In another aspect, the invention provides methods of determining the likelihood that a cancer will develop in a tissue, comprising obtaining a tissue sample, and determining levels of gli gene expression in said sample, wherein, overexpression of a gli gene indicates that cancer is more likely to develop. In another embodiment of this aspect, the present invention provides methods of determining the likelihood that a cancer will develop in a tissue, comprising obtaining a tissue sample, and determining levels of hedgehog gene expression in said sample, wherein, overexpression of a hedgehog gene indicates that cancer is more likely to develop.

In still another aspect, the present invention makes available methods and reagents for inhibiting at least one of undesirable proliferation, growth, differentiation or survival of a cell with an active hedgehog signaling pathway. In one embodiment, the subject methods may be used to inhibit at least one of unwanted cell proliferation, growth, differentiation or survival by determining whether cells overexpress a gli gene, and contacting cells that overexpress a gli gene with an effective amount of a hedgehog antagonist. In still another embodiment, the subject methods may be used to inhibit at least one of unwanted cell proliferation, growth, differentiation or survival by determining whether cells overexpress a hedgehog gene, and contacting cells that overexpress a hedgehog gene with an effective amount of a hedgehog antagonist. In preferred embodiments, the unwanted cell proliferation, growth, differentiation or survival is cancer or benign prostatic hyperplasia.

Exemplary forms of cancer which may be treated by the subject methods include, but are not limited to, prostate cancer, bladder cancer, lung cancer (including either small cell or non-small cell cancer), colon cancer, kidney cancer, liver cancer, breast cancer, cervical cancer, endometrial or other uterine cancer, ovarian cancer, testicular cancer, cancer of the penis, cancer of the vagina, cancer of the urethra, gall bladder cancer, esophageal cancer, or pancreatic cancer. Additional exemplary forms of cancer which may be treated by the subject methods include, but are not limited to, cancer of skeletal or smooth muscle, stomach cancer, cancer of the small intestine, cancer of the salivary gland, anal cancer, rectal cancer, tyroid cancer, parathyroid cancer, pituitary cancer, and nasopharyngeal cancer. Further exemplary forms of cancer which can be treated with the hedgehog antagonists of the present invention include cancers comprising hedgehog expressing cells. Still further exemplary forms of cancer which can be treated with the hedgehog antagonists of the present invention include cancers comprising gli expressing cells. In one embodiment, the cancer is not characterized by a mutation in patched-1.

The present invention further contemplates methods for determining the appropriate treatment regimen for a patient with cancer. Without being bound by any particular theory, cancers which express a hedgehog gene or a gli gene, or which overexpress a hedgehog gene or a gli gene in comparison to non-cancerous cells of the same tissue type, may be more amenable to treatment with the hedgehog antagonists of the present invention. Accordingly, methods of determining the expression of a hedgehog gene or a gli gene can be used to determine whether treatment with a hedgehog antagonist is appropriate (i.e., is likely to be effective).

In one embodiment, the method comprises determining the level of the expression of a hedgehog gene wherein the hedgehog gene is selected from Shh, Ihh or Dhh. In another embodiment, the method comprises determining the level of expression of a gli gene wherein the gli gene is gli-1, gli-2 or gli-3.

In another aspect, the present invention contemplates the use of one or more hedgehog agonists in the manufacture of a medicament for promoting angiogenesis.

In another aspect, the present invention provides the use of one or more hedgehog antagonists in the manufacture of a medicament for inhibiting angiogenesis.

In still another aspect, the present invention provides the use of one or more hedgehog antagonists in the manufacture of a medicament for inhibiting one or more of unwanted growth, proliferation, differentiation, or survival of a cell.

In one embodiment, the one or more hedgehog antagonists are administered as part of a therapeutic regimen with other drugs or therapies.

In still another aspect, the present invention provides the use of one or more hedgehog antagonists in the manufacture of a medicament for treating cancer.

In one embodiment, the one or more hedgehog antagonists are administered as part of a therapeutic regimen with other drugs or therapies.

BRIEF DESCRIPTION OF THE DRAWINGS

FIG. 1 shows an alignment of N-terminal fragments of Human Hedgehog proteins.

FIG. 2 shows a consensus sequence of a hedgehog protein suitable for use in developing the conjugated proteins of the invention, antagonist, where "Xaa" indicates amino acids that differ between the Sonic, Indian and Desert hedgehog proteins.

DETAILED DESCRIPTION OF THE INVENTION

I. Overview

Figure 3:
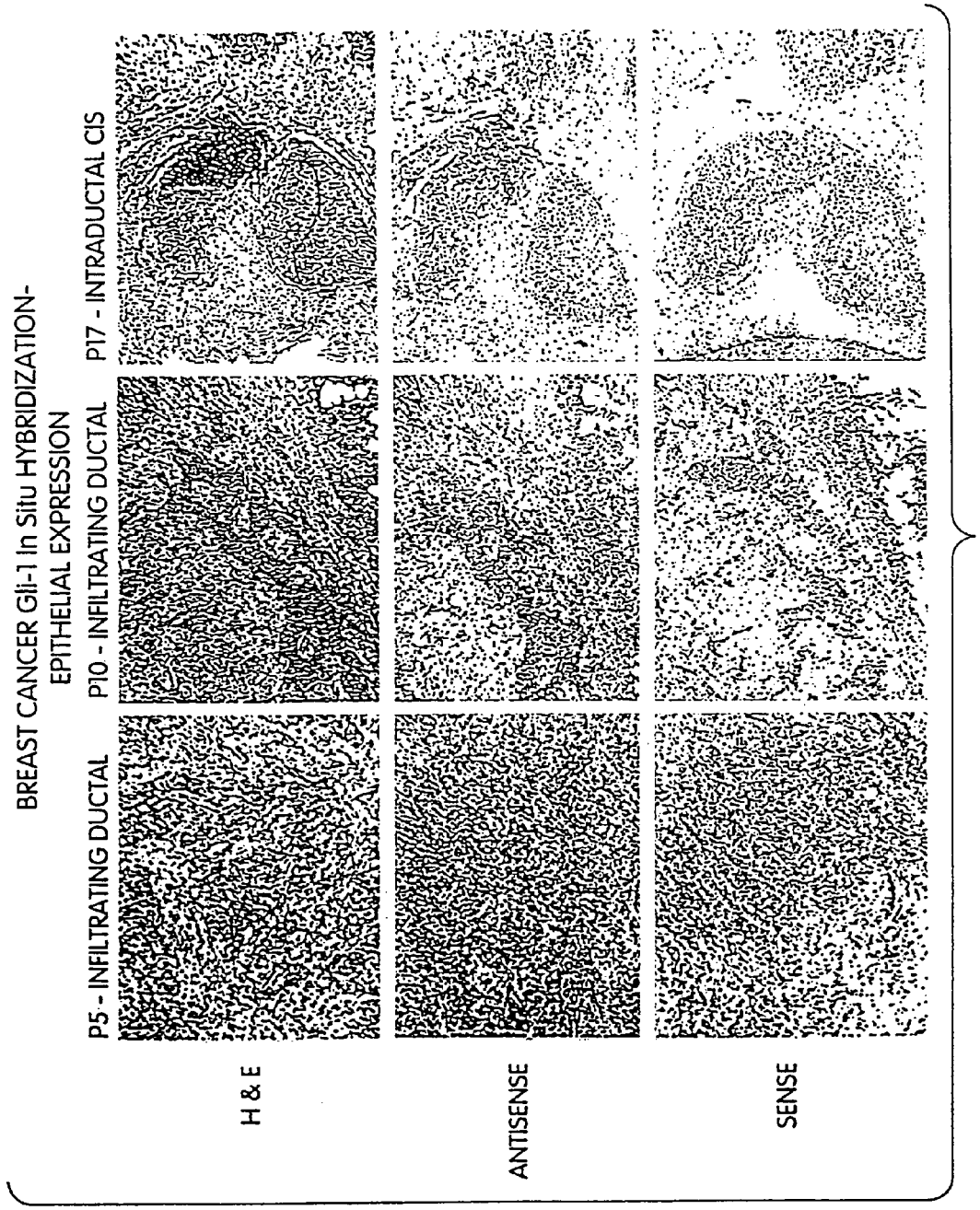
FIG. 3 illustrates gli-1 expression in breast cancer tissue as visualized by in situ hybridization.
Figure 4:
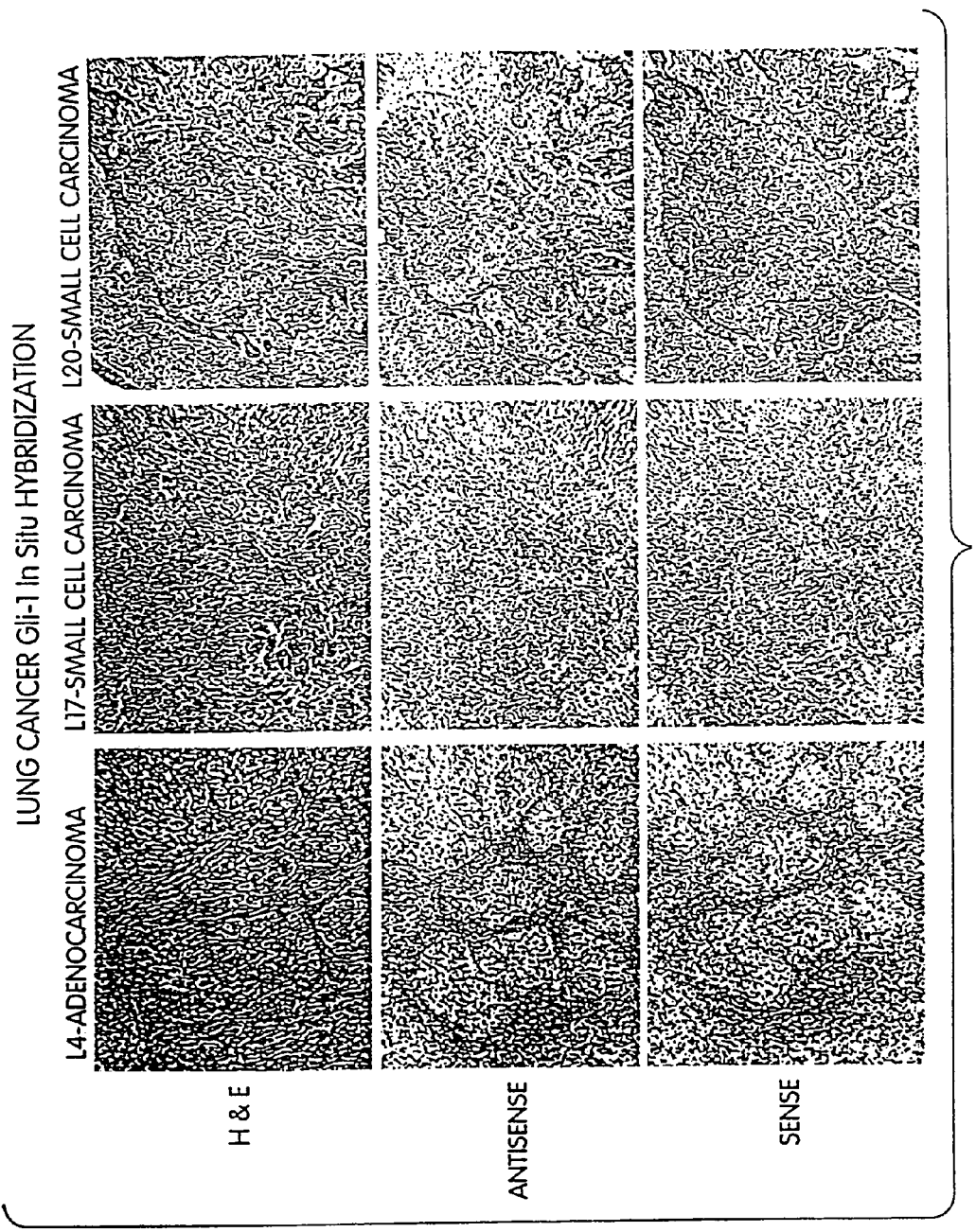
FIG. 4 shows gli-1 expression in lung cancer visualized by in situ hybridization.
Figure 5:
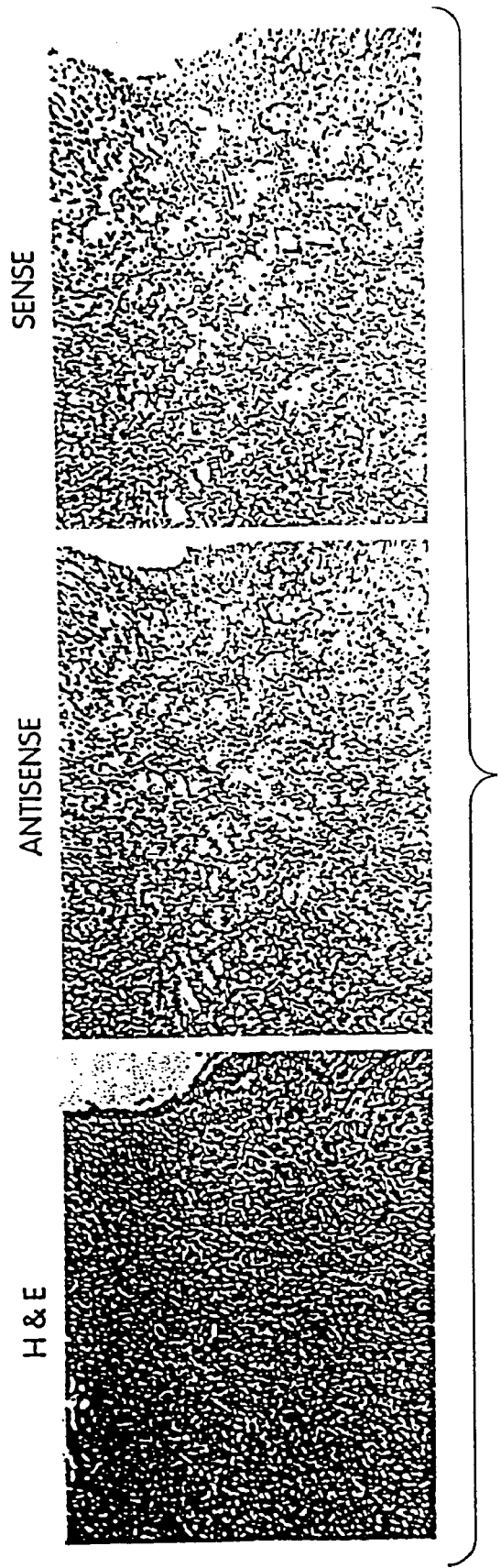
FIG. 5 illustrates gli-1 expression in prostate cancer as visualized by in situ hybridization.
Figure 6:
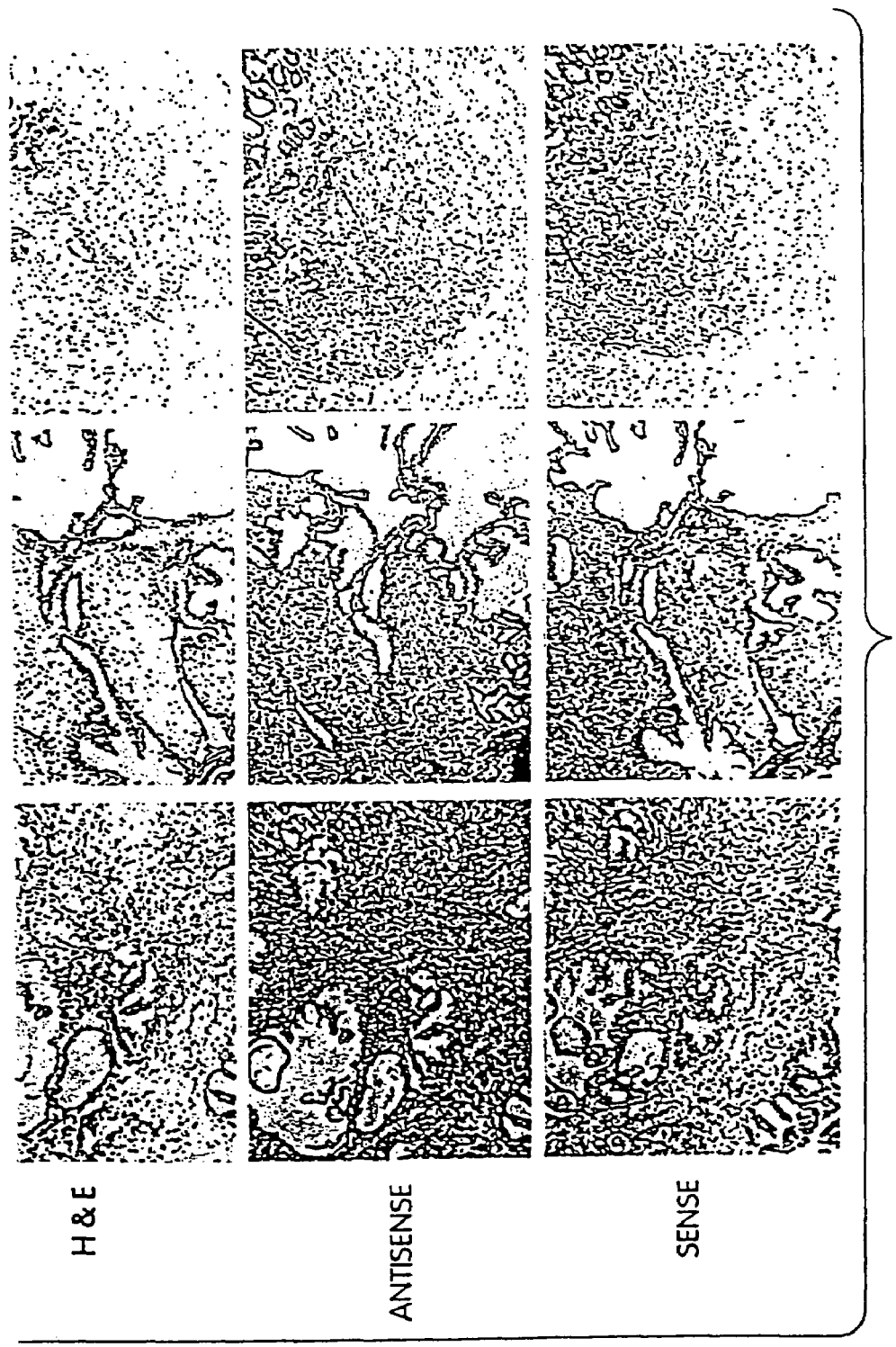
FIG. 6 depicts gli-1 expression in benign prostatic hyperplasia as visualized by in situ hybridization.

The present invention relates to the use of hedgehog protein, nucleic acids, or other hedgehog therapeutic as an agent to induce the growth of new blood vessels, ie angiogenesis, arteriogenesis or vascular growth in adult tissues where the induction of angiogenesis has therapeutic value. The present invention also relates to the use of inhibitors of hedgehog protein or signaling to prevent angiogenesis contributing to pathological conditions such as neoplasia (tumors and gliomas), diabetic retinopathy, rheumatoid arthritis, osteoarthritis, macular degeneration, psoriasis, ulcerative colitis, Chrohn's disease, and inflammation. Such inhibitors of hedgehog signaling (hedgehog antagonists) include antagonistic variants of hedgehog protein, hedgehog antibodies, antisense RNAs, RNAi constructs, ribozymes, and small organic molecules.

The present invention relates to the discovery that signal transduction pathways regulated by hedgehog, patched (ptc), gli and/or smoothened can be inhibited, at least in part, by hedgehog antagonists. While not wishing to be bound by any theory, in the case of small molecule antagonists, the modulation of a receptor may be the mechanism by which these agents act. For example, the ability of these agents to inhibit proliferation of patched loss-of-function ($ptc^{lof}$) cells may be due to the ability of such molecules to interact with hedgehog, patched, or smoothened, or at least to interfere with the ability of those proteins to activate a hedgehog, ptc, and/or smoothened-mediated signal transduction pathway.

It is, therefore, specifically contemplated that these small molecules which interfere with aspects of hedgehog, ptc, or smoothened signal transduction activity will likewise be capable of changing the role of a cell in tissue development from what would otherwise occur. In preferred embodiments, the cell has a substantially wild-type hedgehog signaling pathway. It is also contemplated that hedgehog antagonists are particularly effective in treating disorders resulting from hyperactivation of the hedgehog pathway, either as a result of mutations in components of the hedgehog signaling pathway or as a result of inappropriate activation of the hedgehog signaling pathway in cell which do not comprise a mutation/lesion in a component of the hedgehog signaling pathway. Therefore, it is desirable to have a method for identifying those cells in which the hedgehog pathway is hyperactive such that antagonist treatment may be efficiently targeted. One of skill in the art will readily recognize, that antagonists for use in the present invention can antagonize hedgehog signaling at any point in the hedgehog signaling pathway. That is, an exemplary antagonist can reduce hedgehog signaling by binding to and antagonizing hedgehog, as for example using a hedgehog antibody. Similarly, an exemplary antagonist can interfere with the interaction between hedgehog and the hedgehog receptor patched. Additionally, one of skill in the art will recognize that exemplary antagonists can interfere with hedgehog signaling by acting intracellularly, as for example using a small molecule antagonist that acts on an intracellular component of the hedgehog signaling pathway. It is contemplated that the hedgehog antagonists of the present invention can be used to antagonize hedgehog signaling in a wild-type cell or in a cell comprising a mutation in a component of the hedgehog signaling pathway.

In certain embodiments, the subject antagonists are organic molecules having a molecular weight less than 2500 amu, more preferably less than 1500 amu, and even more preferably less than 750 amu, and are capable of inhibiting at least some of the biological activities of hedgehog proteins, preferably specifically in target cells.

Thus, the methods of the present invention include the use of small molecules that agonize ptc inhibition of hedgehog signaling in the regulation of repair and/or functional performance of a wide range of cells, tissues and organs having the phenotype of hedgehog gain-of-function and in tissues with wild-type hedgehog activity. For instance, the subject method has therapeutic and cosmetic applications ranging from regulation of neural tissues, bone and cartilage formation and repair, regulation of spermatogenesis, regulation of smooth muscle, regulation of lung, liver and tissue of other organs arising from the primitive gut, regulation of hematopoietic function, regulation of skin and hair growth, etc. Moreover, the subject methods can be performed on cells that are provided in culture (in vitro), or on cells in a whole animal (in vivo). See, for example, PCT publications WO 95/18856 and WO 96/17924 (the specifications of which are expressly incorporated by reference herein).

In another aspect, the present invention provides pharmaceutical preparations comprising, as an active ingredient, a hedgehog antagonist or ptc agonist such as described herein, formulated in an amount sufficient to inhibit, in vivo, proliferation or other biological consequences of hedgehog gain-of-function.

The subject treatments using hedgehog antagonists can be effective for both human and animal subjects. Animal subjects to which the invention is applicable extend to both domestic animals and livestock, raised either as pets or for commercial purposes. Examples are dogs, cats, cattle, horses, sheep, hogs, and goats.

All references cited in the Detailed Description are incorporated herein by references, unless stipulated otherwise. The following terms are used herein:

II. Definitions

"Angiogenesis" is defined as any alteration of an existing vascular bed or the formation of new vasculature which benefits tissue perfusion. This includes the formation of new vessels by sprouting of endothelial cells from existing blood vessels or the remodeling of existing vessels to alter size, maturity direction or flow properties to improve blood perfusion of tissue.

Mesenchymal cells are defined as cells of mesenchymal origin including fibroblasts, stromal cells, smooth muscle cells, skeletal muscle cells, cells of osteogenic origin such as chondrocytes, cells of hemaeopoietic origin such as monocytes, macrophages, lymphocytes, granulocytes and cells of adipose origin such as adipocytes.

A hedgehog therapeutic, whether it is a hedgehog angonist or hedgehog antagonist is said to have "therapeutic efficacy" in modulating, for example, angiogenesis and an amount of the therapeutic is said to be a "angiogenic modulatory amount", if administration of that amount of the therapeutic is sufficient to cause a significant modulation (i.e., increase or decrease) in angiogenic activity when administered to a subject (e.g., an animal model or human patient) needing modulation of angiogenesis.

As used herein, a hedgehog therapeutic of the invention is an "agonist" if it "modulates" hedgehog biological activity (i.e., elicits, allows and/or enhances hedgehog biological activity). For the purposes of the invention an agonist also refers to an agent, e.g., a polypeptide such as an hedgehog or patched or a small organic molecule which can elicit, allow and/or enhance hedgehog and/or patched-mediated binding or which can otherwise modulate hedgehog and/or patched function, e.g., by activating hedgehog-ligand mediated hedgehog signal transduction. Such an agonist of the hedgehog/patched interaction is an agent which has one or more of the following properties: (1) it coats, or binds to, a hedgehog protein associated with an extracellular matrix, e.g., heparin, heparin proteoglycans, collagen, fibronectin, vitronectin, thrombospondin, or on the surface of a hedgehog bearing or secreting cell with sufficient specificity to modulate a hedgehog-ligand/hedgehog receptor interaction, e.g., the hedgehog/patched-smoothened interaction; (2) it coats, or binds to, a hedgehog on the surface of a hedgehog-bearing or secreting cell with sufficient specificity to modify, and preferably to modulate, transduction of a hedgehog-mediated signal e.g., hedgehog/patched-smoothened-mediated signaling; (3) it coats, or binds to, a hedgehog receptor or co-receptor, (e.g., patched, smoothened or a heparin proteoglycan) in or on cells with sufficient specificity to modulate the hedgehog/patched-smoothened interaction; (4) it coats, or binds to, a hedgehog receptor (e.g., patched or smoothened) in or on cells with sufficient specificity to modify, and preferably to modulate, transduction of hedgehog receptor mediated hedgehog signaling, e.g., patched, smoothened, fused or gli-mediated hedgehog signaling.

In preferred embodiments an agonist has one or both of properties 1 and 2. In other preferred embodiments the agonist has one or both of properties 3 and 4. Moreover, more than one agonist can be administered to a patient, e.g., an agent which binds to hedgehog can be combined with an agent which binds to patched. Moreover, a hedgehog therapeutic is an "agonist" if it modulates angiogenesis in such a way as to enhance, elicit, accelerate or increase angiogenesis, regardless of the mode of action of such therapeutic.

As used herein, a hedgehog therapeutic is an "antagonist" if it de-activates the hedgehog receptor or inhibits its activity or inhibits activity of the hedgehog protein or otherwise inhibits hedgehog signal transduction. Such an antagonist may additionally have one or more of the following properties: (1) it coats, or binds to, a hedgehog protein on the surface of a hedgehog bearing or secreting cell with sufficient specificity to de-activate or inhibit a hedgehog-ligand/hedgehog interaction, e.g., the hedgehog/patched interaction; (2) it coats, or binds to, a hedgehog protein on the surface of a hedgehog-bearing or secreting cell with sufficient specificity to modify, and preferably to de-activate or inhibit, transduction of a hedgehog-mediated signal e.g., hedgehog/patched, smoothened, fused, or gli-mediated signaling; (3) it coats, or binds to, a hedgehog receptor or coreceptor (e.g., patched or smoothened) in or on cells with sufficient specificity to de-activate or inhibit the hedgehog/patched interaction; (4) it coats, or binds to, a hedgehog receptor or co-receptor (e.g., patched or smoothened) in or on cells with sufficient specificity to modify, and preferably to de-activate or inhibit transduction of hedgehog receptor mediated hedgehog signaling, e.g., patched-mediated hedgehog signaling. In preferred embodiments an antagonist has one or both of properties 1 and 2. In other preferred embodiments the antagonist has one or both of properties 3 and 4. Moreover, more than one antagonist can be administered to a patient, e.g., an agent which binds to hedgehog can be combined with an agent which binds to patched. Moreover, a hedgehog therapeutic is an "antagonist" if it modulates angiogenesis in such a way as to inhibit, decelerate, reverse or otherwise slow angiogenesis, regardless of the mode of action of such therapeutic. For example, antagonist molecules may be antibody homologs (defined below), certain fragments of hedgehog, or small organic molecules that may be administered and modulate hedgehog binding sites on cells.

As discussed herein, the hedgehog therapeutics (i.e., antagonists or agonists) that can be linked or otherwise conjugated to, for instance, an antibody homolog such as an immunoglobulin or fragment thereof are not limited to a particular type or structure of hedgehog or patched or other molecule so that, for purposes of the invention, any agent capable of forming a chimeric protein and capable of effectively modulating hedgehog is considered to be an equivalent of the therapeutics used in the examples herein.

As used herein, the term "antibody homolog" includes intact antibodies consisting of immunoglobulin light and heavy chains linked via disulfide bonds. The term "antibody homolog" is also intended to encompass a hedgehog therapeutic comprising one or more polypeptides selected from immunoglobulin light chains, immunoglobulin heavy chains and antigen-binding fragments thereof which are capable of binding to one or more antigens (i.e., hedgehog or patched). The component polypeptides of an antibody homolog composed of more than one polypeptide may optionally be disulfide-bound or otherwise covalently crosslinked. Accordingly, therefore, "antibody homologs" include intact immunoglobulins of types IgA, IgG, IgE, IgD, IgM (as well as subtypes thereof), wherein the light chains of the immunoglobulin may be of types kappa or lambda or portions of intact antibodies that retain antigen-binding specificity, for example, Fab fragments, Fab' fragments, F(ab')2 fragments, F(v) fragments, heavy chain monomers or dimers, light chain monomers or dimers, dimers consisting of one heavy and one light chain, and the like.

As used herein, a "humanized antibody homolog" is an antibody homolog, produced by recombinant DNA technology, in which some or all of the amino acids of a human immunoglobulin light or heavy chain that are not required for antigen binding have been substituted for the corresponding amino acids from a nonhuman mammalian immunoglobulin light or heavy chain. A "human antibody homolog" is an antibody homolog in which all the amino acids of an immunoglobulin light or heavy chain (regardless of whether or not they are required for antigen binding) are derived from a human source.

"amino acid"—a monomeric unit of a peptide, polypeptide, or protein. There are twenty amino acids found in naturally occurring peptides, polypeptides and proteins, all of which are L-isomers. The term also includes analogs of the amino acids and D-isomers of the protein amino acids and their analogs.

A hedgehog therapeutic has "biological activity" if it has at least one of the following properties: (i) it has the ability to bind to its receptor, patched or it encodes, upon expression, a polypeptide that has this characteristic; and/or (ii) it may induce alkaline phosphatase activity in C3H10T1/2 cells. The hedgehog therapeutic protein meeting this functional test of "biological activity" may meet the hedgehog consensus criteria as defined herein in FIG. 2 (SEQ ID NO: 26). This term "biological activity" includes antagonists and agonists.

The term "bioavailability" refers to the ability of a compound to be absorbed by the body after administration. For instance, a first compound has greater bioavailability than a second compound if, when both are administered in equal amounts, the first compound is absorbed into the blood to a greater extent than the second compound.

The term "chimeric" hedgehog therapeutic is a generic term referring to constructs X-A, where "X" is a polypeptide having the amino acid sequence or portion thereof, consisting of the amino acid sequence of a hedgehog protein and "A" is at least part of a polypeptide other than hedgehog. "A" may include a linker sequence (as defined below) and may be attached to either, or both, of the N- or C-terminii of the hedgehog moiety. Chimeric hedgehog therapeutics of the invention therefore include compounds in which the various moieties are chemically cross-linked or covalently "fused" (as defined below).

As used herein, the term "covalently coupled" means that the specified moieties of the hedgehog therapeutic are either directly covalently bonded to one another, or else are indirectly covalently joined to one another through an intervening moiety or moieties, such as a bridge, spacer, or linkage moiety or moieties. The intervening moiety or moieties are called a "coupling group". The term "conjugated" is used interchangeably with "covalently coupled".

"expression control sequence"—a sequence of polynucleotides that controls and regulates expression of genes when operatively linked to those genes.

"expression vector"—a polynucleotide, such as a DNA plasmid or phage (among other common examples) which allows expression of at least one gene when the expression vector is introduced into a host cell. The vector may, or may not, be able to replicate in a cell.

The phrase "extracellular signaling protein" means any protein that is either secreted from a cell, or is associated with the cell membrane, and upon binding to the receptor for that protein on a target cell, triggers a response in the target cell.

"functional equivalent" of an amino acid residue is (i) an amino acid having similar reactive properties as the amino acid residue that was replaced by the functional equivalent; (ii) an amino acid of a ligand of a polypeptide of the invention, the amino acid having similar properties as the amino acid residue that was replaced by the functional equivalent; (iii) a non-amino acid molecule having similar properties as the amino acid residue that was replaced by the functional equivalent.

A first polynucleotide encoding hedgehog protein is "functionally equivalent" compared with a second polynucleotide encoding hedgehog protein if it satisfies at least one of the following conditions:

(a) the "functional equivalent" is a first polynucleotide that hybridizes to the second polynucleotide under standard hybridization conditions and/or is degenerate to the first polynucleotide sequence. Most preferably, it encodes a mutant hedgehog having the activity of an hedgehog therapeutic;

(b) the "functional equivalent" is a first polynucleotide that codes on expression for an amino acid sequence encoded by the second polynucleotide.

The term "hedgehog therapeutic" includes, but is not limited to, the agonist and/or antagonist agents listed herein as well as their functional equivalents. As used herein, the term "functional equivalent" therefore refers to, for example, an hedgehog protein or a polynucleotide encoding the hedgehog protein that has the same or an improved beneficial effect on the mammalian recipient as the hedgehog of which it is deemed a functional equivalent. As will be appreciated by one of ordinary skill in the art, a functionally equivalent protein can be produced by recombinant techniques, e.g., by expressing a "functionally equivalent DNA". Accordingly, the instant invention embraces hedgehog therapeutics encoded by naturally-occurring DNAs, as well as by non-naturally-occurring DNAs which encode the same protein as encoded by the naturally-occurring DNA. Due to the degeneracy of the nucleotide coding sequences, other polynucleotides may be used to encode hedgehog protein. These include all, or portions of the above sequences which are altered by the substitution of different codons that encode the same amino acid residue within the sequence, thus producing a silent change. Such altered sequences are regarded as equivalents of these sequences. For example, Phe (F) is coded for by two codons, TTC or TTT, Tyr (Y) is coded for by TAC or TAT and His (H) is coded for by CAC or CAT. On the other hand, Trp (W) is coded for by a single codon, TGG. Accordingly, it will be appreciated that for a given DNA sequence encoding a particular hedgehog there will be many DNA degenerate sequences that will code for it. These degenerate DNA sequences are considered within the scope of this invention.

The term "fusion" or "fusion protein" is a species of chimeric hedgehog therapeutic and refers to a co-linear, covalent linkage of two or more proteins or fragments thereof via their individual peptide backbones, most preferably through genetic expression of a polynucleotide molecule encoding those proteins. It is preferred that the proteins or fragments thereof are from different sources (e.g., a 'chimeric' protein). Thus, preferred fusion therapeutics include an hedgehog protein or fragment covalently linked to a second moiety that is not a hedgehog protein. In certain embodiments, the non-hedgehog moiety may be a protein having a domain or region which is homologous to a member of the immunoglobulin gene superfamily. Members of this superfamily inlcude class I and class II major histocompatability antigens, CD4 and T cell receptor chains. Further examples of members of this family and fusion proteins containing them are found in U.S. Pat. No. 5,565,335 (Genentech), incorporated herein by reference.

Non-hedgehog proteins of this type are useful if they contain one or more amino acid sequences at least 20, 50, 75 or 150 residues in length, that are at least 40% homologous to a sequence of an immunoglobulin constant or variable region. A non-hedgehog protein meeting these requirements is said to possess an "Ig-like domain" which may be an "Ig-like constant domain" or an "Ig-like variable domain". Thus, one embodiment of the present invention is a chimeric hedgehog therapeutic in which the non-hedgehog moiety contains at least one Ig-like domain, or portion thereof.

Other embodiments are possible. Specifically, a "hedgehog/Ig fusion" is a hedgehog therapeutic comprising a biologically active hedgehog molecule of the invention (i.e., Sonic hedgehog), or a biologically active fragment thereof (i.e., the N-terminal portion) linked to an N-tenninus of an immunoglobulin chain wherein a portion of the N-terminus of the immunoglobulin is replaced with the hedgehog. A species of hedgehog/Ig fusion is an "hedgehog /Fc fusion" which is a protein comprising an hedgehog molecule of the invention (i.e., hedgehog ) linked to at least a part of the constant domain of an immunoglobulin. Also, the term "fusion protein" means an hedgehog protein chemically linked via a mono- or hetero- functional molecule to a second moiety that is not an hedgehog protein and is made de novo from purified protein as described below. Thus, this invention features a hedgehog therapeutic molecule which includes: (1) a hedgehog moiety, (2) a second peptide, e.g., one which increases solubility or in vivo life time of the hedgehog moiety, e.g., a member of the immunoglobulin super family or fragment or portion thereof, e.g., a portion or a fragment of IgG, e.g., the human IgGl heavy chain constant region, e.g., CH2, CH3, and hinge regions; and a toxin moiety.

"Heterologous promoter"—as used herein is a promoter which is not naturally associated with a gene or a purified nucleic acid.

"Homology" and "identity" each refer to sequence similarity between two polypeptide sequences, and both 'homology' and 'identity' are used interchangeably in this disclosure. Homology can be determined by comparing a position in each sequence which may be aligned for purposes of comparison. When a position in the compared sequence is occupied by the same amino acid residue, then the polypeptides can be referred to as identical at that position; when the equivalent site is occupied by the same amino acid (e.g., identical) or a similar amino acid (e.g., similar in steric and/or electronic nature), then the molecules can be referred to as homologous at that position. A percentage of homology between sequences is a function of the number of matching or homologous positions shared by the sequences. An "unrelated" or "non-homologous" sequence shares less than 40 percent identity, though preferably less than 25 percent identity, with a sequence of the present invention.

For instance, if 6 of 10 of the positions in two sequences are matched or are homologous, then the two sequences are 60% homologous. By way of example, the DNA sequences CTGACT and CAGGTT share 50% homology (3 of the 6 total positions are matched). Generally, a comparison is made when two sequences are aligned to give maximum homology. Such alignment can be provided using, for instance, the method of Needleman et al., J. Mol Biol. 48: 443-453 (1970), implemented conveniently by computer programs described in more detail below. Homologous sequences share identical or similar amino acid residues, where similar residues are conservative substitutions for, or "allowed point mutations" of, corresponding amino acid residues in an aligned reference sequence. In this regard, a "conservative substitution" of a residue in a reference sequence are those substitutions that are physically or functionally similar to the corresponding reference residues, e.g., that have a similar size, shape, electric charge, chemical properties, including the ability to form covalent or hydrogen bonds, or the like. Particularly preferred conservative substitutions are those fulfilling the criteria defined for an "accepted point mutation" in Dayhoff et al., 5: Atlas of Protein Sequence and Structure, 5: Suppl. 3, chapter 22: 354-352, Nat. Biomed. Res. Foundation, Washington, D.C. (1978).

"Percent homology/identity" of two amino acids sequences or two nucleic acid sequences is determined using the alignment algorithm of Karlin and Altschul (Proc. Nat. Acad. Sci., USA 87: 2264 (1990) as modified in Karlin and Altschul (Proc. Nat. Acad. Sci., USA 90: 5873 (1993). Such an algorithm is incorporated into the NBLAST or XBLAST programs of Altschul et aL, J. Mol. Biol. 215: 403 (1990). BLAST searches are performed with the NBLAST program, score=100, wordlength =12, to obtain nucleotide sequences homologous to a nucleic acid of the invention. BLAST protein searches are performed with the XBLAST program, score =50, wordlength =3, to obtain amino acid sequences homologous to a reference polypeptide. To obtain gapped alignments for comparisons, gapped BLAST is used as described in Altschul et al., Nucleic Acids Res., 25: 3389 (1997). When using BLAST and Gapped BLAST, the default parameters of the respective programs (XBLAST and NBLAST) are used.

The term "hedgehog N-terminal fragment" may be used interchangeably with "Hedgehog" and refers to the active mature sequence that is proteolytically cleaved from the hedgehog precursor.

The term "hydrophobic" refers to the tendency of chemical moieties with nonpolar atoms to interact with each other rather than water or other polar atoms. Materials that are "hydrophobic" are, for the most part, insoluble in water. Natural products with hydrophobic properties include lipids, fatty acids, phospholipids, sphingolipids, acylglycerols, waxes, sterols, steroids, terpenes, prostaglandins, thromboxanes, leukotrienes, isoprenoids, retenoids, biotin, and hydrophobic amino acids such as tryptophan, phenylalanine, isoleucine, leucine, valine, methionine, alanine, proline, and tyrosine. A chemical moiety is also hydrophobic or has hydrophobic properties if its physical properties are determined by the presence of nonpolar atoms.

The phrase "internal amino acid" means any amino acid in a peptide sequence that is neither the N-termiinal amino acid nor the C-terminal amino acid.

"Isolated" (used interchangeably with "substantially pure") when applied to nucleic acid i.e., polynucleotide sequences that encode polypeptides, means an RNA or DNA polynucleotide, portion of genomic polynucleotide, cDNA or synthetic polynucleotide which, by virtue of its origin or manipulation: (i) is not associated with all of a polynucleotide with which it is associated in nature (e.g., is present in a host cell as an expression vector, or a portion thereof); or (ii) is linked to a nucleic acid or other chemical moiety other than that to which it is linked in nature; or (iii) does not occur in nature. By "isolated" it is further meant a polynucleotide sequence that is: (i) amplified in vitro by, for example, polymerase chain reaction (PCR); (ii) synthesized chemically; (iii) produced recombinantly by cloning; or (iv) purified, as by cleavage and gel separation.

"Isolated" (used interchangeably with "substantially pure") when applied to polypeptides means a polypeptide or a portion thereof which, by virtue of its origin or manipulation: (i) is present in a host cell as the expression product of a portion of an expression vector; or (ii) is linked to a protein or other chemical moiety other than that to which it is linked in nature; or (iii) does not occur in nature, for example, a protein that is chemically manipulated by appending, or adding at least one hydrophobic moiety to the protein so that the protein is in a form not found in nature. By "isolated" it is further meant a protein that is: (i) synthesized chemically; or (ii) expressed in a host cell and purified away from associated and contaminating proteins. The term generally means a polypeptide that has been separated from other proteins and nucleic acids with which it naturally occurs. Preferably, the polypeptide is also separated from substances such as antibodies or gel matrices (polyacrylamide) which are used to purify it.

"multivalent protein complex" refers to a plurality of hedgehog therapeutics (i.e., one or more).

"mutant" is any change in the genetic material of an organism, in particular any change (i.e., deletion, substitution, addition, or alteration) in a wild type polynucleotide sequence or any change in a wild type protein. The term "mutein" is used interchangeably with "mutant".

"N-terminal end" refers to the first amino acid residue (amino acid number 1) of the mature form of a protein.

"N-terminal cysteine" refers to the amino acid number 1 as shown in SEQ ID NOS. 23-26. In certain embodiments of the hedgehog therapeutic, the N-terminal cysteine has been "modified". The term "modified" in this regard refers to chemical modifications of the N-terminal cysteine such as linkage thereof to another moiety such as a hydrophobic group and/or replacement of the N-terminal cysteine with another moiety, such as a hydrophobic group.

"operatively linked": A polynucleotide sequence (DNA, RNA) is operatively linked to an expression control sequence when the expression control sequence controls and regulates the transcription and translation of that polynucleotide sequence. The term "operatively linked" includes having an appropriate start signal (e.g., ATG) in front of the polynucleotide sequence to be expressed, and maintaining the correct reading frame to permit expression of the polynucleotide sequence under the control of the expression control sequence, and production of the desired polypeptide encoded by the polynucleotide sequence.

"protein" is any polymer consisting essentially of any of the 20 amino acids. Although "polypeptide" is often used in reference to relatively large polypeptides, and "peptide" is often used in reference to small polypeptides, usage of these terms in the art overlaps and is varied. The term "protein" as used herein refers to peptides, proteins and polypeptides, unless otherwise noted.

The terms "peptide(s)", "protein(s)" and "polypeptide(s)" are used interchangeably herein. The terms "polynucleotide sequence" and "nucleotide sequence" are also used interchangeably herein.

"Recombinant," as used herein, means that a protein is derived from recombinant, mammalian expression systems. Since hedgehog is not glycosylated nor contains disulfide bonds, it can be expressed in most prokaryotic and eukaryotic expression systems.

"Spacer" sequence refers to a moiety that may be inserted between an amino acid to be modified with an antibody homolog or fragment and the remainder of the protein. A spacer is designed to provide separation between the modification and the rest of the protein so as to prevent the modification from interfering with protein function and/or make it easier for the modification to link with an antibody homolog moiety or any other moiety.

Thus, "substantially pure nucleic acid" is a nucleic acid which is not immediately contiguous with one or both of the coding sequences with which it is normally contiguous in the naturally occurring genome of the organism from which the nucleic acid is derived. Substantially pure DNA also includes a recombinant DNA which is part of a hybrid gene encoding additional hedgehog sequences.

The phrase "surface amino acid" means any amino acid that is exposed to solvent when a protein is folded in its native form.

"standard hybridization conditions" refer to salt and temperature conditions substantially equivalent to 0.5×SSC to about 5×SSC and 65° C. for both hybridization and wash. The term "standard hybridization conditions" as used herein is therefore an operational definition and encompasses a range of hybridization conditions. Nevertheless, for the purposes of this present disclosure "high stringency" conditions include hybridizing with plaque screen buffer (0.2% polyvinylpyrrolidone, 0.2% Ficoll 400; 0.2% bovine serum albumin, 50 mM Tris-HCl (pH 7.5); 1 M NaCl; 0.1% sodium pyrophosphate; 1% SDS); 10% dextran sulfate, and 100 ug/ml denatured, sonicated salmon sperm DNA at 65° C. for 12-20 hours, and washing with 75 mM NaCl/7.5 mM sodium citrate (0.5×SSC)/1% SDS at 65° C. "Low stringency" conditions include hybridizing with plaque screen buffer, 10% dextran sulfate and 110 ug/ml denatured, sonicated salmon sperm DNA at 55° C for 12-20 hours, and washing with 300 mM NaCl/30 mM sodium citrate (2.0×SSC)/1% SDS at 55° C. See also Current Protocols in Molecular Biology, John Wiley & Sons, Inc. New York, Sections 6.3.1-6.3.6, (1989).

A "therapeutic composition" as used herein is defined as comprising the therapeutics of the invention and other biologically compatible ingredients. The therapeutic composition may contain excipients such as water, minerals and carriers such as protein.

"wild type"—the naturally-occurring polynucleotide sequence of an exon of a protein, or a portion thereof, or protein sequence, or portion thereof, respectively, as it normally exists in vivo.

Practice of the present invention will employ, unless indicated otherwise, conventional techniques of cell biology, cell culture, molecular biology, microbiology, recombinant DNA, protein chemistry, and immunology, which are within the skill of the art. Such techniques are described in the literature. Unless stipulated otherwise, all references cited in the Detailed Description are incorporated herein by reference.

III. General Properties of Isolated Hedgehog Proteins

Hedgehogs are a family of genes which begin expression early in development and are involved in the morphogenesis of a number of organs in the developing embryo (Ingham, 1995, Perrimon, 1995; Johnson and Tabin, 1995; Hammerschmidt et al., 1997).

However, there is currently no evidence that hedgehogs are directly involved in the development of the mammalian vasculature. Knockouts of each of the mammalian hedgehog genes, sonic (Chiang et al., 1996; Litingtung et al., 1998; St-Jacques et al., 1998), indian (St-Jacques et al., 1999; Karp et al., 2000) and desert (Bitgood et al., 1996; Parmantier et al., 1999) hedgehog have not been reported to have defects in vascular development, but do show defects in tissues where they are known to function in development.

The adult functions of the hedgehog proteins are not well understood. Hedgehog is known to be expressed in adult bone/cartilage, central and peripheral nervous system, kidney, eye and several other tissues (Valentine et al., 1997; Traiffort et al., 1998 and 1999; Iwamoto et al., 1999; Jensen et al., 1997; Parmantier et al., 1999). The adult function of the hedgehog pathway is perhaps best understood in bone and cartilage where it regulates the differentiation of chondrocytes by modulating PTHrp (Iwamoto et al., 1999; Karp et al., 2000). Administration of hedgehog locally in the skin also can induce hair growth in adult animals (Sato et al., 1999; Wang et al., 2000).

The various naturally-occurring hedgehog proteins from which the subject therapeutics can be derived are characterized by a signal peptide, a highly conserved N-terminal region (see FIG. 1), and a more divergent C-terminal domain. In addition to signal sequence cleavage in the secretory pathway (Lee, J. J. et al. (1992) Cell 71:33-50; Tabata, T. et al. (1992) Genes Dev. 2635-2645; Chang, D.E. et al. (1994) Development 120:3339-3353), hedgehog precursor proteins naturally undergo an internal autoproteolytic cleavage which depends on conserved sequences in the C-terminal portion (Lee et al. (1994) Science 266:1528-1537; Porter et al. (1995) Nature 374:363-366). This autocleavage leads to a 19 kD N-terminal peptide and a C-terminal peptide of 26-28 kD. The N-terminal peptide stays tightly associated with the surface of cells in which it was synthesized, while the C-terminal peptide is freely diffusible both in vitro and in vivo. Cell surface retention of the N-terminal peptide is dependent on autocleavage, as a truncated form of hedgehog encoded by an RNA which terminates precisely at the normal position of internal cleavage is diffusible in vitro (Porter et al. (1995) supra) and in vivo (Porter, J.A. et al. (1996) Cell 86, 21-34). Biochemical studies have shown that the autoproteolytic cleavage of the hedgehog precursor protein proceeds through an internal thioester intermediate, which subsequently is cleaved in a nucleophilic substitution. It is suggested that the nucleophile is a small lipophilic molecule, more particularly cholesterol, which becomes covalently bound to the C-terminal end of the N-peptide (Porter et al. (1996) supra), tethering it to the cell surface.

The vertebrate family of hedgehog genes includes at least four members, e.g., paralogs of the single drosophila hedgehog gene (reference). Three of these members, herein referred to as Desert hedgehog (Dhh), Sonic hedgehog (Shh) and Indian hedgehog (Ihh), apparently exist in all vertebrates, including fish, birds, and mammals. A fourth member, herein referred to as tiggie-winkle hedgehog (Thh), appears specific to fish. Isolated hedgehog proteins used in the methods of this invention are naturally occurring or recombinant proteins of the hedgehog family and may be obtainable from either invertebrate or from vertebrate sources (see references below). Members of the vertebrate hedgehog protein family share homology with proteins encoded by the Drosophila hedgehog (hh) gene (Mohler and Vani, (1992) Development 115, 957-971). Other members continue to be identified.

Mouse and chicken Shh and mouse Ihh genes (see, for example, U.S. Pat. No. 5,789,543) encode glycoproteins which undergo cleavage, yielding an amino terminal fragment of about 20kDa and a carboxy terminal fragment of about 25kDa. The most preferred 20kDa fragment has the consensus sequence SEQ ID NO: 26 which includes the amino acid sequences of SEQ ID NOS: 23-25. Various other fragments that encompass the 20kDa moiety are considered within the presently claimed invention. Publications disclosing these sequences, as well as their chemical and physical properties, include Hall et al., (1995) Nature 378, 212-216; Ekker et al., (1995) Current Biology 5, 944-955; Fan et al., (1995) Cell 81, 457-465, Chang et al., (1994) Development 120, 3339-3353; Echelard et al., (1993) Cell 75, 1414-1430 34-38; PCT Patent Application WO 95/23223 (Jessell, Dodd, Roelink and Edlund); PCT Patent Publication WO 95/18856 (Ingham, McMahon and Tabin). U.S. Pat. No. 5,759,811 lists the Genbank accession numbers of a complete mRNA sequence encoding human Sonic hedgehog; a partial sequence of human Indian hedgehog mRNA, 5' end; and a partial sequence of human Desert hedgehog mRNA. The hedgehog therapeutic compositions of the subject method can be generated by any of a variety of techniques, including purification of naturally occurring proteins, recombinantly produced proteins and synthetic chemistry. Polypeptide forms of the hedgehog therapeutics are preferably derived from vertebrate hedgehog proteins, e.g., have sequences corresponding to naturally occurring hedgehog proteins, or fragments thereof, from vertebrate organisms. However, it will be appreciated that the hedgehog polypeptide can correspond to a hedgehog protein (or fragment thereof) which occurs in any metazoan organism.

The vertebrate family of hedgehog genes includes at least four members, e.g., paralogs of the single drosophila hedgehog gene (SEQ ID No. 19). Three of these members, herein referred to as Desert hedgehog (Dhh), Sonic hedgehog (Shh) and Indian hedgehog (Ihh), apparently exist in all vertebrates, including fish, birds, and mammals. A fourth member, herein referred to as tiggie-winkle hedgehog (Thh), appears specific to fish. According to the appended sequence listing, (see also Table 1) a chicken Shh polypeptide is encoded by SEQ ID No: 1; a mouse Dhh polypeptide is encoded by SEQ ID No:2; a mouse Ihh polypeptide is encoded by SEQ ID No:3; a mouse Shh polypeptide is encoded by SEQ ID No:4 a zebrafish Shh polypeptide is encoded by SEQ ID No:5; a human Shh polypeptide is encoded by SEQ ID No:6; a human Ihh polypeptide is encoded by SEQ ID No:7; a human Dhh polypeptide is encoded by SEQ ID No. 8; and a zebrafish Thh is encoded by SEQ ID No. 9.

TABLE 1

Guide to hedgehog sequences in Sequence Listing

| | Nucleotide | Amino Acid |
| --- | --- | --- |
| Chicken Shh | SEQ ID No. 1 | SEQ ID No. 10 |
| Mouse Dhh | SEQ ID No. 2 | SEQ ID No. 11 |
| Mouse Ihh | SEQ ID No. 3 | SEQ ID No. 12 |
| Mouse Shh | SEQ ID No. 4 | SEQ ID No. 13 |
| Zebrafish Shh | SEQ ID No. 5 | SEQ ID No. 14 |
| Human Shh | SEQ ID No. 6 | SEQ ID No. 15 |
| Human Ihh | SEQ ID No. 7 | SEQ ID No. 16 |
| Human Dhh | SEQ ID No. 8 | SEQ ID No. 17 |
| zebrafish Thh | SEQ ID No. 9 | SEQ ID No. 18 |
| *Drosophila* HH | SEQ ID No. 19 | SEQ ID No. 20 |

In addition to the sequence variation between the various hedgehog homologs, the hedgehog proteins are apparently present naturally in a number of different forms, including a pro-form, a full-length mature form, and several processed fragments thereof. The pro-form includes an N-terminal signal peptide for directed secretion of the extracellular domain, while the full-length mature form lacks this signal sequence.

As described above, further processing of the mature form occurs in some instances to yield biologically active fragments of the protein. For instance, sonic hedgehog undergoes additional proteolytic processing to yield two peptides of approximately 19 kDa and 27 kDa, the 19 kDa fragment corresponding to an proteolytic N-terminal portion of the mature protein.

In addition to proteolytic fragmentation, the vertebrate hedgehog proteins can also be modified post-translationally, such as by glycosylation and/or addition of lipophilic moieties, such as stents, fatty acids, etc., though bacterially produced (e.g. unmodified) forms of the proteins still maintain certain of the bioactivities of the native protein. Bioactive fragments of hedgehog polypeptides of the present invention have been generated and are described in great detail in, e.g., PCT publications WO 95/18856 and WO 96/17924.

A "hedgehog therapeutic" of the invention is defined in terms of having at least a portion that consists of the consensus amino acid sequence of SEQ ID NO: 26 or at least a portion that consists of SEQ ID NOS: 10-18 or 23-25. The term also means a hedgehog polypeptide, or a functional variant of a hedgehog polypeptide, or homolog of a hedgehog polypeptide, or functional variant, which has biological activity and can modulate angiogenesis.

Members useful in the methods of the invention include any of the naturally-occurring native hedgehog proteins including allelic, phylogenetic counterparts or other variants thereof, whether naturally-sourced or produced chemically including muteins or mutant proteins, as well as recombinant forms and new, active members of the hedgehog family. Particularly useful hedgehog polypeptides have portions that include all or part of SEQ ID NOS: 23-26.

Hedgehog therapeutics may also include polypeptides having an amino acid sequence at least 60%, 80%, 90%, 95%, 98%, or 99% homologous to an amino acid sequence from SEQ ID NOS 10-18 or 23-26. The polypeptide can also include an amino acid sequence essentially the same as an amino acid sequence in SEQ ID NOS: 10-18 or 23-26. The polypeptide is at least 5, 10, 20, 50, 100, or 150 amino acids in length and includes at least 5, preferably at least 10, more preferably at least 20, most preferably at least 50, 100, or 150 contiguous amino acids from SEQ ID NOS: 10-18 or 23-26.

Polypeptides of the invention include those which arise as a result of the existence of multiple genes, alternative transcription events, alternative RNA splicing events, and alternative translational and posttranslational events. The polypeptide can be made entirely by synthetic means or can be expressed in systems, e.g., cultured cells, which result in substantially the same posttranslational modifications present when the protein is expressed in a native cell, or in systems which result in the omission of posttranslational modifications present when expressed in a native cell.

Moreover, mutagenesis can be used to create modified hh polypeptides, e.g., for such purposes as enhancing therapeutic or prophylactic efficacy, or stability (e.g., ex vivo shelf life and resistance to proteolytic degradation in vivo). Such modified peptides can be produced, for instance, by amino acid substitution, deletion, or addition. Modified hedgehog polypeptides can also include those with altered post-translational processing relative to a naturally occurring hedgehog protein, e.g., altered glycosylation, cholesterolization, prenylation and the like.

In one embodiment, a hedgehog therapeutic is a hedgehog polypeptide with one or more of the following characteristics:
(i) it has at least 30, 40, 42, 50, 60, 70, 80, 90 or 95% sequence identity with amino acids of SEQ ID NOS: 23-26;
(ii) it has a cysteine or a functional equivalent as the N-terminal end;
(iii) it may induce alkaline phosphatase activity in C3H10T1/2 cells;
(iv) it has an overall sequence identity of at least 50%, preferably at least 60%, more preferably at least 70, 80, 90, or 95%, with a polypeptide of SEQ ID NOS: 10-18;
(v) it can be isolated from natural sources such as mammalian cells;
(vi) it can bind or interact with patched; and
(vii) it may be modified at at least one amino acid residue by a polyalkylene glycol polymer attached to the residue or, optionally, via a linker molecule to the amino acid residue.

Preferred nucleic acids encode a polypeptide comprising an amino acid sequence at least 60% homologous or identical, more preferably 70% homologous or identical, and most preferably 80% homologous or identical with an amino acid sequence selected from the group consisting of SEQ ID NOS: 10-18 or 23-26. Nucleic acids which encode polypeptides at least about 90%, more preferably at least about 95%, and most preferably at least about 98-99% homology or identity with an amino acid sequence represented in one of SEQ ID Nos: 23-26 are also within the scope of the invention.

In another embodiment, the hedgehog therapeutic is a polypeptide encodable by a nucleotide sequence that hybridizes under stringent conditions to a hedgehog coding sequence represented in one or more of SEQ ID NOS: 1-9, 19 or 23-26.

Preferred nucleic acids encode a hedgehog polypeptide comprising an amino acid sequence at least 60% homologous, more preferably 70% homologous and most preferably 80% homologous with an amino acid sequence selected from the group consisting of SEQ ID Nos:8-14. Nucleic acids which encode polypeptides at least about 90%, more preferably at least about 95%, and most preferably at least about 98-99% homology with an amino acid sequence represented in one of SEQ ID Nos: 10-18 or 20 are also within the scope of the invention.

Hedgehog therapeutics, in addition to native hedgehog proteins, are at least 60% homologous, more preferably 70% homologous and most preferably 80% homologous with an amino acid sequence represented by any of SEQ ID Nos: 10-18 or 20. Polypeptides which are at least 90%, more preferably at least 95%, and most preferably at least about 98-99% homologous with a sequence selected from the group consisting of SEQ ID Nos: 10-18 or 20 are also within the scope of the invention.

With respect to fragments of hedgehog polypeptide, preferred hedgehogs moieties include at least 50 amino acid residues of a hedgehog polypeptide, more preferably at least 100, and even more preferably at least 150.

Another preferred hedgehog polypeptide which can be included in the hedgehog therapeutic is an N-terminal fragment of the mature protein having a molecular weight of approximately 19 kDa.

Preferred human hedgehog proteins include N-terminal fragments corresponding approximately to residues 24-197 of SEQ ID No. 15, 28-202 of SEQ ID No. 16, and 23-198 of SEQ ID No. 17. By "corresponding approximately" it is meant that the sequence of interest is at most 20 amino acid residues different in length to the reference sequence, though more preferably at most 5, 10 or 15 amino acid different in length.

Still other preferred hedgehog therapeutics include an amino acid sequence represented by the formula A-B wherein: (i) A represents all or the portion of the amino acid sequence designated by residues 24-193 of SEQ ID No: 15; and B represents at least one amino acid residue of the amino acid sequence designated by residues 194-250 of SEQ ID No: 15; (ii) A represents all or the portion of the amino acid sequence designated by residues 25-193 of SEQ ID No: 13; and B represents at least one amino acid residue of the amino acid sequence designated by residues 194-250 of SEQ ID No: 13; (iii) A represents all or the portion of the amino acid sequence designated by residues 23-193 of SEQ ID No: 11; and B represents at least one amino acid residue of the amino acid sequence designated by residues 194-250 of SEQ ID No: 11; (iv) A represents all or the portion of the amino acid sequence designated by residues 28-197 of SEQ ID No: 12; and B represents at least one amino acid residue of the amino acid sequence designated by residues 198-250 of SEQ ID No: 12; (v) A represents all or the portion of the amino acid sequence designated by residues 29-197 of SEQ ID No: 16; and B represents at least one amino acid residue of the amino acid sequence designated by residues 198-250 of SEQ ID No: 16; or (vi) A represents all or the portion of the amino acid sequence designated by residues 23-193 of SEQ ID No. 17, and B represents at least one amino acid residue of the amino acid sequence designated by residues 194-250 of SEQ ID No. 17. In certain preferred embodiments, A and B together represent a contiguous polypeptide sequence designated sequence, A represents at least 25, 50, 75, 100, 125 or 150 amino acids of the designated sequence, and B represents at least 5, 10, or 20 amino acid residues of the amino acid sequence designated by corresponding entry in the sequence listing, and A and B together preferably represent a contiguous sequence corresponding to the sequence listing entry. Similar fragments from other hedgehog also contemplated, e.g., fragments which correspond to the preferred fragments from the sequence listing entries which are enumerated above.

IV. Production of Recombinant Polypeptides

Isolated hedgehog polypeptides described herein can be produced by any suitable method known in the art. Such methods range from direct protein synthetic methods to constructing a DNA sequence encoding isolated polypeptide sequences and expressing those sequences in a suitable transformed host.

In one embodiment of a recombinant method, a DNA sequence is constructed by isolating or synthesizing a DNA sequence encoding a wild type protein of interest. Optionally, the sequence may be mutagenized by site-specific mutagenesis to provide functional analogs thereof. See, e.g., U.S. Pat. No. 4,588,585. Another method of constructing a DNA sequence encoding a polypeptide of interest would be by chemical synthesis using an oligonucleotide synthesizer. Such oligonucleotides may be preferably designed based on the amino acid sequence of the desired polypeptide, and preferably selecting those codons that are favored in the host cell in which the recombinant polypeptide of interest will be produced.

Standard methods may be applied to synthesize an isolated polynucleotide sequence encoding an isolated polypeptide of interest. For example, a complete amino acid sequence may be used to construct a back-translated gene. See Maniatis et al., supra. Further, a DNA oligomer containing a nucleotide sequence coding for the particular isolated polypeptide may be synthesized. For example, several small oligonucleotides coding for portions of the desired polypeptide may be synthesized and then ligated. The individual oligonucleotides typically contain 5' or 3' overhangs for complementary assembly.

Once assembled (by synthesis, site-directed mutagenesis, or by another method), the mutant DNA sequences encoding a particular isolated polypeptide of interest will be inserted into an expression vector and operatively linked to an expression control sequence appropriate for expression of the protein in a desired host. Proper assembly may be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

The choice of expression control sequence and expression vector will depend upon the choice of host. A wide variety of expression host/vector combinations may be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from Esherichia coli, including pCRI, pBR322, pMB9 and their derivatives, wider host range plasmids, such as M13 and filamentous single-stranded DNA phages. Preferred E. coli vectors include pL vectors containing the lambda phage pL promoter (U.S. Pat. No. 4,874,702), pET vectors containing the T7 polymerase promoter (Studier et al., Methods in Enzymology 185: 60-89, 1990 1) and the pSP72 vector (Kaelin et al., supra). Useful expression vectors for yeast cells, for example, include the 2 g and centromere plasmids. Further, within each specific expression vector, various sites may be selected for insertion of these DNA sequences. These sites are usually designated by the restriction endonuclease which cuts them. They are well-recognized by those of skill in the art. It will be appreciated that a given expression vector useful in this invention need not have a restriction endonuclease site for insertion of the chosen DNA fragment. Instead, the vector may be joined by the fragment by alternate means.

The expression vector, and the site chosen for insertion of a selected DNA fragment and operative linking to an expression control sequence, is determined by a variety of factors such as: the number of sites susceptible to a particular restriction enzyme, the size of the polypeptide, how easily the polypeptide is proteolytically degraded, and the like. The choice of a vector and insertion site for a given DNA is determined by a balance of these factors.

To provide for adequate transcription of the recombinant constructs of the invention, a suitable promoter/enhancer sequence may preferably be incorporated into the recombinant vector, provided that the promoter/expression control sequence is capable of driving transcription of a nucleotide sequence encoding a hedgehog protein.

Any of a wide variety of expression control sequences may be used in these vectors.

Such useful expression control sequences include the expression control sequences associated with structural genes of the foregoing expression vectors. Examples of useful expression control sequences include, for example, the-early and late promoters of SV40 or adenovirus, the lac system, the trp system, the TAC or TRC system, the major operator and promoter regions of phage lambda, for example pL, the control regions of fd coat protein, the promoter for 3-phosphoglycerate kinase or other glycolytic enzymes, the promoters of acid phosphatase, e.g., Pho5, the promoters of the yeast alpha-mating system and other sequences known to control the expression of genes of prokaryotic or eukaryotic cells and their viruses, and various combinations thereof.

Promoters which may be used to control the expression of immunoglobulin-based fusion protein include, but are not limited to, the SV40 early promoter region (Benoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:144-1445), the regulatory sequences of the metallothionine gene (Brinster et al., 1982, Nature 296:39-42); plant expression vectors comprising the nopaline synthetase promoter region (Herrera-Estrella et al., Nature 303:209-213) or the cauliflower mosaic virus 35S RNA promoter (Gardner, et al., 1981, Nucl. Acids Res. 9:2871), and the promoter for the photosynthetic enzyme ribulose biphosphate carboxylase (Herrera-Estrella et al., 1984, Nature 310:115-120); promoter elements from yeast or other fungi such as the Gal 4 promoter, the ADC (alcohol dehydrogenase) promoter, PGK (phosphoglycerol kinase) promoter, alkaline phophatase promoter, and the following animal transcriptional control regions, which exhibit tissue specificity and have been utilized in transgenic animals: elastase I gene control region which is active in pancreatic cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene enhancers or promoters which are active in pancreatic cells (Hanahan, 1985, Nature 315:115-122); immunoglobulin gene enhancers or promoters which are active in lymphoid cells (Grosschedl et al., 1984, Cell 38:647-658; Adames et al., 1985, Nature 318:533-538; Alexander et al., 1987, Mol. Cell. Biol. 7:1436-1444); the cytomegalovirus early promoter and enhancer regions (Boshart et al., 1985, Cell 41:521-530); mouse mammary tumor virus control region which is active in testicular, breast, lymphoid and mast cells (Leder et al., 1986, Cell 45:485-495); albumin gene control region which is active in liver (Pinkert et al., 1987, Genes and Devel. 1:268-276); alpha-fetoprotein gene control region which is active in liver (Krumlauf et al., 1985, Mol. Cell. Biol. 5:1639-1648; Hammer et al., 1987, Science 235:53-58); alphantitrypsin gene control region which is active in the liver (Kelsey et al, 1987, Genes and Devel. 1:161-171); -globin gene control region which is active in myeloid cells (Mogram et al., 1985, Nature 315:338-340; Kollias et al., 1986, Cell 46:89-94; myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286); and gonadotropic releasing hormone gene control region which is active in the hypothalamus (Mason et al., 1986, Science 234:1372-1378).

Any suitable host may be used to produce in quantity the isolated hedgehog polypeptides described herein, including bacteria, fungi (including yeasts), plants, insects, mammals, or other appropriate animal cells or cell lines, as well as transgenic animals or plants. More particularly, these hosts may include well known eukaryotic and prokaryotic hosts, such as strains of E. coli, Pseudomonas, Bacillus, Streptomyces, fungi, yeast (e.g., Hansenula ), insect cells such as Spodoptera frugiperda (SF9), and High Five TM, animal cells such as Chinese hamster ovary (CHO), mouse cells such as NS/O cells, African green monkey cells, COS 1, COS 7, BSC 1, BSC 40, and BMT 10, and human cells, as well as plant cells.

It should be understood that not all vectors and expression control sequences will function equally well to express a given isolated polypeptide. Neither will all hosts function equally well with the same expression system. However, one of skill in the art may make a selection among these vectors, expression control systems and hosts without undue experimentation. For example, to produce isolated polypeptide of interest in large-scale animal culture, the copy number of the expression vector must be controlled. Amplifiable vectors are well known in the art. See, for example, Kaufman and Sharp, (1982) Mol. Cell. Biol., 2, 1304-1319 and U.S. Pat. Nos. 4,470,461 and 5,122,464.

Such operative linking of a DNA sequence to an expression control sequence includes the provision of a translation start signal in the correct reading frame upstream of the DNA sequence. If the particular DNA sequence being expressed does not begin with a methionine, the start signal will result in an additional amino acid (methionine) being located at the N-terminus of the product. If a hydrophobic moiety is to be linked to the N-terminal methionyl-containing protein, the protein may be employed directly in the compositions of the invention. Nevertheless, since the preferred N-terminal end of the protein is to consist of a cysteine (or functional equivalent) the methionine must be removed before use. Methods are available in the art to remove such N-terminal methionines from polypeptides expressed with them. For example, certain hosts and fermentation conditions permit removal of substantially all of the N-terminal methionine in vivo. Other hosts require in vitro removal of the N-terminal methionine. Such in vitro and in vivo methods are well known in the art.

Successful incorporation of these polynucleotide constructs into a given expression vector may be identified by three general approaches: (a) DNA-DNA hybridization, (b) presence or absence of "marker" gene functions, and (c) expression of inserted sequences. In the first approach, the presence of the hedgehog gene inserted in an expression vector can be detected by DNA-DNA hybridization using probes comprising sequences that are homologous to the inserted fusion protein gene. In the second approach, the recombinant vector/host system can be identified and selected based upon the presence or absence of certain "marker" gene functions (e.g., thymidine kinase activity, resistance to antibiotics such as G418, transformation phenotype, occlusion body formation in baculovirus, etc.) caused by the insertion of foreign genes in the vector. For example, if the polynucleotide is inserted so as to interrupt a marker gene sequence of the vector, recombinants containing the insert can be identified by the absence of the marker gene function. In the third approach, recombinant expression vectors can be identified by assaying the foreign gene product expressed by the recombinant vector. Such assays can be based, for example, on the physical or functional properties of the gene product in bioassay systems.

Recombinant nucleic acid molecules which encode chimeric hedgehog therapeutics may be obtained by any method known in the art (Maniatis et al., 1982, Molecular Cloning; A Laboratory Manual, Cold Spring Harbor Laboratory, Cold Spring Harbor, N.Y.) or obtained from publicly available clones. Methods for the preparation of genes which encode the heavy or light chain constant regions of immunoglobulins are taught, for example, by Robinson, R. et al., PCT Application, Publication No. W087-02671. The cDNA sequence encoding the hedgehog molecule or fragment may be directly joined to the cDNA encoding the heavy Ig contant regions or may be joined via a linker sequence. In further embodiments of the invention, a recombinant vector system may be created to accommodate sequences encoding hedgehog in the correct reading frame with a synthetic hinge region. Additionally, it may be desirable to include, as part of the recombinant vector system, nucleic acids corresponding to the 3' flanking region of an immunoglobulin gene including RNA cleavage/polyadenylation sites and downstream sequences. Furthermore, it may be desirable to engineer a signal sequence upstream of the immunoglobulin fusion protein-encoding sequences to facilitate the secretion of the fused molecule from a cell transformed with the recombinant vector.

The proteins produced by a transformed host can be purified according to any suitable method. Such standard methods include chromatography (e.g., ion exchange, affinity, and sizing column chromatography), centrifugation, differential solubility, or by any other standard technique for protein purification. For immunoaffinity chromatography (See Example ), a protein such as Sonic hedgehog may be isolated by binding it to an affinity column comprising of antibodies that were raised against Sonic hedgehog, or a related protein and were affixed to a stationary support. For example, the hedgehog proteins and fragments may be purified by passing a solution thereof through a column having an hedgehog receptor immobilized thereon (see U.S. Pat. No. 4,725,669). The bound hedgehog molecule may then be eluted by treatment with a chaotropic salt or by elution with aqueous acetic acid. Specific immunoglobulin fusion proteins may be purified by passing a solution containing the fusion protein through a column which contains immobilized protein A or protein G which selectively binds the Fc portion of the fusion protein. See, for example, Reis, K. J., et al., J. Immunol. 132:3098-3102 (1984); PCT Application, Publication No. W087/00329.

Alternatively hedgehog proteins and chimeric molecules may be purified on anti-hedgehog antibody columns, or on anti-immunoglobulin antibody columns to give a substantially pure protein. By the term "substantially pure" is intended that the protein is free of the impurities that are naturally associated therewith. Substantial purity may be evidenced by a single band by electrophoresis. Alternatively, affinity tags such as hexahistidine, maltose binding domain, influenza coat sequence, and glutathione-S-transferase can be attached to the protein to allow easy purification by passage over an appropriate affinity column. Isolated proteins can also be characterized physically using such techniques as proteolysis, nuclear magnetic resonance, and X-ray crystallography.

An example of a useful hedgehog/Ig chimeric protein of this invention is that protein encoded by the nucleotide sequence of SEQ ID NOS: 31-34, which are secreted into the cell culture by eukaryotic cells containing the expression plasmids pUB55, pUB 114, pUB 115 and pUB 116, respectively (See Examples). These proteins consist of the mature human hedgehog fused to a portion of the hinge region and the CH2 and CH3 constant domains of murine or human Ig. Proteins of this group contains a sufficient portion of the immunoglobulin to be recognized by the Fc binding protein, Protein A.

A. Production of Fragments and Analogs

Fragments of an isolated protein (e.g., fragments of SEQ ID NOS: 10-18 or 23-26) can also be produced efficiently by recombinant methods, by proteolytic digestion, or by chemical synthesis using methods known to those of skill in the art. In recombinant methods, internal or terminal fragments of a polypeptide can be generated by removing one or more nucleotides from one end (for a terminal fragment) or both ends (for an internal fragment) of a DNA sequence which encodes for the isolated hedgehog polypeptide. Expression of the mutagenized DNA produces polypeptide fragments. Digestion with "end nibbling" endonucleases can also generate DNAs which encode an array of fragments. DNAs which encode fragments of a protein can also be generated by random shearing, restriction digestion, or a combination of both. Protein fragments can be generated directly from intact proteins. Peptides can be cleaved specifically by proteolytic enzymes, including, but not limited to plasmin, thrombin, trypsin, chymotrypsin, or pepsin. Each of these enzymes is specific for the type of peptide bond it attacks. Trypsin catalyzes the hydrolysis of peptide bonds in which the carbonyl group is from a basic amino acid, usually arginine or lysine. Pepsin and chymotrypsin catalyse the hydrolysis of peptide bonds from aromatic amino acids, such as tryptophan, tyrosine, and phenylalanine. Alternative sets of cleaved protein fragments are generated by preventing cleavage at a site which is susceptible to a proteolytic enzyme. For instance, reaction of the E-amino acid group of lysine with ethyltrifluorothioacetate in mildly basic solution yields blocked amino acid residues whose adjacent peptide bond is no longer susceptible to hydrolysis by trypsin. Proteins can be modified to create peptide linkages that are susceptible to proteolytic enzymes. For instance, alkylation of cysteine residues with (3-haloethylamines yields peptide linkages that are hydrolyzed by trypsin (Lindley, (1956) Nature 178, 647). In addition, chemical reagents that cleave peptide chains at specific residues can be used. For example, cyanogen bromide cleaves peptides at methionine residues (Gross and Witkip, (1961) J. Am. Chem. Soc. 83, 1510). Thus, by treating proteins with various combinations of modifiers, proteolytic enzymes and/or chemical reagents, the proteins may be divided into fragments of a desired length with no overlap of the fragments, or divided into overlapping fragments of a desired length.

Fragments can also be synthesized chemically using techniques known in the art such as the Merrifield solid phase F moc or t-Boc chemistry. Merrifield, Recent Progress in Hormone Research 23: 451 (1967).

Examples of prior art methods which allow production and testing of fragments and analogs are discussed below. These, or analogous methods may be used to make and screen fragments and analogs of an isolated polypeptide (e.g., hedgehog) which can be shown to have biological activity. An exemplary method to test whether fragments and analogs of hedgehog have biological activity is found in Example B. Production of Altered DNA and Peptide Sequences: Random Methods Amino acid sequence variants of a protein can be prepared by random mutagenesis of DNA which encodes the protein or a particular portion thereof. Useful methods include PCR mutagenesis and saturation mutagenesis. A library of random amino acid sequence variants can also be generated by the synthesis of a set of degenerate oligonucleotide sequences. Methods of generating amino acid sequence variants of a given protein using altered DNA and peptides are well-known in the art. The following examples of such methods are not intended to limit the scope of the present invention, but merely serve to illustrate representative techniques. Persons having ordinary skill in the art will recognize that other methods are also useful in this regard.

PCR Mutagenesis: See, for example Leung et al., (1989) Technique 1, 11-15.

Saturation Mutagenesis: One method is described generally in Mayers et al., (1989) Science 229, 242.

Degenerate Olizonucleotide Mutagenesis: See for example Harang, S.A., (1983) Tetrahedron 39, 3; Itakura et al., (1984) Ann. Rev. Biochem. 53, 323 and Itakura et al., Recombinant DNA, Proc. 3rd Cleveland Symposium on Macromolecules, pp. 273-289 (A.G. Walton, ed.), Elsevier, Amsterdam, 1981.

C. Production of Altered DNA and Peptide Sequences: Directed Methods

Non-random, or directed, mutagenesis provides specific sequences or mutations in specific portions of a polynucleotide sequence that encodes an isolated polypeptide, to provide variants which include deletions, insertions, or substitutions of residues of the known amino acid sequence of the isolated polypeptide. The mutation sites may be modified individually or in series, for instance by: (1) substituting first with conserved amino acids and then with more radical choices depending on the results achieved; (2) deleting the target residue; or (3) inserting residues of the same or a different class adjacent to the located site, or combinations of options 1-3.

Clearly, such site-directed methods are one way in which an N-terminal cysteine (or a functional equivalent) can be introduced into a given polypeptide sequence to provide the attachment site for a hydrophobic moiety.

Alanine scanning Mutagenesis: See Cunningham and Wells, (1989) Science 244, 1081-1085).

Oligonucleotide-Mediated Mutagenesis: See, for example, Adelman et al., (1983)DNA2, 183.

Cassette Mutagenesis: See Wells et al., (1985) Gene 34, 315.

Combinatorial Mutagenesis: See, for example, Ladner et al., WO 88/06630

Indeed, it is plain from the combinatorial mutagenesis art that large scale mutagenesis of hedgehog proteins, without any preconceived ideas of which residues were critical to the biological function, and generate wide arrays of variants having equivalent biological activity. Indeed, it is the ability of combinatorial techniques to screen billions of different variants by high throughput analysis that removes any requirement of a priori understanding or knowledge of critical residues.

D. Other Variants of Isolated Polypeptides

Included in the invention are isolated molecules that are: allelic variants, natural mutants, induced mutants, and proteins encoded by DNA that hybridizes under high or low stringency conditions to a nucleic acid which encodes a polypeptide such as the N-terminal fragment of Sonic hedgehog (SEQ ID NO: 23) and polypeptides bound specifically by antisera to hedgehog peptides, especially by antisera to an active site or binding site of hedgehog. All variants described herein are expected to: (i) retain the biological function of the original protein and (ii) retain the ability to link to form a chimeric molecule with a non-hedgehog moiety.

The methods of the invention also feature uses of fragments, preferably biologically active fragments, or analogs of an isolated peptide such as hedgehog. Specifically, a biologically active fragment or analog is one having any in vivo or in vitro activity which is characteristic of the peptide shown in SEQ ID NOS: 10-18 or 23-26 or of other naturally occurring isolated hedgehog. Most preferably, the hydrophobically-modified fragment or analog has at least 10%, preferably 40% or greater, or most preferably at least 90% of the activity of Sonic hedgehog in any in vivo or in vitro assay.

Analogs can differ from naturally occurring isolated protein in amino acid sequence or in ways that do not involve sequence, or both. The most preferred polypeptides of the invention have preferred non-sequence modifications that include in vivo or in vitro chemical derivatization (e.g., of their N-terminal end). Hedgehog polypeptides may also be chemically modified to create hedgehog derivatives by forming covalent or aggregate conjugates with other chemical moieties, such as glycosyl groups, cholesterol, isoprenoids, lipids, phosphate, acetyl groups and the like. Covalent derivatives of hedgehog proteins can be prepared by linking the chemical moieties to functional groups on amino acid sidechains of the protein or at the N-terminus or at the C-terminus of the polypeptide.

For instance, hedgehog proteins can be generated to include a moiety, other than sequence naturally associated with the protein, that binds a component of the extracellular matrix and enhances localization of the analog to cell surfaces. For example, sequences derived from the fibronectin "type-III repeat", such as a tetrapeptide sequence R-G-D-S (Pierschbacher et al. (1984) Nature 309:30-3; and Komblihtt et al. (1985) EMBO 4:1755-9) can be added to the hedgehog polypeptide to support attachment of the chimeric molecule to a cell through binding ECM components (Ruoslahti et al. (1987) Science 238:491-497; Pierschbacheret al. (1987) J. Biol. Chem. 262:17294-8.; Hynes (1987) Cell 48:549-54; and Hynes (1992) Cell 69:11-25).

Other analogs include a protein such as Sonic hedgehog or its biologically active fragments whose sequences differ from the wild type consensus sequence (e.g., SEQ ID NO: 26) by one or more conservative amino acid substitutions or by one or more non conservative amino acid substitutions, or by deletions or insertions which do not abolish the isolated protein's biological activity. Conservative substitutions typically include the substitution of one amino acid for another with similar characteristics such as substitutions within the following groups: valine, alanine and glycine; leucine and isoleucine; aspartic acid and glutamic acid; asparagine and glutamine; serine and threonine; lysine and arginine; and phenylalanine and tyrosine. The non-polar hydrophobic amino acids include alanine, leucine, isoleucine, valine, proline, phenylalanine, tryptophan, and methionine. The polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic acid and glutamic acid. Other conservative substitutions can be readily known by workers of ordinary skill. For example, for the amino acid alanine, a conservative substitution can be taken from any one of D-alanine, glycine, beta-alanine, L-cysteine, and D-cysteine. For lysine, a replacement can be any one of D-lysine, arginine, D-arginine, homo-arginine, methionine, D-methionine, ornithine, or D-ornithine.

Other analogs used within the methods of the invention are those with modifications which increase peptide stability. Such analogs may contain, for example, one or more non-peptide bonds (which replace the peptide bonds) in the peptide sequence. Also included are: analogs that include residues other than naturally occurring L-amino acids, such as D-amino acids or non-naturally occurring or synthetic amino acids such as beta or gamma amino acids and cyclic analogs. Incorporation of D- instead of L-amino acids into the isolated hedgehog polypeptide may increase its resistance to proteases. See, U.S. Pat. No. 5,219,990 supra. The term "fragment", as applied to an isolated hedgehog analog, can be as small as a single amino acid provided that it retains biological activity. It may be at least about 20 residues, more typically at least about 40 residues, preferably at least about 60 residues in length. Fragments can be generated by methods known to those skilled in the art. The ability of a candidate fragment to exhibit isolated hedgehog biological activity can be also assessed by methods known to those skilled in the art as described herein.

V. Antagonists of Hedgehog Activity

A preferred antagonist has at least the following properties: (i) the isolated protein binds the receptor patched-i with an affinity that may be less than, but is preferably at least the same as, the binding of mature hedgehog protein to patched-1; and (ii) the isolated protein blocks alkaline phosphatase (AP) induction by mature hedgehog protein when tested in an in vitro CH310T1/2 cell-based AP induction assay. Antagonists of the invention may also have the additional properties of being (iii) unable to induce ptc-1 and gli-1 expression. Additionally, it is recognized that some antagonists, for example small organic molecules, may act intracellularly to block hedgehog signal transduction at some point in the signaling pathway downstream of the interaction between hedgehog and patched and that some antagonists act by directly binding hedgehog itself. The present invention contemplates that any antagonist which inhibits hedgehog signal transduction may be useful in the methods of the present invention.

Persons having ordinary skill in the art can easily test any putative hedgehog antagonist for these properties. In particular, the mouse embryonic fibroblast line C3H10T1/2 is a mesenchymal stem cell line that is hedgehog responsive. Hedgehog treatment of the cells causes an upregulation of gli-1 and patched-1 (known indicators of hedgehog dependent signaling) and also causes induction of alkaline phosphatase activity, an indicator that the cells have differentiated down the chondrocyte/ bone osteoblast lineage. Several hedgehog variants are unable to elicit a hedgehog-dependent response on C3H10T1/2 cells, but they competed with mature hedgehog for function and therefore serve as functional antagonists. The synthesis and use of such hedgehog antagonist moieties are briefly described below.

A. N-Modified Hedgehog Polypeptides as Antagonists

Certain hedgehog variants that contain N-terminal modifications can block hedgehog function because they lack the ability to elicit a hedgehog-dependent response but retain the ability to bind to hedgehog receptor, patched-1. The critical primary amino acid sequence that defines whether a hedgehog polypeptide (i.e., a Sonic, Indian or Desert hedgehog) is a functional hedgehog antagonist is the N-terminal cysteine residue which corresponds to Cys-1 of the mature hedgehog. So long as the hedgehog polypeptide either lacks this N-terminal cysteine completely or contains this N-terminal cysteine in a modified form (e.g. chemically modified or included as part of an N-terminal extension moiety), the resulting polypeptide can act as a functional hedgehog antagonist. In this regard, the fact that an N-terminal cysteine "corresponds to Cys-1" means: (a) the N-terminal cysteine is the Cys-1 of mature Sonic, Indian or Desert hedgehog; or (b) the N-terminal cysteine occupies the same position as Cys-1 of mature Sonic, Indian or Desert hedgehog. Provided that, for example, a Sonic hedgehog has an N-terminal cysteine corresponding to Cys-1 that is altered or otherwise modified as described herein, it can antagonize the action of any other member of the hedgehog family. Therefore, persons having ordinary skill in the art will understand that it is possible for an Indian hedgehog protein to antagonize the activity of Sonic, Desert or Indian hedgehogs.

Examples of these antagonists with N-terminal modifications are included below and one skilled in the art can alter the disclosed structure of the antagonist, e.g., by producing fragments or analogs, and test the newly produced structures for antagonist activity. These examples in no way limit the structure of any related hedgehog antagonists, but are merely provided for further description. These, or analogous methods, can be used to make and screen fragments and analogs of a antagonist polypeptides. There are several variants that are able to function as antagonists.

1. N-Terminal Extensions

Antagonist polypeptides of the invention may include a hedgehog polypeptide sequence in which the N-terminal cysteine is linked to an N-terminal extension moiety. The isolated antagonist polypeptide can therefore be, as but one example, a recombinant fusion protein having: (a) a first N-terminal polypeptide portion that can be 5' to the hedgehog polypeptide itself, and that contains at least one element (e.g., an amino acid residue) that may be unrelated to hedgehog, linked to (b) an N-terminal cysteine corresponding to Cys-1 of Sonic hedgehog that is part of a hedgehog antagonist of the invention, or a portion of hedgehog antagonist. This N-terminal extension moiety (e.g., the first N-terminal polypeptide portion) can be a histidine tag, a maltose binding protein, glutathione-S-transferase, a DNA binding domain, or a polymerase activating domain. The functional antagonist may include an N-terminal extension moiety that contains an element which replaces the Cys-1 of mature hedgehog or an N-terminal cysteine that corresponds to Cys-1 of a mature Sonic hedgehog.

2. N-Terminal Deletions

Another variation of a functional antagonist is a hedgehog protein that is missing no greater than about 12 amino acids beginning from that N-terminal cysteine corresponding to Cys-1 of a mature hedgehog. Deletions in more than the about the first 12 contiguous amino acid residues do not generate functional antagonists. Preferably, deletions of about 10 contiguous amino acids will provide suitable functional antagonists. One can, however, remove fewer than 10 contiguous residues and still maintain antagonist function. Moreover, one can delete various combinations of non-contiguous residues provided that there are at least about 3 deleted residues in total.

These structures highlight the importance of the N-terminus of hedgehog proteins for function and indeed, underscore the need to conjugate a hedgehog protein at a site other than the N-terminal cysteine. All of the N-terminal deletion variants were indistinguishable from mature Sonic hedgehog (Shh) in their ability to bind patched-1, but were inactive in the in vitro C3H10T1/2 AP induction assay. All these N-terminal variants are unable to promote hedgehog-dependent signaling.

3. N-Terminal Mutations

Yet another functional antagonist has a mutation of the N-terminal cysteine to another amino acid residue. Any non-hydrophobic amino acid residue may be acceptable and persons having ordinary skill in the art following the teachings described herein will be able to perform the mutations and test the effects of such mutations. One example is Shh in which the N-terminal cysteine is replaced with a serine residue. This mutated form is indistinguishable from mature Shh in its ability to bind patched-1, but it blocks AP induction by mature Shh when tested for function in the C3H10T1/2 AP induction assay. Replacements with aspartic acid, alanine and histidine have also shown to serve as antagonists.

4. N-Terminal Cysteine Modifications

Because the primary amino acid sequence of hedgehog contains the Cys-1 that is important for biological activity, certain other modifications will result in inactive antagonist variants of hedgehog protein. Another antagonist is an isolated functional antagonist of a hedgehog polypeptide, comprising a hedgehog polypeptide containing an N-terminal cysteine that corresponds to Cys-1 of a mature Sonic hedgehog, except that the cysteine is in a modified form. Antagonist polypeptides of hedgehog may have non-sequence modifications that include in vivo or in vitro chemical derivatization of their N-terminal cysteine, as well as possible changes in acetylation, methylation, phosphorylation, amidation, or carboxylation. As an example, the functional antagonist can have an N-terminal cysteine in an oxidized form. Thus, a functional antagonist can have an N-terminal cysteine that is effectively modified by including it as part of an N-terminal extension moiety.

The functional antagonist polypeptides can include amino acid sequences that are at least 60% homologous to a hedgehog protein. The antagonist must exhibit at least the following functional antagonist properties: (i) the isolated protein binds the receptor patched-1 with an affinity that may be less than, but is preferably at least the same as, the binding of mature hedgehog protein to patched-1; and (ii) the isolated protein blocks alkaline phosphatase (AP) induction by mature hedgehog protein when tested in an in vitro CH310T1/2 cell-based AP induction assay.

Antagonists useful in the present invention also include those which arise as a result of the existence of multiple genes, alternative transcription events, alternative RNA splicing events, and alternative translational and posttranslational events. The polypeptide can be made entirely by synthetic means or can be expressed in systems, e.g., cultured cells, which result in substantially the same posttranslational modifications present when the protein is expressed in a native cell, or in systems which result in the omission of posttranslational modifications present when expressed in a native cell.

In a preferred embodiment, isolated antagonist is a polypeptide with one or more of the following characteristics:
  (i) it has at least 60, more preferably 90 and most preferably 95% sequence identity with amino acids of SEQ ID NOS: 10-18 and 23-26;
  (ii) it either has a modified N-terminal cysteine or lacks an N-terminal cysteine or has an N-terminal cysteine in a position different from the N-terminal cysteine corresponding to Cys-1 of the hedgehog;
  (iii) it blocks alkaline phosphatase induction by mature hedgehog in CH310T1/2 cells;
  (iv) it binds or interacts with its receptor patched-1 with an affinity that may be less than, but is preferably at least the same as, the binding of mature hedgehog protein to patched-1;
  (v) it is unable to induce ptc-1 and gli-1 expression in vitro in CH310T1/2 cells;

or
  (vi) it is unable to induce AP in CH310T1/2 assays.

B. Antibody Homologs as Antagonists

It is anticipated that antibodies can act as hedgehog antagonists. Antibodies can have extraordinary affinity and specificity for particular epitopes. Antibodies that bind to any protein in the hedgehog signaling pathway may have the capacity to act as antagonists. Antibodies that bind to hedgehog, smoothened or gli-1 may act by simply sterically hindering the proper protein-protein interactions or occupying active sites. Antibodies that bind to patched proteins may act as antagonists if they cause hyperactivation of the patched protein, for example stimulating patched association with smoothened. Proteins with extracellular domains are readily bound by exogenously supplied antibodies.

One aspect of the present invention are methods and compositions comprising hedgehog antibodies which antibodies are hedgehog antagonists. Preferred antibodies are specifically immunoreactive with a vertebrate hedgehog protein. For example, by using immunogens derived from hedgehog protein, monoclonal or polyclonal antibodies can be made using standard protocols (See, for example, Antibodies: A laboratory manual ed. by Harlow and Lane (Cold Spring Harbor Press: 1988)). A mammal, such as a mouse, a hamster or rabbit can be immunized with an immunogenic form of the peptide (e.g., a vertebrate hedgehog polypeptide or an antigenic fragment which is capable of eliciting an antibody response). Techniques for conferring immunogenicity on a protein or peptide include conjugation to carriers or other techniques well known in the art. An immunogenic portion of a hedgehog protein can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of a hedgehog protein of a vertebrate organism. In yet a further preferred embodiment the present invention provides, for example, antibodes which are immunospecific for discrete hedgehog family member, e.g. Shh versus Dhh versus Ihh. Antibodies which are immunospecific for hedgehog, or for a specific hedgehog family member do not substantially cross-react with non-homolgous protein. By not substantially cross react is meant that the antibody has a binding affinity for a non-homologous protein which is at least one order of magnitude, more preferably at least 2 orders of magnitude, and even more preferably at least 3 orders of magnitude less than the binding affinity of the antibody for the protein or proteins for which the antibody is immunospecific. In one embodiment, the antibody does not substantially cross-react with an invertebrate hedgehog protein.

The term antibody as used herein is intended to include fragments thereof which are also specifically reactive with one or more of the vertebrate hedgehog polypeptides. Antibodies can be fragmented using conventional techniques and the fragments screened for utility in the same manner as described above for whole antibodies. For example, F(ab)2 fragments can be generated by treating antibody with pepsin. The resulting F(ab)2 fragment can be treated to reduce disulfide bridges to produce Fab fragments. The antibody of the present invention is further intended to include bispecific and chimeric molecules having affinity for a hedgehog protein conferred by at least one CDR region of the antibody.

Both monoclonal and polyclonal antibodies immunoreactive with hedgehog polypeptides can be used as hedgehog antagonists. Although not all hedgehog antibodies function as hedgehog antagonists, antibodies with hedgehog antagonist activity can be identified in much the same way as other hedgehog antagonists. For example, candidate antibodies can be administered to cells expressing a hedgehog reporter gene, and antibodies that cause decreased reporter gene expression are antagonists.

In one variation, antibodies of the invention can be single chain antibodies (scFv), comprising variable antigen binding domains linked by a polypeptide linker. Single chain antibodies are expressed as a single polypeptide chain and can be expressed in bacteria and as part of a phage display library. In this way, phage that express the appropriate scFv will have hedgehog antagonist activity. The nucleic acid encoding the single chain antibody can then be recovered from the phage and used to produce large quantities of the scFv. Construction and screening of scFv libraries is extensively described in various publications (U.S. Pat. Nos. 5,258,498; 5,482,858; 5,091,513; 4,946,778; 5,969,108; 5,871,907; 5,223,409; 5,225,539).

An illustrative example of a hedgehog antibody which functions as a hedgehog antagonist is 5E1. 5E1 was deposited by Applicants with the ATCC (American Type Tissue Collection, P.O. Box 1549, Manassas, Va. 20108) under provisions of the Budapest Treaty on Aug. 13, 2002 (Patent Deposit Designation PTA-4595). As noted in the Examples provided herein, 5E1 functions in vitro and in vivo as a hedgehog antagonist. The invention specifically contemplates the use of 5E1, or an antibody which recognizes the same epitope as 5E1 in the subject methods.

The technology for producing monoclonal antibodies is well known. The preferred antibody homologs contemplated herein can be expressed from intact or truncated genomic or cDNA or from synthetic DNAs in prokaryotic or eukaryotic host cells. The dimeric proteins can be isolated from the culture media and/or refolded and dimerized in vitro to form biologically active compositions. Heterodimers can be formed in vitro by combining separate, distinct polypeptide chains. Alternatively, heterodimers can be formed in a single cell by co-expressing nucleic acids encoding separate, distinct polypeptide chains. See, for example, WO93/09229, or U.S. Pat. No. 5,411,941, for several exemplary recombinant heterodimer protein production protocols. Currently preferred host cells include, without limitation, prokaryotes including E. coli, or eukaryotes including yeast, Saccharomyces, insect cells, or mammalian cells, such as CHO, COS or BSC cells. One of ordinary skill in the art will appreciate that other host cells can be used to advantage. For example, anti-hedgehog antibodies may be identified by immunoprecipitation of 125I-labeled cell lysates from hedgehog-expressing cells. Anti-hedgehog antibodies may also be identified by flow cytometry, e.g., by measuring fluorescent staining of cells incubated with an antibody believed to recognize hedgehog protein. The lymphocytes used in the production of hybridoma cells typically are isolated from immunized mammals whose sera have already tested positive for the presence of anti-hedgehog antibodies using such screening assays.

Typically, the immortal cell line (e.g., a myeloma cell line) is derived from the same mammalian species as the lymphocytes. Preferred immortal cell lines are mouse myeloma cell lines that are sensitive to culture medium containing hypoxanthine, aminopterin and thymidine ("HAT medium"). Typically, HAT-sensitive mouse myeloma cells are fused to mouse splenocytes using 1500 molecular weight polyethylene glycol ("PEG 1500"). Hybridoma cells resulting from the fusion are then selected using HAT medium, which kills unfused and unproductively fused myeloma cells (unfused splenocytes die after several days because they are not transformed). Hybridomas producing a desired antibody are detected by screening the hybridoma culture supernatants. For example, hybridomas prepared to produce anti-hedgehog or patched antibodies may be screened by testing the hybridoma culture supernatant for secreted antibodies having the ability to bind to a recombinant hedgehog or patched expressing cell line.

To produce antibody homologs that are intact immunoglobulins, hybridoma cells that tested positive in such screening assays were cultured in a nutrient medium under conditions and for a time sufficient to allow the hybridoma cells to secrete the monoclonal antibodies into the culture medium. Tissue culture techniques and culture media suitable for hybridoma cells are well known. The conditioned hybridoma culture supernatant may be collected and the anti-hedgehog or patched antibodies optionally further purified by well-known methods.

Alternatively, the desired antibody may be produced by injecting the hybridoma cells into the peritoneal cavity of an unimmunized mouse. The hybridoma cells proliferate in the peritoneal cavity, secreting the antibody which accumulates as ascites fluid. The antibody may be harvested by withdrawing the ascites fluid from the peritoneal cavity with a syringe. Several anti-hedgehog or patched monoclonal antibodies have been previously described. These anti-hedgehog or patched monoclonal antibodies and others will be useful in the methods of treatment according to the present invention.

Fully human monoclonal antibody homologs against hedgehog or patched are another preferred binding agent which may block or coat hedgehog ligands in the method of the invention. In their intact form these may be prepared using in vitro-primed human splenocytes, as described by Boerner et al., 1991, J. Immunol., 147, 86-95. Alternatively, they may be prepared by repertoire cloning as described by Persson et al., 1991, Proc. Nat. Acad. Sci. USA, 88: 2432-2436 or by Huang and Stollar, 1991, J. Immunol. Methods 141, 227-236. U.S. Pat. No. 5,798,230 (Aug. 25, 1998, "Process for the preparation of human monoclonal antibodies and their use") who describe preparation of human monoclonal antibodies from human B cells. According to this process, human antibody-producing B cells are immortalized by infection with an Epstein-Barr virus, or a derivative thereof, that expresses Epstein-Barr virus nuclear antigen 2 (EBNA2). EBNA2 function, which is required for immortalization, is subsequently shut off, which results in an increase in antibody production.

In yet another method for producing fully human antibodies, U.S. Pat. No. 5,789,650 (Aug. 4, 1998, "Transgenic non-human animals for producing heterologous antibodies") describes transgenic non-human animals capable of producing heterologous antibodies and transgenic non-human animals having inactivated endogenous immunoglobulin genes. Endogenous immunoglobulin genes are suppressed by antisense polynucleotides and/or by antiserum directed against endogenous immunoglobulins. Heterologous antibodies are encoded by immunoglobulin genes not normally found in the genome of that species of non-human animal. One or more transgenes containing sequences of unrearranged heterologous human immunoglobulin heavy chains are introduced into a non-human animal thereby forming a transgenic animal capable of functionally rearranging transgenic immunoglobulin sequences and producing a repertoire of antibodies of various isotypes encoded by human immunoglobulin genes. Such heterologous human antibodies are produced in B-cells which are thereafter immortalized, e.g., by fusing with an immortalizing cell line such as a myeloma or by manipulating such B-cells by other techniques to perpetuate a cell line capable of producing a monoclonal heterologous, fully human antibody homolog.

Large nonimmunized human phage display libraries may also be used to isolate high affinity antibodies that can be developed as human therapeutics using standard phage technology (Vaughan et al, 1996).

Yet another preferred binding agent which may block or coat hedgehog ligands in the method of the invention is a humanized recombinant antibody homolog having anti-hedgehog or patched specificity. Following the early methods for the preparation of true "chimeric antibodies" (where the entire constant and entire variable regions are derived from different sources), a new approach was described in EP 0239400 (Winter et al.) whereby antibodies are altered by substitution (within a given variable region) of their complementarity determining regions (CDRs) for one species with those from another. This process may be used, for example, to substitute the CDRs from human heavy and light chain Ig variable region domains with alternative CDRs from murine variable region domains. These altered Ig variable regions may subsequently be combined with human Ig constant regions to create antibodies which are totally human in composition except for the substituted murine CDRs. Such CDR-substituted antibodies would be predicted to be less likely to elicit an immune response in humans compared to true chimeric antibodies because the CDR-substituted antibodies contain considerably less non-human components. The process for humanizing monoclonal antibodies via CDR "grafting" has been termed "reshaping". (Riechmann et al., 1988, Nature 332, 323-327; Verhoeyen et al., 1988, Science 239, 1534-1536).

Typically, complementarity determining regions (CDRs) of a murine antibody are transplanted onto the corresponding regions in a human antibody, since it is the CDRs (three in antibody heavy chains, three in light chains) that are the regions of the mouse antibody which bind to a specific antigen. Transplantation of CDRs is achieved by genetic engineering whereby CDR DNA sequences are determined by cloning of murine heavy and light chain variable (V) region gene segments, and are then transferred to corresponding human V regions by site directed mutagenesis. In the final stage of the process, human constant region gene segments of the desired isotype (usually gamma I for CH and kappa for CL) are added and the humanized heavy and light chain genes are co-expressed in mammalian cells to produce soluble humanized antibody.

The transfer of these CDRs to a human antibody confers on this antibody the antigen binding properties of the original murine antibody. The six CDRs in the murine antibody are mounted structurally on a V region "framework" region. The reason that CDR-grafting is successful is that framework regions between mouse and human antibodies may have very similar 3-D structures with similar points of attachment for CDRS, such that CDRs can be interchanged. Such humanized antibody homologs may be prepared, as exemplified in Jones et al., 1986, Nature 321, 522-525; Riechmann, 1988, Nature 332, 323-327; Queen et al., 1989, Proc. Nat. Acad. Sci. USA 86, 10029; and Orlandi et al., 1989, Proc. Nat. Acad. Sci. USA 86, 3833.

Nonetheless, certain amino acids within framework regions are thought to interact with CDRs and to influence overall antigen binding affinity. The direct transfer of CDRs from a murine antibody to produce a recombinant humanized antibody without any modifications of the human V region frameworks often results in a partial or complete loss of binding affinity. In a number of cases, it appears to be critical to alter residues in the framework regions of the acceptor antibody in order to obtain binding activity.

Queen et al., 1989 (supra) and WO 90/07861 (Protein Design Labs) have described the preparation of a humanized antibody that contains modified residues in the framework regions of the acceptor antibody by combining the CDRs of a murine MAb (anti-Tac) with human immunoglobulin framework and constant regions. They have demonstrated one solution to the problem of the loss of binding affinity that often results from direct CDR transfer without any modifications of the human V region framework residues; their solution involves two key steps. First, the human V framework regions are chosen by computer analysts for optimal protein sequence homology to the V region framework of the original murine antibody, in this case, the anti-Tac MAb. In the second step, the tertiary structure of the murine V region is modelled by computer in order to visualize framework amino acid residues which are likely to interact with the murine CDRs and these murine amino acid residues are then superimposed on the homologous human framework. See also U.S. Pat. Nos. 5,693,762; 5,693,761; 5,585,089; and 5,530,101 (Protein Design Labs).

One may use a different approach (Tempest et al.,1991, Biotechnology 9, 266-271) and utilize, as standard, the V region frameworks derived from NEWM and REI heavy and light chains respectively for CDR-grafting without radical introduction of mouse residues. An advantage of using the Tempest et al., approach to construct NEWM and REI based humanized antibodies is that the 3dimensional structures of NEWM and REI variable regions are known from x-ray crystallography and thus specific interactions between CDRs and V region framework residues can be modeled.

Regardless of the approach taken, the examples of the initial humanized antibody homologs prepared to date have shown that it is not a straightforward process. However, even acknowledging that such framework changes may be necessary, it is not possible to predict, on the basis of the available prior art, which, if any, framework residues will need to be altered to obtain functional humanized recombinant antibodies of the desired specificity. Results thus far indicate that changes necessary to preserve specificity and/or affinity are for the most part unique to a given antibody and cannot be predicted based on the humanization of a different antibody.

C. Small Organic Molecules as Antagonists

In other embodiments, a hedgehog antagonist may be a small organic molecule. Such a small organic molecule may antagonize hedgehog signal transduction via an interaction with but not limited to hedgehog, patched (ptc), gli, and/or smoothened. It is, therefore, specifically contemplated that these small molecules which intefere with aspects of hedgehog, ptc, or smoothened signal transduction activity will likewise be capable of inhibiting angiogenesis (or other biological consequences) in normal cells and/or mutant cells. Thus, it is contemplated that in certain embodiments, these compounds may be useful for inhibiting hedgehog activity in normal cells. In other embodiments, these compounds may be useful for inhibitng hedgehog activity in abnormal cells. In preferred embodiments, the subject inhibitors are organic molecules having a molecular weight less than 2500 amu, more preferably less than 1500 amu, and even more preferably less than 750 amu, and are capable of antagonizing hedgehog signaling, preferably specifically in target cells.

For example, compounds useful in the subject methods include compounds may be represented by general forumla (I):

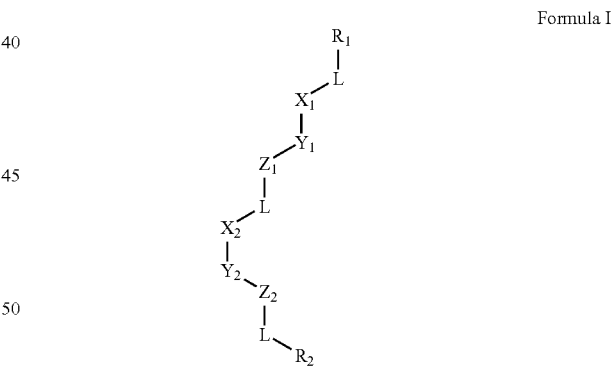

Formula I wherein, as valence and stability permit, $R_1$ and $R_2$, independently for each occurrence, represent H, lower alkyl, aryl (e.g., substituted or unsubstituted), aralkyl (e.g., substituted or unsubstituted, e.g., —$(CH_2)_n$aryl), or heteroaryl (e.g., substituted or unsubstituted), or heteroaralkyl (e.g., substituted or unsubstituted, e.g., —$(CH_2)_n$heteroaralkyl-);

L, independently for each occurrence, is absent or represents —$(CH_2)_n$-alkyl, -alkenyl-, -alkynyl-, —$(CH_2)_n$alkenyl-, —$(CH_2)_n$alkynyl-, —$(CH_2)_nO(CH_2)_p$—, —$(CH_2)_n$ $NR_2(CH_2)_p$—, —$(CH_2)_nS(CH_2)_p$—, —$(CH_2)_n$alkenyl $(CH_2)_p$—, —$(CH_2)_n$alkynyl$(CH_2)_p$—, —$O(CH_2)_n$—, —$NR_2$ $(CH_2)_n$—, or —$S(CH_2)_n$—;

$X_1$ and $X_2$ can be selected, independently, from —$N(R_8)$—, —O—, —S—, —Se—, —N=N—, —ON=CH—, —$(R_8)N$—$N(R_8)$—, —$ON(R_8)$—, a heterocycle, or a direct bond between L and $Y_1$ or $Y_2$, respectively;

$Y_1$ and $Y_2$ can be selected, independently, from —C(=O)—, —C(=S)—, —S($O_2$)—, —S(O)—, —C(=NCN)—, —P(=O)($OR_2$)—, a heteroaromatic group, or a direct bond between $X_1$ and $Z_1$ or $X_2$ and $Z_2$, respectively;

$Z_1$ and $Z_2$ can be selected, independently, from —$N(R_8)$—, —O—, —S—, —Se—, —N=N—, —ON=CH—, —$R_8N$—$NR_8$—, —$ONR_8$—, a heterocycle, or a direct bond between $Y_1$ or $Y_2$, respectively, and L;

$R_8$, independently for each occurrence, represents H, lower alkyl, —$(CH_2)_n$aryl (e.g., substituted or unsubstituted), —$(CH_2)_n$heteroaryl (e.g., substituted or unsubstituted), or two $R_8$ taken together may form a 4- to 8-membered ring, e.g., with $X_1$ and $Z_1$ or $X_2$ and $Z_1$, which ring may include one or more carbonyls;

p represents, independently for each occurrence, an integer from 0 to 10, preferably from 0 to 3; and n, individually for each occurrence, represents an integer from 0 to 10, preferably from 0 to 5.

In certain embodiments, $R_1$ represents a substituted or unsubstituted heteroaryl group.

In certain embodiments, $X_1$ and $X_2$ can be selected from —$N(R_8)$—, —O—, —S—, a direct bond, and a heterocycle, $Y_1$ and $Y_2$ can be selected from —C(=O)—, —C(=S)—, and —S($O_2$)—, and $Z_1$ or $Z_2$ can be selected from —$N(R_8)$—, —O—, —S—, a direct bond, and a heterocycle.

In certain related embodiments, $X_1$-$Y_1$-$Z_1$ or $X_2$-$Y_2$-$Z_2$ taken together represents a urea (N—C(O)—N) or an amide (N—C(O) or C(O)—N).

In certain embodiments, $X_1$ or $X_2$ represents a diazacarbocycle, such as a piperazine.

In certain embodiments, $R_1$ represents a fused cycloalkyl-aryl or cycloalkyl-heteroaryl system, for example:

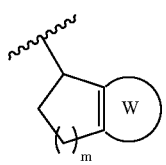

wherein W is a substituted or unsubstituted aryl or heteroaryl ring fused to the cycloalkyl ring and m is an integer from 1-4 inclusive, e.g., from 1-3, or from 1-2. The fused system may be bound to L from any carbon of the fused system, including the position depicted above. In certain embodiments, $R_1$ may represent a tetrahydronaphthyl group, and preferably $Y_1$-$X_1$-L-$R_1$ taken together represent a tetrahydronaphthyl amide group, such as:

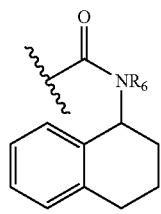

In embodiments wherein $Y_1$ and $Z_1$ are absent and $X_1$ comprises a pyrimidone, compounds useful in the present invention may be represented by general formula (II):

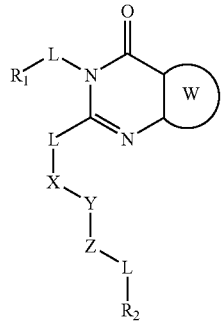

Formula II wherein, as valence and stability permit, $R_1$ and $R_2$, independently for each occurrence, represent H, lower alkyl, —$(CH_2)_n$aryl (e.g., substituted or unsubstituted), or —$(CH_2)_n$heteroaryl (e.g., substituted or unsubstituted);

L, independently for each occurrence, is absent or represents —$(CH_2)_n$-alkyl, -alkenyl-, -alkynyl-, —$(CH_2)_n$alkenyl-, —$(CH_2)_n$alkynyl-, —$(CH_2)_nO(CH_2)_p$—, —$(CH_2)_nNR_2(CH_2)_p$—, —$(CH_2)_nS(CH_2)_p$—, —$(CH_2)_n$alkenyl$(CH_2)_p$—, —$(CH_2)_n$alkynyl$(CH_2)_p$—, —$O(CH_2)_n$—, —$NR_2(CH_2)_n$—, or —$S(CH_2)_n$—;

X can be selected from —$N(R_8)$—, —O—, —S—, —Se—, —N=N—, —ON=CH—, —$(R_8)N$—$N(R_8)$—, —$ON(R_8)$—, a heterocycle, or a direct bond between L and Y;

Y can be selected from —C(=O)—, —C(=S)—, —S($O_2$)—, —S(O)—, —C(=NCN)—, —P(=O)($OR_2$)—, a heteroaromatic group, or a direct bond between X and Z;

Z can be selected from —$N(R_8)$—, —O—, —S—, —Se—, —N=N—, —ON=CH—, —$R_8N$—$NR_8$—, —$ONR_8$—, a heterocycle, or a direct bond between Y and L;

$R_8$, independently for each occurrence, represents H, lower alkyl, —$(CH_2)_n$aryl (e.g., substituted or unsubstituted), —$(CH_2)_n$heteroaryl (e.g., substituted or unsubstituted), or two $R_8$ taken together may form a 4- to 8-membered ring, e.g., with X and Z, which ring may include one or more carbonyls;

W represents a substituted or unsubstituted aryl or heteroaryl ring fused to the pyrimidone ring;

p represents, independently for each occurrence, an integer from 0 to 10, preferably from 0 to 3; and n, individually for each occurrence, represents an integer from 0 to 10, preferably from 0 to 5.

In embodiments wherein $Y_1$ and $Z_1$ are absent and $X_1$ comprises a pyrimidone, compounds useful in the present invention may be represented by general formula (III):

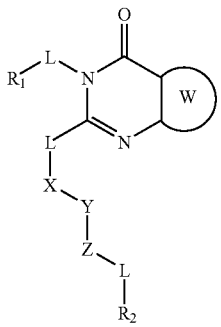

Formula III wherein, as valence and stability permit, $R_1$ and $R_2$, independently for each occurrence, represent H, lower alkyl, aryl (e.g., substituted or unsubstituted), aralkyl (e.g., substituted or unsubstituted, e.g., —$(CH_2)_n$aryl), or heteroaryl (e.g., substituted or unsubstituted), or heteroaralkyl (e.g., substituted or unsubstituted, e.g., —$(CH_2)_n$heteroaralkyl-);

L, independently for each occurrence, is absent or represents —$(CH_2)_n$-alkyl, -alkenyl-, -alkynyl-, —$(CH_2)_n$alkenyl-, —$(CH_2)_n$alkynyl-, —$(CH_2)_nO(CH_2)_p$—, —$(CH_2)_n$ $NR_2(CH_2)_p$—, —$(CH_2)_nS(CH_2)_p$—, —$(CH_2)_n$alkenyl $(CH_2)_p$—, —$(CH_2)_n$alkynyl$(CH_2)_p$—, —$O(CH_2)_n$—, —$NR_2$ $(CH_2)_n$—, or —$S(CH_2)_n$—, which may optionally be substitued with a group selected from H, substituted or unsubstituted lower alkyl, alkenyl, or alkynyl, cycloalkylalkyl (e.g., substituted or unsubstituted, e.g., —$(CH_2)_n$cycloalkyl), (e.g., substituted or unsubstituted), aryl (e.g., substituted or unsubstituted), aralkyl (e.g., substituted or unsubstituted, e.g., —$(CH_2)_n$aryl), or heteroaryl (e.g., substituted or unsubstituted), or heteroaralkyl (e.g., substituted or unsubstituted, e.g., —$(CH_2)_n$heteroaralkyl-), preferably from H, lower alkyl, —$(CH_2)_n$aryl (e.g., substituted or unsubstituted), or —$(CH_2)_n$heteroaryl (e.g., substituted or unsubstituted);

X can be selected from —$N(R_8)$—, —O—, —S—, —Se—, —N=N—, —ON=CH—, —$(R_8)N$—$N(R_8)$—, —$ON(R_8)$—, a heterocycle, or a direct bond between L and Y;

Y can be selected from —C(=O)—, —C(=S)—, —$S(O_2)$—, —S(O)—, —C(=NCN)—, —P(=O)($OR_2$)—, a heteroaromatic group, or a direct bond between X and Z;

Z can be selected from —$N(R_8)$—, —O—, —S—, —Se—, —N=N—, —ON=CH—, —$R_8N$—$NR_8$—, —$ONR_8$—, a heterocycle, or a direct bond between Y and L;

$R_8$, independently for each occurrence, represents H, lower alkyl, aryl (e.g., substituted or unsubstituted), aralkyl (e.g., substituted or unsubstituted, e.g., —$(CH_2)_n$aryl), or heteroaryl (e.g., substituted or unsubstituted), or heteroaralkyl (e.g., substituted or unsubstituted, e.g., —$(CH_2)_n$heteroaralkyl-), or two $R_8$ taken together may form a 4- to 8-membered ring, e.g., with X and Z, which ring may include one or more carbonyls;

W represents a substituted or unsubstituted aryl or heteroaryl ring fused to the pyrimidone ring;

p represents, independently for each occurrence, an integer from 0 to 10, preferably from 0 to 3; and n, individually for each occurrence, represents an integer from 0 to 10, preferably from 0 to 5.

In certain embodiments, $R_1$ represents a substituted or unsubstituted aryl or heteroaryl group, e.g., a phenyl ring, a pyridine ring, etc. In certain embodiments wherein -$LR_1$ represents a substituted aryl or heteroaryl group, $R_1$ is preferably not substituted with an isopropoxy ($Me_2CHO$—) group. In certain embodiments wherein -$LR_1$ represents a substituted aryl or heteroaryl group, $R_1$ is preferably not substituted with an ether group. In certain embodiments, substituents on $R_1$ (e.g., other than hydrogen) are selected from halogen, cyano, alkyl, alkenyl, alkynyl, aryl, hydroxyl, (unbranched alkyl-O—), silyloxy, amino, nitro, thiol, amino, imino, amido, phosphoryl, phosphonate, phosphine, carbonyl, carboxyl, carboxamide, anhydride, silyl, thioether, alkylsulfonyl, arylsulfonyl, sulfoxide, selenoether, ketone, aldehyde, ester, or —$(CH_2)_m$—$R_8$. In certain embodiments, non-hydrogen substituents are selected from halogen, cyano, alkyl, alkenyl, alkynyl, aryl, nitro, thiol, imino, amido, carbonyl, carboxyl, anhydride, thioether, alkylsulfonyl, arylsulfonyl, ketone, aldehyde, and ester. In certain embodiments, non-hydrogen substituents are selected from halogen, cyano, alkyl, alkenyl, alkynyl, nitro, amido, carboxyl, anhydride, alkylsulfonyl, ketone, aldehyde, and ester.

In certain embodiments, X can be selected from —$N(R_8)$—, —O—, —S—, a direct bond, and a heterocycle, Y can be selected from —C(=O)—, —C(=S)—, and —$S(O_2)$—, and Z can be selected from —$N(R_8)$—, —O—, —S—, a direct bond, and a heterocycle. In certain such embodiments, at least one of Z and X is present.

In certain related embodiments, X-Y-Z taken together represents a urea (NC(O)N) or an amide (NC(O) or C(O)N).

In certain embodiments, W is a substituted or unsubstituted benzene ring.

In certain embodiments, X represents a diazacarbocycle, such as a piperazine, e.g., substituted or unsubstituted.

In certain embodiments, X can be selected from —$N(R_8)$—, —O—, —S—, and a direct bond, Y can be selected from —C(=O)—, —C(=S)—, and —$S(O_2)$—, and Z can be selected from —$N(R_8)$—, —O—, —S—, and a direct bond, such that at least one of X and Z is present.

In certain embodiments $R_8$ represents H, lower alkyl, aralkyl, heteroaralkyl, aryl, or heteroaryl, e.g., H or lower alkyl.

In certain embodiments, X represents —NH—.

In certain embodiments, -L-X- represents -(unbranched lower alkyl)-NH—, e.g., —$CH_2$—NH—, —$CH_2CH_2$—NH—, etc.

In certain other embodiments, compounds useful in the subject methods include compounds may be represented by general forumla (IV):

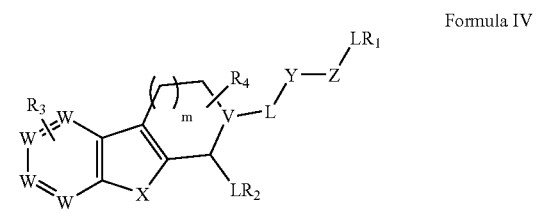

Formula IV wherein, as valence and stability permit, $R_1$ and $R_2$, independently for each occurrence, represent H, substituted or unsubstituted lower alkyl, alkenyl, or alkynyl, —$(CH_2)_n$cycloalkyl (e.g., substituted or unsubstituted), —$(CH_2)_n$aryl (e.g., substituted or unsubstituted), or —$(CH_2)_n$ heterocyclyl (e.g., substituted or unsubstituted);

L, independently for each occurrence, is absent or represents —$(CH_2)_n$-alkyl, -alkenyl-, -alkynyl-, —$(CH_2)_n$alkenyl-, —$(CH_2)_n$alkynyl-, —$(CH_2)_nO(CH_2)_p$—, —$(CH_2)_n$ $NR_2(CH_2)_p$—, —$(CH_2)_nS(CH_2)_p$—, —$(CH_2)_n$alkenyl $(CH_2)_p$—, —$(CH_2)_n$alkynyl$(CH_2)_p$—, —$O(CH_2)_n$—, —$NR_2$ $(CH_2)_n$—, or —$S(CH_2)_n$—;

V represents N or CH;

W, independently for each occurrence, represents N or CH, such that preferably no more than one occurrence of W represents N;

X and Z, independently, can be selected from —CH—, —$N(R_8)$—, —O—, —S—, or —Se—;

Y can be selected from —C(=O)—, —C(=S)—, —$S(O_2)$—, —S(O)—, —C(=NCN)—, or —P(=O) ($OR_2$)—;

$R_8$, independently for each occurrence, represents H, substituted or unsubstituted lower alkyl, —$(CH_2)_n$cycloalkyl (e.g., substituted or unsubstituted), —$(CH_2)_n$aryl (e.g., substituted or unsubstituted), —$(CH_2)_n$heterocyclyl (e.g., substituted or unsubstituted), or two $R_8$ taken together may form a 4- to 8-membered ring, e.g., with $X_1$ and $Z_1$ or $X_2$ and $Z_1$, which ring may include one or more carbonyls;

$R_3$ and $R_4$, independently represent from 1-4 substituents on the ring to which they are attached, selected from, independently for each occurrence, hydrogen, halogens, alkyls, alkenyls, alkynyls, aryls, hydroxyl, =O, =S, alkoxyl, syliloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, selenoethers, ketones, aldehydes, esters, or —$(CH_2)_m$—$R_8$;

m represents an integer from 0-3;

p represents, independently for each occurrence, an integer from 0 to 10, preferably from 0 to 3; and n, individually for each occurence, represents an integer from 0 to 10, preferably from 0 to 5.

In certain embodiments, $R_1$ and $R_2$ are independently selected from substituted or unsubstituted aryl, heterocyclyl, branched or unbranched alkyl, or cycloalkyl. In embodiments wherein $R_1$ or $R_2$ is aryl or heterocyclyl, substituents are preferably selected from H, alkyl, acyl, carboxy, ester, amide, cyano, ether, thioether, amino, halogen, nitro, and trihalomethyl.

In certain embodiments, $R_3$ is absent or represents one or two substituents selected from alkyl, acyl, carboxy, ester, amide, cyano, ether, thioether, amino, acyl, halogen, nitro, and trihalomethyl.

In certain embodiments, $R_4$ is absent or represents one or two substituents selected from ether, amino, thioether, alkyl, aryl, (=O), or carbonyl (e.g., carboxy, ester, ketone, aldehyde, etc.).

In certain embodiments, L is absent for each occurrence, or represents —$CH_2$— or —$CH_2CH_2$—.

In certain embodiments, X represents $NR_8$. $R_8$ preferably represents H.

In certain embodiments, Z represents $NR_8$. $R_8$ preferably represents H.

In certain embodiments, Y represents —C(=O)—, —C(=S)—, or —$S(O_2)$—.

In certain embodiments, m is 1.

In certain embodiments, W represents CH in all occurrences.

In certain embodiments, V represents N.

In certain embodiments, compounds useful in the present invention may be represented by general formula (V):

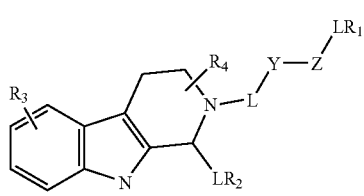

Formula V wherein, as valence and stability permit, $R_1$ and $R_2$, independently for each occurrence, represent H, substituted or unsubstituted lower alkyl, alkenyl, or alkynyl, —$(CH_2)_n$cycloalkyl (e.g., substituted or unsubstituted), —$(CH_2)_n$aryl (e.g., substituted or unsubstituted), or —$(CH_2)_n$ heterocyclyl (e.g., substituted or unsubstituted);

L, independently for each occurrence, is absent or represents —$(CH_2)_n$-alkyl, -alkenyl-, -alkynyl-, —$(CH_2)_n$alkenyl-, —$(CH_2)_n$alkynyl-, —$(CH_2)_nO(CH_2)_p$—, —$(CH_2)_n NR_2(CH_2)_p$—, —$(CH_2)_nS(CH_2)_p$—, —$(CH_2)_n$alkenyl$(CH_2)_p$—, —$(CH_2)_n$alkynyl$(CH_2)_p$—, —$O(CH_2)_n$—, —$NR_2(CH_2)_n$—, or —$S(CH_2)_n$—;

X and Z, independently, can be selected from —CH—, —$N(R_8)$—, —O—, —S—, or —Se—;

Y can be selected from —C(=O)—, —C(=S)—, —$S(O_2)$—, —S(O)—, —C(=NCN)—, or —P(=O)($OR_2$)—;

$R_8$, independently for each occurrence, represents H, substituted or unsubstituted lower alkyl, —$(CH_2)_n$cycloalkyl (e.g., substituted or unsubstituted), —$(CH_2)_n$aryl (e.g., substituted or unsubstituted), —$(CH_2)_n$heterocyclyl (e.g., substituted or unsubstituted), or two $R_8$ taken together may form a 4- to 8-membered ring, e.g., with $X_1$ and $Z_1$ or $X_2$ and $Z_1$, which ring may include one or more carbonyls;

$R_3$ and $R_4$, independently represent from 1-4 substituents on the ring to which they are attached, selected from, independently for each occurrence, hydrogen, halogens, alkyls, alkenyls, alkynyls, aryls, hydroxyl, =O, =S, alkoxyl, syliloxy, amino, nitro, thiol, amines, imines, amides, phosphoryls, phosphonates, phosphines, carbonyls, carboxyls, carboxamides, anhydrides, silyls, ethers, thioethers, alkylsulfonyls, arylsulfonyls, selenoethers, ketones, aldehydes, esters, or —$(CH_2)_m$—R;

p represents, independently for each occurrence, an integer from 0 to 10, preferably from 0 to 3; and n, individually for each occurence, represents an integer from 0 to 10, preferably from 0 to 5.

In certain embodiments, $R_1$ and $R_2$ are independently selected from substituted or unsubstituted aryl, heterocyclyl, branched or unbranched alkyl, or cycloalkyl. In embodiments wherein $R_1$ or $R_2$ is aryl or heterocyclyl, substituents are preferably selected from H, alkyl, acyl, carboxy, ester, amide, cyano, ether, thioether, amino, halogen, nitro, and trihalomethyl.

In certain embodiments, $R_3$ is absent or represents one or two substituents selected from alkyl, acyl, carboxy, ester, amide, cyano, ether, thioether, amino, acyl, halogen, nitro, and trihalomethyl.

In certain embodiments, $R_4$ is absent or represents one or two substituents selected from ether, amino, thioether, alkyl, aryl, (=O), or carbonyl (e.g., carboxy, ester, ketone, aldehyde, etc.).

In certain embodiments, L is absent for each occurrence, or represents —$CH_2$— or —$CH_2CH_2$—.

In certain embodiments, X represents $NR_8$. $R_8$ preferably represents H.

In certain embodiments, Z represents $NR_8$. $R_8$ preferably represents H.

In certain embodiments, Y represents —C(=O)—, —C(=S)—, or —$S(O_2)$—.

In still other embodiments, compounds which may be useful in the subject methods include compounds may be represented by general formula (VI):

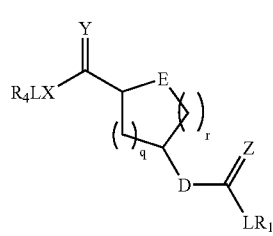

Formula VI wherein, as valence and stability permit, $R_1$, $R_2$, $R_3$, and $R_4$, independently for each occurrence, represent H, lower alkyl, —$(CH_2)_n$aryl (e.g., substituted or unsubstituted), or —$(CH_2)_n$heteroaryl (e.g., substituted or unsubstituted);

L, independently for each occurrence, is absent or represents —(CH$_2$)$_n$—, -alkenyl-, -alkynyl-, —(CH$_2$)$_n$alkenyl-, —(CH$_2$)$_n$alkynyl-, —(CH$_2$)$_n$O(CH$_2$)$_p$—, —(CH$_2$)$_n$NR$_8$(CH$_2$)$_p$—, —(CH$_2$)$_n$S(CH$_2$)$_p$—, —(CH$_2$)$_n$alkenyl(CH$_2$)$_p$—, —(CH$_2$)$_n$alkynyl(CH$_2$)$_p$—, —O(CH$_2$)$_n$—, NR$_8$(CH$_2$)$_n$—, or —S(CH$_2$)$_n$—;

X and D, independently, can be selected from —N(R$_8$)—, —O—, —S—, —(R$_8$)N—N(R$_8$)—, —ON(R$_8$)—, or a direct bond;

Y and Z, independently, can be selected from O or S;

E represents O, S, or NR$_5$, wherein R$_5$ represents LR$_8$ or —(C=O)LR$_8$.

R$_8$, independently for each occurrence, represents H, lower alkyl, —(CH$_2$)$_n$aryl (e.g., substituted or unsubstituted), —(CH$_2$)$_n$heteroaryl (e.g., substituted or unsubstituted), or two R$_8$ taken together may form a 4- to 8-membered ring;

p represents, independently for each occurrence, an integer from 0 to 10, preferably from 0 to 3;

n, individually for each occurrence, represents an integer from 0 to 10, preferably from 0 to 5; and q and r represent, independently for each occurrence, an integer from 0-2.

In certain embodiments, D does not represent N-lower alkyl. In certain embodiments, D represents an aralkyl- or heteroaralkyl-substituted amine.

In certain embodiments, R$_1$ represents a lower alkyl group, such as a branched alkyl, a cycloalkyl, or a cycloalkylalkyl, for example, cyclopropyl, cyclopropylmethyl, neopentyl, cyclobutyl, isobutyl, isopropyl, sec-butyl, cyclobutylmethyl, etc.

In certain embodiments, Y and Z are O.

In certain embodiments, the sum of q and r is less than 4, e.g., is 2 or 3.

In certain embodiments, XLR$_4$, taken together, include a cyclic amine, such as a piperazine, a morpholine, a piperidine, a pyrrolidine, etc.

In certain embodiments, at least one of R$_1$, R$_2$, and R$_3$ includes an aryl or heteroaryl group. In certain related embodiments, at least two of R$_1$, R$_2$, and R$_3$ include an aryl or heteroaryl group. In certain embodiments, R$_1$ is lower alkyl.

In certain embodiments, L attached to R$_1$ represents O, S, or NR$_8$, such as NH.

In certain embodiments, E is NR$_8$. In certain embodiments, E represents an aralkyl- or heteroaralkyl-substituted amine, e.g., including polycyclic R$_8$.

In certain embodiments, X is not NH. In certain embodiments, X is included in a ring, or, taken together with —C(=Y)—, represents a tertiary amide.

In certain embodiments, compounds useful in the present invention may be represented by general formula (VII):

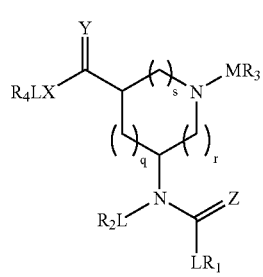

Formula VII wherein, as valence and stability permit,

R$_1$, R$_2$, R$_3$, R$_4$, R$_8$, L, X, Y, Z, n, p, q, and r are as defined above;

M is absent or represents L, —SO$_2$L-, or —(C=O)L-; and s represents, independently for each occurrence, an integer from 0-2.

In certain embodiments, Y and Z are O.

In certain embodiments, R$_1$ represents a lower alkyl group, such as a branched alkyl, a cycloalkyl, or a cycloalkylalkyl, for example, cyclopropyl, cyclopropylnethyl, neopentyl, cyclobutyl, isobutyl, isopropyl, sec-butyl, cyclobutylmethyl, etc.

In certain embodiments, the sum of q, r, and s is less than 5, e.g., is 2, 3, or 4.

In certain embodiments, XLR$_4$, taken together, include a cyclic amine, such as a piperazine, a morpholine, a piperidine, a pyrrolidine, etc.

In certain embodiments, L attached to R$_1$ represents O, S, or NR$_8$, such as NH.

In certain embodiments, at least one of R$_1$, R$_2$, and R$_3$ includes an aryl or heteroaryl group. In certain related embodiments, at least two of R$_1$, R$_2$, and R$_3$ include an aryl or heteroaryl group.

In certain embodiments, M is absent.

In certain embodiments, X is not NH. In certain embodiments, X is included in a ring, or, taken together with —C(=Y)—, represents a tertiary amide.

In certain embodiments, compounds useful in the present invention may be represented by general formula (VIII):

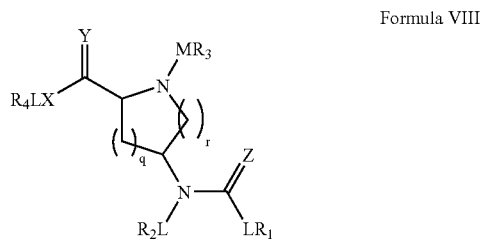

Formula VIII wherein, as valence and stability permit,

R$_1$, R$_2$, R$_3$, R$_4$, R$_8$, L, M, X, Y, Z, n, p, q, and r are as defined above.

In certain embodiments, Y and Z are O.

In certain embodiments, R$_1$ represents a lower alkyl group, preferably a branched alkyl, a cycloalkyl, or a cycloalkylalkyl, for example, cyclopropyl, cyclopropylmethyl, neopentyl, cyclobutyl, isobutyl, isopropyl, sec-butyl, cyclobutylmethyl, etc.

In certain embodiments, the sum of q and r is less than 4, e.g., is 2 or 3.

In certain embodiments, XLR$_4$, taken together, include a cyclic amine, such as a piperazine, a morpholine, a piperidine, a pyrrolidine, etc.

In certain embodiments, at least one of R$_1$, R$_2$, and R$_3$ includes an aryl or heteroaryl group. In certain related embodiments, at least two of R$_1$, R$_2$, and R$_3$ include an aryl or heteroaryl group. In certain embodiments, R$_1$ is lower alkyl.

In certain embodiments, L attached to R$_1$ represents O, S, or NR$_8$, such as NH.

In certain embodiments, M is absent.

In certain embodiments, X is not NH. In certain embodiments, X is included in a ring, or, taken together with —C(=Y)—, represents a tertiary amide.

In certain embodiments, compounds useful in the present invention may be represented by general formula (IX):

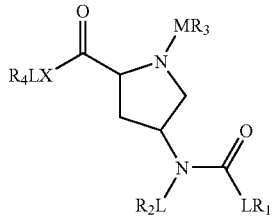

Formula IX wherein, as valence and stability permit, $R_1$, $R_2$, $R_3$, $R_4$, $R_8$, L, M, X, n, and p are as defined above.

In certain embodiments, $XLR_4$, taken together, include a cyclic amine, such as a piperazine, a morpholine, a piperidine, a pyrrolidine, etc.

In certain embodiments, $R_1$ represents a lower alkyl group, preferably a branched alkyl, a cycloalkyl, or a cycloalkylalkyl, for example, cyclopropyl, cyclopropylmethyl, neopentyl, cyclobutyl, isobutyl, isopropyl, sec-butyl, cyclobutylmethyl, etc.

In certain embodiments, at least one of $R_1$, $R_2$, and $R_3$ includes an aryl or heteroaryl group. In certain related embodiments, at least two of $R_1$, $R_2$, and $R_3$ include an aryl or heteroaryl group. In certain embodiments, $R_1$ is lower alkyl.

In certain embodiments, L attached to $R_1$ represents O, S, or $NR_8$, such as NH.

In certain embodiments, M is absent.

In certain embodiments, X is not NH. In certain embodiments, X is included in a ring, or, taken together with —C(=Y)—, represents a tertiary amide.

In certain embodiments L represents a direct bond for all occurrences.

In certain embodiments, compounds useful in the present invention may be represented by general formula (X):

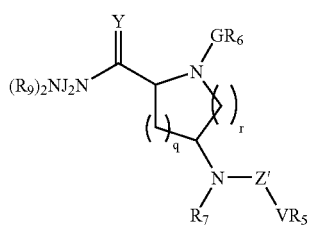

Formula X wherein, as valence and stability permit,

Y, n, p, q, and r are as defined above;

Z' represents —C(=O)—, —C(=S)—, —C(=NH)—, $SO_2$, or SO, preferably —C(=O)—, —C(=S)—;

V is absent or represents O, S, or $NR_8$;

G is absent or represents —C(=O)— or —$SO_2$—;

J, independently for each occurrence, represents H or substituted or unsubstituted lower alkyl or alkylene, such as methyl, ethyl, methylene, ethylene, etc., attached to NC(=Y), such that both occurrences of N adjacent to J are linked through at least one occurrence of J, and $R_9$, independently for each occurrence, is absent or represents H or lower alkyl, or two occurrences of J or one occurrence of J taken together with one occurrence of $R_9$, forms a ring of from 5 to 7 members, which ring includes one or both occurrences of N;

$R_5$ represents substituted or unsubstituted alkyl (e.g., branched or unbranched), alkenyl (e.g., branched or unbranched), alkynyl (e.g., branched or unbranched), cycloalkyl, or cycloalkylalkyl;

$R_6$ represents substituted or unsubstituted aryl, aralkyl, heteroaryl, heteroaralkyl, heterocyclyl, heterocyclylalkyl, cycloalkyl, or cycloalkylalkyl, including polycyclic groups; and $R_7$ represents substituted or unsubstituted aryl, aralkyl, heteroaryl, or heteroaralkyl.

In certain embodiments, Y is O. In certain embodiments, Z' represents $SO_2$, —C(=O)—, or —C(=S)—.

In certain embodiments, the sum of q and r is less than 4.

In certain embodiments, $NJ_2N$, taken together, represent a cyclic diamine, such as a piperazine, etc., which may be substituted or unsubstituted, e.g., with one or more substitutents such as oxo, lower alkyl, lower alkyl ether, etc. In certain other embodiments, $NJ_2$ or $NJR_9$ taken together represent a substituted or unsubstituted heterocyclic ring to which the other occurrence of N is attached. In certain embodiments, one or both occurrences of J are substituted with one or more of lower alkyl, lower alkyl ether, lower alkyl thioether, amido, oxo, etc. In certain embodiments, a heterocyclic ring which comprises an occurrence of J has from 5 to 8 members.

In certain embodiments, $R_5$ represents a branched alkyl, cycloalkyl, or cycloalkylalkyl.

In certain embodiments, $R_6$ includes at least one heterocyclic ring, such as a thiophene, furan, oxazole, benzodioxane, benzodioxole, pyrrole, indole, etc.

In certain embodiments, $R_7$ represents a phenyl alkyl, such as a benzyl group, optionally substituted with halogen, hydroxyl, lower alkyl, nitro, cyano, lower alkyl ether (e.g., optionally substituted, such as $CHF_2CF_2O$), or lower alkyl thioether (e.g., optionally substituted, such as $CF_3S$).

In certain embodiments, $R_8$, when it occurs in V, represents H or lower alkyl, preferably H.

In certain embodiments, compounds useful in the present invention may be represented by general formula (XI):

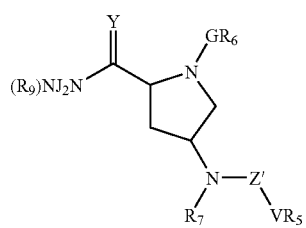

Formula XI wherein, as valence and stability permit, $R_5$, $R_6$, $R_7$, $R_8$, $R_9$, $R_{10}$, G, J, V, Y, Z', n, and p are as defined above.

In certain embodiments, Y is O. In certain embodiments, Z' represents $SO_2$, —C(=O)—, or —C(=S)—.

In certain embodiments, $NJ_2N$, taken together, represent a heterocyclic ring, such as a piperazine, etc., which may be substituted or unsubstituted, e.g., with one or more substitutents such as oxo, lower alkyl, lower alkyl ether, etc. In certain other embodiments, $NJ_2$ or $NJR_9$ taken together represent a substituted or unsubstituted heterocyclic ring to which the other occurrence of N is attached. In certain embodiments, one or both occurrences of J are substituted with one or more of lower alkyl, lower alkyl ether, lower alkyl thioether, amido, oxo, etc. In certain embodiments, a heterocyclic ring which comprises an occurrence of J has from 5 to 8 members.

In certain embodiments, $R_5$ represents a branched alkyl, cycloalkyl, or cycloalkylalkyl.

In certain embodiments, $R_6$ includes at least one heterocyclic ring, such as a thiophene, furan, oxazole, benzodioxane, benzodioxole, pyrrole, indole, etc.

In certain embodiments, $R_7$ represents a phenyl alkyl, such as a benzyl group, optionally substituted with halogen, hydroxyl, lower alkyl, nitro, cyano, lower alkyl ether (e.g., optionally substituted, such as $CHF_2CF_2O$), or lower alkyl thioether (e.g., optionally substituted, such as $CF_3S$).

In certain embodiments, $R_8$, when it occurs in V, represents H or lower alkyl, preferably H.

In certain preferred embodiments, the subject inhibitors inhibit hedgehog-mediated signal transduction with an $IC_{50}$ of 1 mM or less, more preferably of 1 μM or less, and even more preferably of 1 nM or less.

Moreover, the subject methods can be performed on cells which are provided in culture (in vitro), or on cells in a whole animal (in vivo). See, for example, PCT publications WO 95/18856 and WO 96/17924 (the specifications of which are expressly incorporated by reference herein).

V. Agonists of Hedgehog Biological Activity

Preferred hedgehog therapeutics useful in methods of the invention are agonists that are derived from several sources of hedgehog protein. In one embodiment, the agonist is not N-terminally clipped (as described above). Other embodiments of a hedgehog therapeutic suitable for the present methods are based, in part, on the discovery disclosed in U.S. patent application Ser. No. 60/067,423 (Dec. 3, 1997 :PCT Publication that human Sonic hedgehog, expressed as a full-length construct in either insect or in mammalian cells, has a hydrophobic palmitoyl group appended to the alpha-amine of the N-terminal cysteine. This is the first example of an extracellular signaling protein being modified in such a manner, and, in contrast to thiol-linked palmitic acid modifications whose attachment is readily reversible, this novel N-linked palmitoyl moiety is likely to be very stable by analogy with myristic acid modifications.

The agonists have at least one of the following properties: (i) the isolated protein binds the receptor patched-1 with an affinity that is at similar to, but is preferably higher than, the binding of mature hedgehog protein to patched-1; or (ii) the isolated protein binds to a hedgehog protein in such a way as to increase the proteins binding affinity to patched-1 when tested in an in vitro CH310T1/2 cell-based AP induction assay. Agonists of the invention may also have the additional properties of being (iii) able to solely induce ptc-1 and gli-1 expression.

The preferred agonists for use in conjugation with a non-hedgehog conjugate (e.g., immunoglobulin or fragment thereof) include a derivitized hedgehog polypeptide sequence as well as other N-terminal and/or C-terminal amino acid sequence or it may include all or a fragment of a hedgehog amino acid sequence. Agonist polypeptides of the invention include those that arise as a result of the existence of multiple genes, alternative transcription events, alternative RNA splicing events, and alternative translational and posttranslational events. The polypeptide can be made entirely by synthetic means or can be expressed in systems, e.g., cultured cells, which result in substantially the same posttranslational modifications present when the protein is expressed in a native cell, or in systems which result in the omission of posttranslational modifications present when expressed in a native cell.

In one embodiment, the agonist is a hedgehog polypeptide with one or more of the following characteristics:

(i) it has at least 30, 40, 42, 50, 60, 70, 80, 90 or 95% sequence identity with a hedgehog sequence such as SEQ ID NOS: 10-18 or 23-26;

(ii) it has a cysteine or a functional equivalent as the N-terminal end;

(iii) it may induce alkaline phosphatase activity in C3H10T1/2 cells;

(iv) it has an overall sequence identity of at least 50%, preferably at least 60%, more preferably at least 70, 80, 90, or 95%, with a polypeptide of a hedgehog sequence;

(v) it can be isolated from natural sources such as mammalian cells;

(vi) it can bind or interact with patched; and (vii) it may be hydrophobically-modified (i.e., it has at least one hydrophobicmoiety attached to the polypeptide).

Increasing the overall hydrophobic nature of a hedgehog protein increases the biological activity of the protein. The potency of a signaling protein such as hedgehog can be increased by: (a) chemically modifying, such as by adding a hydrophobic moiety to, the sulfhydryl and/or to the alpha-amine of the N-terminal cysteine (see U.S. Ser. No. 60/067,423); (b) replacing the N-terminal cysteine with a hydrophobic amino acid (see U.S. Ser. No. 60/067,423); or (c) replacing the N-terminal cysteine with a different amino acid and then chemically modifying the substituted residue so as to add a hydrophobic moiety at the site of the substitution.

Additionally, modification of a hedgehog protein at an internal residue on the surface of the protein with a hydrophobic moiety by: (a) replacing the internal residue with a hydrophobic amino acid; or (b) replacing the internal residue with a different amino acid and then chemically modifying the substituted residue so as to add a hydrophobic moiety at the site of the substitution will retain or enhance the biological activity of the protein.

Additionally, modification of a protein such as a hedgehog protein at the C-terminus with a hydrophobic moiety by: (a) replacing the C-terminal residue with a hydrophobic amino acid; or (b) replacing the C-terminal residue with a different amino acid and then chemically modifying the substituted residue so as to add a hydrophobic moiety at the site of the substitution, will retain or enhance the biological activity of the protein.

For hydrophobically-modified hedgehog obtained by chemically modifying the soluble, unmodified protein, palmitic acid and other lipids can be added to soluble Shh to create a lipid-modified forms with increased potency in the C3H10T1/2 assay. Another form of protein encompassed by the invention is a protein derivatized with a variety of lipid moieties. The principal classes of lipids that are encompassed within this invention are fatty acids and sterols (e.g., cholesterol). Derivatized proteins of the invention contain fatty acids which are cyclic, acyclic (i.e., straight chain), saturated or unsaturated, mono-carboxylic acids. Exemplary saturated fatty acids have the generic formula: $CH_3 (CH_2)_n COON$. Table 2 below lists examples of some fatty acids that can be derivatized conveniently using conventional chemical methods.

TABLE 2

Exemplary Saturated and Unsaturated Fatty Acids

| | Common Name |
|---|---|
| Saturated Acids: CH3 (CH2)n COOH: | |
| Value of n | |
| 2 | butyric acid |
| 4 | caproic acid |
| 6 | caprylic acid |
| 8 | capric acid |
| 10 | lauric acid |
| 12 | myristic acid* |
| 14 | palmitic acid* |
| 16 | stearic acid* |
| 18 | arachidic acid* |
| 20 | behenic acid |
| 22 | lignoceric acid |
| Unsaturated Acids: | |
| CH3CH=CHCOOH | crotonic acid |
| CH3(CH2)3CH=CH(CH2)7COOH | myristoleic acid* |
| CH3(CH2)5CH=CH(CH2)7COOH | palmitoleic acid* |
| CH3(CH2)7CH=CH(CH2)7COOH | oleic acid* |
| CH3(CH2)3(CH2CH=CH)2(CH2)7COOH | linoleic acid |
| CH3(CH2CH=CH)3(CH2)7COOH | linolenic acid |
| CH3(CH2)3(CH2CH=CH)4(CH2)3COOH | arachidonic acid |

The asterisk (*) denotes fatty acids detected in recombinant hedgehog protein secreted from a soluble construct (Pepinsky et al., supra).

Other lipids that can be attached to the protein include branched-chain fatty acids and those of the phospholipid group such as the phosphatidylinositols (i.e., phosphatidylinositol 4-monophosphate and phosphatidylinositol 4,5-biphosphate), phosphatidylcholine, phosphatidylethanolamine, phosphatidylserine, and isoprenoids such as farnesyl or geranyl groups. Lipid-modified hedgehog proteins can be purified from either a natural source, or can be obtained by chemically modifying the soluble, unmodified protein.

For protein purified from a natural source, we showed that when full-length human Sonic hedgehog (Shh) was expressed in insect cells and membrane-bound Shh purified from the detergent-treated cells using a combination of SP-Sepharose chromatography and immunoaffinity chromatography, that the purified protein migrated on reducing SDS-PAGE gels as a single sharp band with an apparent mass of 20 kDa. See PCT The soluble and membrane-bound Shh proteins were readily distinguishable by reverse phase HPLC, where the tethered forms eluted later in the acetonitrile gradient. We then demonstrated that human Sonic hedgehog is tethered to cell membranes in two forms, one form that contains a cholesterol, and therefore is analogous to the data reported previously for Drosophila hedgehog, and a second novel form that contains both a cholesterol and a palmitic acid modification. Both modified forms were equally as active in the C3H10T1/2 alkaline phosphatase assay, but both were about 30-times more potent than soluble human Shh lacking the tether(s). The hydrophobic modifications did not significantly affect the apparent binding affinity of Shh for its receptor, patched.

For specific lipid-modified hedgehog obtained by chemically modifying the soluble, unmodified protein, palmitic acid and other lipids can be added to soluble Shh to create a lipid-modified forms with increased potency in the C3H10T1/2 assay. Generally, therefore, the reactive lipid moiety can be in the form of thioesters of saturated or unsaturated carboxylic acids such as a Coenzyme A thioesters. Such materials and their derivatives may include, for example, commercially available Coenzyme A derivatives such as palmitoleoyl Coenzyme A, arachidoyl Coenzyme A, arachidonoyl Coenzyme A, lauroyl Coenzyme A and the like. These materials are readily available from Sigma Chemical Company (St. Louis, Mo., 1998 catalog pp. 303-306).

There are a wide range of hydrophobic moieties with which hedgehog polypeptides can be derivatived. A hydrophobic group can be, for example, a relatively long chain alkyl or cycloalkyl (preferably n-alkyl) group having approximately 7 to 30 carbons. The alkyl group may terminate with a hydroxy or primary amine "tail". To further illustrate, such molecules include naturally-occurring and synthetic aromatic and non-aromatic moieties such as fatty acids, esters and alcohols, other lipid molecules, cage structures such as adamantane and buckminsterfullerenes, and aromatic hydrocarbons such as benzene, perylene, phenanthrene, anthracene, naphthalene, pyrene, chrysene, and naphthacene.

Particularly useful as hydrophobic molecules are alicyclic hydrocarbons, saturated and unsaturated fatty acids and other lipid and phospholipid moieties, waxes, cholesterol, isoprenoids, terpenes and polyalicyclic hydrocarbons including adamantane and buckminsterfullerenes, vitamins, polyethylene glycol or oligoethylene glycol, (C1-C18)-alkyl phosphate diesters, —O—CH2—CH(OH)—O—(C12-C18)-alkyl, and in particular conjugates with pyrene derivatives. The hydrophobic moiety can be a lipophilic dye suitable for use in the invention include, but are not limited to, diphenylhexatriene, Nile Red, N-phenyl-1-naphthylamine, Prodan, Laurodan, Pyrene, Perylene, rhodamine, rhodamine B, tetramethylrhodamine, Texas Red, sulforhodamine, 1,1'-didodecyl-3,3,3',3'tetramethylindocarbocyanine perchlorate, octadecyl rhodamine B and the BODIPY dyes available from Molecular Probes Inc.

Other exemplary lipophilic moieties include aliphatic carbonyl radical groups include 1- or 2-adamantylacetyl, 3-methyladamant-1-ylacetyl, 3-methyl-3-bromo-1-adamantylacetyl, 1-decalinacetyl, camphoracetyl, camphaneacetyl, noradamantylacetyl, norbornaneacetyl, bicyclo[2.2.2.]-oct-5-eneacetyl, 1-methoxybicyclo[2.2.2.]-oct-5-ene-2-carbonyl, cis-5-norbornene-endo-2,3-dicarbonyl, 5-norbornen-2-ylacetyl, (1R)-(-)-myrtentaneacetyl, 2-norbornaneacetyl, anti-3-oxo-tricyclo[2.2.1.0<2,6>]-heptane-7-carbonyl, decanoyl, dodecanoyl, dodecenoyl, tetradecadienoyl, decynoyl or dodecynoyl.

1. Chemical Modifications of the N-terminal Cysteine of Hedgehog

If an appropriate amino acid is not available at a specific position, site-directed mutagenesis can be used to place a reactive amino acid at that site. Reactive amino acids include cysteine, lysine, histidine, aspartic acid, glutamic acid, serine, threonine, tyrosine, arginine, methionine, and tryptophan. Mutagenesis could also be used to place the reactive amino acid at the N- or C-terminus or at an internal position.

For example, it is possible to chemically modify an N-terminal cysteine of a biologically active protein, such as a hedgehog protein, or eliminate the N-terminal cysteine altogether and still retain the protein's biological activity. The replacement or modification of the N-terminal cysteine of hedgehog with a hydrophobic amino acid results in a protein with increased potency in a cell-based signaling assay. By replacing the cysteine, this approach eliminates the problem of suppressing other unwanted modifications of the cysteine that can occur during the production, purification, formulation, and storage of the protein. The generality of this approach is supported by the finding that three different hydrophobic amino acids, phenylalanine, isoleucine, and methionine, each give a more active form of hedgehog, and thus, an agonist.

This is also important for conjugation with non-hedgehog moieties (e.g., immunoglobulin) as described below in which we introduce two isoleucine residues to the N-terminal cysteine end of Sonic and Desert hedgehog. This effectively allows us to use the thiol of C-terminal cysteine as the reactive site for covalent coupling. Thus, replacement of the N-terminal cysteine with any other hydrophobic amino acid should result in an active protein. Furthermore, since we have found a correlation between the hydrophobicity of an amino acid or chemical modification and the potency of the corresponding modified protein in the C3H10T1/2 assay (e.g. Phe>Met, long chain length fatty acids>short chain length), it could be envisioned that adding more than one hydrophobic amino acid to the hedgehog sequence would increase the potency of the agonist beyond that achieved with a single amino acid addition. Indeed, addition of two consecutive isoleucine residues to the N-terminus of human Sonic hedgehog results in an increase in potency in the C3H10T1/2 assay as compared to the mutant with only a single isoleucine added. Thus, adding hydrophobic amino acids at the N- or C-terminus of a hedgehog protein, in a surface loop, or some combination of positions would be expected to give a more active form of the protein. The substituted amino acid need not be one of the 20 common amino acids. Methods have been reported for substituting unnatural amino acids at specific sites in proteins and this would be advantageous if the amino acid was more hydrophobic in character, resistant to proteolytic attack, or could be used to further direct the hedgehog protein to a particular site in vivo that would make its activity more potent or specific. Unnatural amino acids can be incorporated at specific sites in proteins during in vitro translation, and progress is being reported in creating in vivo systems that will allow larger scale production of such modified proteins.

There are many modifications of the N-terminal cysteine which protect the thiol and append a hydrophobic moiety. One of skill in the art is capable of determining which modification is most appropriate for a particular therapeutic use. Factors affecting such a determination include cost and ease of production, purification and formulation, solubility, stability, potency, pharmacodynamics and kinetics, safety, immunogenicity, and tissue targeting.

2. Chemical Modification of Other Amino Acids.

There are specific chemical methods for the modification of many other amino acids. Therefore, another route for synthesizing a more active form of hedgehog would be to chemically attach a hydrophobic moiety to an amino acid in hedgehog other than to the N-terminal cysteine. If an appropriate amino acid is not available at the desired position, site-directed mutagenesis could be used to place the reactive amino acid at that site in the hedgehog structure, whether at the N- or C-terminus or at another position. Reactive amino acids would include cysteine, lysine, histidine, aspartic acid, glutamic acid, serine, threonine, tyrosine, arginine, methionine, and tryptophan. Thus the goal of creating a better hedgehog agonist could be attained by many chemical means and we do not wish to be restricted by a particular chemistry or site of modification since our results support the generality of this approach.

The hedgehog polypeptide can be linked to the hydrophobic moiety in a number of ways including by chemical coupling means, or by genetic engineering. To illustrate, there are a large number of chemical cross-linking agents that are known to those skilled in the art. For the present invention, the preferred cross-linking agents are heterobifunctional cross-linkers, which can be used to link the hedgehog polypeptide and hydrophobic moiety in a stepwise manner. Heterobifunctional cross-linkers provide the ability to design more specific coupling methods for conjugating to proteins, thereby reducing the occurrences of unwanted side reactions such as homo-protein polymers. A wide variety of heterobifunctional cross-linkers are known in the art. These include: succinimidyl 4-(N-maleimidomethyl) cyclohexane-1-carboxylate (SMCC), m-Maleimidobenzoyl-N-hydroxysuccinimide ester (MBS); N-succinimidyl (4-iodoacetyl) aminobenzoate (SIAB), succinimidyl 4-(p-maleimidophenyl) butyrate (SMPB), 1-ethyl-3-(3-dimethylaminopropyl) carbodiimide hydrochloride (EDC); 4-succinimidyloxycarbonyl-a-methyl-a-(2-pyridyldithio)-tolune (SMPT), N-succinimidyl 3-(2-pyridyldithio) propionate (SPDP), succinimidyl 6-[3-(2-pyridyldithio) propionate] hexanoate (LC-SPDP). Those cross-linking agents having N-hydroxysuccinimide moieties can be obtained as the N-hydroxysulfosuccinimide analogs, which generally have greater water solubility. In addition, those cross-linking agents having disulfide bridges within the linking chain can be synthesized instead as the alkyl derivatives so as to reduce the amount of linker cleavage in vivo.

One particularly useful class of heterobifunctional cross-linkers, included above, contain the primary amine reactive group, N-hydroxysuccinimide (NHS), or its water soluble analog N-hydroxysulfosuccinimide (sulfo-NHS). Primary amines (lysine epsilon groups) at alkaline pH's are unprotonated and react by nucleophilic attack on NHS or sulfo-NHS esters. This reaction results in the formation of an amide bond, and release of NHS or sulfo-NHS as a by-product.

Another reactive group useful as part of a heterobifunctional cross-linker is a thiol reactive group. Common thiol reactive groups include maleimides, halogens, and pyridyl disulfides. Maleimides react specifically with free sulfhydryls (cysteine residues) in minutes, under slightly acidic to neutral (pH 6.5-7.5) conditions. Halogens (iodoacetyl functions) react with —SH groups at physiological pH's. Both of these reactive groups result in the formation of stable thioether bonds.

Generally, the structure of an agonistic hedgehog therapeutic useful in this invention is a chimeric molecule that has the general formula: X-Y-Z, where wherein X is a polypeptide having the amino acid sequence, or portion thereof, consisting of the amino acid sequence of hedgehog; Y is an optional linker moiety; and Z is a polypeptide comprising at least a portion of a polypeptide other than hedgehog. Preferably, X includes at least a biologically active N-terminal fragment of is human Sonic, Indian or Desert hedgehog. In the more preferred embodiments, Z is a protein with an 19-like constant and/or variable domain. Most preferably, Z is at least a portion of a constant region of an immunoglobulin and can be derived from an immunoglobulin of the class selected from IgM, IgG, IgD, IgA, and IgE. If the class is IgG, then it is selected from one of IgG1, IgG2, IgG3 and IgG4. The constant region of human IgM and IgE contain 4 constant regions (CHI, (hinge), CH2, CH3 and CH4, whereas the constant region of human IgG, IgA and IgD contain 3 constant regions (CHI, (hinge), CH2 and CH3. In the most preferred fusion proteins of the invention, the constant region contains at least the hinge, CH2 and CH3 domains.

In another embodiment, the chimeric molecule has the structure D-[Sp]-B-[Sp]-C, where D is a non-hedgehog moiety such as described herein; [Sp] is an optional spacer peptide sequence; B is a hedgehog protein (which optionally may be a mutein as described herein); and C is an optional hydrophobic moiety linked (optionally by way of the spacer peptide) to the hedgehog protein D or another residue such as a surface site of the protein.

The present invention provides for multimeric hedgehog therapeutic molecules. Such multimers may be generated by using those Fc regions, or portions thereof, of Ig molecules which are usually multivalent such as IgM pentamers or IgA dimers. It is understood that a J chain polypeptide may be needed to form and stabilize IgM pentamers and IgA dimers. Alternatively, multimers of hedgehog therapeutic proteins may be formed using a protein with an affinity for the Fc region of Ig molecules, such as Protein A. For instance, a plurality of hedgehog/immunoglobulin fusion proteins may be bound to Protein A-agarose beads.

These multivalent forms are useful since they possess multiple hedgehog receptor binding sites. For example, a bivalent soluble hedgehog therapeutic may consist of two tandem repeats of those amino acids encoded by nucleic acids of SEQ. ID NOS: 1-9 or 21, 22 or 27 (moiety X in the generic formula) separated by a linker region (moiety Y), the repeats bound to at least a portion of an immunoglobulin constant domain (moiety Z). Alternate polyvalent forms may also be constructed, for example, by chemically coupling chimeric hedgehog therapeutics of the invention to any clinically acceptable carrier molecule, a polymer selected from the group consisting of Ficoll, polyethylene glycol or dextran using conventional coupling techniques. Alternatively, hedgehog may be chemically coupled to biotin, and the biotin-hedgehog chimera then allowed to bind to avidin, resulting in tetravalent avidin/biotin/hedgehog molecules. Chimeric hedgehog proteins may also be covalently coupled to dinitrophenol (DNP) or trinitrophenol (TNP) and the resulting conjugate precipitated with anti-DNP or anti-TNP-IgM, to form decameric conjugates with a valency of 10 for hedgehog receptor binding sites Polymer Conjugates of Hedgehog Therapeutics One unique property of polyalkylene glycol-derived polymers of value for therapeutic applications of the present invention is their general biocompatibility. These polymers have various water solubility properties and are not toxic. They are believed non-immunogenic and non-antigenic and do not interfere with the biological activities of the hedgehog protein moiety when conjugated under the conditions described herein. They have long circulation in the blood and are easily excreted from living organisms.

Hedgehog therapeutics are conjugated most preferably via a terminal reactive group on the polyalkylene glycol polymer although conjugations can also be branched from non-terminal reactive groups. The polymer with the reactive group(s) is designated herein as "activated polymer". The reactive group would be expected to selectively react with free amino or other reactive groups on the hedgehog protein. In theory, the activated polymer(s) are reacted so that attachment could occur at any available hedgehog amino group such as alpha amino groups or the epsilon-amino groups of lysines, or —SH groups of cysteines. Free carboxylic groups, suitably activated carbonyl groups, hydroxyl, guanidyl, oxidized carbohydrate moieties and mercapto groups of the hedgehog protein (if available) can also be used as attachment sites.

In particular, the chemical modification of any N-terminal cysteine to protect the thiol, with concomitant conjugation with a polyalkylene glycol moiety (i.e., PEG), can be carried out in numerous ways by someone skilled in the art. See U.S. Pat. No. 4,179,337. The sulfhydryl moiety, with the thiolate ion as the active species, is the most reactive functional group in a protein. There are many reagents that react faster with the thiol than any other groups. See Chemistry of Protein Conjugation and Cross-Linking (S. S. Wong, CRC Press, Boca Raton, Fla., 1991). The thiol of an N-terminal cysteine, such as found in all hedgehog proteins, would be expected to be more reactive than internal cysteines within the sequence. This is because the close proximity to the alpha-amine will lower the pKa of the thiol resulting in a greater degree of proton dissociation to the reactive thiolate ion at neutral or acid pH. In addition, the cysteine at the N-terminus of the structure is more likely to be exposed than the other two cysteines in the hedgehog sequence that are found buried in the protein structure.

Other examples of methods that provide linkage between a polyalkylene glycol and the N-terminal cysteine would be reactions with other alpha-haloacetyl compounds, organomercurials, disulfide reagents, and other N-substituted maleimides. Numerous derivatives of these active species are available commercially (e.g., ethyl iodoacetate (Aldrich, Milwaukee Wis.), phenyl disulfide (Aldrich), and N-pyrenemaleimide (Molecular Probes, Eugene Oreg.)) or could be synthesized readily (e.g., N-alkyliodoacetamides, N-alkylmaleimides, and organomercurials). Another aspect to the reactivity of an N-terminal cysteine is that it can take part in reaction chemistries unique to its 1,2-aminothiol configuration. One example is the reaction with thioester groups to form an N-terminal amide group via a rapid S to N shift of the thioester. This reaction chemistry can couple together synthetic peptides and can be used to add single or multiple, natural or unnatural, amino acids or other hydrophobic groups via the appropriately activated peptide. Another example, is the reaction with aldehydes to form the thiazolidine adduct. Numerous hydrophobic derivatives of thiol esters (e.g., C2-C24 saturated and unsaturated fatty acyl Coenzyme A esters (Sigma Chemical Co., St. Louis Mo.)), aldehydes (e.g., butyraldehyde, n-decyl aldehyde, and n-myristyl aldehyde (Aldrich)), and ketones (e.g., 2-, 3-, and 4-decanone (Aldrich)) are available commercially or could be synthesized readily. In a similar manner, thiomorpholine could be prepared from a variety of alpha-haloketone starting materials.

Several observations suggest that the C-terminus or amino acids near the C-terminus would be preferred targets for modification with a polyalkylene glycol moiety. Briefly, we have shown that: (i) The wild-type protein is naturally modified with cholesterol at the C-terminus, indicating that it is exposed and available for modification. Indeed, we showed that treatment with thrombin results in selective release of the C-terminal 3 amino acids (See U.S. Ser. No. 60/106,703, filed Nov. 2, 1998, now PCT Number incorporated herein by reference); (ii) We performed extensive SAR analyses and discovered that the C-terminal 11 amino acids could be deleted without harmful effects on folding or function; (iii) We have made hedgehog/Ig fusion proteins by attaching an Ig moiety to the C-terminus of hedgehog without harmful effects on folding or function (data not presented here).

While there is no simple chemical strategy for targeting a polyalkylene glycol polymer such as PEG to the C-terminus of hedgehog, it is straightforward to genetically engineer a site that can be used to target the polymer moiety, as discussed above with regard to site-directed mutagenesis. For example, incorporation of a Cys at a site that is at or near the C-terminus allows specific modification using a maleimide, vinylsulfone or haloacetate-activated polyalkylene glycol (e.g., PEG). As discussed above in Section A, these derivatives can be used specifically for modification of the engineered C-terminal cysteines due to the high selectively of these reagents for Cys. Other strategies such as incorporation of a histidine tag which can be targeted (Fancy et al., (1996) Chem. & Biol. 3: 551) or an additional glycosylation site, represent other alternatives for modifying the C-terminus of hedgehog. A single polymer molecule may be employed for conjugation with the hedgehog protein and modified versions thereof as discussed above, although it is also contemplated that more than one polymer molecule can be attached as well. Conjugated hedgehog compositions of the invention may find utility in both in vivo as well as non-in vivo applications. Additionally, it will be recognized that the conjugating polymer may utilize any other groups, moieties, or other conjugated species, as appropriate to the end use application. By way of example, it may be useful in some applications to covalently bond to the polymer a functional moiety imparting UV-degradation resistance, or antioxidation, or other properties or characteristics to the polymer. As a further example, it may be advantageous in some applications to functionalize the polymer to render it reactive or cross-linkable in character, to enhance various properties or characterisics of the overall conjugated material. Accordingly, the polymer may contain any functionality, repeating groups, linkages, or other constituent structures which do not preclude the efficacy of the conjugated hedgehog composition for its intended purpose. Other objectives and advantages of the present invention will be more fully apparent from the ensuing disclosure and appended claims.

Illustrative polymers that may usefully be employed to achieve these desirable characteristics are described herein below in exemplary reaction schemes. In covalently bonded peptide applications, the polymer may be functionalized and then coupled to free amino acid(s) of the peptide(s) to form labile bonds.

Generally from about 1.0 to about 10 moles of activated polymer per mole of protein is employed, depending on the particular reaction chemistry and the protein concentration. The final amount is a balance between maximizing the extent of the reaction while minimizing non-specific modifications of the product and, at the same time, defining chemistries that will maintain optimum activity, while at the same time optimizing, if possible, the half-life of the protein. Preferably, at least about 50% of the biological activity of the protein is retained, and most preferably 100% is retained.

The reactions may take place by any suitable method used for reacting biologically active materials with inert polymers. Generally the process involves preparing an activated polymer (that may have at least one terminal hydroxyl group) and thereafter reacting the protein with the activated polymer to produce the soluble protein suitable for formulation. The above modification reaction can be performed by several methods, which may involve one or more steps.

Suitable methods of attaching a polyalkylene glycol moiety to a C-terminal cysteine involve using such moieties that are activated with a thiol reactive group, as generally discussed above. Common thiol reactive groups include maleimides, vinylsulfones or haloacetates. These derivatives can be used specifically for modification of cysteines due to the high selectively of these reagents for —SH. Maleimides react specifically with free sulfhydryls (cysteine residues) in minutes, under slightly acidic to neutral (pH 6.0-7.5) conditions. This pH range is preferred although the reaction will proceed, albeit slowly, at pH 5.0. Halogens (iodoacetyl functions) react with —SH groups at physiological pH's to slightly basic conditions. Both of these reactive groups result in the formation of stable thioether bonds.

In the practice of the methods of the present invention, polyalkylene glycol residues of C1-C4 alkyl polyalkylene glycols, preferably polyethylene glycol (PEG), or poly(oxy) alkylene glycol residues of such glycols are advantageously incorporated in the polymer systems of interest. Thus, the polymer to which the protein is attached can be a homopolymer of polyethylene glycol (PEG) or is a polyoxyethylated polyol, provided in all cases that the polymer is soluble in water at room temperature. Non-limiting examples of such polymers include polyalkylene oxide homopolymers such as PEG or polypropylene glycols, polyoxyethylenated glycols, copolymers thereof and block copolymers thereof, provided that the water solubility of the block copolymer is maintained. Examples of polyoxyethylated polyols include, for example, polyoxyethylated glycerol, polyoxyethylated sorbitol, polyoxyethylated glucose, or the like. The glycerol backbone of polyoxyethylated glycerol is the same backbone occurring naturally in, for example, animals and humans in mono-, di-, and triglycerides. Therefore, this branching would not necessarily be seen as a foreign agent in the body.

As an alternative to polyalkylene oxides, dextran, polyvinyl pyrrolidones, polyacrylamides, polyvinyl alcohols, carbohydrate-based polymers and the like may be used. Moreover, heteropolymers (i.e., polymers consisting of more than one species of monomer such as a copolymer) as described in U.S. Pat. No. 5,359,030 may be used (e.g., proteins conjugated to polymers comprising a polyalkylene glycol moiety and one or more fatty acids) Those of ordinary skill in the art will recognize that the foregoing list is merely illustrative and that all polymer materials having the qualities described herein are contemplated. The polymer need not have any particular molecular weight, but it is preferred that the molecular weight be between about 300 and 100,000, more preferably between 10,000 and 40,000. In particular, sizes of 20,000 or more are best at preventing protein loss due to filtration in the kidneys. Moreover, in another aspect of the invention, one can utilize hedgehog covalently bonded to the polymer component in which the nature of the conjugation involves cleavable covalent chemical bonds. This allows for control in terms of the time course over which the polymer may be cleaved from the hedgehog. This covalent bond between the hedgehog protein drug and the polymer may be cleaved by chemical or enzymatic reaction. The polymer-hedgehog protein product retains an acceptable amount of activity. Concurrently, portions of polyethylene glycol are present in the conjugating polymer to endow the polymer-hedgehog protein conjugate with high aqueous solubility and prolonged blood circulation capability. As a result of these improved characteristics the invention contemplates parenteral, aerosol, and oral delivery of both the active polymer-hedgehog protein species and, following hydrolytic cleavage, bioavailability of the hedgehog protein per se, in in vivo applications.

It is to be understood that the reaction schemes described herein are provided for the purposes of illustration only and are not to be limiting with respect to the reactions and structures which may be utilized in the modification of the hedgehog protein, e.g., to achieve solubility, stabilization, and cell membrane affinity for parenteral and oral administration. Generally speaking, the concentrations of reagents used are not critical to carrying out the procedures provided hererin except that the molar amount of activated polymer should be at least equal to, and preferably in excess of, the molar amount of the reactive group (e.g., thiol) on the hedgehog amino acid(s). The reaction of the polymer with the hedgehog to obtain the most preferred conjugated products is readily carried out using a wide variety of reaction schemes. The activity and stability of the hedgehog protein conjugates can be varied in several ways, by using a polymer of different molecular size. Solubilities of the conjugates can be varied by changing the proportion and size of the polyethylene glycol fragment incorporated in the polymer composition.

3. Small Molecule Agonists

In other embodiments, a hedgehog agonist may be a small organic molecule. Such a small organic molecule may agonize hedgehog signal transduction via an interaction with but not limited to hedgehog, patched (ptc), gli, and/or smoothened. It is, therefore, specifically contemplated that these small molecules which enhance or potentiate aspects of hedgehog, ptc, or smoothened signal transduction will likewise be capable of enhancing angiogenesis (or other biological consequences) in normal cells and/or mutant cells. Thus, it is contemplated that in certain embodiments, these compounds may be useful for enhancing or potentiating hedgehog activity. In other embodiments, these compounds may be useful for inhibitng hedgehog activity in abnormal cells. In preferred embodiments, the subject agonists are organic molecules having a molecular weight less than 2500 amu, more preferably less than 1500 amu, and even more preferably less than 750 amu, and are capable of agonizing hedgehog signaling, preferably specifically in target cells.

For example, agonist compounds useful in the subject methods include compounds represented by general formula (XII):

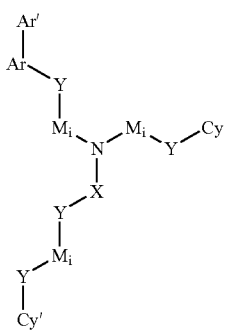

Formula XII wherein, as valence and stability permit,

Ar and Ar' independently represent substituted or unsubstituted aryl or heteroaryl rings;

Y, independently for each occurrence, may be absent or represent —N(R)—, —O—, —S—, or —Se—;

X can be selected from —C(=O)—, —C(=S)—, —S(O$_2$)—, —S(O)—, —C(=NCN)—, —P(=O)(OR$_2$)—, and a methylene group optionally substituted with 1-2 groups such as lower alkyl, alkenyl, or alkynyl groups;

M represents, independently for each occurrence, a substituted or unsubstituted methylene group, such as —CH$_2$—, —CHF—, —CHOH—, —CH(Me)—, —C(=O)—, etc., or two M taken together represent substituted or unsubstituted ethene or ethyne;

R represents, independently for each occurrence, H or substituted or unsubstituted aryl, heterocyclyl, heteroaryl, aralkyl, heteroaralkyl, alkynyl, alkenyl, or alkyl, or two R taken together may form a 4- to 8-membered ring, e.g., with N;

Cy and Cy' independenly represent substituted or unsubstituted aryl, heterocyclyl, heteroaryl, or cycloalkyl, including polycyclic groups;

i represents, independently for each occurrence, an integer from 0 to 5, preferably from 0 to 2; and n, individually for each occurence, represents an integer from 0 to 10, preferably from 0 to 5.

In certain embodiments, M represents, independently for each occurrence, a substituted or unsubstituted methylene group, such as —CH$_2$—, —CHF—, —CHOH—, —CH(Me)—, —C(=O)—, etc.

In certain embodiments, Ar and Ar' represent phenyl rings, e.g., unsubstituted or substituted with one or more groups including heteroatoms such as O, N, and S. In certain embodiments, at least one of Ar and Ar' represents a phenyl ring. In certain embodiments, at least one of Ar and Ar' represents a heteroaryl ring, e.g., a pyridyl, thiazolyl, thienyl, pyrimidyl, etc. In certain embodiments, Y and Ar' are attached to Ar in a meta and/or 1,3-relationship.

In certain embodiments, Y is absent from all positions. In embodiments wherein Y is present in a position, i preferably represents an integer from 1-2 in an adjacent $M_i$ if i=0 would result in two occurrences of Y being directly attached, or an occurrence of Y being directly attached to N.

In certain embodiments, Cy' is a substituted or unsubstituted aryl or heteroaryl. In certain embodiments, Cy' is directly attached to X. In certain embodiments, Cy' is a substituted or unsubstituted bicyclic or heteroaryl ring, preferably both bicyclic and heteroaryl, such as benzothiophene, benzofuran, benzopyrrole, benzopyridine, etc. In certain embodiments, Cy' is a monocyclic aryl or heteroaryl ring substituted at least with a substituted or unsubstituted aryl or heteroaryl ring, e.g., forming a biaryl system. In certain embodiments, Cy' includes two substituted or unsubstituted aryl or heteroaryl rings, e.g., the same or different, directly connected by one or more bonds, e.g., to form a biaryl or bicyclic ring system.

In certain embodiments, X is selected from —C(=O)—, —C(=S)—, and —S(O$_2$)—.

In certain embodiments, Cy represents a substituted or unsubstituted non-aromatic carbocyclic or heterocyclic ring, i.e., including at least one sp$^3$ hybridized atom, and preferably a plurality of sp$^3$ hybridized atoms. In certain embodiments, Cy includes an amine within the atoms of the ring or on a substitutent of the ring, e.g., Cy is pyridyl, imidazolyl, pyrrolyl, piperidyl, pyrrolidyl, piperazyl, etc., and/or bears an amino substituent. In certain embodiments, Cy is a 5- to 7-membered ring. In certain embodiments, Cy is directly attached to N. In embodiments wherein Cy is a six-membered ring directly attached to N and bears an amino substituent at the 4 position of the ring relative to N, the N and amine substituents may be disposed trans on the ring.

In certain embodiments, substituents on Ar or Ar' are selected from halogen, lower alkyl, lower alkenyl, aryl, heteroaryl, carbonyl, thiocarbonyl, ketone, aldehyde, amino, acylamino, cyano, nitro, hydroxyl, azido, sulfonyl, sulfoxido, sulfate, sulfonate, sulfamoyl, sulfonamido, phosphoryl, phosphonate, phosphinate, —(CH$_2$)$_p$alkyl, —(CH$_2$)$_p$alkenyl, —(CH$_2$)$_p$alkynyl, —(CH$_2$)$_p$aryl, —(CH$_2$)$_p$aralkyl, —(CH$_2$)$_p$OH, —(CH$_2$)$_p$O-lower alkyl, —(CH$_2$)$_p$O-lower alkenyl, —O(CH$_2$)$_n$R, —(CH$_2$)$_p$SH, —(CH$_2$)$_p$S-lower alkyl, —(CH$_2$)$_p$S-lower alkenyl, —S(CH$_2$)$_n$R, —(CH$_2$)$_p$N(R)$_2$, —(CH$_2$)$_p$NR-lower alkyl, —(CH$_2$)$_p$NR-lower alkenyl, —NR(CH$_2$)$_n$R, and protected forms of the above, wherein p, individually for each occurence, represents an integer from 0 to 10, preferably from 0 to 5.

In certain embodiments, compounds useful in the present invention may be represented by general formula (XIII):

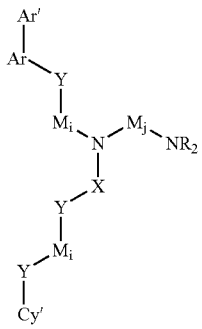

Formula XIII wherein, as valence and stability permit,

Ar and Ar' independently represent substituted or unsubstituted aryl or heteroaryl rings;

Y, independently for each occurrence, may be absent or represent —N(R)—, —O—, —S—, or —Se—;

X can be selected from —C(=O)—, —C(=S)—, —S(O$_2$)—, —S(O)—, —C(=NCN)—, —P(=O)(OR$_2$)—, and a methylene group optionally substituted with 1-2 groups such as lower alkyl, alkenyl, or alkynyl groups;

M represents, independently for each occurrence, a substituted or unsubstituted methylene group, such as —CH$_2$—, —CHF—, —CHOH—, —CH(Me)—, —C(=O)—, etc., or two M taken together represent substituted or unsubstituted ethene or ethyne, wherein some or all occurrences of M in M$_j$ form all or part of a cyclic structure;

R represents, independently for each occurrence, H or substituted or unsubstituted aryl, heterocyclyl, heteroaryl, aralkyl, heteroaralkyl, alkynyl, alkenyl, or alkyl, or two R taken together may form a 4- to 8-membered ring, e.g., with N;

Cy' represents a substituted or unsubstituted aryl, heterocyclyl, heteroaryl, or cycloalkyl, including polycyclic groups;

j represents, independently for each occurrence, an integer from 0 to 10, preferably from 2 to 7;

i represents, independently for each occurrence, an integer from 0 to 5, preferably from 0 to 2; and n, individually for each occurence, represents an integer from 0 to 10, preferably from 0 to 5.

In certain embodiments, M represents, independently for each occurrence, a substituted or unsubstituted methylene group, such as —CH$_2$—, —CHF—, —CHOH—, —CH(Me)—, —C(=O)—, etc.

In certain embodiments, Ar and Ar' represent phenyl rings, e.g., unsubstituted or substituted with one or more groups including heteroatoms such as O, N, and S. In certain embodiments, at least one of Ar and Ar' represents a phenyl ring. In certain embodiments, at least one of Ar and Ar' represents a heteroaryl ring, e.g., a pyridyl, thiazolyl, thienyl, pyrimidyl, etc. In certain embodiments, Y and Ar' are attached to Ar in a meta and/or 1,3-relationship.

In certain embodiments, Y is absent from all positions. In embodiments wherein Y is present in a position, i preferably represents an integer from 1-2 in an adjacent M$_i$ if i=0 would result in two occurrences of Y being directly attached, or an occurrence of Y being directly attached to N or NR$_2$.

In certain embodiments, Cy' is a substituted or unsubstituted aryl or heteroaryl. In certain embodiments, Cy' is directly attached to X. In certain embodiments, Cy' is a substituted or unsubstituted bicyclic or heteroaryl ring, preferably both bicyclic and heteroaryl, such as benzothiophene, benzofuran, benzopyrrole, benzopyridine, etc. In certain embodiments, Cy' is a monocyclic aryl or heteroaryl ring substituted at least with a substituted or unsubstituted aryl or heteroaryl ring, e.g., forming a biaryl system. In certain embodiments, Cy' includes two substituted or unsubstituted aryl or heteroaryl rings, e.g., the same or different, directly connected by one or more bonds, e.g., to form a biaryl or bicyclic ring system.

In certain embodiments, X is selected from —C(=O)—, —C(=S)—, and —S(O$_2$)—.

In certain embodiments, NR$_2$ represents a primary amine or a secondary or tertiary amine substituted with one or two lower alkyl groups, aryl groups, or aralkyl groups, respectively, preferably a primary amine.

In certain embodiments, substituents on Ar or Ar' are selected from halogen, lower alkyl, lower alkenyl, aryl, heteroaryl, carbonyl, thiocarbonyl, ketone, aldehyde, amino, acylamino, cyano, nitro, hydroxyl, azido, sulfonyl, sulfoxido, sulfate, sulfonate, sulfamoyl, sulfonamido, phosphoryl, phosphonate, phosphinate, —(CH$_2$)$_p$alkyl, —(CH$_2$)$_p$alkenyl, —(CH$_2$)$_p$alkynyl, —(CH$_2$)$_p$aryl, —(CH$_2$)$_p$aralkyl, —(CH$_2$)$_p$OH, —(CH$_2$)$_p$O-lower alkyl, —(CH$_2$)$_p$O-lower alkenyl, —O(CH$_2$)$_{n_R}$, —(CH$_2$)$_p$SH, —(CH$_2$)$_p$S-lower alkyl, —(CH$_2$)$_p$S-lower alkenyl, —S(CH$_2$)$_n$R, —(CH$_2$)$_p$N(R)$_2$, —(CH$_2$)$_p$NR-lower alkyl, —(CH$_2$)$_p$NR-lower alkenyl, —NR(CH$_2$)$_n$R, and protected forms of the above, wherein p, individually for each occurence, represents an integer from 0 to 10, preferably from 0 to 5.

In certain embodiments, compounds useful in the present invention may be represented by general formula (XIV):

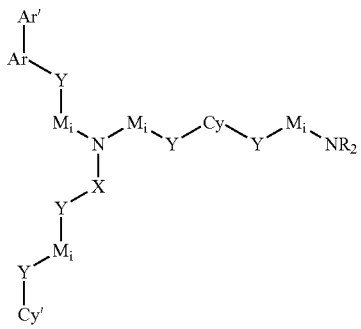

Formula XIV wherein, as valence and stability permit,

Ar and Ar' independently represent substituted or unsubstituted aryl or heteroaryl rings;

Y, independently for each occurrence, may be absent or represent —N(R)—, —O—, —S—, or —Se—;

X can be selected from —C(=O)—, —C(=S)—, —S(O$_2$)—, —S(O)—, —C(=NCN)—, —P(=O)(OR$_2$)—, and a methylene group optionally substituted with 1-2 groups such as lower alkyl, alkenyl, or alkynyl groups;

M represents, independently for each occurrence, a substituted or unsubstituted methylene group, such as —CH$_2$—, —CHF—, —CHOH—, —CH(Me)—, —C(=O)—, etc., or two M taken together represent substituted or unsubstituted ethene or ethyne;

R represents, independently for each occurrence, H or substituted or unsubstituted aryl, heterocyclyl, heteroaryl, aralkyl, heteroaralkyl, alkynyl, alkenyl, or alkyl, or two R taken together may form a 4- to 8-membered ring, e.g., with N;

Cy and Cy' independenly represent substituted or unsubstituted aryl, heterocyclyl, heteroaryl, or cycloalkyl, including polycyclic groups;

i represents, independently for each occurrence, an integer from 0 to 5, preferably from 0 to 2; and n, individually for each occurence, represents an integer from 0 to 10, preferably from 0 to 5.

In certain embodiments, M represents, independently for each occurrence, a substituted or unsubstituted methylene group, such as —CH$_2$—, —CHF—, —CHOH—, —CH(Me)—, —C(=O)—, etc.

In certain embodiments, Ar and Ar' represent phenyl rings, e.g., unsubstituted or substituted with one or more groups including heteroatoms such as O, N, and S. In certain embodiments, at least one of Ar and Ar' represents a phenyl ring. In certain embodiments, at least one of Ar and Ar' represents a heteroaryl ring, e.g., a pyridyl, thiazolyl, thienyl, pyrimidyl, etc. In certain embodiments, Y and Ar' are attached to Ar in a meta and/or 1,3-relationship.

In certain embodiments, Y is absent from all positions. In embodiments wherein Y is present in a position, i preferably represents an integer from 1-2 in an adjacent $M_i$ if i=0 would result in two occurrences of Y being directly attached, or an occurrence of Y being directly attached to N or $NR_2$.

In certain embodiments, Cy' is a substituted or unsubstituted aryl or heteroaryl. In certain embodiments, Cy' is directly attached to X. In certain embodiments, Cy' is a substituted or unsubstituted bicyclic or heteroaryl ring, preferably both bicyclic and heteroaryl, such as benzothiophene, benzofuran, benzopyrrole, benzopyridine, etc. In certain embodiments, Cy' is a monocyclic aryl or heteroaryl ring substituted at least with a substituted or unsubstituted aryl or heteroaryl ring, e.g., forming a biaryl system. In certain embodiments, Cy' includes two substituted or unsubstituted aryl or heteroaryl rings, e.g., the same or different, directly connected by one or more bonds, e.g., to form a biaryl or bicyclic ring system.

In certain embodiments, X is selected from —C(=O)—, —C(=S)—, and —S(O$_2$)—.

In certain embodiments, NR$_2$ represents a primary amine or a secondary or tertiary amine substituted with one or two lower alkyl groups, aryl groups, or aralkyl groups, respectively, preferably a primary amine.

In certain embodiments, Cy represents a substituted or unsubstituted non-aromatic carbocyclic or heterocyclic ring, i.e., including at least one sp$^3$ hybridized atom, and preferably a plurality of sp$^3$ hybridized atoms. In certain embodiments, Cy is directly attached to N and/or to NR$_2$. In certain embodiments, Cy is a 5- to 7-membered ring. In embodiments wherein Cy is a six-membered ring directly attached to N and bears an amino substituent at the 4 position of the ring relative to N, the N and amine substituents may be disposed trans on the ring.

In certain embodiments, substituents on Ar or Ar' are selected from halogen, lower alkyl, lower alkenyl, aryl, heteroaryl, carbonyl, thiocarbonyl, ketone, aldehyde, amino, acylamino, cyano, nitro, hydroxyl, azido, sulfonyl, sulfoxido, sulfate, sulfonate, sulfamoyl, sulfonamido, phosphoryl, phosphonate, phosphinate, —(CH$_2$)$_p$alkyl, —(CH$_2$)$_p$alkenyl, —(CH$_2$)$_p$alkynyl, —(CH$_2$)$_p$aryl, —(CH$_2$)$_p$aralkyl, —(CH$_2$)$_p$OH, —(CH$_2$)$_p$O-lower alkyl, —(CH$_2$)$_p$O-lower alkenyl, —O(CH$_2$)$_n$R, —(CH$_2$)$_p$SH, —(CH$_2$)$_p$S-lower alkyl, —(CH$_2$)$_p$S-lower alkenyl, —S(CH$_2$)$_n$R, —(CH$_2$)$_p$N(R)$_2$, —(CH$_2$)$_p$NR-lower alkyl, —(CH$_2$)$_p$NR-lower alkenyl, —NR(CH$_2$)$_n$R, and protected forms of the above, wherein p, individually for each occurence, represents an integer from 0 to 10, preferably from 0 to 5.

In certain embodiments, compounds useful in the subject methods include compounds represented by general forumla (XV):

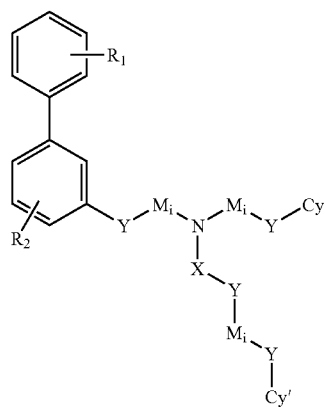

Formula XV wherein, as valence and stability permit,

Cy' represents a substituted or unsubstituted aryl or heteroaryl ring, including polycyclics;

Y, independently for each occurrence, may be absent or represent —N(R)—, —O—, —S—, or —Se—;

X can be selected from —C(=O)—, —C(=S)—, —S(O$_2$)—, —S(O)—, —C(=NCN)—, —P(=O)(OR$_2$)—, and a methylene group optionally substituted with 1-2 groups such as lower alkyl, alkenyl, or alkynyl groups;

M represents, independently for each occurrence, a substituted or unsubstituted methylene group, such as —CH$_2$—, —CHF—, —CHOH—, —CH(Me)—, —C(=O)—, etc., or two M taken together represent substituted or unsubstituted ethene or ethyne;

R represents, independently for each occurrence, H or substituted or unsubstituted aryl, heterocyclyl, heteroaryl, aralkyl, heteroaralkyl, alkynyl, alkenyl, or alkyl, or two R taken together may form a 4- to 8-membered ring, e.g., with N;

R$_1$ and R$_2$ represent, independently and as valency permits, from 0-5 substituents on the ring to which it is attached, selected from halogen, lower alkyl, lower alkenyl, aryl, heteroaryl, carbonyl, thiocarbonyl, ketone, aldehyde, amino, acylamino, amido, amidino, cyano, nitro, hydroxyl, azido, sulfonyl, sulfoxido, sulfate, sulfonate, sulfamoyl, sulfonamido, phosphoryl, phosphonate, phosphinate, —(CH$_2$)$_p$alkyl, —(CH$_2$)$_p$alkenyl, —(CH$_2$)$_p$alkynyl, —(CH$_2$)$_p$aryl, —(CH$_2$)$_p$aralkyl, —(CH$_2$)$_p$OH, —(CH$_2$)$_p$O-lower alkyl, —(CH$_2$)$_p$O-lower alkenyl, —O(CH$_2$)$_n$R, —(CH$_2$)$_p$SH, —(CH$_2$)$_p$S-lower alkyl, —(CH$_2$)$_p$S-lower alkenyl, —S(CH$_2$)$_n$ R, —(CH$_2$)$_p$N(R)$_2$, —(CH$_2$)$_p$NR-lower alkyl, —(CH$_2$)$_p$NR-lower alkenyl, —NR(CH$_2$)$_n$R, and protected forms of the above;

Cy represents substituted or unsubstituted aryl, heterocyclyl, heteroaryl, or cycloalkyl, including polycyclic groups;

i represents, independently for each occurrence, an integer from 0 to 5, preferably from 0 to 2; and p and n, individually for each occurrence, represent integers from 0 to 10, preferably from 0 to 5.

In certain embodiments, M represents, independently for each occurrence, a substituted or unsubstituted methylene group, such as —CH$_2$—, —CHF—, —CHOH—, —CH(Me)—, —C(=O)—, etc.

In certain embodiments, Cy' represents a substituted or unsubstituted bicyclic or heterocyclic ring system, preferably both bicyclic and heteroaryl, such as benzothiophene, benzofuran, benzopyrrole, benzopyridine, etc. In certain embodiments, Cy' is directly attached to X. In certain embodiments, Cy' is a monocyclic aryl or heteroaryl ring substituted at least with a substituted or unsubstituted aryl or heteroaryl ring, e.g., forming a biaryl system. In certain embodiments, Cy' includes two substituted or unsubstituted aryl or heteroaryl rings, e.g., the same or different, directly connected by one or more bonds, e.g., to form a biaryl or bicyclic ring system.

In certain embodiments, Y is absent from all positions. In embodiments wherein Y is present in a position, i preferably represents an integer from 1-2 in an adjacent $M_i$ if i=0 would result in two occurrences of Y being directly attached, or an occurrence of Y being directly attached to N.

In certain embodiments, X is selected from —C(=O)—, —C(=S)—, and —S(O$_2$)—.

In certain embodiments, Cy represents a substituted or unsubstituted non-aromatic carbocyclic or heterocyclic ring, i.e., including at least one sp$^3$ hybridized atom, and preferably a plurality of sp$^3$ hybridized atoms. In certain embodiments, Cy includes an amine within the atoms of the ring or on a substituent of the ring, e.g., Cy is pyridyl, imidazolyl, pyrrolyl, piperidyl, pyrrolidyl, piperazyl, etc., and/or bears an amino substituent. In certain embodiments, Cy is directly attached to N. In certain embodiments, Cy is a 5- to 7-membered ring. In embodiments wherein Cy is a six-membered ring directly attached to N and bears an amino substituent at the 4 position of the ring relative to N, the N and amine substituents may be disposed trans on the ring.

In certain embodiments, $R_1$ and $R_2$ represent, independently and as valency permits, from 0-5 substituents on the ring to which it is attached, selected from halogen, lower alkyl, lower alkenyl, carbonyl, thiocarbonyl, ketone, aldehyde, amino, acylamino, cyano, nitro, hydroxyl, azido, sulfonyl, sulfoxido, sulfate, sulfonate, sulfamoyl, sulfonamido, phosphoryl, phosphonate, phosphinate, —(CH$_2$)$_p$alkyl, —(CH$_2$)$_p$alkenyl, —(CH$_2$)$_p$alkynyl, —(CH$_2$)$_p$aryl, —(CH$_2$)$_p$aralkyl, —(CH$_2$)$_p$OH, —(CH$_2$)$_p$O-lower alkyl, —(CH$_2$)$_p$O-lower alkenyl, —O(CH$_2$)$_n$R, —(CH$_2$)$_p$SH, —(CH$_2$)$_p$S-lower alkyl, —(CH$_2$)$_p$S-lower alkenyl, —S(CH$_2$)$_n$R, —(CH$_2$)$_p$N(R)$_2$, —(CH$_2$)$_p$NR-lower alkyl, —(CH$_2$)$_p$NR-lower alkenyl, —NR(CH$_2$)$_n$R, and protected forms of the above, wherein p, individually for each occurence, represents an integer from 0 to 10, preferably from 0 to 5.

In certain embodiments, compounds useful in the present invention may be represented by general formula (XVI):

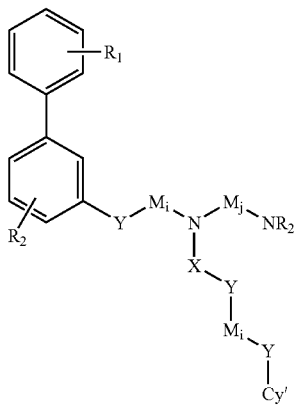

Formula XVI wherein, as valence and stability permit,

Cy' represents a substituted or unsubstituted aryl or heteroaryl ring, including polycyclics;

Y, independently for each occurrence, may be absent or represent —N(R)—, —O—, —S—, or —Se—;

X can be selected from —C(=O)—, —C(=S)—, —S(O$_2$)—, —S(O)—, —C(=NCN)—, —P(=O)(OR$_2$)—, and a methylene group optionally substituted with 1-2 groups such as lower alkyl, alkenyl, or alkynyl groups;

M represents, independently for each occurrence, a substituted or unsubstituted methylene group, such as —CH$_2$—, —CHF—, —CHOH—, —CH(Me)—, —C(=O)—, etc., or two M taken together represent substituted or unsubstituted ethene or ethyne;

R represents, independently for each occurrence, H or substituted or unsubstituted aryl, heterocyclyl, heteroaryl, aralkyl, heteroaralkyl, alkynyl, alkenyl, or alkyl, or two R taken together may form a 4- to 8-membered ring, e.g., with N;

$R_1$ and $R_2$ represent, independently and as valency permits, from 0-5 substituents on the ring to which it is attached, selected from halogen, lower alkyl, lower alkenyl, aryl, heteroaryl, carbonyl, thiocarbonyl, ketone, aldehyde, amino, acylamino, amido, amidino, cyano, nitro, hydroxyl, azido, sulfonyl, sulfoxido, sulfate, sulfonate, sulfamoyl, sulfonamido, phosphoryl, phosphonate, phosphinate, —(CH$_2$)$_p$alkyl, —(CH$_2$)$_p$alkenyl, —(CH$_2$)$_p$alkynyl, —(CH$_2$)$_p$aryl, —(CH$_2$)$_p$aralkyl, —(CH$_2$)$_p$OH, —(CH$_2$)$_p$O-lower alkyl, —(CH$_2$)$_p$O-lower alkenyl, —O(CH$_2$)$_n$R, —(CH$_2$)$_p$SH, —(CH$_2$)$_p$S-lower alkyl, —(CH$_2$)$_p$S-lower alkenyl, —S(CH$_2$)$_n$R, —(CH$_2$)$_p$N(R)$_2$, —(CH$_2$)$_p$NR-lower alkyl, —(CH$_2$)$_p$NR-lower alkenyl, —NR(CH$_2$)$_n$R, and protected forms of the above;

Cy' represents a substituted or unsubstituted aryl, heterocyclyl, heteroaryl, or cycloalkyl, including polycyclic groups;

j represents, independently for each occurrence, an integer from 0 to 10, preferably from 2 to 7;

i represents, independently for each occurrence, an integer from 0 to 5, preferably from 0 to 2; and p and n, individually for each occurrence, represent integers from 0 to 10, preferably from 0 to 5.

In certain embodiments, M represents, independently for each occurrence, a substituted or unsubstituted methylene group, such as —CH$_2$—, —CHF—, —CHOH—, —CH(Me)—, —C(=O)—, etc.

In certain embodiments, Cy' represents a substituted or unsubstituted bicyclic or heterocyclic ring system, preferably both bicyclic and heteroaryl, such as benzothiophene, benzofuran, benzopyrrole, benzopyridine, etc. In certain embodiments, Cy' is directly attached to X. In certain embodiments, Cy' is a monocyclic aryl or heteroaryl ring substituted at least with a substituted or unsubstituted aryl or heteroaryl ring, e.g., forming a biaryl system. In certain embodiments, Cy' includes two substituted or unsubstituted aryl or heteroaryl rings, e.g., the same or different, directly connected by one or more bonds, e.g., to form a biaryl or bicyclic ring system.

In certain embodiments, Y is absent from all positions. In embodiments wherein Y is present in a position, i preferably represents an integer from 1-2 in an adjacent $M_i$ if i=0 would result in two occurrences of Y being directly attached, or an occurrence of Y being directly attached to N or NR$_2$.

In certain embodiments, X is selected from —C(=O)—, —C(=S)—, and —S(O$_2$)—.

In certain embodiments, NR$_2$ represents a primary amine or a secondary or tertiary amine substituted with one or two lower alkyl groups, aryl groups, or aralkyl groups, respectively, preferably a primary amine.

In certain embodiments, $R_1$ and $R_2$ represent, independently and as valency permits, from 0-5 substituents on the ring to which it is attached, selected from halogen, lower alkyl, lower alkenyl, carbonyl, thiocarbonyl, ketone, aldehyde, amino, acylamino, cyano, nitro, hydroxyl, azido, sulfonyl, sulfoxido, sulfate, sulfonate, sulfamoyl, sulfonamido, phosphoryl, phosphonate, phosphinate, —(CH$_2$)$_p$alkyl, —(CH$_2$)$_p$alkenyl, —(CH$_2$)$_p$alkynyl, —(CH$_2$)$_p$aryl, —(CH$_2$)$_p$aralkyl, —(CH$_2$)$_p$OH, —(CH$_2$)$_p$O-lower alkyl, —(CH$_2$)$_p$O-lower alkenyl, —O(CH$_2$)$_n$R, —(CH$_2$)$_p$SH, —(CH$_2$)$_p$S-lower alkyl, —(CH$_2$)$_p$S-lower alkenyl, —S(CH$_2$)$_n$R, —(CH$_2$)$_p$N(R)$_2$, —(CH$_2$)$_p$NR-lower alkyl, —(CH$_2$)$_p$NR-lower alkenyl, —NR(CH$_2$)$_n$R, and protected forms of the above, wherein p, individually for each occurence, represents an integer from 0 to 10, preferably from 0 to 5.

In certain embodiments, compounds useful in the present invention may be

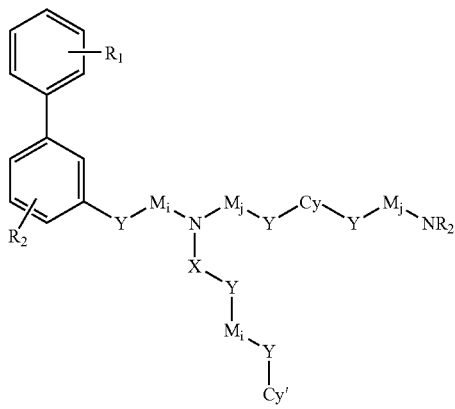

represented by general formula (XVII):

Formula XVII wherein, as valence and stability permit,

Cy' represents a substituted or unsubstituted aryl or heteroaryl ring, including polycyclics;

Y, independently for each occurrence, may be absent or represent —N(R)—, —O—, —S—, or —Se—;

X can be selected from —C(═O)—, —C(═S)—, —S(O$_2$)—, —S(O)—, —C(═NCN)—, —P(═O)(OR$_2$)—, and a methylene group optionally substituted with 1-2 groups such as lower alkyl, alkenyl, or alkynyl groups;

M represents, independently for each occurrence, a substituted or unsubstituted methylene group, such as —CH$_2$—, —CHF—, —CHOH—, —CH(Me)—, —C(═O)—, etc., or two M taken together represent substituted or unsubstituted ethene or ethyne;

R represents, independently for each occurrence, H or substituted or unsubstituted aryl, heterocyclyl, heteroaryl, aralkyl, heteroaralkyl, alkynyl, alkenyl, or alkyl, or two R taken together may form a 4- to 8-membered ring, e.g., with N;

Cy represents substituted or unsubstituted aryl, heterocyclyl, heteroaryl, or cycloalkyl, including polycyclic groups;

i represents, independently for each occurrence, an integer from 0 to 5, preferably from 0 to 2; and n and p, individually for each occurrence, represent integers from 0 to 10, preferably from 0 to 5.

In certain embodiments, M represents, independently for each occurrence, a substituted or unsubstituted methylene group, such as —CH$_2$—, —CHF—, —CHOH—, —CH(Me)—, —C(═O)—, etc.

In certain embodiments, Cy' represents a substituted or unsubstituted bicyclic or heteroaryl ring system, preferably both bicyclic and heteroaryl, e.g., benzothiophene, benzofuran, benzopyrrole, benzopyridyl, etc. In certain embodiments, Cy' is directly attached to X. In certain embodiments, Cy' is a monocyclic aryl or heteroaryl ring substituted at least with a substituted or unsubstituted aryl or heteroaryl ring, e.g., forming a biaryl system. In certain embodiments, Cy' includes two substituted or unsubstituted aryl or heteroaryl rings, e.g., the same or different, directly connected by one or more bonds, e.g., to form a biaryl or bicyclic ring system.

In certain embodiments, Y is absent from all positions. In embodiments wherein Y is present in a position, i preferably represents an integer from 1-2 in an adjacent $M_i$ if i=0 would result in two occurrences of Y being directly attached, or an occurrence of Y being directly attached to N or NR$_2$.

In certain embodiments, X is selected from —C(═O)—, —C(═S)—, and —S(O$_2$)—.

In certain embodiments, NR$_2$ represents a primary amine or a secondary or tertiary amine substituted with one or two lower alkyl groups, aryl groups, or aralkyl groups, respectively, preferably a primary amine.

In certain embodiments, Cy represents a substituted or unsubstituted non-aromatic carbocyclic or heterocyclic ring, i.e., including at least one sp$^3$ hybridized atom, and preferably a plurality of sp$^3$ hybridized atoms. In certain embodiments, Cy is directly attached to N and/or to NR$_2$. In certain embodiments, Cy is a 5- to 7-membered ring. In embodiments wherein Cy is a six-membered ring directly attached to N and bears an amino substituent at the 4 position of the ring relative to N, the N and amine substituents may be disposed trans on the ring.

In certain embodiments, $R_1$ and $R_2$ represent, independently and as valency permits, from 0-5 substituents on the ring to which it is attached, selected from halogen, lower alkyl, lower alkenyl, carbonyl, thiocarbonyl, ketone, aldehyde, amino, acylamino, cyano, nitro, hydroxyl, azido, sulfonyl, sulfoxido, sulfate, sulfonate, sulfamoyl, sulfonamido, phosphoryl, phosphonate, phosphinate, —(CH$_2$)$_p$alkyl, —(CH$_2$)$_p$alkenyl, —(CH$_2$)$_p$alkynyl, —(CH$_2$)$_p$aryl, —(CH$_2$)$_p$aralkyl, —(CH$_2$)$_p$OH, —(CH$_2$)$_p$O-lower alkyl, —(CH$_2$)$_p$O-lower alkenyl, —O(CH$_2$)$_n$R, —(CH$_2$)$_p$SH, —(CH$_2$)$_p$S-lower alkyl, —(CH$_2$)$_p$S-lower alkenyl, —S(CH$_2$)$_n$R, —(CH$_2$)$_p$N(R)$_2$, —(CH$_2$)$_p$NR-lower alkyl, —(CH$_2$)$_p$NR-lower alkenyl, —NR(CH$_2$)$_n$R, and protected forms of the above, wherein p, individually for each occurence, represents an integer from 0 to 10, preferably from 0 to 5.

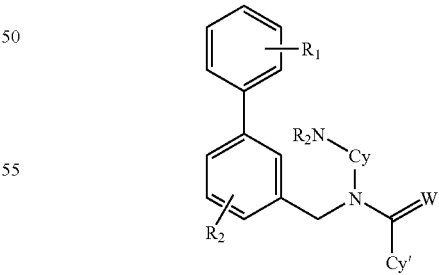

In certain embodiments, a subject compound has the structure of Formula XVIII:

wherein, as valence and stability permit,

Cy represents a substituted or unsubstituted heterocyclyl or cycloalkyl;

Cy' is a substituted or unsubstituted aryl or heteroaryl ring;

W is O or S;

R represents, independently for each occurrence, H or substituted or unsubstituted aryl, heterocyclyl, heteroaryl, aralkyl, heteroaralkyl, alkynyl, alkenyl, or alkyl, or two R taken together may form a 4- to 8-membered ring, e.g., with N;

$R_1$ and $R_2$ represent, independently and as valency permits, from 0-5 substituents on the ring to which it is attached, selected from halogen, lower alkyl, lower alkenyl, aryl, heteroaryl, carbonyl, thiocarbonyl, ketone, aldehyde, amino, acylamino, amido, amidino, cyano, nitro, hydroxyl, azido, sulfonyl, sulfoxido, sulfate, sulfonate, sulfamoyl, sulfonamido, phosphoryl, phosphonate, phosphinate, —$(CH_2)_p$alkyl, —$(CH_2)_p$alkenyl, —$(CH_2)_p$alkynyl, —$(CH_2)_p$aryl, —$(CH_2)_p$aralkyl, —$(CH_2)_p$OH, —$(CH_2)_p$O-lower alkyl, —$(CH_2)_p$O-lower alkenyl, —$O(CH_2)_n$R, —$(CH_2)_p$SH, —$(CH_2)_p$S-lower alkyl, —$(CH_2)_p$S-lower alkenyl, —$S(CH_2)_n$R, —$(CH_2)_p$N(R)$_2$, —$(CH_2)_p$NR-lower alkyl, —$(CH_2)_p$NR-lower alkenyl, —$NR(CH_2)_n$R, and protected forms of the above;

n and p, individually for each occurrence, represent integers from 0 to 10.

In certain embodiments, Cy' represents a substituted or unsubstituted bicyclic or heteroaryl ring system, preferably both bicyclic and heteroaryl, e.g., benzothiophene, benzofuran, benzopyrrole, benzopyridyl, etc. In certain embodiments, Cy' is directly attached to X.

In certain embodiments, $NR_2$ represents a primary amine or a secondary or tertiary amine substituted with one or two lower alkyl groups, aryl groups, or aralkyl groups, respectively, preferably a primary amine.

In certain embodiments, Cy represents a substituted or unsubstituted saturated carbocyclic or heterocyclic ring, i.e., composed of a plurality of $sp^3$ hybridized atoms. In certain embodiments, Cy is a 5- to 7-membered ring. In embodiments wherein Cy is a six-membered ring directly attached to N and bears an amino substituent at the 4 position of the ring relative to N, the N and amine substituents may be disposed trans on the ring.

In certain embodiments, $R_1$ and $R_2$ represent, independently and as valency permits, from 0-5 substituents on the ring to which it is attached, selected from halogen, lower alkyl, lower alkenyl, carbonyl, thiocarbonyl, ketone, aldehyde, amino, acylamino, cyano, nitro, hydroxyl, sulfonyl, sulfoxido, sulfate, sulfonate, sulfamoyl, sulfonamido, —$(CH_2)_p$alkyl, —$(CH_2)_p$alkenyl, —$(CH_2)_p$alkynyl, —$(CH_2)_p$aryl, —$(CH_2)_p$aralkyl, —$(CH_2)_p$OH, —$(CH_2)_p$O-lower alkyl, —$(CH_2)_p$O-lower alkenyl, —$O(CH_2)_n$R, —$(CH_2)_p$SH, —$(CH_2)_p$S-lower alkyl, —$(CH_2)_p$S-lower alkenyl, —$S(CH_2)_n$R, —$(CH_2)_p$N(R)$_2$, —$(CH_2)_p$NR-lower alkyl, —$(CH_2)_p$NR-lower alkenyl, —$NR(CH_2)_n$R, and protected forms of the above.

In certain embodiments, a subject compound has a structure of Formula XIX:

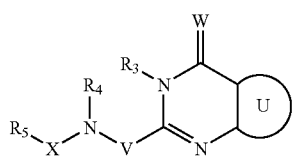

wherein, as valence and stability permit,

U represents a substituted or unsubstituted aryl or heteroaryl ring fused to the nitrogen-containing ring;

V represents a lower alkylene group, such as methylene, 1,2-ethylene, 1,1-ethylene, 1,1-propylene, 1,2-propylene, 1,3-propylene, etc.;

W represents S or O, preferably O;

X represents C=O, C=S, or SO$_2$;

$R_3$ represents substituted or unsubstituted aryl, heteroaryl, lower alkyl, lower alkenyl, lower alkynyl, carbocyclyl, carbocyclylalkyl, heterocyclyl, heterocyclylalkyl, aralkyl, or heteroaralkyl;

$R_4$ represents substituted or unsubstituted aralkyl or lower alkyl, such as phenethyl, benzyl, or aminoalkyl, etc.;

$R_5$ represents substituted or unsubstituted aryl, heteroaryl, aralkyl, or heteroaralkyl, including polycyclic aromatic or heteroaromatic groups.

In certain embodiments, U represents a phenyl ring fused to the nitrogen-containing ring.

In certain embodiments, $R_3$ is selected from substituted or unsubstituted aryl, heteroaryl, lower alkyl, lower alkenyl, aralkyl, and heteroaralkyl.

In certain embodiments, $R_4$ is an unsubstituted lower alkyl group, or is a lower alkyl group substituted with a secondary or tertiary amine.

In certain embodiments, $R_5$ is selected from substituted or unsubstituted phenyl or naphthyl, or is a diarylalkyl group, such as 2,2-diphenylethyl, diphenylmethyl, etc.

Moreover, the subject methods can be performed on cells which are provided in culture (in vitro), or on cells in a whole animal (in vivo). See, for example, PCT publications WO 95/18856 and WO 96/17924 (the specifications of which are expressly incorporated by reference herein).

VI. Testing for Biological Activity

While many bioassays have been used to demonstrate hedgehog activity, the C3H10T1/2 cell line provides a simple system for assessing hedgehog function without the complication of having to work with primary cell cultures or organ explants. The mouse embryonic fibroblast line C3H10T1/2 is a mesenchymal stem cell line that, under defined conditions, can differentiate into adipocytes, chondrocytes, and bone osteoblasts (Taylor, S. M., and Jones, P. A., Cell 17: 771-779 (1979) and Wang, E. A., et al., Growth Factors 9: 57-71 (1993)). Bone morphogenic proteins drive the differentiation of C3H 10T 1/2 cells into the bone cell lineage and alkaline phosphatase induction has been used as a marker for this process (Wang et al., supra). Shh has a similar effect on C3H10T1/2 cells (Kinto, N. et al., FEBS Letts. 404: 319-323 (1997)) and we routinely use the alkaline phosphatase induction by Shh as a quantitative measure of its in vitro potency. Shh treatment also produces a dose-dependent increase in gli-1 and ptc-1 expression, which can be readily detected by a PCR-based analysis.

We found that hedgehog protein can upregulate fibroblast expression of angiogenic growth factors, including VEGF121, VEGF165, VEGF189, Ang-1, and Ang-2 (Example 4). Thus, the procedure outlined in Example 4 provides a new method of measuring the in vitro angiogenic potential of hedgehog. Without wishing to be bound by any particular theory, this upregulation may explain the mechanism whereby hedgehog exerts its angiogenic effect.

Similarly, this cell line provides a simple bioassay to test the agonistic or antagonistic properties of the hedgehog therapeutics of the present invention. In preferred embodiments, agonists would be expected to induce alkaline phosphatase in CSH10T1/2 cells. In other embodiments, antagonists would be expected to inhibit the induction of alkaline phosphatase by exogenous hedgehog.

Further, persons having ordinary skill in the art will recognize means for determining if the hedgehog agents used in the present methods are efficacious in vivo. For instance, clinicians have available to them a variety of non-invasive tests such as echograms, electrocardiograms, CAT scans, MRI to determine vascular and cardiac functioning. Other methods include angiography and other more invasive physiological testing methods. For patients with neuropathies, nerve conduction velocity tests may be routinely performed. To test for the anti-angiogenic function of hedgehog antagonists, persons of ordinary skill in the art way use a variety of imaging methods such as CAT and MRI scans, as well as more invasive tests to look at blood chemistry and tumor metabolism.

VII. Subjects for Treatment

As a general matter, the methods of the present invention may be utilized for any mammalian subject needing modulation of angiogenesis. Mammalian subjects which may be treated according to the methods of the invention include, but are not limited to, human subjects or patients. In addition, however, the invention may be employed in the treatment of domesticated mammals which are maintained as human companions (e.g., dogs, cats, horses), which have significant commercial value (e.g., dairy cows, beef cattle, sporting animals), which have significant scientific value (e.g., captive or free specimens of endangered species), or which otherwise have value. In addition, as a general matter, the subjects for treatment with the methods of the present invention need not present indications for treatment with the agents of the invention other than those indications associated with need for modulation of angiogenesis. That is, the subjects for treatment are expected to be otherwise free of indications for treatment with the hedgehog therapeutic agents of the invention.

In another aspect, the present methods, specifically the administration of hedgehog antagonists, can be used to inhibit unwanted cellular behavior such as unwanted growth, proliferation, differentiation and/or survival. Such unwanted cellular behavior is often observed in cancer. Exemplary forms of cancer which may be treated by the subject methods include, but are not limited to, prostate cancer, bladder cancer, lung cancer (including either small cell or non-small cell cancer), colon cancer, kidney cancer, liver cancer, breast cancer, cervical cancer, endometrial or other uterine cancer, ovarian cancer, testicular cancer, cancer of the penis, cancer of the vagina, cancer of the urethra, gall bladder cancer, esophageal cancer, or pancreatic cancer. Additional exemplary forms of cancer which may be treated by the subject methods include, but are not limited to, cancer of skeletal or smooth muscle, stomach cancer, cancer of the small intestine, cancer of the salivary gland, anal cancer, rectal cancer, tyroid cancer, parathyroid cancer, pituitary cancer, and nasopharyngeal cancer. Further exemplary forms of cancer which can be treated with the hedgehog antagonists of the present invention include cancers comprising hedgehog expressing cells. Still further exemplary forms of cancer which can be treated with the hedgehog antagonists of the present invention include cancers comprising gli expressing cells. In one embodiment, the cancer is not characterized by a mutation in patched-1.

One of ordinary skill in the medical or veterinary arts is trained to recognize subjects which may need modulation of angiogenesis. In particular, clinical and non-clinical trials, as well as accumulated experience, relating to the presently disclosed and other methods of treatment, are expected to inform the skilled practitioner in deciding whether a given subject is in need of modulation and whether any particular treatment is best suited to the subject's needs, including treatment according to the present invention.

VIII. Utilities, Formulations and Methods of Treatment

A. General

We show that hedgehog receptor (ptc1) is normally expressed in the vasculature. We used a mouse which carries the lacZ reporter gene under the control of the endogenous ptc1 promotor to determine the expression of ptc1 in normal adult animals (Example 1). We further determined that mice injected with hedgehog protein for 3 days showed no obvious physical or behavioral differences compared to vehicle-treated or untreated littermates. The vascular and cardiovascular staining pattern for ptc1 seen in normal animals intensifies significantly in animals injected with increasing doses of hedgehog protein. Our data show that systemic administration of hedgehog can induce ptc1 upregulation and indicate that these vascular tissues are responsive to hedgehog protein.

We further determined that hedgehog induces neovascularization in a corneal model of angiogenesis (Example 3) as well as a matrigel plug model of angiogenesis (Example 2). We further found that there was a striking qualitative difference in the appearance of vessels induced by hedgehog compared to VEGF. VEGF induced a fine mesh of capillaries which are short tortous sprouts from the extended branches of the preexisting limbus vessels at the base of the eye. In contrast, hedgehog induced much larger vessels which extended all the way to the pellet and contained numerous anastamoses between the venous and arterial circulation Moreover, we employed surgical ligation of the femoral artery and removal of a segment of the artery distal to the ligation in mice to induce limb ischemia (Example 5). We found that hedgehog improves recovery from such ischemic limb injury.

In yet another clinically relevant animal model, we placed an ameroid constrictor around the left circumflex coronary artery of pigs. We determined that hedgehog protein or gene therapy can also improve these measures of cardiac perfusion, viability and function following ischemia in this model (Example 6). We determined that hedgehog protein is overexpressed in several human gastrointestinal tumor cell lines compared to normal human gastrointestinal epithelial cells or fibroblasts (Example 7) and that inhibition of hedgehog using, for example, anti-hedgehog blocking antibody, may decrease tumor growth rate and/or tumor angiogenesis (Example 7).

Accordingly, the methods of this invention may employ hedgehog therapeutics or biologically active portions thereof, to promote angiogenesis, such as, to repair damage of myocardial tissue as a result of myocardial infarction. Such methods may also include the repair of the cardiac vascular system after ischemia including the growth of collateral vasculature. Methods utilizing hedgehog therapeutics may be employed to stimulate the growth of transplanted tissue and collateral vasculature where coronary bypass surgery is performed. Methods may also treat damaged vascular tissue as a result of coronary artery disease and peripheral or central nervous system vascular disease or ischemia.

Methods of the invention may also promote wound healing, particularly to re-vascularize damaged tissues or stimulate collateral blood flow during ischemia and where new capillary angiogenesis is desired. Other methods of the invention may be employed to treat full-thickness wounds such as dermal ulcers, including pressure sores, venous ulcers, and diabetic ulcers. In addition, methods employing hedgehog therapeutics may be employed to treat full-thickness burns and injuries where a skin graft or flap is used to repair such burns and injuries. Such hedgehog therapeutics may also be employed for use in plastic surgery, for example, for the repair of lacerations, burns, or other trauma. In urology, methods of the invention may assist in recovery of erectile function. In the field of female reproductive health, methods of the invention may assist in the modulation of menstruation, ovulation, endometrial lining formation and maintanence, and placentation.

Since angiogenesis is important in keeping wounds clean and non-infected, methods may be employed in association with surgery and following the repair of cuts. They may also be employed for the treatment of abdominal wounds where there is a high risk of infection. Methods using hedgehog therapeutics described herein may be employed for the promotion of endothelialization in vascular graft surgery. In the case of vascular grafts using either transplanted or synthetic material, hedgehog therapeutics can be applied to the surface of the graft or at the junction to promote the growth of vascular smooth muscle and adventitial cells in conjunction with endothelial cells.

Methods of the invention may also be employed to coat artificial prostheses or natural organs which are to be transplanted in the body to minimize rejection of the transplanted material and to stimulate vascularization of the transplanted materials and may also be employed for vascular tissue repair, for example, that occurring during arteriosclerosis and required following balloon angioplasty where vascular tissues are damaged. Specifically, methods of the invention may be employed to promote recovery from arterial wall injury and thereby inhibit restenosis.

Nucleic acid sequences encoding hedgehog therapeutics may also be employed for in vitro purposes related to scientific research, synthesis of DNA and manufacture of DNA vectors, and for the production of diagnostics and therapeutics to treat human disease. For example. methods of the invention may involve in vitro culturing of vascular smooth muscle cells, fibroblasts, hematopoietic cells, muscle, myotendonous junction, bone or cartilage-derived cells and other mesenchymal cells, where a hedgehog therapeutic is added to the conditional medium in a concentration from 10 ng/ml to 20 ug/ml.

Antagonistic hedgehog therapeutics may be employed to limit angiogenesis necessary for solid tumor metastasis. The identification of antagonists can be used for the generation of certain inhibitors of vascular endothelial growth factor. Without being bound by a particular theory, since angiogenesis and neovascularization are essential steps in solid tumor growth, inhibition of angiogenic activity of the vascular endothelial growth factor is very useful to prevent the further growth, retard, or even regress solid tumors. Gastrointestinal tumors and gliomas are also a type of neoplasia which may be treated with the antagonists of the present invention. In addition to the inhibition of angiogenesis, the evidence presented herein indicates that hedgehog antagonists can be used to decrease proliferation, growth, differentiation and/or survival of a diverse range of tumor cell types. In a preferred embodiment, the tumor expressed and/or overexpresses a hedgehog gene and/or a gli gene (e.g., has hyper-activation of a hedgehog signaling pathway).

The invention contemplates that hedgehog antagonists may be useful for treating a diverse range of tumors and conditions of unwanted cell growth, proliferation, differentiation and/or survival. These include cells which comprise mutations/lesions in one or more component of the hedgehog signaling pathway, as well as wildtype cells (e.g., which do not comprise a lesion in one or more components of the hedgehog signaling pathway). Similarly, the present invention contemplates that hedgehog antagonists may be useful for treating a diverse range of tumors and conditions of unwanted cell growth, proliferation, differentiation and/or survival wherein the cells are characterized by express or overexpress of a hedgehog gene and/or a gli gene (e.g., has hyper-activation of a hedgehog signaling pathway). It is appreciated that such hyperactivation of the hedgehog signaling pathway may occur in cells which either comprise or do not comprise a mutation in a component of the hedgehog signaling pathway.

In addition to these disorders, the antagonists may also be employed to treat retinopathy associated with diabetes, rheumatoid arthritis, osteoarthritis, macular degeneration, glaucoma, Keloid formation, ulcerative colitis, Krohn's disease, psoriasis, and other conditions caused are exacerbated by increased angiogenic activity. The antagonists may be employed in a composition with a pharmaceutically acceptable carrier, e.g., as described herein.

These therapeutic agents may be administered by any route which is compatible with the particular agent employed. The hedgehog therapeutic agents of the invention may be provided to an individual by any suitable means, preferably directly (e.g., locally, as by injection or topical administration to a tissue locus) or systemically (e.g., parenterally or orally). Where the agent is to be provided parenterally, such as by intravenous, intraarterial, subcutaneous, or intramuscular, administration, the agent preferably comprises part of an aqueous solution. The solution is physiologically acceptable so that in addition to delivery of the desired agent to the subject, the solution does not otherwise adversely affect the subject's electrolyte and/or volume balance. The aqueous medium for the hedgehog therapeutic may comprise normal physiologic saline (e.g., 9.85% NaCl, 0.15M, pH 7-7.4).

The hedgehog therapeutics are preferably administered as a sterile pharmaceutical composition containing a pharmaceutically acceptable carrier, which may be any of the numerous well known carriers, such as water, saline, phosphate buffered saline, dextrose, glycerol, ethanol, and the like, or combinations thereof. The compounds of the present invention may be used in the form of pharmaceutically acceptable salts derived from inorganic or organic acids and bases. Included among such acid salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, tris(hydroxymethyl)methylamine and salts with amino acids such as arginine, lysine, and so forth. Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

Pharmaceutical compositions of hedgehog therapeutics comprise any of the compounds of the present invention, or pharmaceutically acceptable derivatives thereof, together with any pharmaceutically acceptable carrier. The term "carrier" as used herein includes acceptable adjuvants and vehicles. Pharmaceutically acceptable carriers that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to this invention, the pharmaceutical compositions may be in the form of a sterile injectable preparation, for example a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as do natural pharmaceutically-acceptable oils, such as olive oil or castor oil, especially in their polyoxyethylated versions. These oil solutions or suspensions may also contain a long-chain alcohol diluent or dispersant.

Controlled release administration of a particular hedgehog therapeutic may be useful. For example, the therapeutic may be administered using intravenous infusion, an implantable osmotic pump, a transdermal patch, liposomes, or other modes of administration. In one embodiment, a pump may be used [Langer et al., eds., Medical Applications of Controlled Release, CRC Pres., Boca Raton, Fla. (1974); Sefton, CRC Crit. Ref. Biomed. Eng., 14:201 (1987); Buchwald et al., Surgery, 88:507 (1980); Saudek et al., N. Engl. J. Med., 321:574 (1989)]. In another embodiment, polymeric materials can be used [see, Langer, 1974, supra; Sefton, 1987, supra; Smolen et al., eds., Controlled Drug Bioavailability, Drug Product Design and Performance, Wiley, N.Y. (1984); Ranger et al., J. Macromol. Sci. Rev. Macromol. Chem., 23:61 (1983); see also Levy et al., Science, 228:190 (1985); During et al., Ann. Neurol., 25:351 (1989); Howard et al., J. Neurosurg., 71:105 (1989)]. In yet another embodiment, a controlled release system can be placed in proximity of the therapeutic target, e.g., a tumor, thus requiring only a fraction of the systemic dose [see. e.g., Goodson, in Medical Applications of Controlled Release, vol. 2, pp. 115-138 (1984)]. Other controlled release systems are discussed in the review by Langer, Science, 249:1527-1533 (1990). In another embodiment, the therapeutic compound can be delivered in a vesicle, in particular a liposome (see Langer, 1990, supra); Treat et al., in Liposomes in the Therapy of Infectious Disease and Cancer, Lopez-Berestein and Fidler (eds.), Liss, New York, pp. 353-365 (1989); Lopez-Berestein, pp. 317-327; see generally id.).

B. Oral Delivery

Contemplated for use herein are oral solid dosage forms, which are described generally in Martin, Chapter 89, 1990, supra, which is herein incorporated by reference. Solid dosage forms include tablets, capsules, pills, troches or lozenges, cachets or pellets. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given by Marshall, in Modern Pharmaceutics, Chapter 10, Banker and Rhodes ed., (1979), herein incorporated by reference. In general, the formulation will include the therapeutic (or chemically modified form), and inert ingredients which allow for protection against the stomach environment, and release of the biologically active material in the intestine.

For the protein (or derivative) the location of release may be the stomach, the small intestine (the duodenum, the jejunem, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the protein (or derivative) or by release of the biologically active material beyond the stomach environment, such as in the intestine. To ensure full gastric resistance, a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films. A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multiparticulates in the form of granules or pellets of particle size about 1 mm. The formulation of the material for capsule administration could also be as a powder, lightly compressed plugs or even as tablets. The therapeutic could be prepared by compression. Colorants and flavoring agents may all be included. For example, the protein (or derivative) may be formulated (such as by liposome or microsphere encapsulation) and then further contained within an edible product, such as a refrigerated beverage containing colorants and flavoring agents. One may dilute or increase the volume of the therapeutic with an inert material. These diluents could include carbohydrates, especially mannitol, alpha-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell. Disintegrants may be included in the formulation of the therapeutic into a solid dosage form. Materials used as disintegrants include but are not limited to starch including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants. Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic. An antifrictional agent may be included in the formulation of the therapeutic to prevent sticking during the formulation process. Lubricants may be used as a layer between the therapeutic and the die wall, and these can include but are not limited to: stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, and Carbowax 4000 and 6000. Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment, a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios. Additives which potentially enhance uptake of the protein (or derivative) are for instance the fatty acids oleic acid, linoleic acid and linolenic acid.

C. Pulmonary Delivery

Also contemplated herein is pulmonary delivery of the present proteins (or derivatives thereof). The protein (or derivative) is delivered to the lungs of a mammal while inhaling and traverses across the lung epithelial lining to the bloodstream. Other reports of this include Adjei et al., Pharmaceutical Research, 7(6):565-569 (1990); Adjei et al., International Journal of Pharmaceutics, 63:135-144 (1990) (leuprolide acetate); Braquet et al., Journal of Cardiovascular Pharmacology, 13(suppl. 5):143-146 (1989) (endothelia-1); Hubbard et al., Annals of Internal Medicine, 3(3):206-212 (1989) (alpha 1-antitrypsin); Smith et al., J. Clin. Invest., 84:1145-1146 (1989) (alpha 1-proteinase); Os wein et al., "Aerosolization of Proteins", Proceedings of Symposium on Respiratory Drug Delivery II, Keystone, Colo., (March 1990) (recombinant human growth hormone); Debs et al., J. Immunol., 140:3482-3488 (1988) (interferon-gamma and tumor necrosis factor alpha) and Platz et al., U.S. Pat. No. 5,284,656 (granulocyte colony stimulating factor). Contemplated for use in the practice of this invention are a wide range of mechanical devices designed for pulmonary delivery of therapeutic products, including but not limited to nebulizers, metered-dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered-dose inhaler, manufactured by Glaxo Inc., Research Triangle Park, N.C.; and the Spinhaler powder inhaler, manufactured by Fisons Corp., Bedford, Mass. All such devices require the use of formulations suitable for the dispensing of protein (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified protein may also be prepared in different formulations depending on the type of chemical modification or the type of device employed.

Formulations suitable for use with a nebulizer, either jet or ultrasonic, will typically comprise protein (or derivative) dissolved in water at a concentration of about 0.1 to 25 mg of biologically active protein per ml of solution. The formulation may also include a buffer and a simple sugar (e.g., for protein stabilization and regulation of osmotic pressure). The nebulizer formulation may also contain a surfactant, to reduce or prevent surface induced aggregation of the protein caused by atomization of the solution in forming the aerosol.

Formulations for use with a metered-dose inhaler device will generally comprise a finely divided powder containing the protein (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing protein (or derivative) and may also include a bulking agent, such as lactose, sorbitol, sucrose, or mannitol in amounts which facilitate dispersal of the powder from the device, e.g., 50 to 90% by weight of the formulation. The protein (or derivative) should most advantageously be prepared in particulate form with an average particle size of less than 10 mum (or microns), most preferably 0.5 to 5 mum, for most effective delivery to the distal lung.

D. Dosages

For all of the above molecules, as further studies are conducted, information will emerge regarding appropriate dosage levels for treatment of various conditions in various patients, and the ordinary skilled worker, considering the therapeutic context, age and general health of the recipient, will be able to ascertain the proper dosage. Generally, for injection or infusion, dosage will be between 0.01 μg of biologically active protein/kg body weight, (calculating the mass of the protein alone, without chemical modification), and 10 mg/kg (based on the same). The dosing schedule may vary, depending on the circulation half-life of the protein or derivative used, whether the polypeptide is delivered by bolus dose or continuous infusion, and the formulation used.

E. Administration with Other Compounds

For therapy associated with modulating angiogenesis, one may administer the present hedgehog therapeutics (or derivatives) in conjunction with one or more pharmaceutical compositions used for treating other clinical complications of the need for angiogenic modulation, such as those used for treatment of cancer (e.g., chemotherapeutics), cachexia, high blood pressure, high cholesterol, and other adverse conditions. Administration may be simultaneous or may be in seriatim. Similarly, one may administer more than one hedgehog therapeutic (or derivatives), having the same or differing mode of action, to attain an additive or synergistic effect on angiogenesis.

For therapy associated with inhibiting unwanted cellular behavior including growth, proliferation, differentiation and/or survival (e.g., cancer), one may administer the hedgehog antagonists in combination with other agents. For example, one may administer two or more hedgehog antagonists such as two different hedgehog antibodies (e.g., antibodies which bind to different epitopes), or one or more hedgehog antibodies in combination with one or more non-hedgehog antagonists. Said combination of hedgehog antagonists may act additively or synergistically.

In any of the foregoing embodiment, the invention contemplates that the pharmaceutical preparations and or therapeutic compositions may be non-pyrogenic.

F. Nucleic Acid-Based Therapeutic Treatment

Nucleic acid sequences encoding an antagonisitic hedgehog therapeutic could be introduced into human tumor or blood vessel cells to develop gene therapy. Similarly, nucleic acid sequences encoding an agonistic hedgehog therapeutic could be introduced into human cells as a gene therapy based treatment.

In one embodiment, a nucleic acid sequence encoding a hedgehog therapeutic is introduced in vivo in a viral vector. Such vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral geries, are preferred. Defective virus is not infective after introduction into a cell. Use of defective viral vectors allows for administration to cells in a specific, localized area, without concern that the vector can infect other cells. Thus, adipose tissue can be specifically targeted. Examples of particular vectors include, but are not limited to, a defective herpes virus 1 (HS V 1) vector [Kaplitt et al., Molec. Cell. Neurosci., 2:320-330 (1991)], an attenuated adenovirus vector, such as the vector described by Stratford-Perricaudet et al., J. Clin. Invest., 90:626-630 (1992), and a defective adeno-associted virus vector [Samulski et al., J. Virol., 61:3096-3101 (1987); Samulski et al., J. Virol., 63:3822-3828 (1989)]. In another embodiment, the nucleic acid can be introduced in a retroviral vector, e.g., as described in Anderson et al., U.S. Pat. No. 5,399,346; Mann et al., Cell, 33:153 (1983); Temin et al., U.S. Pat. No. 4,650,764; Temin et al., U.S. Pat. No. 4,980,289; Markowitz et al., J. Virol., 62:1120 (1988); Temin et al., U.S. Pat. No. 5,124,263; International Patent Publication No. WO 95/07358, published Mar. 16, 1995, by Dougherty et al.; and Kuo et al., Blood, 82:845 (1993).

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker [Felgner et al., Proc. Natl. Acad. Sci. USA, 84:7413-7417 (1987); see Mackey et al., Proc. Natl. Acad. Sci. USA, 85:8027-8031 (1988)]. The use of cationic lipids may promote encapsulation of negatively charged nucleic acids, and also promote fusion with negatively charged cell membranes [Felgner et al., Science, 337:387-388 (1989)]. The use of lipofection to introduce exogenous genes into specific organs in vivo has certain practical advantages. Molecular targeting of liposomes to specific cells represents one area of benefit. It is clear that directing transfection to particular cell types would be particularly advantageous in a tissue with cellular heterogeneity, such as the pancreas, liver, kidney, and brain. Lipids may be chemically coupled to other molecules for the purpose of targeting (see Mackey et al., 1988, supra). Targeted peptides, e.g., hormones or neurotransmitters, and proteins such as antibodies, or non-peptide molecules could be coupled to liposomes chemically.

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter (see, e.g., Wu et al., J. Biol. Chem., 267:963-967 (1992); Wu et al., J. Biol. Chem., 263:14621-14624 (1988); Hartmut et al., Canadian Patent Application No. 2,012,311, filed Mar. 15, 1990).

It is also possible to introduce the vector in vivo in conjuction with a catheter or other device. See Vale et al., 1999: Kornowski et al., 2000.

H. Diagnostics

A diagnostic method useful in the present invention comprises examining a cellular sample or medium by means of an assay including an effective amount of an antagonist to a hedgehog protein, such as an anti-hedgehog antibody homolog, preferably an affinity-purified polyclonal antibody, and more preferably a mAb. In addition, it is preferable for the anti-hedgehog antibody molecules used herein be in the form of Fab, Fab', F(ab)2 or F(v) portions or whole antibody molecules. As previously discussed, patients capable of benefiting from this method include those suffering from cancer or other conditions where abnormal angiogenesis is a characteristic or factor. Methods for isolating hedgehog protein and inducing anti-hedgehog antibodies and for determining and optimizing the ability of anti-hedgehog antibodies to assist in the examination of the target cells are all well-known in the art.

The present invention will be illustrated by the following, non-limiting examples. These are described in further detail in the pending publication, Pola et al., 2001, Nature Medicine, which is hereby incorporated by reference in its entirety.

EXAMPLE 1

Hedgehog Responsive Cells in Normal Vasculature

The Expression of Hedgehog Receptor in Normal Vasculature

The hedgehog receptor which is coupled directly to the hedgehog signalling pathway is patched 1 (ptc1). In addition to being the primary hedgehog receptor in the signalling pathway, ptc1 gene expression is also induced by signalling through the hedgehog pathway. The expression of the ptc1 gene in cells can thus indicate that the cell is potentially responsive to hedgehog proteins and can also show that the cell is in the process of responding to hedgehog stimulation.

We used a mouse which carries the lacZ reporter gene under the control of the endogenous ptc1 promotor to determine the expression of ptc1 in normal adult animals Ptc1-lacZ mice carry a non disruptive insertion of the lacZ reporter gene containing a nuclear localization signal upstream of the ptc1 coding region. LacZ expression corresponds to ptc1 expression (Goodrich et al., 1997; M. Scott, Ontogeny, personal communication). Ptc1 expression does not appear to be altered by LacZ insertion and expression corresponds to ptc1 expression in embryos (M. Scott, Ontogeny, personal communication). Heterozygous Ptc1-lacZ mice and their wild type littermate controls are generated by mating heterozygote lacZ positive males with standard C57BL/6J female mice (Taconic, Germantown, N.Y.). Adult Ptc1-lacZ mice were fixed by cardiac perfusion followed by drop fixation of heart or vascular tissues for 1-2 hours in 0.2% gluteraldehyde, 5 mM EDTA, 2 mM $MgCl_2$, 0.1M sodium phosphate, pH8. Pup tissues and small tissues were directly drop fixed in gluteraldehyde for 1-2 hours. Following fixation, the tissues were washed 3 times for 20-30 min in 2 mM $MgCl_2$, 0.01 deoxycholate, 0.02% NP40, 50 mM sodium phosphate pH8. The tissues were then stained overnight at 37° C. in 1 mg/ml 5-Bromo-4-chloro-3-indolyl-D-galactopyranoside (Xgal) (Sigma, St. Louis, Mo.), 5 mM potassium ferricyanide, 5 mM potassium ferrocyanide, 2 mM $MgCl_2$, 0.01% deoxycholate, 0.02% NP40, 50 mM sodium phosphate pH8. The tissues were visualized either as whole mounts or embedded in paraffin and prepared as light eosin-stained 5 micron sections.

Patched 1 is expressed in the endothelial cells of the aorta, some vascular smooth muscle cells (vSMC) and adventitial fibroblasts of the aorta (photomicrographs not presented here). In addition, coronary vasculature and cardiomyocytes of the atria and ventricles also express ptc1. These expression patterns suggest that cells in normal vascular and cardiovascular tissues may be responsive to or responding to hedgehog.

Normal Vasculature and Cardiovascular Tissues are Hedgehog Responsive

We determined that normal vascular and cardiovascular tissues are indeed responsive to exogenous hedgehog administration by injecting Ptc1-lacZ mice systemically with hedgehog. Ptc1-lacZ mice were injected daily subcutaneously with the indicated amounts of polyethylene glycol 20,000-conjugated A192C sonic hedgehog n-terminal protein (PEG-Shh) (Pepinsky et al, 2000) or its vehicle (PBS). This form of the protein also contains a mutation of the n-terminal cysteine residue to isoleucine-isoleucine which significantly improves the specific activity of hedgehog protein (Pepinsky et al, 1998; Taylor et al, in prep).

Mice injected with hedgehog protein for 3 days showed no obvious physical or behavioural differences compared to vehicle-treated or untreated littermates. Specifically, Ptc1-lacZ mice were injected (s.c.) once daily with PEG-Shh for 3 days starting at postnatal day 6 then sacrificed at postnatal day 9; selected organs were dissected and whole mount stained by X-Gal histochemistry. Mice were treated with vehicle, 3 mg/kg PEG-Shh or 6 mg/kg PEG-Shh for 3 days and were sacrificed on the fourth day. Vascular and cardiovascular tissues were dissected and whole-mount stained with Xgal. The vascular and cardiovascular staining pattern for ptc1 seen in normal animals intensifies significantly in animals injected with increasing doses of hedgehog protein (data not presented here). Whole mount Xgal staining of the coronary arteries, atria and ventricles are increased in a dose dependent manner in the hearts and in the aortic wall of the Ptc1-lacZ mice injected with hedgehog. In contrast, wild type littermate mice injected with the highest dose of hedgehog (6 mg/kg) show no staining suggesting that the staining seen in the Ptc1-lacZ animals is not due to endogenous betagalactosidase. Histological sections of these tissues show that the lacZ positive cells in the Ptc1-lacZ mice treated with hedgehog are similar to those which are positive in the vehicle-injected group and in normal adult hearts and aortas from untreated animals. Though the same type of cells appear to stain with Xgal in the treated animals, there appears to be an increase in the number of these cells especially in the adventitia. These data show that systemic administration of hedgehog can induce ptc1 upregulation and indicate that these vascular tissues are responsive to hedgehog protein.

EXAMPLE 2

Hedgehog Induces Neovascularization in Matrigel Plug Model of Angiogenesis

Hedgehog was also found to induce angiogenesis in the subcutaneous matrigel plug assay (Passaniti et al., 1992). Doses of 2 to 10 ug/ml of octyl, myr, PEG II or II-Fc fusion forms of human recombinant Shh were prepared in 0.5 ml of matrigel containing 40 IU/ml of heparin and injected subcutaneously into C57BL6 mice (3-5 mo. old, 5 mice/treatment group). The mice were sacrificed between 6-7 days after injection and the matrigel plug was dissected for visual inspection and histological analysis. Plugs containing hedgehog induced significant angiogenesis in the plug and surrounding tissue in 4 of 6 plugs at 2 ug/ml and 5 of 6 plugs at 10 ug/ml whereas only 2 of 9 vehicle containing plugs showed any evidence of angiogenesis (data not presented here). Recombinant human bFGF, a known angiogenic protein, also showed significant hemoglobin content in 3 of 5 implants (data not shown). The results of the matrigel plug support the finding that hedgehog can induce angiogenesis in vivo.

EXAMPLE 3

Hedgehog Induces Neovascularization in Corneal Model of Angiogenesis

The mouse cornea is avascular and can be used to demonstrate angiogenic activity by measuring the amount of vessel growth into this avascular tissue after surgical placement of a polymer pellet containing an angiogenic substance or growth factor into the cornea (Kenyon et al., 1996; Asahara et al., 1997). To confirm the angiogenic activity of hedgehog in another well accepted model of angiogenesis, we tested the ability of hedgehog protein to induce neovascularization in the mouse corneal model pocket model of angiogenesis.

Animals were anesthetized by pentobarbital intraperitoneal injection (160 mg/kg). Corneal pockets were created in the eyes of each mouse and a 0.34×0.34 mm sucrose albumin sulfate (Bukh Meditec, Vaerlose, DK) pellet coated with hydron polymer type NCC (Interferon Sciences, New Brunswick, N.J.) containing 1 of the agents indicated below was implanted into the corneal pocket. C57BL/fJ mice were divided into 5 groups: control buffer alone; VEGF 300 ng/pellet; Myr-Shh vehicle alone; Myr-Shh 1.5 microg/pellet 39; Myr-Shh+VEGF (1.5 microg/pellet +300 ng/pellet, respectively). Pellets were positioned 1.0 mm from the corneal limbus, and erythromycin ophthalmic ointment (E. Fourera) was applied to each operated eye. The corneas of all mice were routinely examined by slit-lamp biomicroscopy on postoperative day 6 after pellet implantation.

On the same day vessel length and corneal circumferential neovascularity (in degrees) were measured. After completing these measurements, C57BL/6J mice received an intravenous injection of 500 pg of BS-1 lectin FITC-conjugated (Vector Laboratories, Burlingame, Calif.). Thirty minutes later, the animals were sacrificed. The eyes were enucleated and fixed in 1% paraformaldehyde solution. After fixation, the corneas were placed on glass slides and examined by fluorescence microscopy. Several C57BL/6J mice in each group did not receive BS-1 lectin injection; instead, the eyes were excised and fixed in 100% methanol solution for immunohistochemical staining.

There was significant neovascular growth in the Shh and in the VEGF groups but not the vehicle-containing pellet groups. There was a striking qualitative difference in the appearance of vessels induced by hedgehog compared to VEGF (photomicrographs not presented here). VEGF induced a fine mesh of capillaries which are short tortous sprouts from the extended branches of the preexisting limbus vessels at the base of the eye. In contrast, hedgehog induced much larger vessels which extended all the way to the pellet and contained numerous anastamoses between the venous and arterial circulation. Histological analysis confirmed that hedgehog induced larger diameter vessels than VEGF. Hedgehog induced vessels often were filled with red blood cells whereas VEGF induced vessels had few or no red blood cells.

Measurements (mean standard error of the mean) of the VEGF and hedgehog vessels confirmed that hedgehog-induced vessel diameters (mean 33±17 um) were significantly larger than VEGF vessel diameters (mean 8±3 um) ($p<0.0001$)). The maximum vessel lengths induced by hedgehog (1020+200 um) were also significantly greater than the maximum length of vessels induced by VEGF (700±70 um) ($p<0.0001$). The density of vessels induced by hedgehog was slightly lower than the density of vessels in the corneal tissue exposed to VEGF as may be expected from the large number of small capillaries formed by VEGF ($p<0.0001$). All group differences were analysed by ANOVA and differences with $p<0.05$ were considered statistically significant.

In summary, neovascularization induced by Shh was characterized by a statistically significant increase in vessel length, circumferential neovascularity and diameter of the lumens; the mean number of vascular lumens per cross section was higher in the VEGF-treated corneas. Neovascularization induced by Shh+VEGF showed a large variability in the lumen diameter of these vessels ranging from small capillaries (6-7 gm) to large diameter vessels (80 gm). The combination of VEGF and Shh appears to create a composite of characteristics of both VEGF and Shh neovascular growth. These results confirm hedgehog protein can induce angiogenesis in vivo and suggest that hedgehog either alone or in combination with VEGF or other angiogenic growth factors such as bFGF, the angiopoietins and TWEAK [Lynch CN, Wang Y C, Lund J K, Chen Y W, Leal J A, Wiley S R. TWEAK induces angiogenesis and proliferation of endothelial cells. J Biol Chem. 1999 March 26;274(13):8455-9] can have therapeutic utility by inducing functional neovasculature.

EXAMPLE 4

Biological Activities Induced By Hedgehog-Responsive Mesenchymal Cells

Hedgehog induces Stromal Fibroblasts and VEGF Upregulation in the Corneal Model of Angiogenesis To determine the mechanism by which Shh induces angiogenesis both Shh and VEGF-stimulated corneas (see Example 3) were excised and X-gal stained as described in Example 1 after fixation of the whole eye for 1 hour in 1% paraformaldehyde followed by enucleation and fixation of the corneal hemisphere in 1% paraformaldehyde for 30 minutes. VEGF-induced corneas did not stain with X-gal, indicating that VEGF does not induce Ptc 1 expression during neovascularization. In contrast, strong X-gal staining was detected in the neovascular regions of Ptc1-lacZ corneas treated with Shh (data not presented here). Histologic analysis following paraffin embedding of X-gal-stained corneas and preparation of immunostained 5 um sections with showed that the X-gal positive cells were not endothelial cells or smooth muscle cells, but fibroblasts surrounding the neovessels. Endothelial cell immunostaining was done with a rat monoclonal antibody against mouse CD-31 (Pharmigen, San Diego, Calif.) followed by a biotinylated goat anti-rat immunoglobulin secondary antibody. Smooth muscle cells and pericytes were identified with a mouse monoclonal antibody against SM a-actin conjugated with alkaline-phosphatase (Sigma, St. Louis, Mo.) and fibroblasts were identified using an anti-vimentin antibody (Sigma, St. Louis, Mo.).

We then immunostained the Shh-induced corneas with a rabbit polyclonal anti-VEGF antibody (Santa Cruz Biotechnology, Santa Cruz, Calif.) with a biotinylated goat anti-rabbit immunoglobulin as secondary antibody. The results show that VEGF protein is in the fibroblasts and matrix immediately adjacent to the neovascular area. These results suggested that hedgehog may induce resident fibroblasts in the cornea to produce angiogenic factors such as VEGF.

Fibroblasts in vitro Respond to Hedgehog Stimulation by Upregulation of Ptc1 and Angiogenic Growth Factors To determine if hedgehog can directly induce fibroblasts to produce VEGF or other angiogenic factors, we treated normal human fibroblasts (CCD37) with Myr-Shh and the ability of fibroblasts to respond was evaluated by competitive RT-PCR for ptc 1 and several angiogenic growth factors. Total RNA was prepared from cells treated as described above using Trizol (Life Technologies, Rockville, Md.). Four micrograms of total RNA was used to prepare cDNA using the SuperScript™ preamplification system (Cat. No. 18089-011, Life Technologies, Rockville, Md.). The PCR reaction using buffer reagents from the SuperScript™ preamplification system (Life Technologies, Rockville, Md.) was quantitated with 20S rRNA competitive primers (Ambion). Primers for the amplification of Ptc 1 were 5'-TCAGGATGCATTTGA-CAGTGACTGG-3' (SEQ ID NO: 38) and 5'-ACTC-CGAGTCGGAGGAATCAGACCC-3' (SEQ ID NO: 39) which are based on ptc1 cDNA sequence (GenBank Accession Number U46155). All amplification for Ptc1 were done with 25 cycles of 94° C. for 30 sec; 55° C. for 1 min; 72° C. for 1 min. The cDNA from the same cells was also used as a template for VEGF, bFGF, Angiopoietin 1, and Angiopoietin II amplification. The following primer pairs and PCR cycles were used: VEGF: 5'CGAAGTGGTGAAGTTCATG-GATG3' (SEQ ID NO: 40) and 5'TTCTGTATCAGTCTTTC-CTGGTGAG3' (SEQ ID NO: 41) which are based on the human VEGF cDNA sequence (GenBank Accession Number E15157). VEGF product was amplified with 30 cycles of 94° C. for 30 sec; 62° C. for 1 min; 72° C. for 1 min; bFGF: 5'TACAACTTCAAGCAGAAGAG3' (SEQ ID NO: 42) and 5'CAGCTCTTAGCAGACATTGG3' (SEQ ID NO: 43) which is based on the human bFGF cDNA sequence (GenBank Accession Number M27968). bFGF product was amplified with with 25 cycles of 94° C. for 30 sec; 62° C. for 1 min; 72° C. for 1 min; Angiopoietin I 5'CAACA-CAAACGCTCTGCAGAGAGA3' (SEQ ID NO: 44) and 5'CTCCAGTTGCTGCTTCTGAAGGAC 3' (SEQ ID NO: 45) which is based on human Angiopoietin I cDNA sequence (GenBank Accession Number U83508). Angiopoietin I product was amplified with 25 cycles of 94° C. for 30 sec; 64° C. for 90 sec; Angiopoietin II: 5'AGCGACGTGAGGATG-GCAGCGTT3' (SEQ ID NO:46) and 5'ATTTCCTGGTTG-GCTGATGCTGCTT3' (SEQ ID NO: 47) which are based on human Angiopoietin II cDNA sequence (GenBank Accesion Number AB009865). Angiopoietin II product was amplified with with 32 cycles of 94° C. for 30 sec; 64° C. for 90 sec. As internal control for sample preparation, gel loading, and random variations in RT-PCR, 18S rRNA primers and 18S rRNA competimers (Ambion, Austin, Tex.), used to modify 18S cDNA amplification efficiency, were included in each PCR reaction with target gene-specific primers. The linear range of amplification and optimal 18S primer/Competimer ratio was determined for each target gene following the manufacturer's recommendations (Ambion, Austin, Tex.).

A time course of Shh induction shows that human fibroblast respond to Shh by upregulating the Ptc1 gene (data not shown) indicating that these cells can respond via the known Hh signalling pathway. Neither human umbilical vein and microvascular endothelial cells respond to Hh (data not shown).

We next found that Hh can upregulate fibroblast expression of angiogenic growth factors, including VEGF, bFGF, Ang-1, and Ang-2 (data not shown). VEGF mRNA from human fibroblasts was significantly increased by Shh: all the three VEGF isoforms (VEGF121, 165, and 189) were strongly upregulated. VEGF 121, 165, and 189 upregulation began at 12 hours and was maximal after 48 hours of incubation of the cells with Shh. No bFGF upregulation was detectable at any time-points. Moreover, quantitative RT-PCR for Ang-1 and Ang-2 showed upregulation of both genes, with maximal increase after 36 hours stimulation. To show that the upregulation of VEGF mRNA correlated with an increase in protein production, the concentration of VEGF165 in cell media was measured by ELISA. Cells were stimulated with recombinant human myristolated Shh protein as described above. At harvest, the cell conditioned media was collected, centrifuged to remove cell debris (15 minutes at 1500×g) and production of VEGF165 protein was evaluated by using an ELISA kit (Quantikine human VEGF, R&D Systems, Minneapolis, Minn.). Total VEGF protein level underwent a progressive increase following Hh stimulation and a significant upregulation in the VEGF production was detectable at 72 hours (data not shown).

Smooth Muscle Cells Upregulate ptc1 and are induced to Proliferate in vitro in Response to Hedgehog We found that smooth muscle cells can also respond to Hh proteins in vitro. Eighty five percent confluent monolayers of vascular smooth muscle cells (PAC 1) were induced for 2 days with 1 ug/ml of myrShh or an equivalent volume of vehicle in normal media (M 199 complete media with 10% fetal bovine serum). For comparison, primary normal human lung fibroblasts and normal prostate stromal cells were grown in complete FBM and similarly stimulated (Clonetics/Bio-Whittaker, Walkersville, Md.). The cells were harvested and RNA from the cells was prepared and analysed by RT-PCR as above. All of these cells showed increased ptc 1 expression following induction with myrShh, but not myrShh vehicle alone suggesting that each of these cell types are responsive to hedgehog (data not shown). In addition, hedgehog protein induced DNA synthesis in quiescent vascular SMCs and human fibroblasts. PAC-1 (Rothman et al., 1992), WKY (Lemire et al., 1994), primary pulmonary artery SMCs or aortic SMCs (Clonetics/Bio-Whittaker, Walkersville, Md.) were plated (5×103/well) in 96 well plates and allowed to adhere for 2-3 hours in 0.18 ml of complete media (M 199 with 10% fetal bovine serum for PAC 1 cells, DMEM with 10% fetal bovine serum for WKY cells or smGM-2 for primary human pulmonary artery or aortic SMCs). The cells were then starved for 18-24 hours in complete media with 0.5% fetal bovine serum. Quiescent cells were stimulated with 0.1 to 40 ug/ml of Hh proteins in 0.2 ml starvation media for 48 hours after which the cells were pulse labeled with 4.5 uCi/ml 3H-thymidine (Amersham,) for 4-8 hours at 37° C. The media was then removed, the cells washed with PBS then trypsinized. 3H-thymidine uptake into cells was determined by scintillation counting using a 1205 Betaplate counter (Wallac, Gaithersburg, Md.). Vascular SMCs showed increased 3H-thymidine uptake 3 to 4-fold when induced by either myrShh (myristylated Sonic hedgehog) Dhh or basic FGF (obtained from Upstate Biotechnology, Lake Placid, N.Y.).

These results show that both SMCs and fibroblasts respond to hedgehog. Although no smooth muscle cells were found in the, hedgehog-stimulated corneas (see Example 1 and 4), the responsiveness of SMCs to Hh in vitro correlates well to normal ptc1 expression and increased ptc1 in the response by normal vascular SMCs to systemically administered Hh protein (See Example 3).

EXAMPLE 5

Hedgehog Improves Recovery from Ischemic Limb Injury

Peripheral vascular disease caused by atherosclerosis and/or diabetes can be modeled in rodents and rabbits by surgical ligation of the femoral artery and removal of a segment of the artery distal to the ligation (Takeshita et al., 1994 and 1996; Rivard et al., 1999; Couffinhal et al., 1999). The limb ischemia produced by the ligation also results in limb neuropathy (Schratzberger et al., 2000). Ischemic injury of healthy animals and humans activates a number of pathways which subsequently induce the regeneration and recovery of the damaged tissue. For example, VEGF is induced in response to hindlimb ischemia and can accelerate recovery when given pharmacologically following this ischemic insult (Schratzberger et al., 2000). We investigated the possibility that the hedgehog pathway is activated in response to limb ischemia in normal animals and is beneficial both in the endogenous and pharmacological settings to revascularization and recovery from ischemic neuropathy.

The expression of ptc1 following hindlimb ischemia was investigated in 3-4 month old Ptc1-lacZ mice (Rivard et al., 1999). The mice were anesthetized with pentobarbital (160 mg/kg i.p.) and an incision was made in the skin overlying the middle portion of the left hindlimb. Both the proximal end of the femoral artery and the distal portion of the saphenous artery were ligated and the artery and all side branches were dissected free and excised. The skin was closed with a surgical stapler and the animals were allowed to recover. The mice were either left untreated or injected daily or every other day i.m. in the ischemic limb with 1 mg/kg of Il-Shh/mouse IgGl Fc fusion protein. Seven days after induction of ischemia, the animals were sacrificed and the upper hindlimb was isolated and whole mount stained with Xgal. Comparison of the contralateral upper hindlimbs (right) to the ischemic hindlimbs (left) shows a significant upregulation of ptc1 expression (data not shown). Ischemia alone induced upregulation of ptc1 expression in the ischemic limb and increasing frequency of hedgehog injection further increased ptc1 expression in the ischemic limb muscle. Histological sections of the ischemic and control hindlimb muscle showed muscle fiber degeneration and edema in the ischemic versus nonischemic tissue (data not shown). In addition, the ischemic muscle has a number of ptc1-expressing (Xgal-stained) stromal cells in the interstitial areas between the muscle fibers. These cells which appear to be responding to hedgehog were shown to be fibroblasts identified by costaining with vimentin and X-gal or monocytes/macrophages identified by costaining with the moma2 antibody and X-gal (see Example 4 for Methods). These results show that the hedgehog pathway may be part of the normal response to ischemia which may be augmented by pharmacological administration of hedgehog protein.

The relevance of hedgehog upregulation following ischemia is determined by inhibiting hedgehog action with a blocking antibody to hedgehog. Unilateral hindlimb ischemia was induced in normal mice (C57BL6, 3-4 months of age, female). The mice are treated with 10 mg/kg daily 3 days prior to ischemia and 2.5-5 mg/kg every 3 days following ischemia for 3 weeks with either the blocking antibody to hedgehog, 5E1, or an isotype matched control mouse monoclonal antibody.

The vascular perfusion of the ischemic vs contralateral limb is assessed at days 4, 7, 14, 21 and 28 days by lasar doppler (Lisca, Inc. laser Doppler perfusion imager system) (Rivard et al., 1999). Nerve vascular perfusion is determined by exposing the sciatic nerve and scanning the nerve surface area using lasar doppler or by injection of Fluoresceinated-BS 1 lectin (Vector Laboratories, Burlingame, Calif.) 30 minutes prior to sacrifice and visualizing the vaso nervorum by whole mount fluorescence microscopy postmortem (as described above). Vascular density is assessed at these times by histological staining for CD31 positive vasculature in sections (anti-murine CD31, Pharmingen, San Diego, Calif.) (Rivard et al., 1999). Neuropathy is assessed at these time points by nerve conduction measurements of the sciatic/peroneal nerves using standard orthodromic surface recording techniques and a Teca TD-10 portable recording system (Oxford Instruments, Concord, Mass.). Angiogenesis as measured both by vascular perfusion or vascular density is decreased in ischemic limbs of animals treated with hedgehog blocking antibody, 5E1, compared to ones treated with the isotype matched control, 1E6. Nerve conduction measurements are also decreased in 5E1-treated mice compared to control antibody-treated mice. Finally, nerve vascular perfusion is decreased in the 5E1-treated mice. These results suggest that the upregulation of the hedgehog pathway following ischemia is a beneficial compensatory response to ischemic injury.

The utility of treating ischemia by activating the hedgehog pathway is tested in aged mice (>2 yrs old) or apoE null mice with surgically induced limb ischemia since these mice are deficient in their repair and regeneration processes following limb ischemia. These mice are made ischemic then injected (i.v., i.p., s.c. or i.m.) with doses ranging from 0-10mg/kg of hedgehog protein or equivalent volumes of vehicle control or control protein beginning on the day of surgery and with a frequency of daily to 3 times per week. The vascular perfusion, vascular density and neuronal conduction and neuronal vascularity (vaso nervorum) of the ischemic vs contralateral limb are assessed at days 4, 7, 14, 21 and 28 postsurgery as described above. The results show that hedgehog-treated animals show significant improvements in vascular perfusion, vascular density as well as motor nerve conduction and their vaso nervorum compared to control treated animals (data not presented).

Hedgehog can also be delivered using gene therapy. Either full length or soluble Nterminal Shh adenovirus ($10^6$ to $101^{10}$ particles) is injected i.m. at day 1 postinjury in the inguinal area of the upper hindlimb following surgery. Alternatively, the full length or soluble n-terminal Shh adenoassociated virus (AAV) or a control LacZ AAV is administered 4 weeks prior to surgery. Similar doses of adenovirus containing full length or n-terminal Shh or LacZ containing control adenovirus can be administered in place of AAV-Shh. Above endpoints for vascular and motor neuron conduction improvements are also seen with viral gene therapy.

Together these results show that the hedgehog pathway is a crucial component of the normal angiogenic response, tissue regeneration and recovery from ischemia injury and that hedgehog proteins can induce angiogenesis and improve recovery from ischemia when used pharmacologically.

EXAMPLE 6

Hedgehog Induces Collateral Vessel formation and Improved Myocardial Function following Surgically Induced Myocardial Ischemia Chronic myocardial ischemia and collateral vessel formation can be modeled in pigs through the placement of an ameroid constrictor around the left circumflex coronary artery. Treatment of these ischemic hearts with angiogenic proteins can increase myocardial vascularity, perfusion and function in the ischemic area as well as overall heart function. We determine that hedgehog protein or gene therapy can also improve these measures of cardiac perfusion, viability and function following ischemia in the following experiments.

Ameroid constrictors are placed around the left circumflex coronary artery (LCX) of anesthetized Yorkshire pigs (5-6 weeks old, 15-18 kg, male or female) (Laham et al., 2000; Harada et al., 1994; Unger et al., 1994). The animals are allowed to recover for 3 weeks to allow time for ameroid closure. Either immediately after or 3 weeks post-ameroid placement, the animals are randomized into one of several groups (10 animals/group). Hedgehog or control is administered by one of the following routes:

1. direct injection of ischemic myocardium with hedgehog or saline
2. intrapericardial administration of hedgehog protein or saline
3. systemic administration of hedgehog protein or saline (s.c., i.m. or i.v. injection)
4. myocardial injection of hedgehog in (0.1-5 mg) heparin or heparin alone following thoracotomy or via an injection catheter (Cordis-Webster)
5. intrapericardial injection of hedgehog in (0.1-5 mg) heparin
6. intracoronary catheter delivery device
7. viral gene therapy via above methods using $10^6$-$10^{12}$ Particles of full length or n-terminal Shh adenovirus in a single or several bolus injections (0.1 ml-1 ml/injection). Heart muscle perfusion and function are monitored using several techniques immediately prior to the Hedgehog treatments and 2-4 weeks post-Hedgehog treatments. Coronary perfusion was determined by right and left coronary angiography.

To obtain a collateral index, left to left and right to left coronary collaterals are measured. Regional resting myocardial blood flow is measured using colored microspheres. Magnetic resonance imaging of wall thickening is used to determine global ventricular, ischemic/normal regional function and myocardial perfusion. Electromechanical left ventricular mapping is done using the NOGA system (Biosense, Johnson&Johnson, Warren, N.J.) to determine localized heart function (Vale et al., 1999, Kornowski, Hong and Leon, 1998). In addition, complete autopsies and histopathology is done on each animal for coronary tissues (pericardium, epicardial coronary artery, myocardium in the left anterior descending artery distribution (normal tissue), left circumflex artery distribution, (ischemic tissue) and peripheral organs (gastrointestinal tract, lung, liver, kidney, bone, bone marrow)). Improvements in heart muscle perfusion and function as well as histological analysis of coronary tissue vascularization are assessed. Hedgehog treatments can show improvement in these parameters when compared to control treatments suggesting therapeutic utility for hedgehog treatments in myocardial infarction and coronary artery disease.

EXAMPLE 7

Inhibition of Hedgehog (Anti-Hedgehog Blocking Antibody) Decreases Tumor Growth Rate and/or Tumor Angiogenesis To determine if tumor cell lines overexpress hedgehog protein, anti-hedgehog antibody was used to immunoprecipitate cell lysates of various tumor cell lines. We used gastrointestinal epithelial cell lines as an example: T84 (human colon epithelial carcinoma, CCL-284, ATCC, Manassas, Va.); Caco2 and SW480 (human colon epithelial adenocarcinomas, HTB-37 and CCL-228, ATCC, Manassas, Va.). Briefly, one milligram amounts of cell lysis supernatant were immunoprecipitated with either anti-hedgehog antibody, 5E1 (+) or an isotype matched control antibody, 9E10 (C). The immunoprecipitated samples were analysed by western blotting with an anti-hedgehog rabbit polyclonal antibody, r1200.

More specifically, confluent monolayers of each cell line in T150 flasks were lysed in 3 mL of cold lysis buffer (1% Triton X-100, 0.5% sodium deoxycholate, 0.% SDS, 150 mM NaCl, 1 mM sodium vanadate, 10% glycerol, lOmM Tris-HCL, pH 8.0) containing a 2× concentration of Complete protease inhibitor cocktail (Boehringer Mannheim, Indianapolis, Ind.). The lysate was rocked for 30' at 4° C. then scraped into a microfuge tube and debris pelleted in a microfuge for 10'. The supernatant was stored at −80° C. Protein concentration of the supernatants were determined using Bio-Rad Protein Assay reagent and equivalent milligram amounts of supernatant were used for each immunoprecipitation. Each sample was gently agitated overnight at 4° C. with 2.5 ug of either anti-hedgehog antibody, 5E1, or an isotype matched control antibody, 9E 10 (anti-human c-myc, Calbiochem, San Diego, Calif.) (Fan et al., 1998). Protein A conjugated Sepharose beads (30 microliters packed beads/sample) were added to each sample and the samples were gently agitated at 4° C. for 30-40 minutes. The beads and associated immune complexes were then spun down in a microfuge for 10 seconds and washed 4 times with 1 ml of ice cold lysis buffer. The buffer was then removed from the beads, reducing SDS-PAGE sample buffer was added, the samples were heated to 90° C. for 5 minutes then analyzed by SDS-PAGE (4-20% Tris-glycine gels, Novex, San Diego, Calif.). The proteins were transferred to nitrocellulose filters and western blot analysis was performed at room temperature.

The nitrocellulose filters was incubated with blocking solution (5% dry milk in Tris-buffered saline with 0.3% Tween-20) for 1 hour followed by blocking solution containing a 1:10,000 dilution of anti-hedgehog rabbit polyclonal, r1200, for 2-3 hours at room temperature or overnight incubation at 4° C. The nitrocellulose filters were washed 3 times with Tris-buffered saline with 0.3% Tween-20; incubated for 1 hour in 1:5000 dilution of horseradish peroxidase-conjugated goat anti-rabbit antibody (Jackson Immunoresearch) then visualized using ECL western blotting detection reagents (Amersham Pharmacia Biotech).

Hedgehog protein is overexpressed in several human gastrointestinal tumor cell lines compared to normal human gastrointestinal epithelial cells or fibroblasts (data not shown). The anti-hedgehog antibody immunoprecipitations show a hedgehog rabbit polyclonal antibody-reactive band at 19 kD, the expected molecular weight for hedgehog protein. The control antibody (9E10) immunoprecipitation shows no hedgehog polyclonal antibody-reactive band comigrating with hedgehog protein standard at 19 kD. Normal gastrointestinal epithelial also express a low level of hedgehog protein, but normal gastrointestinal fibroblasts do not show any expression. None of the epithelial cell lines tested respond to hedgehog (data not shown), but the hedgehog produced by these tumor cells may activate angiogenesis via induction of stromal tissue in the tumor.

The ability of hedgehog-blocking or hedgehog pathway-blocking reagents such as the anti-hedgehog blocking antibodies (SE1, ARG6, ALC9 or BH.E4) to inhibit tumor angiogenesis and tumor growth are determined in subcutaneously-implanted tumor models in athymic Swiss (Cr:NIH(S)-nu) or athymic random bred (NCr-nu) mice of a single sex (males >18 g or females >17 g, all within a 4 g weight range). Carcinoma cell lines of gastrointestinal origin such as SW480, HT29 or T84 are passaged in nude mice as subcutaneous tumors or are passsaged in culture as cell monolayers. Either $2\times10^6$ cells or tumor 20-40 mg fragments of a passaged tumor are implanted subcutaneously in the axillary region of 6-10 athymic mice. Tumors were monitored frequently for progressive growth. Treatments are initiated when individual tumors range between 100 mg-700 mg. Mice are randomized into test and vehicle control groups and treated with either hedgehog blocking antibodies, control isotype-matched antibody, no treatement or cisplatinum. Antibodies were administered (25-100 mg/kg bolus i.p. injections) at a frequency of every day to 3 times a week for the follow-up period. Cisplatinum was administered subcutaneously three times a week (2 mg/kg). Body weights and tumor measurements (width and length) are recorded at 3-5 day intervals following treatment for 7-21 days. Tumors are collected on the final day for histological analysis. Mean tumor weight change and/or mean vascular density are decreased in the hedgehog blocking antibody-treated group compared to the control antibody-treated group. In addition, hedgehog blocking antibodies may be administered prior to tumor implantation and tumor growth rate is monitored as described to determine if early tumor growth rates are decreased by blocking hedgehog signalling.

EXAMPLE 8

Gli-1 Expression in Human Tumors

Hedgehog Pathway Activation in Human Tumors

Hedgehog signaling plays a causative role in the generation of basal cell carcinoma (BCC). Hedgehog signaling was analyzed to determine whether this pathway is active in other human tumors, more specifically prostate, lung and breast cancer, as well as benign prostate hyperplasia. Hedgehog proteins are known proliferative agents for a variety of cell types. Since hedgehogs have a known proliferative effect on a variety of cell types, hedgehog antagonists may be valuable therapeutics for cancers in which high level hedgehog signaling is present.

The question of hedgehog activation in the tumor types was addressed by conducting radioactive in situ hybridization experiments with gli-1, a known transcriptional effector gene of hedgehog signaling.

Briefly, sections of paraformaldehyde-fixed, paraffin-embedded tissue were cleared, re-hydrated, digested with proteinase K, acetylated and hybridized with [33P]-labeled RNA probes over night. After high stringency post-hybridization washes, slides were dipped in photo-emulsion, incubated for up to three weeks, developed, and imaged using dark field illumination. Dark-field signals were filled in with artificial color (red) and superimposed with bright-field images. Gli-1 expression was graded on a scale from "−" to "+" through "++++". Gli-1 expression was rated "−" when expression was no higher in hyperproliferative cells than in other non-proliferative cells present in the slide. Ratings of "+" through "++++" were given for increased expression levels, with any cell rated "++" or above considered to have substantially increased gli-1 expression. When the signal was not interpretable, a sample is indicated as "ND".

The data for these experiments are summarized in table 1-4 below. In brief, 8 out of 18 breast cancer samples showed substantially increased gli-1 expression. 7 out of 11 lung cancer samples, 11 of 19 benign prostatic hypertrophy samples (BPH), and 6 of 15 prostate cancer samples all showed strong gli-1 expression.

TABLE 1

Results of Gli-1 in situ hybridization in breast cancer tissue

| Tissue | Diagnosis | Sample Number | Age/Sex | Signal |
|---|---|---|---|---|
| Breast | Inf Ductal Carcinoma | 1 | 93F | ND |
| Breast | Inf Ductal Carcinoma | 2 | 37F | +++ |
| Breast | Inf Ductal Carcinoma | 3 | 54F | + |
| Breast | Inf Ductal Carcinoma | 4 | 39F | ++ |
| Breast | Inf Ductal Carcinoma | 5 | 73F | +++ |
| Breast | Inf Ductal Carcinoma | 6 | 65F | ++++ |
| Breast | Inf Ductal Carcinoma | 7 | 58F | ND |
| Breast | Inf Ductal Carcinoma | 8 | 48F | + |
| Breast | Inf Ductal Carcinoma | 9 | 27F | ++ |
| Breast | Inf Ductal Carcinoma | 10 | NA | +++ |
| Breast | Inf Ductal Carcinoma | 11 | 34F | + |
| Breast | Inf Lobular Carcinoma | 12 | 46F | + |
| Breast | Inf Lobular Carcinoma | 13 | F | − |
| Breast | Inf Lobular Carcinoma | 14 | 56F | + |
| Breast | Inf Lobular Carcinoma | 15 | 70F | − |
| Breast | Intraductal Carcinoma | 16 | 40F | +++ |
| Breast | Intraductal Carcinoma | 17 | 55F | +++ |
| Breast | Medullary Carcinoma | 18 | NA | + |
| Breast | Tubular Carcinoma | 19 | 75F | − |
| Breast | Tubular Carcinoma | 20 | 60F | − |

TABLE 2

Results of Gli-1 in situ hybridization in lung cancer tissue

| Tissue | Diagnosis | Sample Number | Age/Sex | Signal |
|---|---|---|---|---|
| Lung | Adenocarcinoma | 1 | 54F | +++++ |
| Lung | Adenocarcinoma | 2 | 61M | ND |
| Lung | Adenocarcinoma | 3 | 61F | ++++ |
| Lung | Adenocarcinoma | 4 | 58F | +++ |
| Lung | Adenocarcinoma | 5 | 77M | ND |
| Lung | Adenocarcinoma | 6 | 65M | ++ |
| Lung | Adenocarcinoma | 7 | 73M | ND |
| Lung | Adenocarcinoma | 8 | 69M | ND |
| Lung | Adenocarcinoma | 9 | 82M | ND |
| Lung | Adenocarcinoma | 10 | NA | − |
| Lung | Adenocarcinoma | 11 | F | ND |
| Lung | Adenocarcinoma | 12 | 56F | + |
| Lung | Broncho-alveolar adenocar | 13 | 70F | + |
| Lung | Broncho-alveolar adenocar | 14 | 76F | − |
| Lung | Small Cell Carcinoma | 15 | 68M | ++ |
| Lung | Small Cell Carcinoma | 16 | 61M | ND |
| Lung | Small Cell Carcinoma | 17 | 70M | +++++ |
| Lung | Small Cell Carcinoma | 18 | NA | ND |
| Lung | SCC | 19 | 60F | ND |
| Lung | SCC | 20 | 63M | +++++ |

TABLE 3

Results of Gli-1 in situ hybridization in benign prostate hyperplasia

| Tissue | Diagnosis | Sample Number | Age/Sex | Signal |
|---|---|---|---|---|
| Prostate | BPH | 1 | 65M | + |
| Prostate | BPH | 2 | 86M | ++++ |
| Prostate | BPH | 3 | 53M | + |
| Prostate | BPH | 4 | 65M | ++++ |
| Prostate | BPH | 5 | 68M | ++ |
| Prostate | BPH | 6 | 70M | ++ |
| Prostate | BPH | 7 | 54M | − |
| Prostate | BPH | 8 | M | ++ |
| Prostate | BPH | 9 | 69M | − |
| Prostate | BPH | 10 | M | − |
| Prostate | BPH | 11 | 73M | +++ |
| Prostate | BPH | 12 | 53M | ++++ |
| Prostate | BPH | 13 | 84M | − |
| Prostate | BPH | 14 | 67M | − |
| Prostate | BPH | 15 | 66M | ++ |
| Prostate | BPH | 16 | 69M | ++ |
| Prostate | BPH | 17 | 72M | ++++ |
| Prostate | BPH | 18 | M | ++ |
| Prostate | BPH | 19 | 60M | − |
| Prostate | BPH | 20 | 60M | − |

TABLE 4

Results of Gli-1 in situ hybridization in prostate cancer tissue

| Tissue | Diagnosis | Sample Number | Age/Sex | Signal |
|---|---|---|---|---|
| Prostate | Adenocarcinoma | 1 | 79M | + |
| Prostate | Adenocarcinoma | 2 | 72M | + |
| Prostate | BPH next to Adenocarcinoma | 3 | 81M | ND |
| Prostate | Adenocarcinoma | 4 | 79M | ++ |
| Prostate | Adenocarcinoma | 5 | 81M | ND |
| Prostate | Adenocarcinoma | 6 | 73M | − |
| Prostate | Adenocarcinoma | 7 | 79M | ++ |
| Prostate | Adenocarcinoma | 8 | M | +++ |
| Prostate | Adenocarcinoma | 9 | 69M | ND |
| Prostate | Adenocarcinoma | 10 | 53M | +++ |
| Prostate | Adenocarcinoma | 11 | 65M | + |
| Prostate | Adenocarcinoma | 12 | 60M | ++ |
| Prostate | Adenocarcinoma | 13 | 66M | ND |
| Prostate | Adenocarcinoma | 14 | 66M | + |
| Prostate | Adenocarcinoma | 15 | 92M | − |
| Prostate | Adenocarcinoma | 16 | 80M | − |
| Prostate | Adenocarcinoma | 17 | 78M | ND |
| Prostate | Adenocarcinoma | 18 | 85M | − |
| Prostate | Adenocarcinoma | 19 | 78M | − |
| Prostate | Adenocarcinoma | 20 | 93M | +++ |

In summary, high level Gli-1 expression, i.e., hedgehog signaling activation, can be observed in human prostate cancer and benign prostatic hyperplasia, lung cancer and breast cancer (FIGS. 3-6). Hedgehog pathway activation in these tumor types has never before been described. The presence of an exceptionally active hedgehog pathway in these proliferating cells strongly suggests a causal link between the hedgehog pathway and hyperproliferation in these disorders. It is expected that hedgehog antagonists will be effective as antiproliferative agents in these cancer types.

EXAMPLE 9

Steroidal Hedgehog Antagonists

Studies were performed to determine the site in the hedgehog signaling pathway at which cyclopamine (an alkaloid steroidal hedgehog antagonist) operates, and therefore better understand the spectrum of tumors caused by Shh pathway-activating lesions that could potentially be treated with this compound. These studies are presented in greater detail in U.S. patent application Beachy et al. entitled "Hedgehog signaling pathways, compositions and uses related thereto" filed Oct. 10, 2000, the contents of which are herein incorporated by reference.

These studies involve the use of mouse embryonic fibroblasts (MEFs) that were generated by trypsin digestion of E8.5 embryos from patched (ptc) ±matings. The mouse ptc gene was disrupted by homologous recombination in which part of exon 1 and all of exon 2 were replaced with the bacterial lacZ gene (Goodrich et al, (1997) *Science* 277: 1109). As Ptc protein suppresses Shh signaling, a loss of its function activates the Shh signaling pathway. Shh signaling, through a cascade of events, is mediated by the Gli transcription factors. One of the target genes of Shh signaling is ptc, through Gli-binding sites in the ptc promoter region, and this serves as a feedback mechanism for down regulation of signaling. Thus, in these ptc-/- embryos, the Shh signaling pathway is activated in many tissues, and the lacZ gene product β-galactosidase is expressed in all of those tissues as a report of pathway activation.

These MEFs were obtained to determine whether cyclopamine acts on Ptc or another component of the cascade to inhibit Shh signaling. If the target of cyclopamine is Ptc, then one would expect that when the Shh pathway is activated by the loss of ptc function, it could no longer be inhibited by cyclopamine. The Shh signaling pathway can be activated in these fibroblasts in cell culture, and that the level of β-galactosidase activity does reflect the degree of pathway activation. The MEF line 23-4 is heterozygous for ptc-lacZ, and thus contains one functional ptc allele capable of maintaining a repressed state of the pathway, but will express lacZ when the pathway is activated by addition of Shh protein.

In contrast, the β-galactosidase activity in MEFs homozygous for ptc-lacZ, (cell line 23-1) is markedly elevated, because in these cells the pathway is constitutively activated by the loss of a functional ptc allele. When these cells are cultured with cyclopamine, β-galactosidase activity is decreased, indicating that when the Shh signaling pathway is unregulated by Ptc repression, it is still sensitive to cyclopamine inhibition. The reduction of β-galactosidase activity appears to result from the specific inhibition of Shh signaling, rather than from cell toxicity because enzymatic activity is normalized to whole protein content of the sample. Also, the reduction of β-galactosidase activity can be obtained with exposure to cyclopamine over a period of time that is shorter than the average cell cycle, and so does not appear to be due solely to an inhibition of cell proliferation.

A final indication that this represents specific inhibition of Shh signaling is that it cannot be achieved with a non-inhibitory, but structurally related compound tomatidine.

EXAMPLE 10

Lead Compound Discovery/High-throughput Screening Assay

The methodologies described herein can be used to identify a wide assortment of small molecule hedgehog antagonists.

Compounds to be tested are dissolved in DMSO to a concentration of 10 mM, and stored at −20° C. To activate the Hedgehog pathway in the assay cells, an octylated (lipid-modified) form of the N-terminal fragment of the Sonic Hedgehog protein (OCT-SHH) is used. This N-terminal SHH fragment is produced bacterially.

Compounds may be tested in the "Gli-Luc" assay below, using the cell line 10T(s12), wherein the cells contain a Hedgehog-responsive reporter construct utilizing Luciferase as the reporter gene. In this way, Hedgehog pathway signaling activity can be measured via the Gli-Luc response.

10t1/2(s12) cells are plated in a 96-well micro-titer plate (MTP) at 20,000 cells/well in full medium [DMEM with 10% FBS]. Then plates are placed in the incubator for incubation overnight (O/N), at 37° C. and 5% $CO_2$. After 24 h, the medium is replaced with Luciferase-assay medium (DMEM with 0.5% FBS). Compounds are thawed and diluted in assay medium at 3:1000 (about 300-fold) resulting in a starting concentration of about 30 μM.

Subsequently, 150 μl of each 30 μM sample is added to the first wells (in triplicate). The MTP samples are then diluted at 3-fold dilutions to a total of seven wells, ultimately resulting in a regiment of seven dilutions in triplicate, for each compound. Next, the protein ligand OCT-SHH is diluted in Luciferase-assay medium and added to each well at a final concentration of 0.3 μg/ml. Plates are then returned to the incubator for further incubation O/N, at 37° C. and 5% $CO_2$. After about 24 h, plates are removed from the incubator and the medium is aspirated/discarded. Wells are washed once with assay buffer [PBS+1 mM $Mg^{2+}$ and 1 mM $Ca^{2+}$]. Then 50 μl of assay buffer is added to each well. The Luciferase assay reagent is prepared as described by the vendor (LucLite kit from Packard), and 50 μl is added to each well. Plates are incubated at room temperature (RT) for about 30 minutes after which the signals are read, again at RT, on a Topcount (Packard).

The discovery of compounds that inhibit Shh-induced Gli-transcription exemplifies the utility of the claims in this patent. Activities for these compounds are presented in Table 1 below.

TABLE 1

| Compound | $IC_{50}$ |
|---|---|
| 31 | <10 μM |
| 32 | <5 μM |
| 34 | <5 μM |
| 11 | <5 μM |
| 36 | <5 μM |
| 38 | <5 μM |
| 39 | <5 μM |
| 40 | <10 μM |
| 41 | <10 μM |
| 42 | <5 μM |
| 43 | <10 μM |
| 44 | <1 μM |

TABLE 1-continued

| Compound | IC$_{50}$ |
|---|---|
| 45 | <5 µM |
| 46 | <0.5 µM |
| 47 | <5 µM |
| 48 | <0.5 µM |
| 49 | <1 µM |
| 50 | <1 µM |
| 51 | <5 µM |
| 52 | <1 µM |
| 53 | <1 µM |
| 54 | <5 µM |
| 55 | <5 µM |
| 56 | <10 µM |
| 57 | <10 µM |
| 58 | <5 µM |
| 59 | <5 µM |
| 60 | <5 µM |
| 61 | <1 µM |
| 62 | <1 µM |
| 63 | <10 µM |
| 64 | <10 µM |
| 65 | <10 µM |
| 66 | <10 µM |
| 67 | <5 µM |
| 68 | <1 µM |
| 69 | <0.5 µM |
| 5 | <0.1 µM |
| 71 | <10 µM |
| 6 | <0.5 µM |
| 73 | <5 µM |
| 74 | <5 µM |
| 75 | <5 µM |

Mouse #456 is a Ptc-knockout heterozygote that received UV irradiation for 6 months. The mouse developed many small BCC lesions, which were blue after X-gal staining. The mouse was sacrificed and the skin was excised with a 2 mm skin punch. Those skin punches were then cultured for 6 days. Comparing to vehicle (DMSO), compound A can decrease the number and size of BCC lesions (blue spots in the picture). This experiment suggests that compound A is able to inhibit murine BCC lesions in mouse #456.

In yet another experiment, E12.5 old ptc-1 (d11) lacZ lungs were harvested and transgenic embryos identified by lacZ detection using tails. Lung explants were grown submerged in mouse explant medium (DMEM based, additives optimized for the culture of mouse lungs) for 48 hrs, fixed in lacZ fixative, rinsed and stained for lacZ O/N at 37° C. Control tissue was untreated, while test tissue was treated with compound A. Strong lacZ expression can be observed in distal and proximal mesenchyme. Treatment with compound A leads to significantly decreased reporter gene expression, as evidenced especially by the weak signal surrounding the distal branching tips of the growing lung epithelium.

EXAMPLE 11

Bladder Cancer

Cytogenetic and Mutational Data Suggest Hedgehog Activation Plays a Causative Role in Bladder Cancer The cytogenetic and molecular alterations found in bladder cancer are heterogeneous. In establishing the primary, specific mutations in cancers, it is often useful to examine near-diploid cancers, which do not yet have complex, multiple chromosome changes accompanied by hyperdiploidy. Gibas et al., found monosomy of chromosome 9 in 4 out of 9 cases of transitional cell carcinoma of the bladder (Gibas et al. (1984) *Cancer Research* 44:1257-1264). In three of these, the karyotype was near diploid, and in one, monosomy 9 was the only abnormality observed. Therefore, monosomy of chromosome 9 may initiate malignant transformation in a subgroup of such cancers.

More evidence that this change appears as an early event was presented by two other group who reported that deletions of chromosome 9 are the only genetic changes present frequently in superficial papillary tumors (Dalbagni et al. (1993) *Lancet* 342: 469-471). In fact, 9q deletions are estimated to occur in approximately 60-70 percent of bladder tumors (Cairns et al. (1992) *Oncogene* 8: 1083-1085; Dalbagni et al., supra). One study reported that deletion of 9q22 occurs in 35% of informative cases (Simoneau et al. 1999). The hedgehog signaling pathway component patched-1 is located on 9q22.

LOH of all other chromosomes is infrequent (less than 10%) in low-grade, non-invasive cancers. Likewise, alteration in bladder-cancer associated oncogenes (ERBB2, EGFR) are also rare in superficial, low-grade tumors (Cairns et al., supra).

On the basis of these cytogenetic findings, the following model for bladder carcinogenesis has been proposed: Initiation occurs by deletion of tumor-suppressor genes on chromosome 9, leading to superficial papillary or occasionally flat tumors, a few of which may then acquire further mutations (e.g., p53) and progress to invasion.

Three groups observed trisomy 7 in a low percentage of bladder cancers (Sandberg, supra; Berger et al. supra; Smeets et al., supra). Shh, which according to our own experiments continues to be expressed in bladder epithelium throughout adult life, localizes to chromosome 7. Berger et al. also observed deletions of 10q24, the locus of su(fu) (Berger et al (1986) *Cancer Genetics and Cytogenetics* 23: 1-24). Likewise, Smeets et al. suggested that 10q loss may be a primary event in the development of bladder cancer (Smeets et al. (1987) *Cancer Genetics and Cytogenetics* 29: 29-41).

This data suggests mechanisms by which the baseline expression of hedgehog signaling present in the adult bladder epithelium may be increased, thus leading to increased proliferation of urothelial cells. This hypothesis is supported by the cytological data, as well as by the finding of McGarvey et al. that described ptc-1, smo and gli-3 expression in normal human urothelium and two transitional cell carcinoma lines (McGarvey et al. (1998) *Oncogene* 17: 1167-1172).

Figure 7:
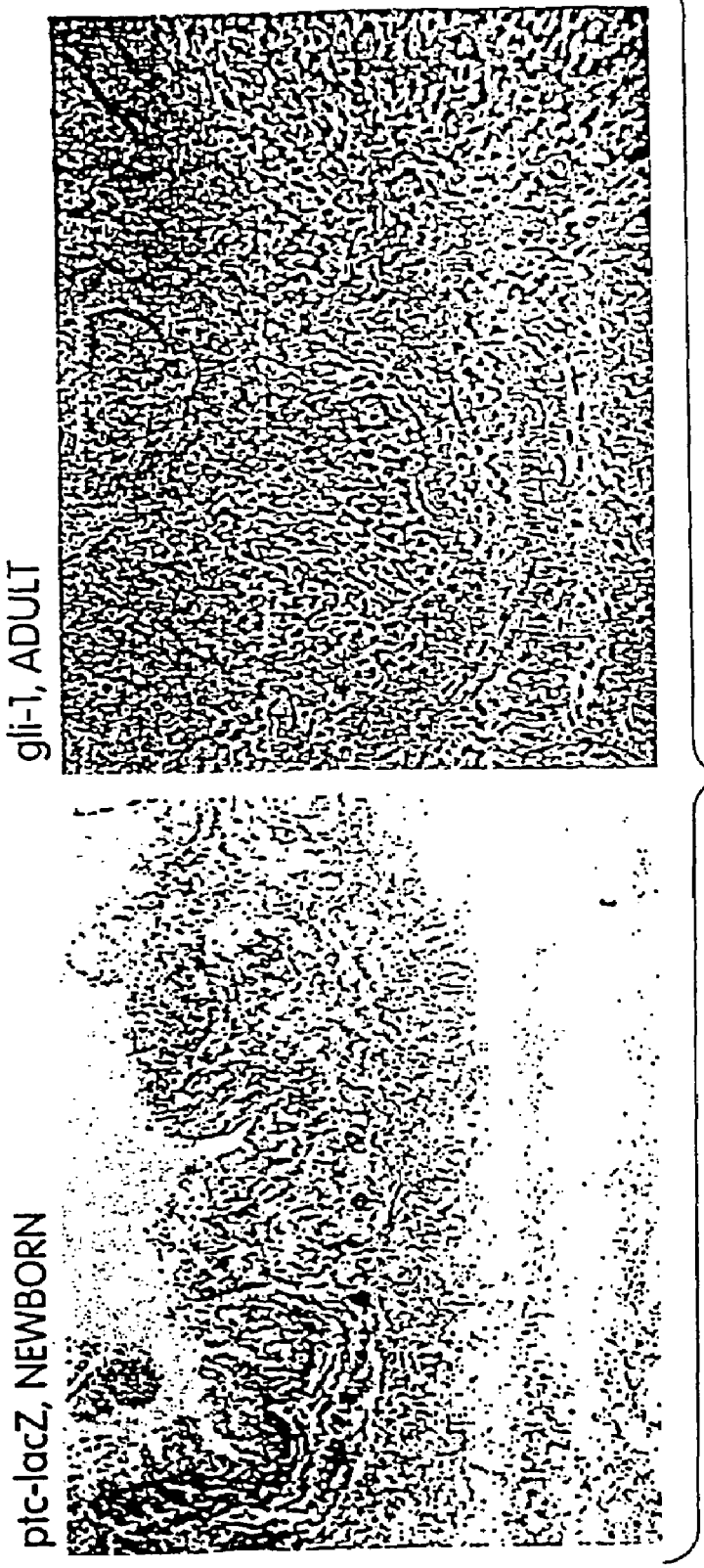
FIG. 7 shows (A) Ptc-lacZ transgene expression in newborn mouse ptc-1 (d11) lacZ bladder epithelium. LacZ expression can be detected in the proliferating urothelial cells and, more weakly, in adjacent mesenchymal cells. (B) Gli-1 expression in adult mouse bladder epithelium. Gli-1 expression can be detected in the proliferating urothelial cells.

Hedgehog signaling was examined in the mouse bladder, and found to be present in normal bladder. In Ptc-lacZ transgenic newborn mice (ptc-1 (d11) lacZ), LacZ expression can be detected in the proliferating urothelial cells of the bladder epithelium, and more weakly, in adjacent mesenchymal cells (FIG. 7A). Additional in situ hybridization analysis of adult mouse bladder indicates expression of gli-1 in the bladder epithelium, and specifically in the proliferating urothelial cells (FIG. 7B). METHODS: For lacZ staining, ptc-1 (d11) lacZ bladder was harvested from the transgenic newborn mouse pups identified by lacZ detection using tails. Bladders were fixed in lacZ fixative, rinsed and stained for lacZ O/N at 37° C., then processed for standard histology. Sections were counter-stained with eosin. For in situ hybridization, sections of paraformaldehyde-fixed, paraffin-embedded tissue were cleared, re-hydrated, digested with proteinase K, acetylated and hybridized with [33P]-labeled gli-1 RNA probe over night. After high stringency post-hybridization washes, slides were dipped in photo-emulsion, incubated for up to three weeks, developed, and imaged using dark field illumination. Dark-field signals were filled in with artificial color (red) and superimposed with bright-field images.

Hedgehog Signaling in Bladder Cancer

Hedgehog signaling and hedgehog pathway gene expression was analyzed in a human bladder cancer, and in several bladder cancer cell lines. Gene expression in these tissues was measured using Quantitative Real-Time PCR (Q-RT-PCR). These results are summarized in FIGS. 8-10, and demonstrate that hedgehog pathway genes are expressed in bladder cancer cell lines.

Figure 8:
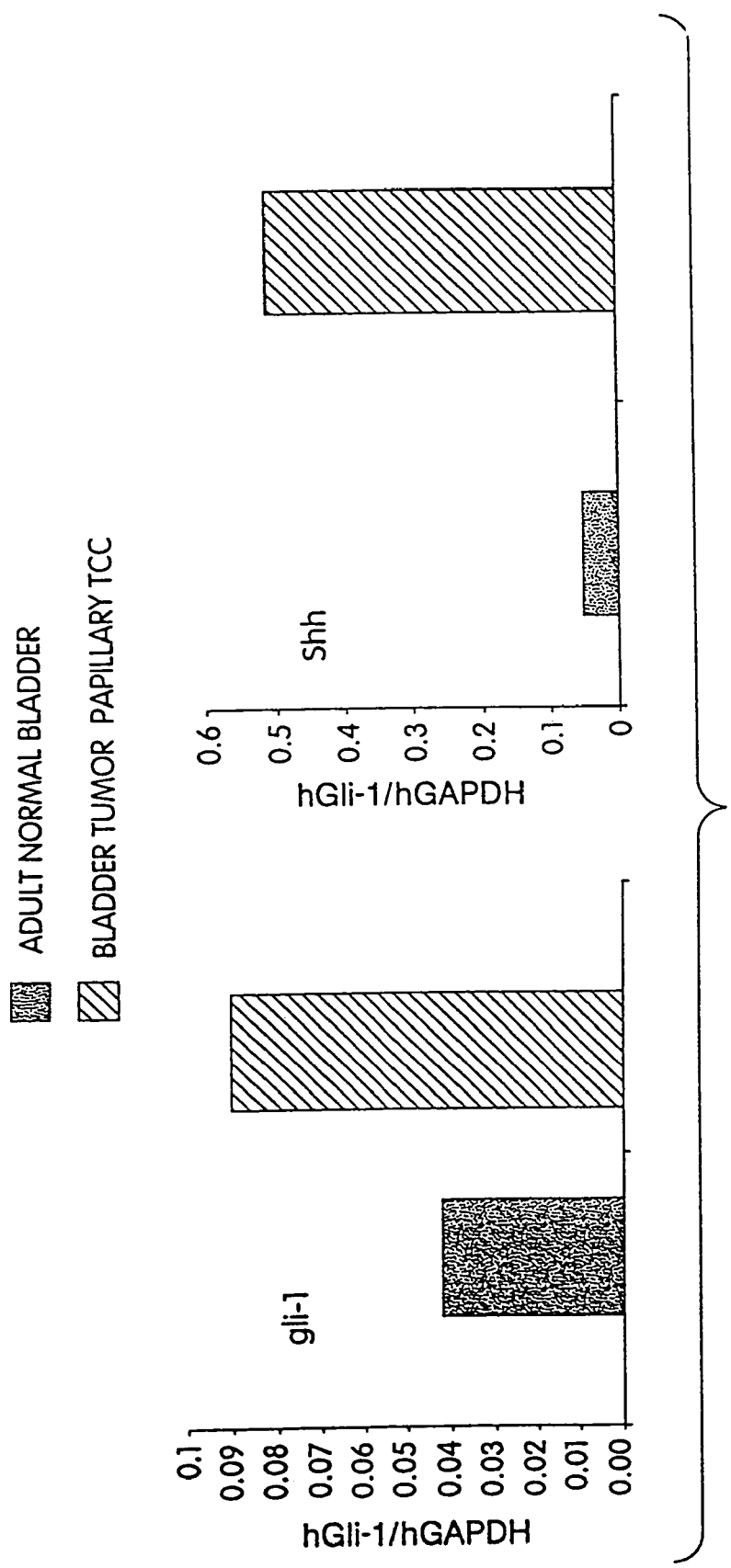
FIG. 8 shows the expression of gli-1 and shh in normal adult bladder and in a commercially available bladder tumor.
Figure 9:
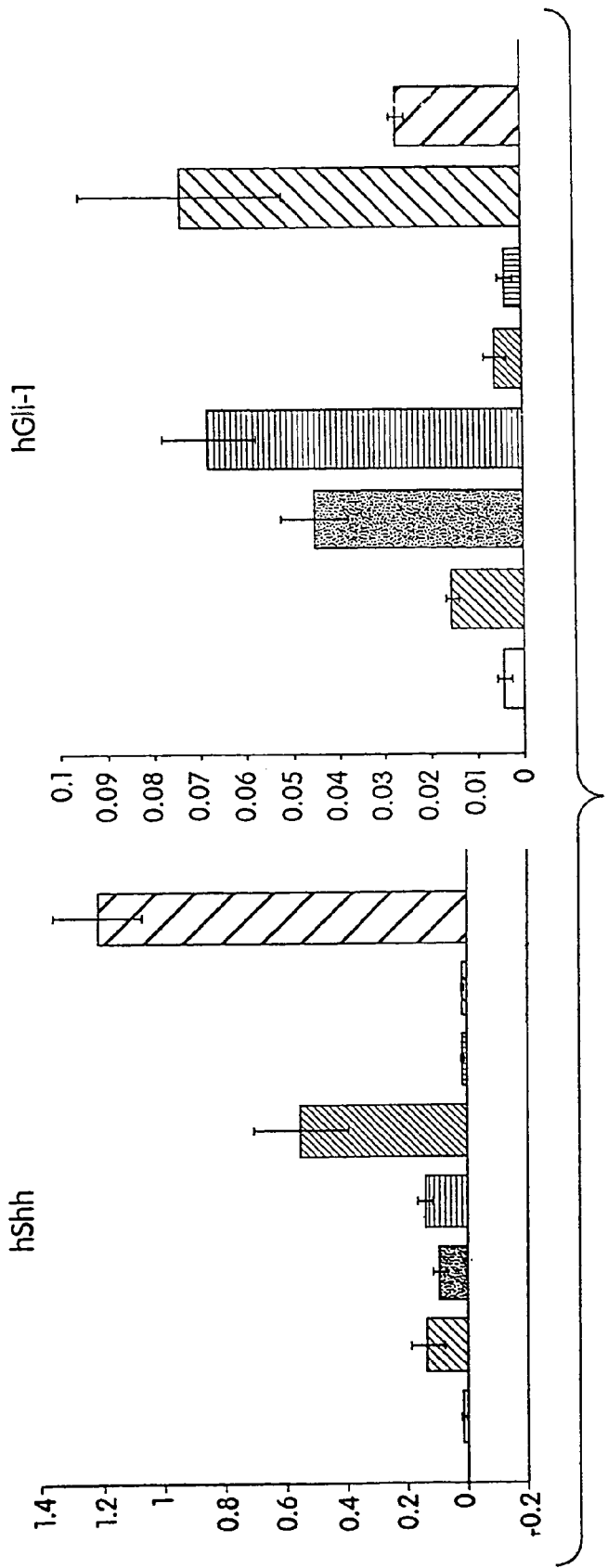
FIG. 9 shows the expression of shh and gli-1 in eight commercially available bladder cancer cell lines. All eight cell lines examined express genes involved in hedgehog signaling.
Figure 10:
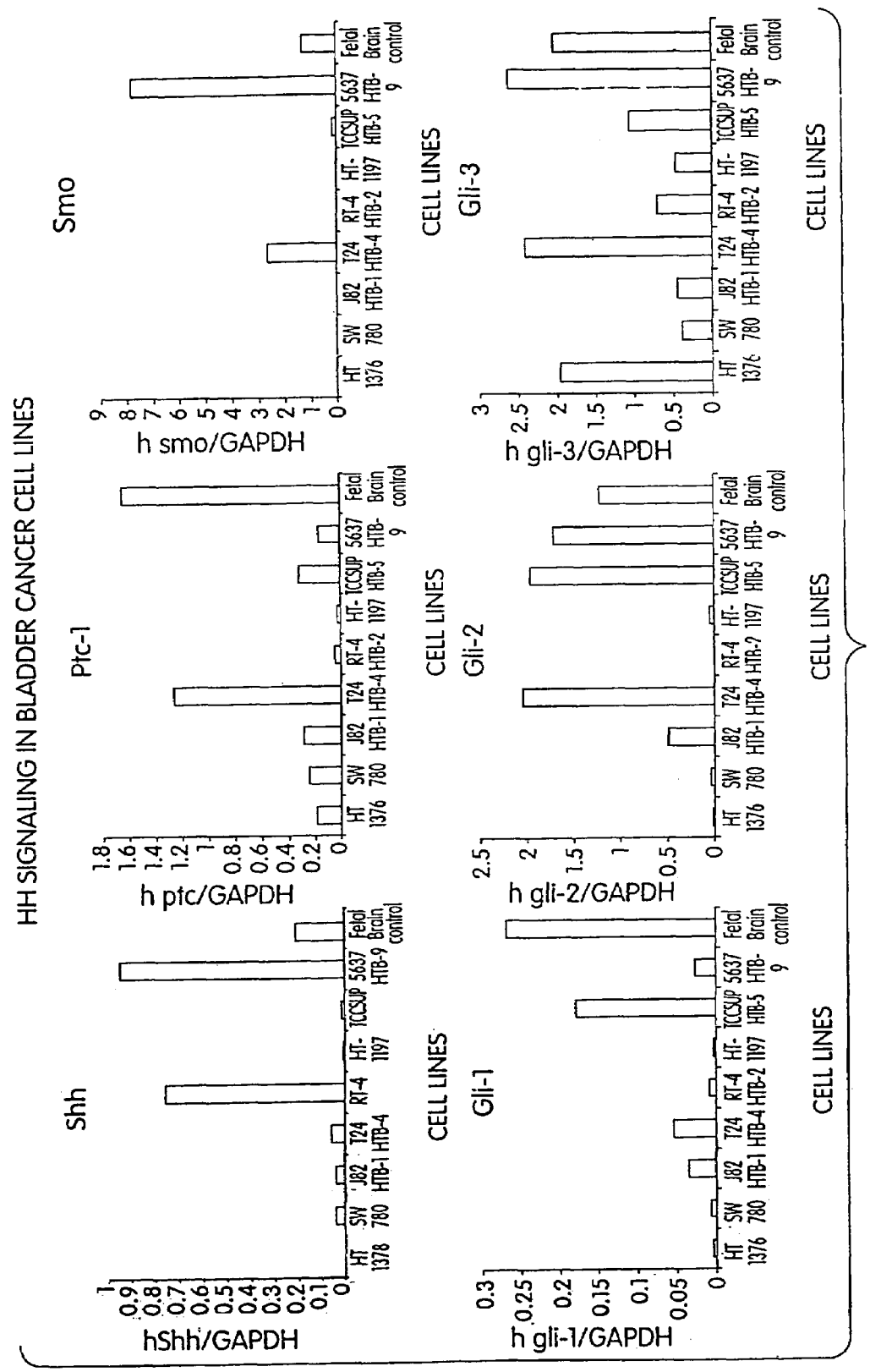
FIG. 10 shows the expression of shh, ptc-1, smo, gli-1, gli-2, and gli-3 in eight commercially available bladder cancer cell lines, as well as in fetal brain.

FIG. 8 demonstrates that shh expression is increased 12-fold and gli-1 expression is increased 2.5 fold in a bladder tumor sample when compared to normal adult bladder. FIG. 9 examines shh and gli-1 expression in eight human bladder cancer cell lines, and FIG. 10 examines expression of shh, ptc-1, smo, gli-1, gli-2, and gli-3 in the same eight human bladder cancer cell lines. These results indicate that components of the hedgehog pathway are expressed in eight out of eight cell lines examined.

METHODS: Experiment 1 (FIG. 8)—evaluation of hedgehog signaling in a bladder tumor.

For Quantitative Real-Time Polymerase Chain Reaction (Q-RT-PCR) experiments, commercially available cDNA (Clontech) was amplified using an ABI Prism 7700 Sequence Detection System (TaqMan) from Perkin Elmer and gene-specific primers. The housekeeping gene GAPDH was used to normalize RNA concentration and PCR efficiency, and GAPDH primers were added to the same reactions. Since probes for both genes are labeled with different fluorophores, the specific signal and that of GAPDH can be detected in the same tube. Signal intensities were calculated using the algorithms provided in Sequence Detector v1.7, the software provided by the manufacturer. Experiment 2 (FIGS. 9-10)—hedgehog signaling in eight bladder cancer cell lines. Bladder cancer cell lines were purchased from ATCC (American Type Culture Collection) and maintained as recommended in the product description. At confluency, cells were rinsed and switched to medium containing 1% serum, a treatment that increases hedgehog signaling. Cells were then grown 2 more days, collected in Trizol (GIBCO-BRL) and RNA isolated according to the manufacturer's protocol. The RNA was then transcribed into first strand cDNA according to standard protocols, and amplified using an ABI Prism 7700 Sequence Detection System (TaqMan) from Perkin Elmer and gene-specific primers. The housekeeping gene GAPDH was used to normalize RNA concentration and PCR efficiency, and GAPDH primers were added to the same reactions. Since probes for both genes are labeled with different fluorophores, the specific signal and that of GAPDH can be detected in the same tube. Signal intensities were calculated using the algorithms provided in Sequence Detector v1.7, the software provided by the manufacturer.

In vitro Assay to Examine Hedgehog Signaling in Bladder Cancer Cell Lines

Figure 11:
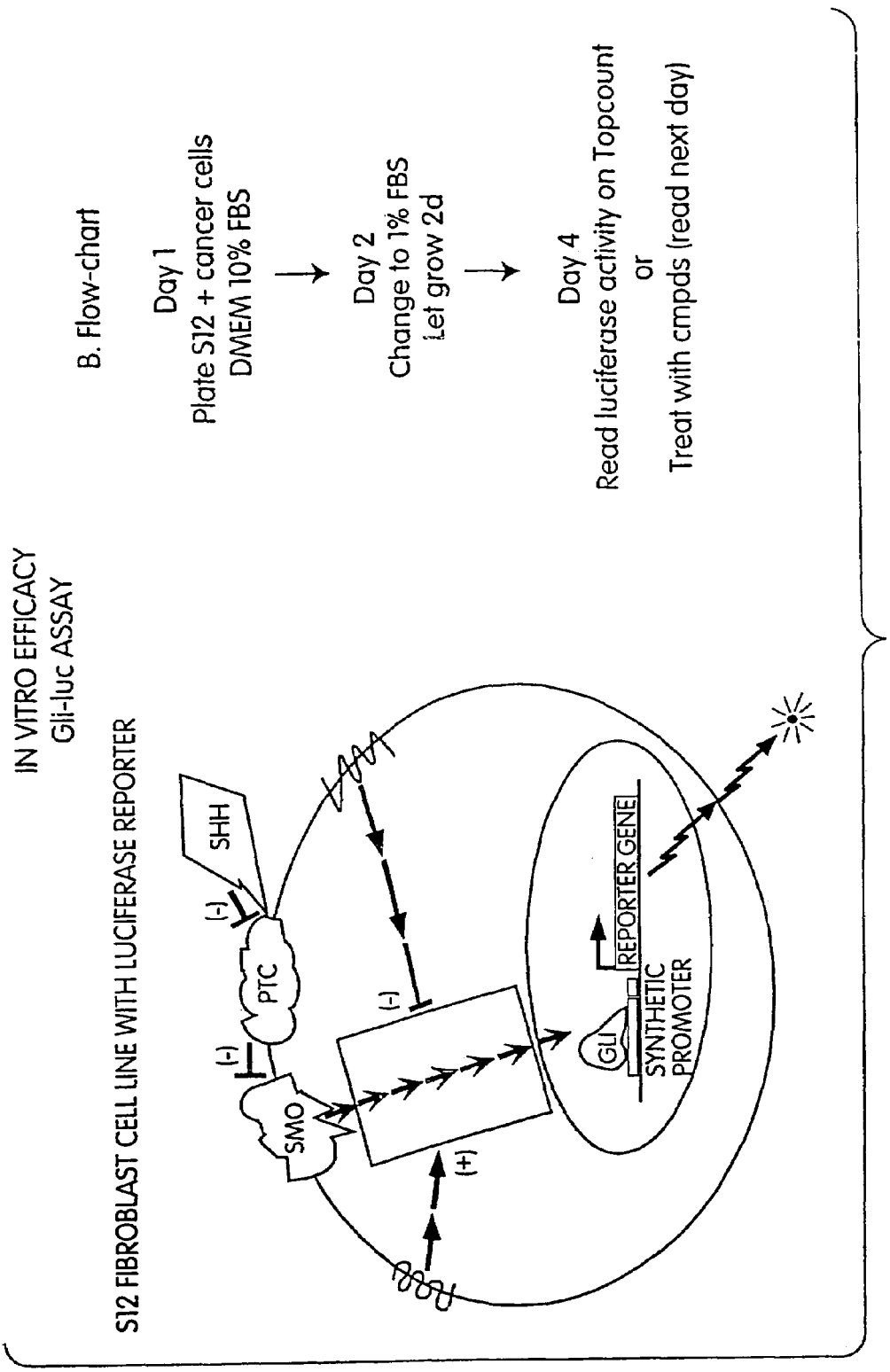
FIG. 11 shows a schematic representation of the gli-Luc assay.

The expression of components of the hedgehog signaling pathway in the eight bladder cancer cell lines examined suggested that hedgehog signaling is active in bladder cancer cells. However the gene expression observed may not be indicative of functional signaling. To assess whether functional hedgehog signaling occurs in bladder cancer cell lines, a gli-Luc in vitro assay was used. This assay is summarized schematically in FIG. 11. Briefly, 10T ½ (S12) fibroblasts expressing a luciferase reporter gene responsive to hedgehog serve as an indicator of hedgehog signaling. When these cells are contacted with functional hedgehog protein, the hedgehog signaling pathway is activated in the S12 cells, and luciferase is expressed. In the experiments presented here, S12 cells are co-cultured with bladder cancer cells. If the bladder cancer cell line secretes functional hedgehog protein, luciferase expression will be activated in the adjacent S12 cells.

Figure 12:
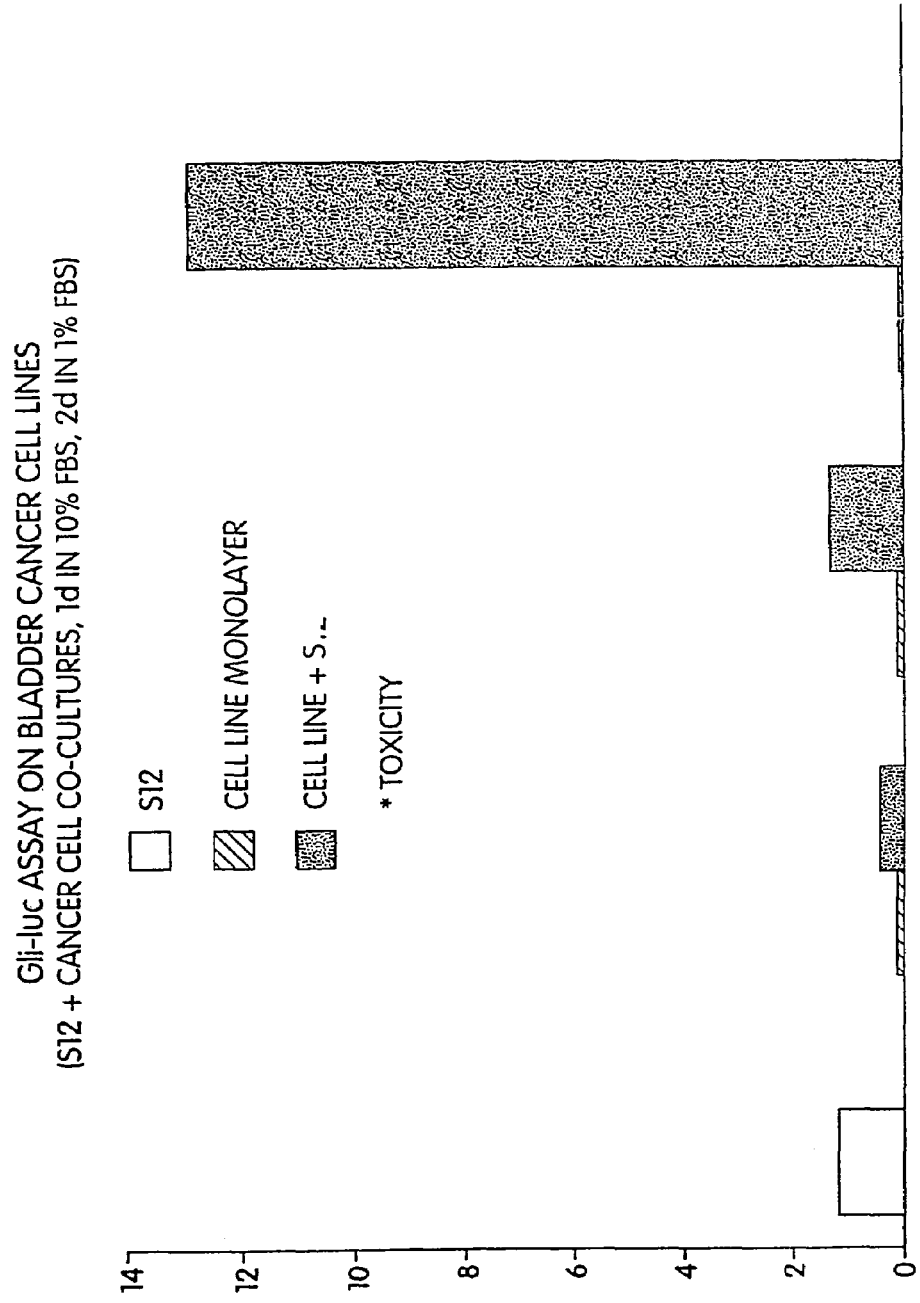
FIG. 12 shows the results of the gli-Luc assay on bladder cancer cell co-cultures. Co-culture of S12 cells with either cell line 5637 or cell line RT4 results in activation of the reporter gene indicating that these cell lines can activate hedgehog signaling.

FIG. 12 shows luciferase induction in S12 cells alone, and in S12 cells co-cultured with three bladder cancer cell lines. Two of the three cell lines examined induced expression of luciferase in S12 cells indicating that these bladder cancer cell lines secrete functional hedgehog protein.

Figure 13:
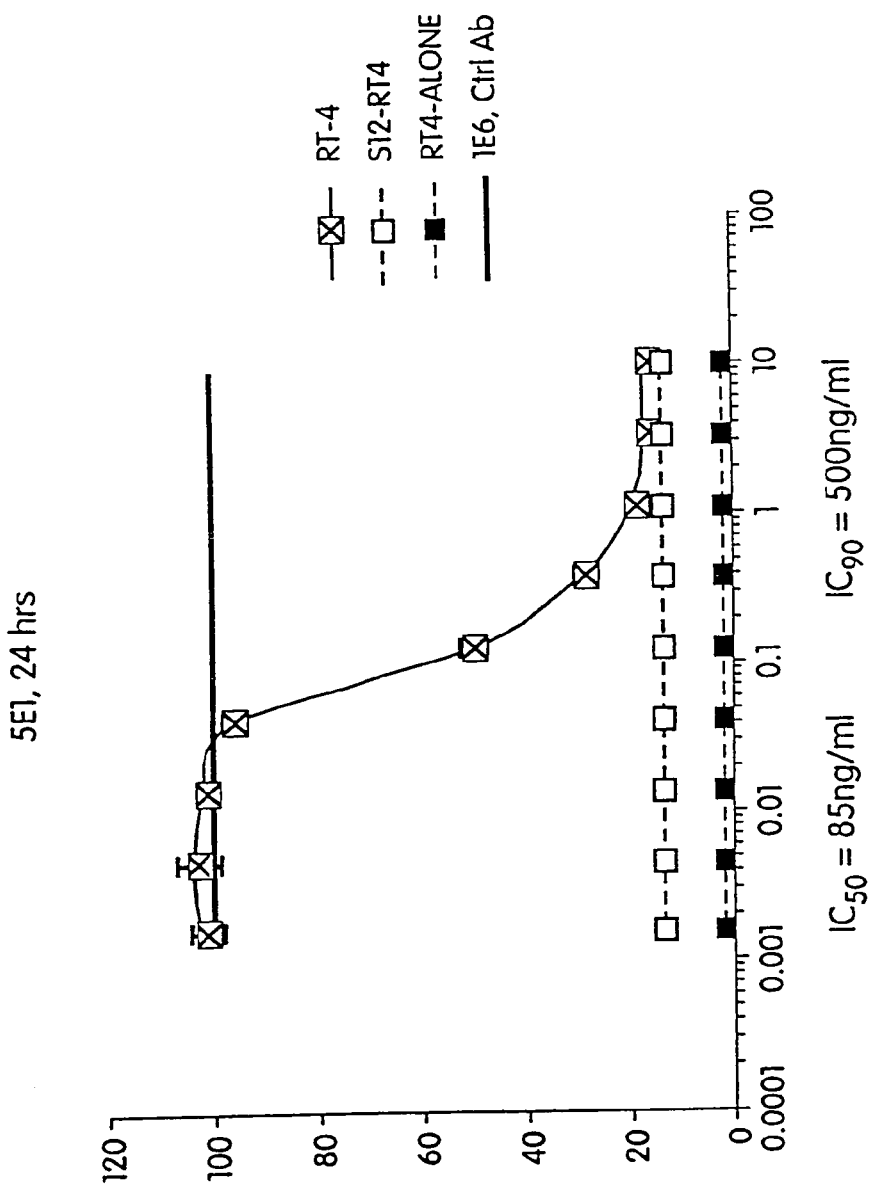
FIG. 13 shows that the Shh antibody 5E1 inhibits activation of the reporter gene in RT-4/S12 co-cultures.

To confirm the specificity of this activation of hedgehog signaling by bladder cancer cell lines, S12/RT-4 co-cultures were treated with the Shh blocking antibody (5E1). FIG. 13 demonstrates that 5E1 treatment of co-cultures inhibits expression of luciferase in S12 cells with an $IC_{50}$ of 85 ng/ml and an $IC_{90}$ of 500 ng/ml. It should be noted that this model also provides a means for evaluating the in vitro efficacy of other hedgehog antagonists including small molecule and polypeptide antagonists.

Hedgehog Signaling in an in vivo Mouse Bladder Tumor Model

Figure 14:
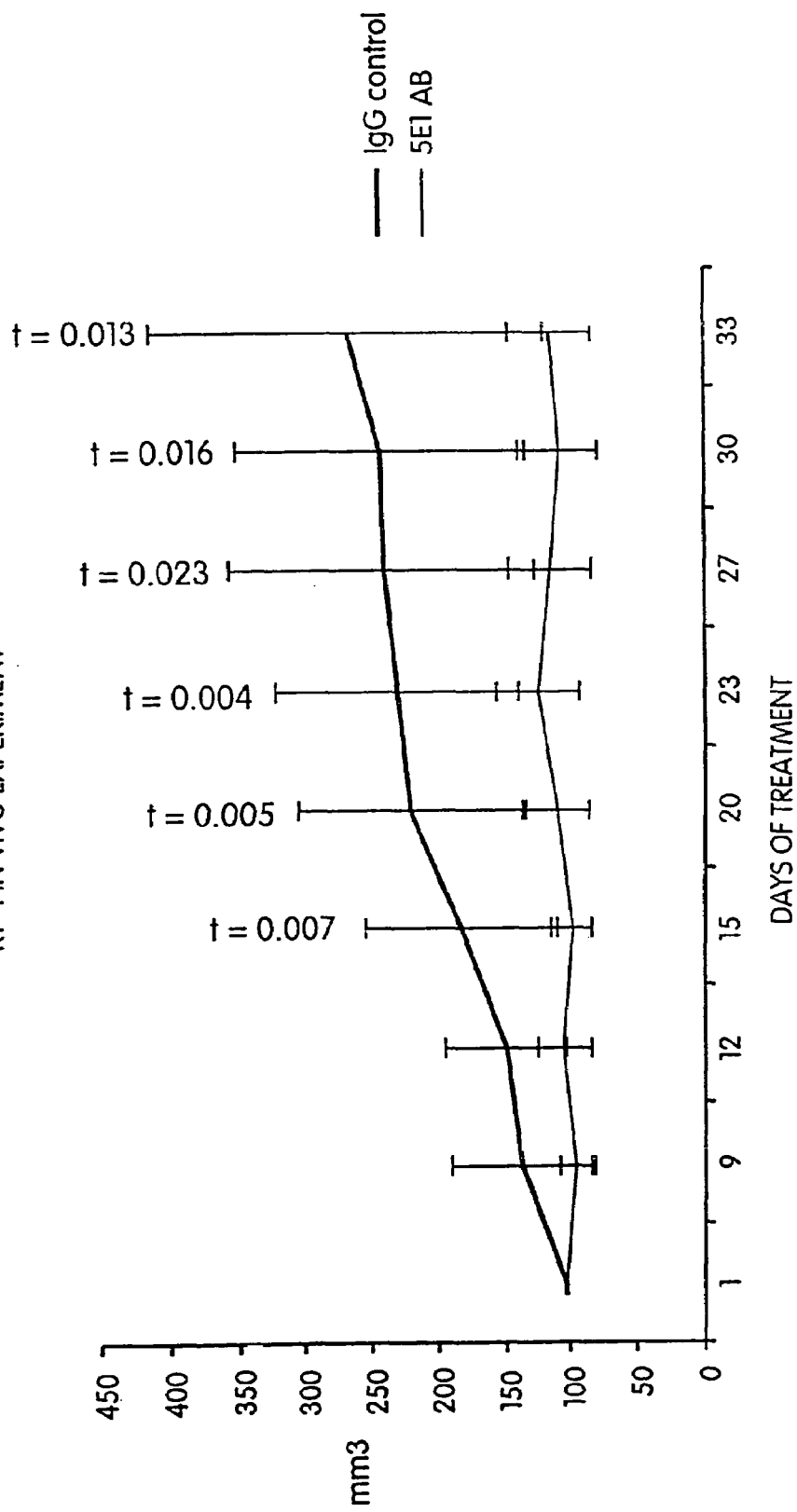
FIGS. 14 and 15 show that administration of the Shh antibody 5E1 inhibits tumor growth in vivo in a nude mouse bladder cancer model.
Figure 15:
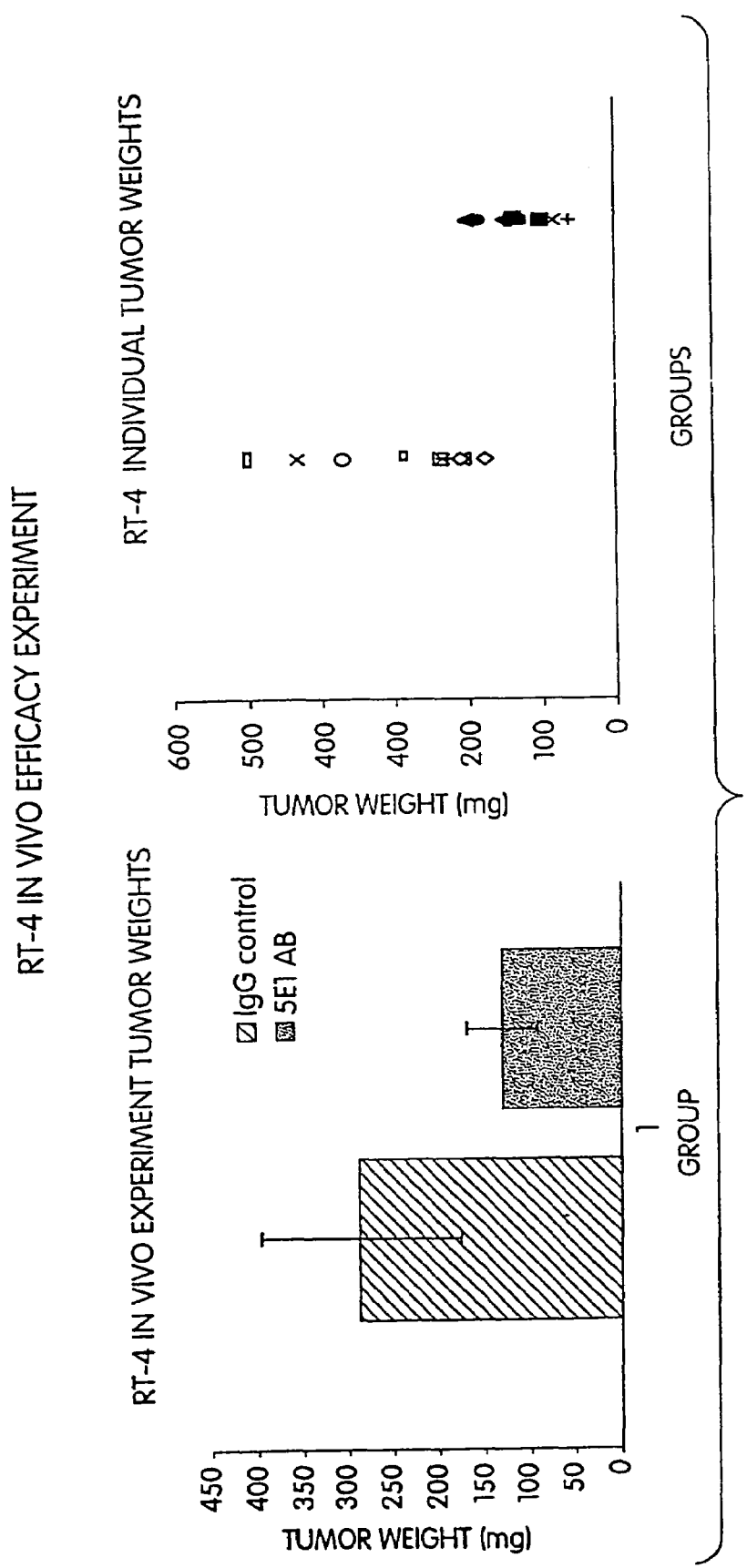

Injection of bladder tumor cells into nude mice induces tumor formation. Based on the ability of the Shh antibody 5E1 to inhibit hedgehog signaling in the in vitro gli-Luc assay described in detail above, the ability of 5E1 to inhibit bladder cell tumor growth in vivo was examined. Briefly, nude mice were injected subcutaneously with $10^7$ RT-4 cells. The mice were divided into two groups and treated with either 5E1 or with a control IgG antibody. FIGS. 14 and 15 show that treatment with 5E1 significantly decreased the size of the tumor in comparison to treatment with the IgG control. It is important to note that due to the procedure used in this particular experiment (injection of tumor cells with Matrigel) the tumors start out with an average size of 100 $mm^3$ due to the Matrigel matrix (=100 μl injection volume). Matrigel is a liquid when kept on wet ice, but solidifies upon injection. Thus, the average tumor size in the 5E1 group at the end of the experiment is roughly equal to that at the beginning of treatment. Results are highly statistically significant (Student's t-test: p=0.017). It should be noted that this model also provides a means for evaluating the in vivo efficacy of other hedgehog antagonists including small molecule and polypeptide antagonists.

Figure 16:
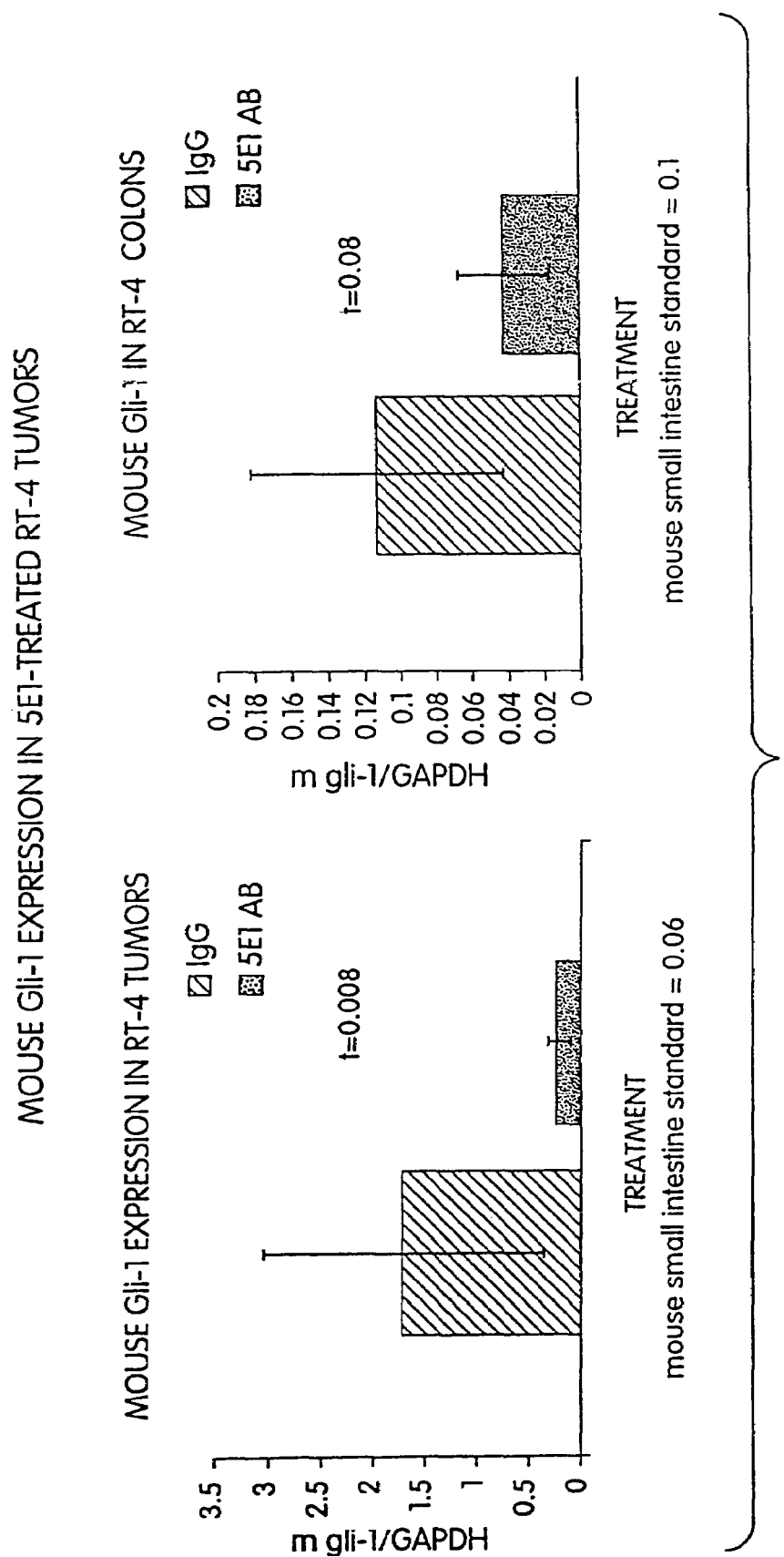
FIG. 16 shows that administration of the Shh antibody 5E1 decreases expression of gli-1 in vivo in a nude mouse bladder cancer model.

In addition to evaluating the effect of 5E1 treatment on tumor size, expression of gli-1 in both the RT-4 tumors and in the surrounding tissue was also evaluated. 5E1 treatment decreased expression of gli-1 in both the RT-4 tumors and in adjacent tissue (FIG. 16). This finding is significant because the in vitro experiments outlined above indicate that these hedgehog-expressing cells can activate hedgehog signaling in adjacent cell. Given the complex nature of cancer progression, it is possible that hedgehog signaling influences cancer both directly and indirectly. The indirect effects may include the induction of proliferative factors, angiogenic factors, or anti-apoptotic factors, to name a few. The induction of such factors may occur within the cancer cells themselves or in adjacent cells. Thus, the demonstration that a hedgehog antagonist 5E1 can inhibit hedgehog signaling in both cancer cells and in surrounding cells has significant implications.

METHODS: Exponentially growing RT-4 cultures were trypsinized, spun down, and resuspended in a small volume of culture medium. The proportion of viable tumor cells was determined by trypan blue exclusion. $10^7$ cells/animal were resuspended in 100 μl Matrigel (a commercially available preparation of basement membrane components) and injected subcutaneously in the right side of the flank of 6-8 week-old athymic male BALB/c nu/nu nude mice. Treatment was begun the day after injection of the cells. Mice were divided into two groups containing 16 animals/group. The control group (IgG control antibody) and the 5E1-treated group were injected 3×/week intraperitoneally with 10 mg/kg antibody. Tumors were measured 2×/week by caliper in 2 dimensions and measurements converted to tumor mass using the formula for a prolate ellipsoid ($axb^2x/2$). As noted above, in this particular example the tumors were injected in combination with Matrigel. Therefore, the tumors have an initial size of 100 mm$^3$ and the inhibition of tumor size observed following 5E1 treatment is nearly a complete inhibition of tumor growth.

Expression of gli-1 was measured using Q-RT-PCR as described throughout the application.

The inhibition of tumor growth by the hedgehog antagonist 5E1 supports the utility of the claimed invention. It is expected that antagonism of hedgehog signaling using a range of agents would have similar effects in decreasing tumor growth, and the efficacy of any candidate compound could be easily assessed using the in vitro and in vivo methods described above.

EXAMPLE 12

Prostate Cancer

Hedgehog signaling plays an important role in normal prostate development. Sonic hedgehog is required for prostate growth, and expression of Shh is strongly correlated with prostate ductal branching (Podlasek et al. (1999) *Developmental Biology* 209: 28-39). Recent evidence supporting the essential role of shh in proper prostate branching demonstrates that treatment of embryonic prostate with the hedgehog antagonist cyclopamine inhibits growth and branching (W. Bushman, unpublished result). Additionally, the maintenance of low levels of hedgehog signaling in the adult mouse prostate suggests additional roles for hedgehog signaling beyond this early role in the initial growth and branching of the embryonic prostate.

Recent studies have examined the correlation between the expression of components of the hedgehog pathway and prostate cancer. These results show a correlation between increased expression of shh and/or gli-1 and prostate cancer. Additional cytological data supports the idea that mis-regulation of the hedgehog pathway plays a role in prostate cancer. Two studies have described deletions of a fragment of chromosome 10 containing the Su(fu) locus in prostate cancers (Carter et al. (1990) *PNAS* 87: 8751-8755; Li et al. (1997) *Science* 275: 1943-1947). Given the evidence in the literature suggestive of a role for hedgehog signaling in prostate cancer, hedgehog signaling in several prostate cancer cell lines was examined. Additionally, the ability of hedgehog antagonists to decrease activation of hedgehog signaling in prostate tumor cell lines was demonstrated. These results suggest that, like in bladder cancer cells, antagonism of hedgehog signaling has utility in decreasing growth and proliferation of prostate cancer cells.

Hedgehog Signaling in Prostate Cancer

Figure 17:
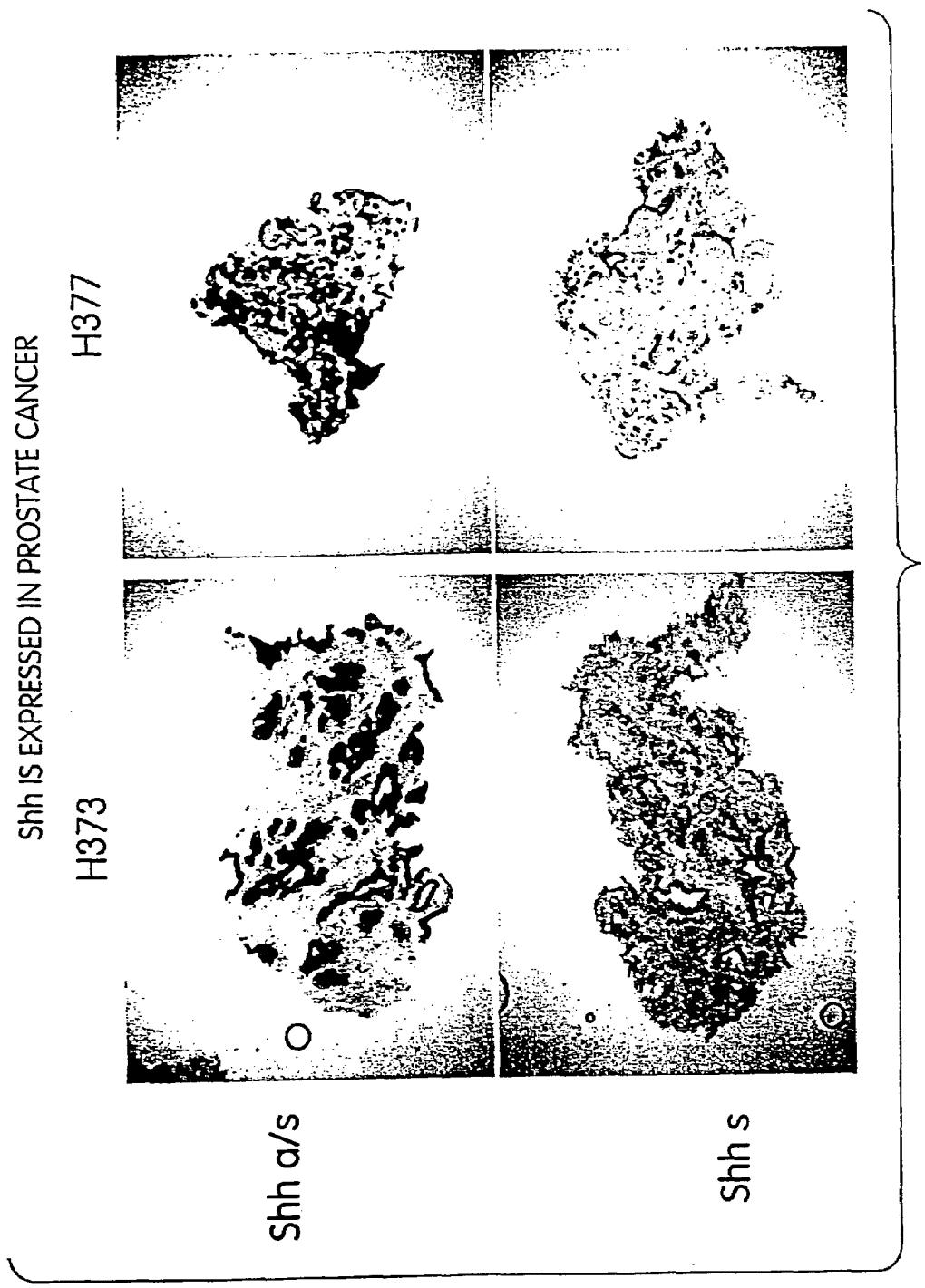
FIG. 17 shows that shh is expressed in prostate cancer samples as visualized by in situ hybridization.
Figure 18:
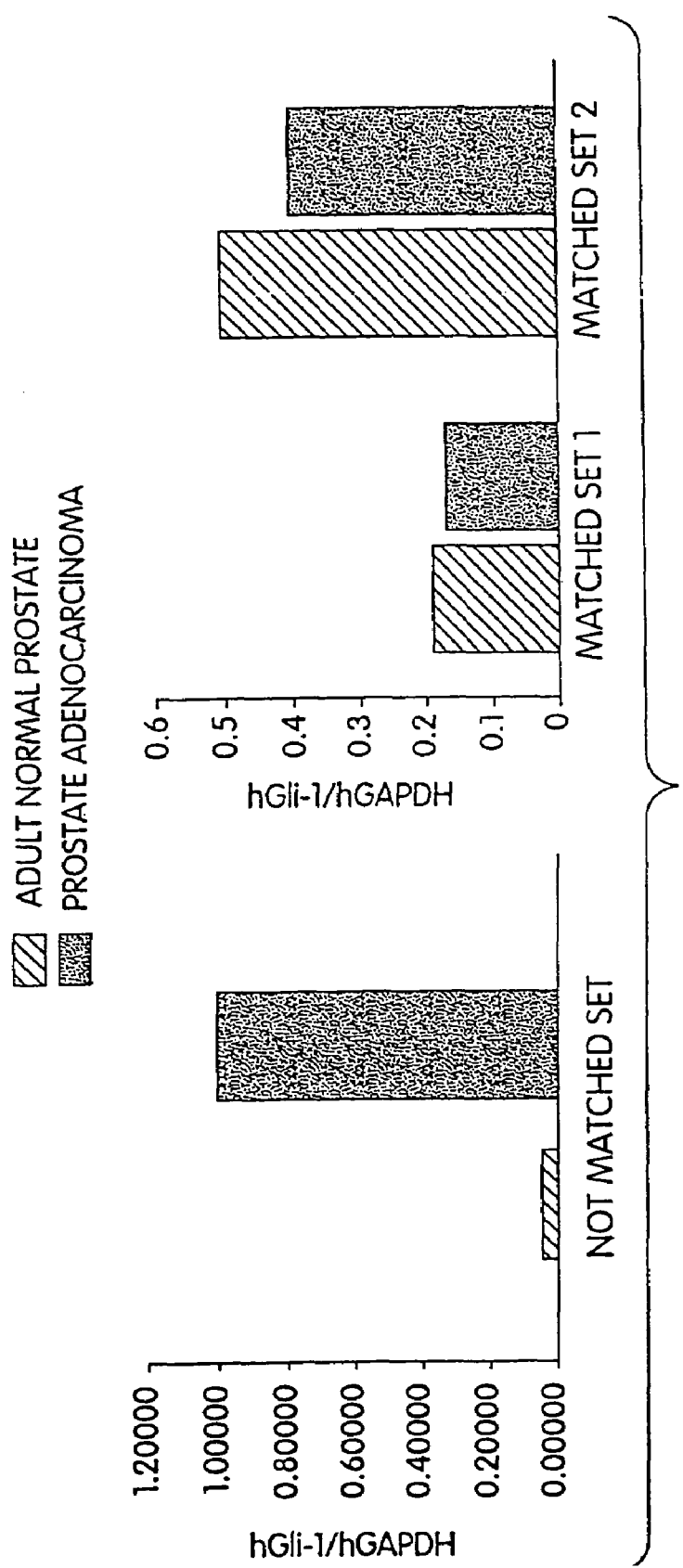
FIG. 18 shows by Q-RT-PCR the expression of gli-1 in normal adult prostate and in a prostate adenocarcinoma.
Figure 19:
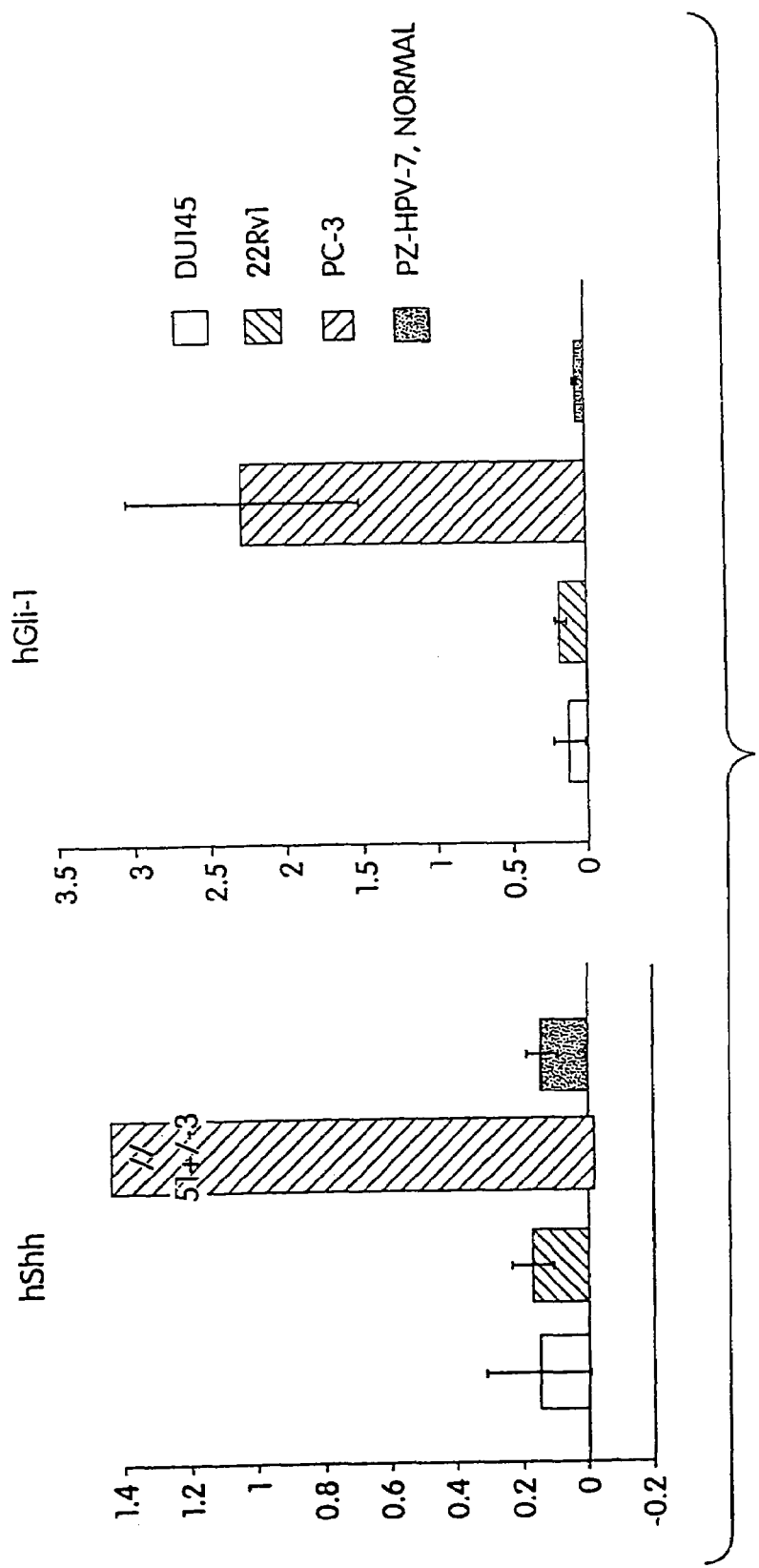
FIG. 19 shows the expression of shh and gli-1 in three prostate cancer cell lines in comparison with expression in a normal prostate cell line.

Expression of shh and gli-1 in both human prostate cancer samples and in commercially available prostate cancer cell lines was examined. FIG. 17 shows in situ hybridization analysis of human prostate cancer samples, and demonstrates the abundant expression of shh. Similarly, FIG. 18 demonstrates high levels of gli-1 expression in prostate cancer cells as measured by Q-RT-PCR. Finally, FIG. 19 examined expression of both shh and gli-1 by Q-RT-PCR in three commercially available prostate cancer cell lines. These results indicate hedgehog signaling occurs in all three commercially available cell lines.

METHODS: In situ hybridization: Paraformaldehyde-fixed tissue is cryo-sectioned into 30 µm sections, digested with proteinase K, hybridized overnight with digoxigenin-labeled RNA probe. After high stringency post-hybridization washes, sections are incubated with an anti-digoxigenin antibody which is labeled with alkaline phosphatase. The signal is visualized by addition of BM purple, a commercially available chromagen solution that reacts with the alkaline phosphatase to form a purple precipitate. Prostate cancer cell lines were purchased from ATCC (American Type Culture Collection) and maintained as recommended in the product description. At confluency, cells were rinsed and switched to medium containing 1% serum, a treatment that increases hedgehog signaling. Cells were then grown 2 more days, collected in Trizol (GIBCO-BRL) and RNA isolated according to the manufacturer's protocol. The RNA was then transcribed into first strand cDNA according to standard protocols, and amplified using an ABI Prism 7700 Sequence Detection System (TaqMan) from Perkin Elmer and gene-specific primers. The housekeeping gene GAPDH was used to normalize RNA concentration and PCR efficiency, and GAPDH primers were added to the same reactions. Since probes for both genes are labeled with different fluorophores, the specific signal and that of GAPDH can be detected in the same tube. Signal intensities were calculated using the algorithms provided in Sequence Detector v1.7, the software provided by the manufacturer.

In vitro Assay to Examine Hedgehog Signaling in Prostate Cancer Cell Lines

The expression of components of the hedgehog signaling pathway in prostate cancer samples and cell lines suggests that hedgehog signaling is active in prostate cancer. However the gene expression observed may not be indicative of functional signaling. To assess whether functional hedgehog signaling occurs in prostate cancer cell lines, the gli-Luc in vitro assay was employed. This assay was summarized above. Briefly, 10T ½ (S12) fibroblasts expressing a luciferase reporter gene responsive to hedgehog serves as an indicator of hedgehog signaling. When these cells are contacted with functional hedgehog protein, the hedgehog signaling pathway is activated in the S12 cells, and luciferase is expressed. In the experiments presented here, S12 cells are co-cultured with prostate cancer cells. If the prostate cancer cell line secretes functional hedgehog protein, luciferase expression will be activated in the adjacent S12 cells.

Figure 20:
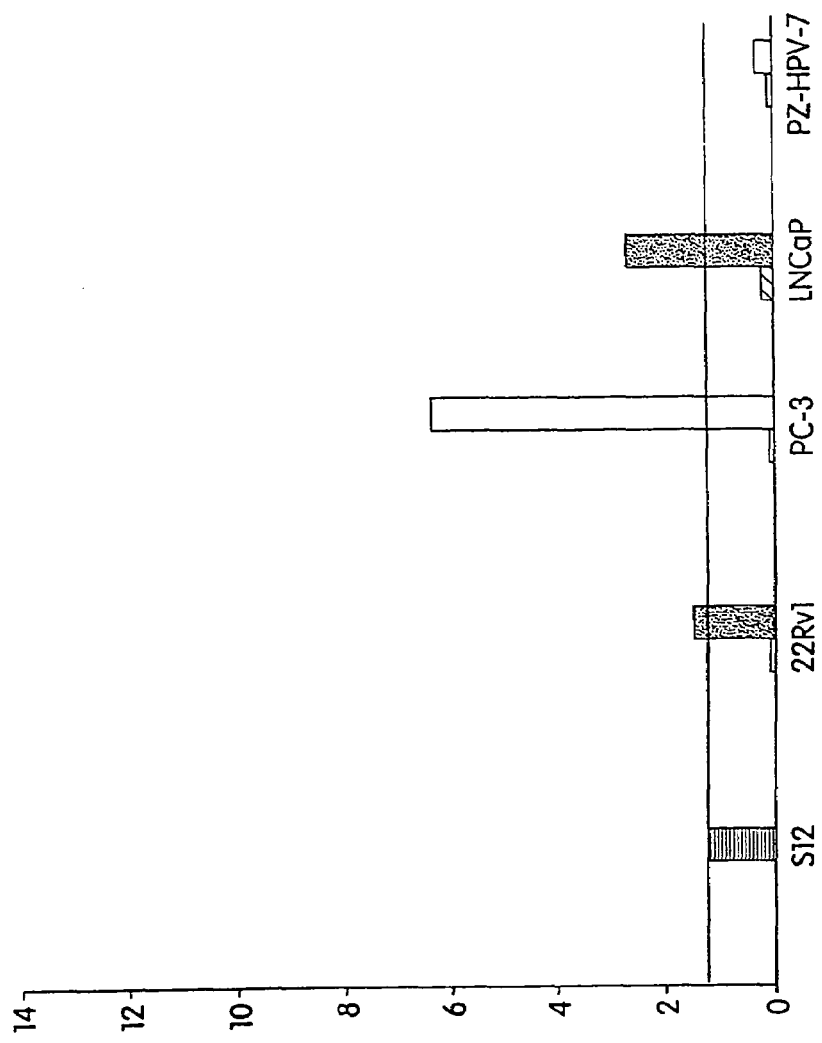
FIG. 20 shows that prostate cancer cell lines induce expression of luciferase when co-cultured with S12 cells in the gli-Luc in vitro assay.

FIG. 20 shows no induction of luciferase in S12 cells cultured alone, or in S12 cells cultured with PZ-HPV-7 (normal) cells. However, luciferase induction is observed when S12 cells are cultured with any of three prostate cancer cell lines: 22Rv1, PC-3, or LNCaP. This result indicates that these prostate cancer cell lines secrete functional hedgehog protein.

Figure 21:
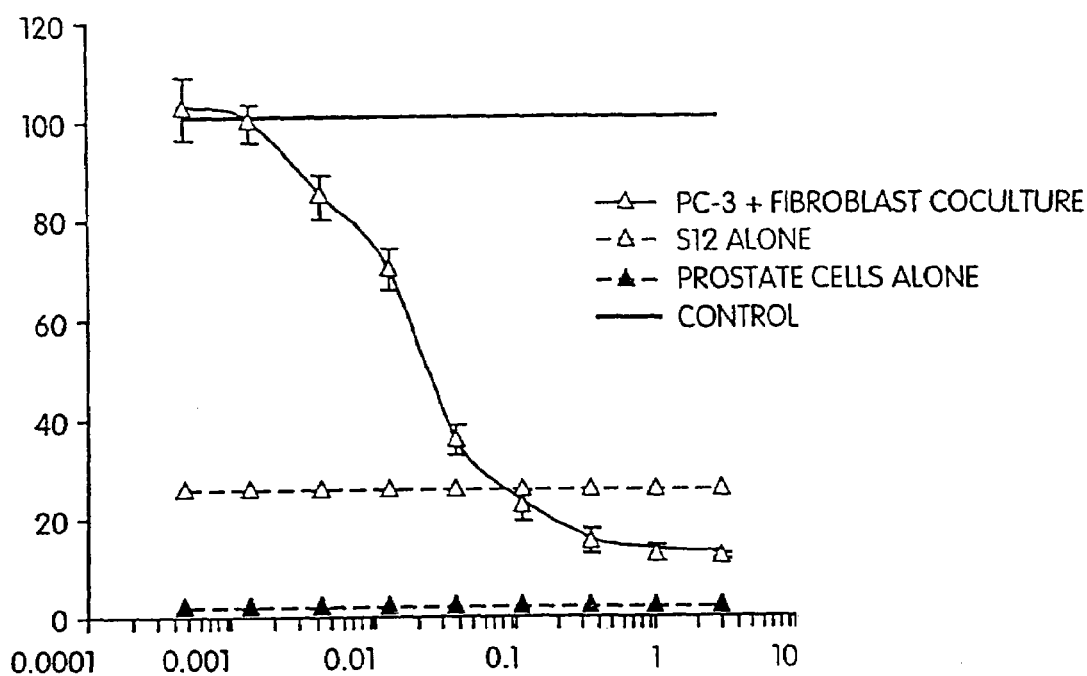
FIG. 21 shows that the antagonizing antibody 5E1 inhibits the induction of luciferase in by prostate cancer cells in the gli-Luc in vitro assay.

To confirm the specificity of this activation of hedgehog signaling by prostate cancer cell lines, S12/prostate cancer co-cultures were treated with the Shh blocking antibody (5E1). FIG. 21 demonstrates that 5E1 treatment of co-cultures inhibits expression of luciferase in S 12 cells.

METHODS: S12 cultures and co-cultures, and luciferase assays were performed as detailed above.

EXAMPLE 13

Benign Prostatic Hyperplasia (BPH)

As detailed above, hedgehog signaling appears to have both an important role in early prostate patterning, and a role in maintenance of the adult prostate. Although prostate cancer is one potential affect of misregulation of hedgehog signaling in the adult prostate, another common condition of the prostate that seems to correlate with hedgehog expression is benign prostatic hyperplasia (BPH).

BPH is a disease of the central prostate, and is characterized by increased smooth muscle around the prostatic urethra. Interestingly, shh is expressed in a gradient in the adult prostate with highest expression in the central zone of the prostate. Additionally, shh is involved in smooth muscle differentiation in other tissues including the gut and lung (Apelqvist et al. (1997) Current Biology 7: 801-804; Pepicelli et al. (1998) Current Biology 8: 1083-1086). This evidence identified hedgehog signaling as a good candidate for involvement in the etiology of BPH. Finally, transcription of shh is increased by exposure to dihydro-testosterone (DHT) (Podlasek et al., supra). This is significant because the concentration of 5-alpha-reductase, an enzyme which converts testosterone to DHT, is elevated in BPH stroma (Wilkin et al. (1980) *Acta Endocrinology* 94: 284-288). This data suggests that misregulation of hedgehog signaling may be involved in BPH, and thus that the present invention provides utility for the treatment of BPH.

Hedgehog Signaling in BPH

Figure 22:
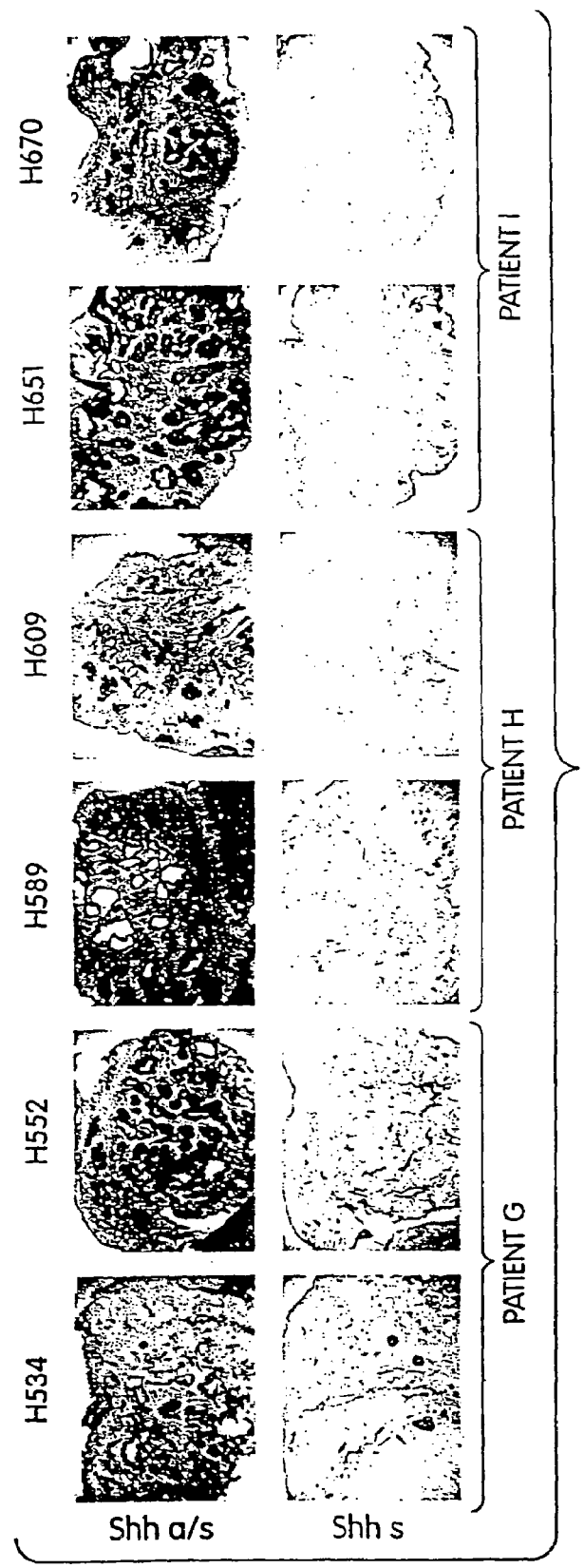
FIG. 22 shows the expression of shh in prostatic epithelium and stroma in human BPH samples.
Figure 23:
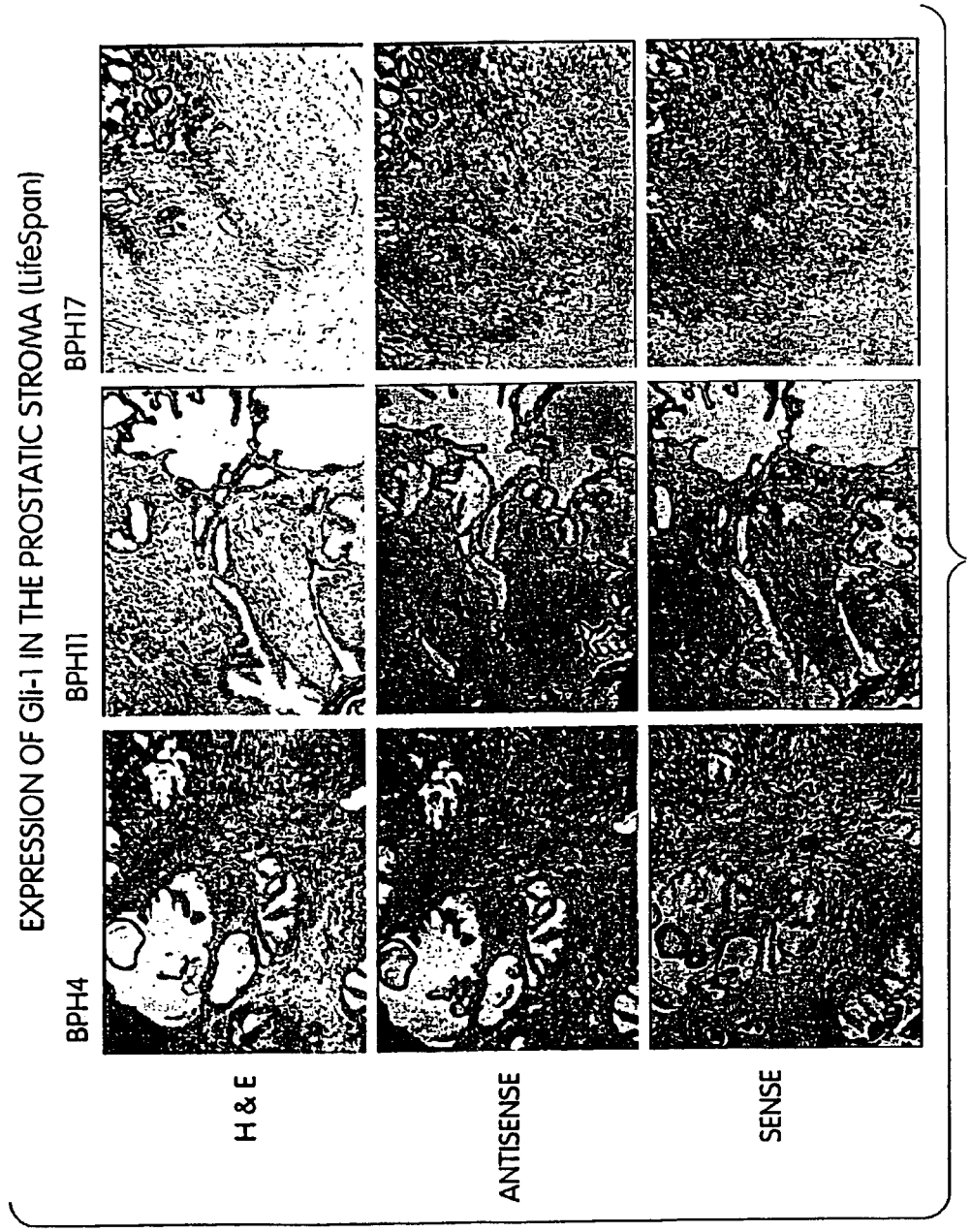
FIG. 23 shows the expression of gli-1 in the prostatic stroma of human BPH samples as measured by radioactive in situ hybridization.
Figure 24:
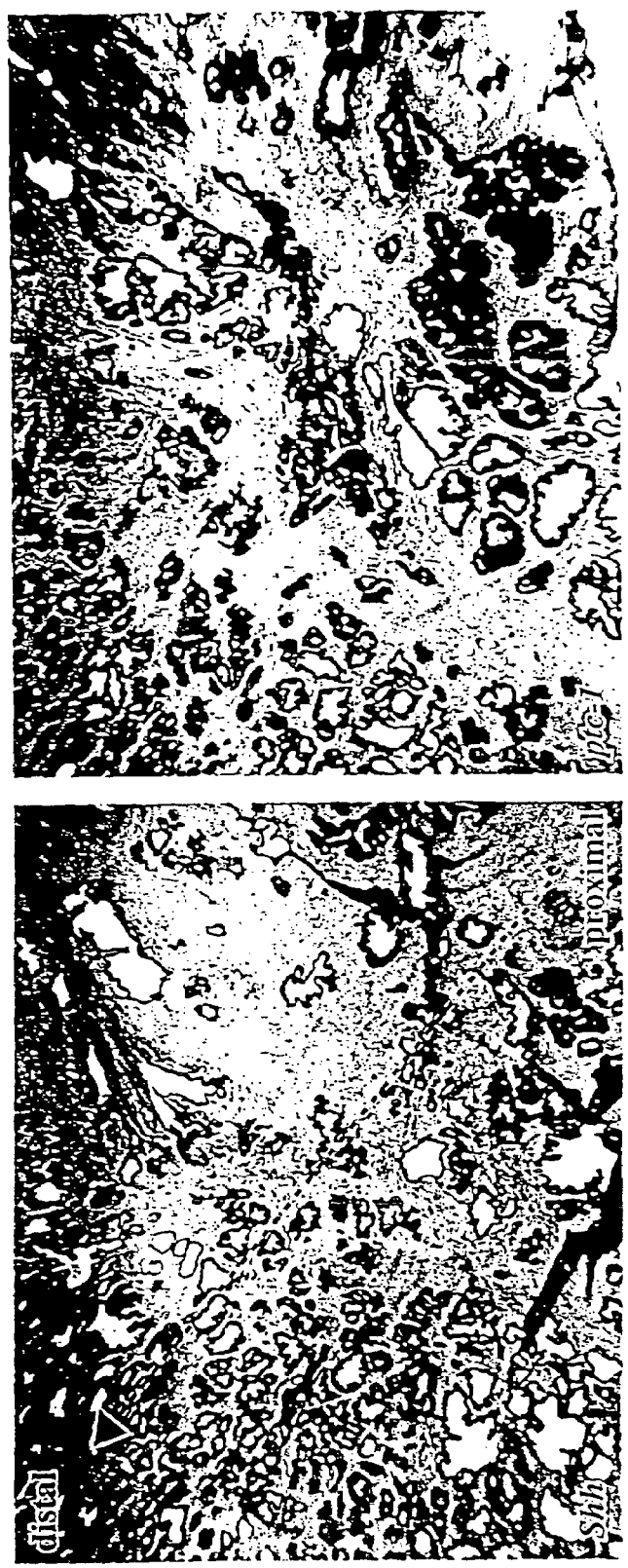
FIG. 24 shows that shh and patched-1 are expressed in a proximo-distal pattern in normal prostate tissue with the highest levels of gene expression occurring in the proximo or central region.

Expression of sonic hedgehog and gli-1 expression in human BPH samples was examined. FIGS. 22 and 23 show in situ hybridization analysis of human BPH samples, and demonstrate that both shh and gli-1 are abundantly expressed in BPH. Furthermore, FIG. 24 demonstrates that shh is not ubiquitously expressed throughout the prostate, but is instead present in a gradient with the highest level of both hedgehog and ptc-1 transcripts present in the proximal central zone of the prostate.

Figure 25:
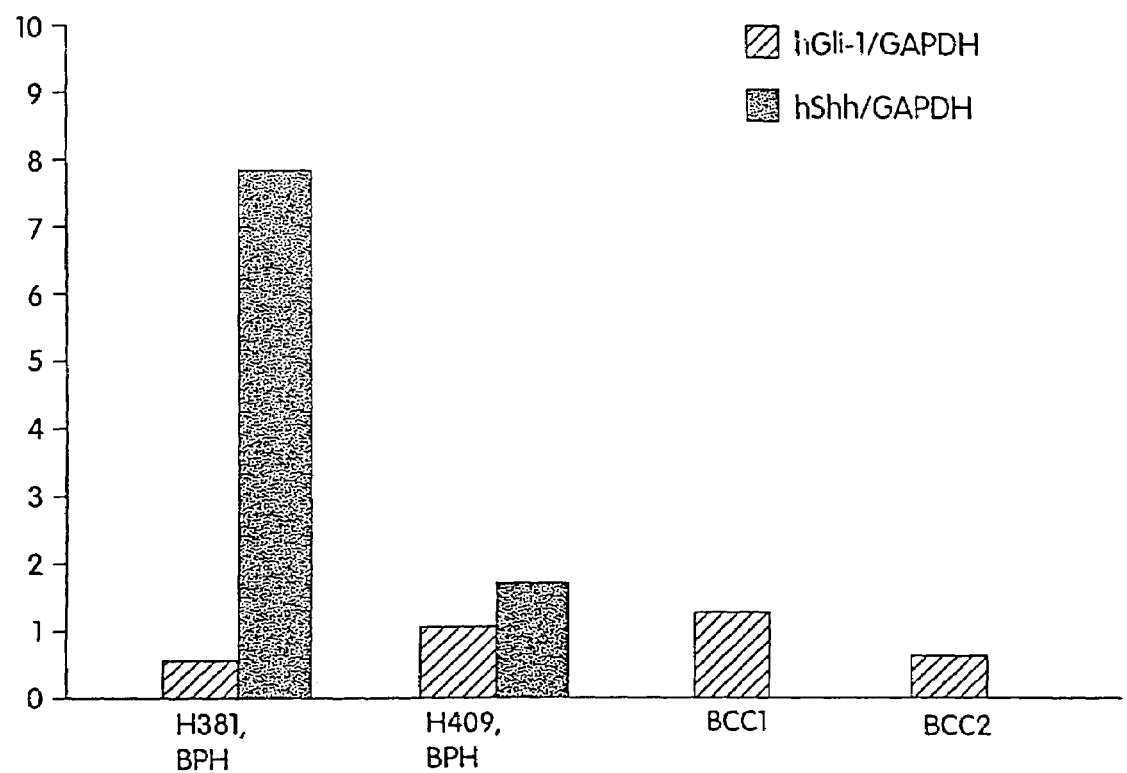
FIG. 25 shows the expression of shh and gli-1 in BPH samples, and compares the levels of gene expression to BCC samples.
Figure 26:
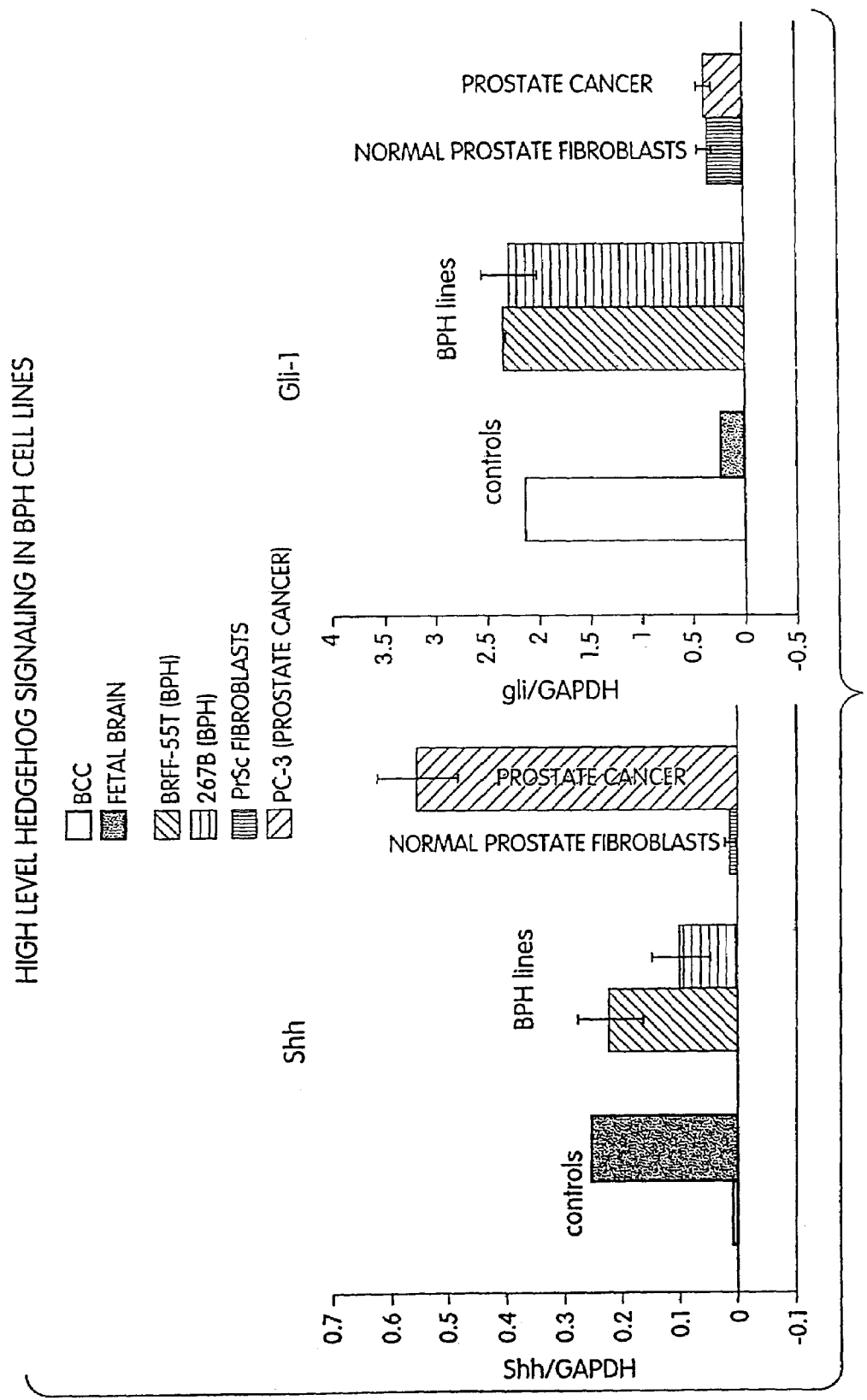
FIG. 26 shows the expression of shh and gli-1 in BPH cell lines, and compares the levels of gene expression to that of BCC samples, normal prostate, and prostate cancer.

Additionally, the expression of shh and gli-1 by Q-RT-PCR was analyzed. FIG. 25 shows that both shh and gli-1 are expressed in BPH samples. Expression of shh and gli-1 in basal cell carcinoma (BCC) samples is provided for comparison. These results demonstrate that gli-1 is expressed in BPH samples at a level similar to that found in a cancer type known to be caused by a hedgehog pathway mutation. Finally, FIG. 26 shows the expression of shh and gli-1 in BPH cell lines, and compares expression to that observed in BCC, prostate cancer cell lines, and normal prostate fibroblasts. Note that gli-1 is expressed at similar levels in both BPH cell lines and in BCC samples. These results are suggestive of a role for hedgehog signaling in BPH and further suggests that antagonism of hedgehog signaling has significant utility in the treatment of BPH.

METHODS: In situ hybridization (FIGS. 22 and 24): Paraformaldehyde-fixed tissue is cryo-sectioned into 30 μm sections, digested with proteinase K, hybridized overnight with digoxigenin-labeled RNA probe. After high stringency post-hybridization washes, sections are incubated with an anti-digoxigenin antibody which is labeled with alkaline phosphatase. The signal is visualized by addition of BM purple, a commercially available chromagen solution that reacts with the alkaline phosphatase to form a purple precipitate.

Radioactive In situ hybridization (FIG. 23): Briefly, 7 mm sections of paraformaldehyde-fixed, paraffin-embedded tissue containing large basal cell islands are cleared, re-hydrated, digested with proteinase K, acetylated and hybridized overnight with 33P-labeled RNA probes. After high stringency post-hybridization washes, slides were dipped in photo emulsion and incubated in the dark for 14 days at 4° C. After developing, slides were counter-stained with hematoxylin and eosin and imaged using dark-field illumination. Dark-field images were converted to red artificial color and superimposed with bright-field images.Q-RT-PCR: Samples were collected in Trizol (GIBCO-BRL) and RNA isolated according to the manufacturer's protocol. The RNA was then transcribed into first strand cDNA according to standard protocols, and amplified using an ABI Prism 7700 Sequence Detection System (TaqMan) from Perkin Elmer and gene-specific primers. The housekeeping gene GAPDH was used to normalize RNA concentration and PCR efficiency, and GAPDH primers were added to the same reactions. Since probes for both genes are labeled with different fluorophores, the specific signal and that of GAPDH can be detected in the same tube. Signal intensities were calculated using the algorithms provided in Sequence Detector v1.7, the software provided by the manufacturer.

EXAMPLE 14

Additional Analysis of Hedgehog Expression in Normal and Hyperproliferative Tissue To further access the range of tissues in which the methods and compositions of the present invention may be useful in inhibiting the proliferation, growth, differentiation or survival of cells, hedgehog expression was analyzed in a range of normal and cancerous human tissues. Expression was examined at both the level of hedgehog mRNA using quantitative RT-PCR and at the level of hedgehog protein by immunohistochemistry.

Figure 27:
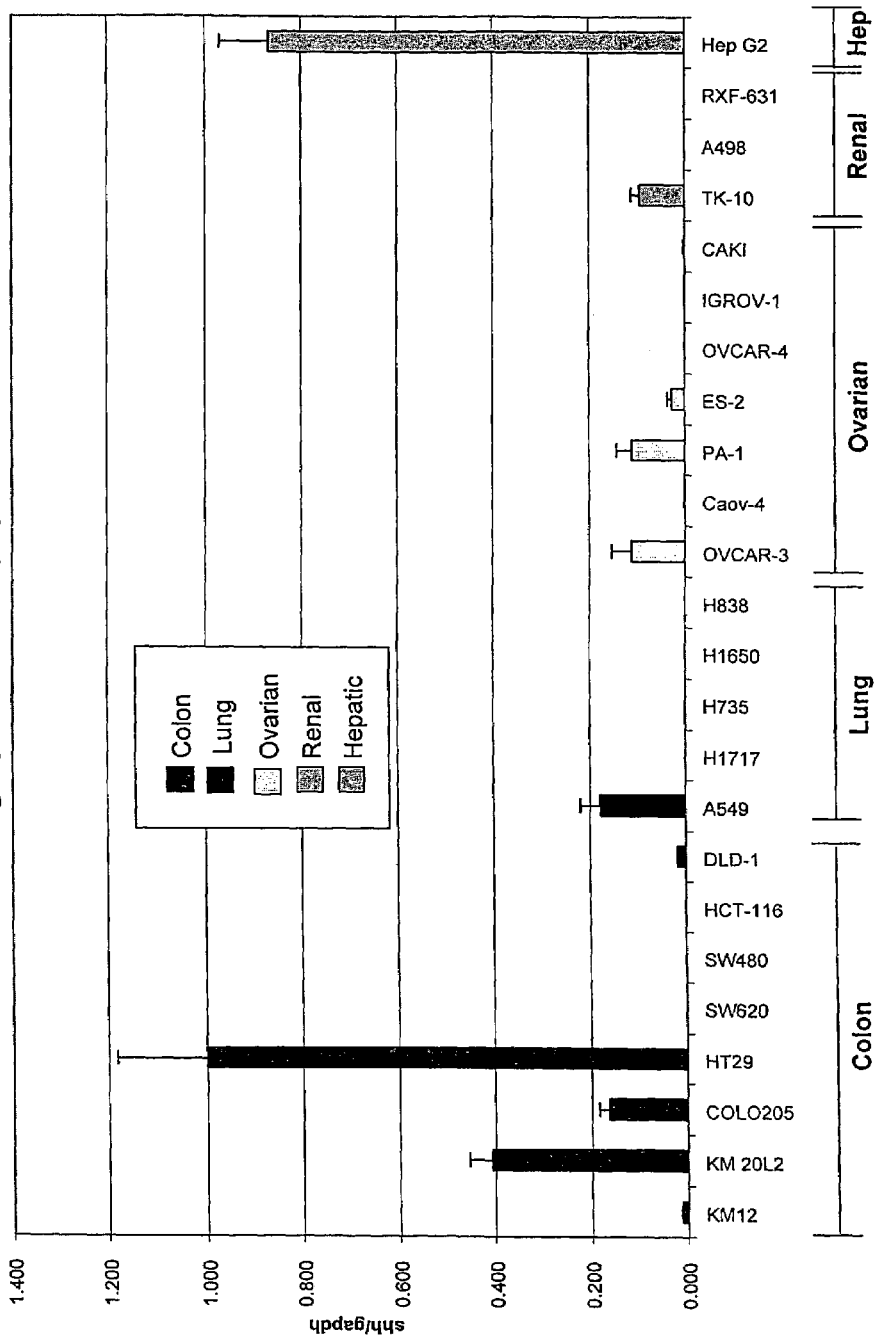
FIG. 27 shows the expression of shh in a variety of colon, lung, ovarian, renal and hepatic human cancer cell lines. Expression of shh is measured using Q-RT-PCR which demonstrates that shh is expressed, to a varying degree, in human cancer cell lines derived from several diverse tissue types.

FIG. 27 presents Q-RT-PCR analysis of Sonic hedgehog (shh) expression in a variety of human cancer cell lines. Shh expression was examined in human colon, lung, ovarian, renal and hepatic cell lines, and these results indicate that shh is expressed, at varying concentrations, in cell lines derived from each of these tissues.

Figure 28:
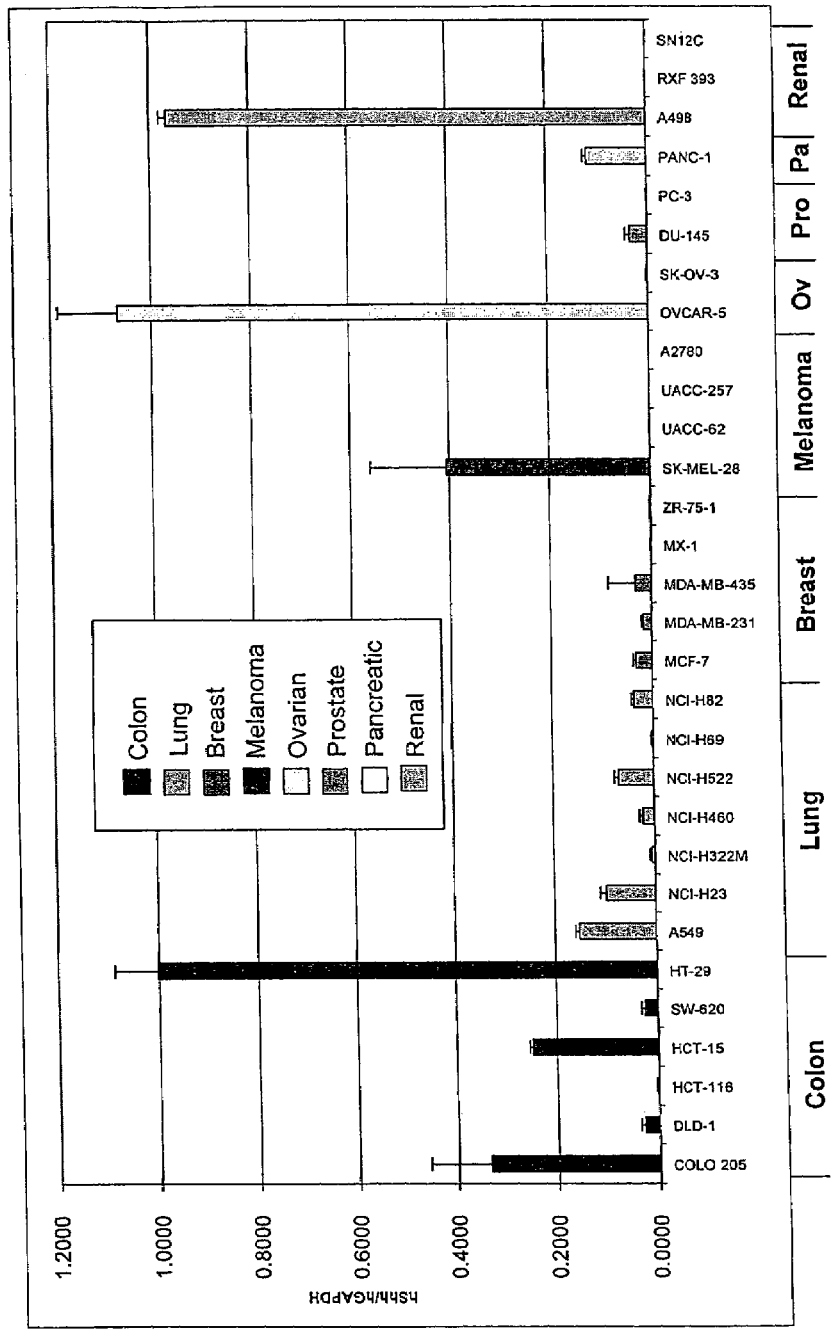
FIG. 28 shows the expression of shh in a variety of passaged tumors derived from colon, lung, breast, melanoma, ovarian, prostate, pancreatic and renal tissue. Expression of shh is measured using Q-RT-PCR which demonstrates that shh is expressed, to a varying degree, in passaged tumors derived from several diverse tissue types.

FIG. 28 presents Q-RT-PCR analysis of shh expression in passaged colon, lung, breast, melanoma, ovarian, prostate, pancreatic and renal tumors. The results demonstrate that shh is expressed, at varying levels, in passaged tumors derived from each of these tissues.

Figure 29:
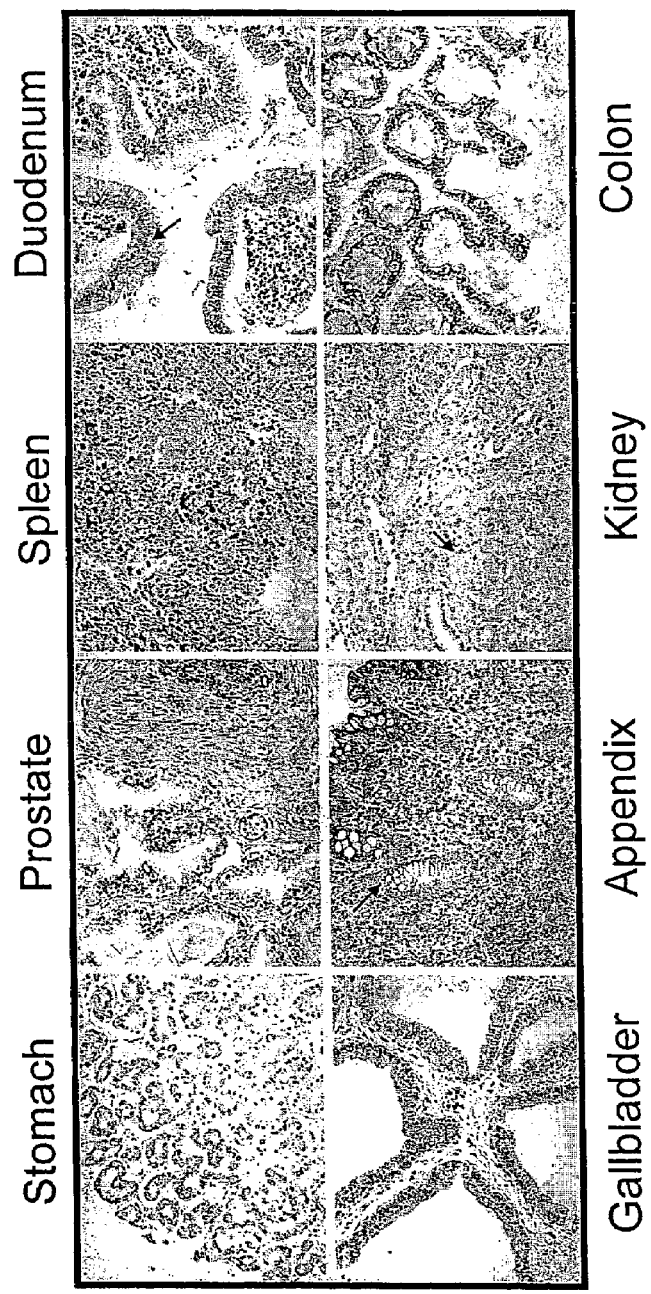
FIG. 29 shows the expression of hedgehog protein in normal human stomach, prostate, spleen, small intestine, large intestine, gall bladder, appendix and kidney tissue. Hedgehog protein expression was examined by immunohistochemistry using a polyclonal anti-hedgehog antibody.

Although the expression of shh RNA in a sample provides evidence that hedgehog signaling may be active in a cell, further information may be gleaned by examing the expression of hedgehog protein in a cell. In order to address this question, immunohistochemistry using a polyclonal anti-hedgehog primary antibody was performed on both normal and cancerous human tissue samples. FIG. 29 shows that hedgehog protein is expressed in normal human tissue harvested from a variety of sources including the stomach, prostate, spleen, small intestine, large intestine, gall bladder, kidney and appendix. It is interesting to note that hedgehog expression is observed in normal adult tissue derived from either the mesoderm or endoderm.

Figure 30:
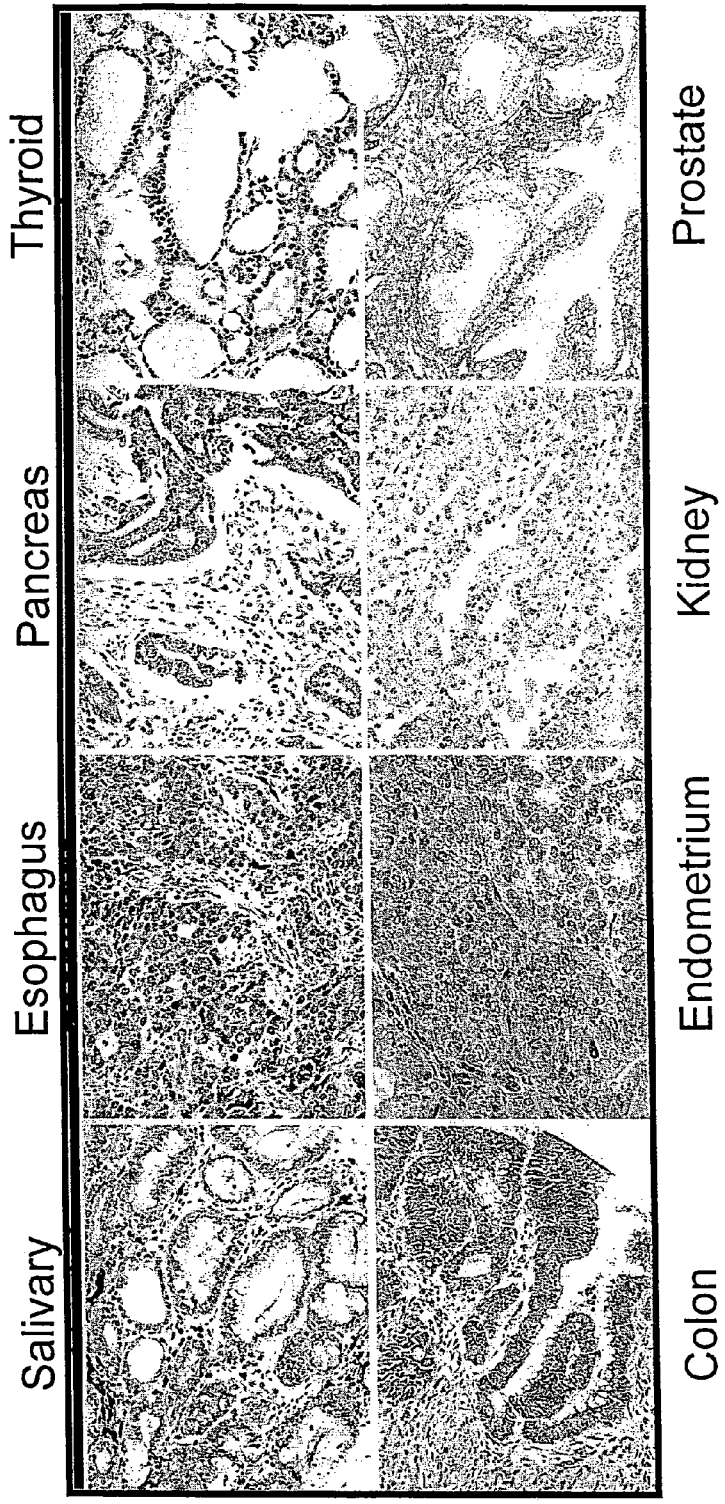
FIG. 30 shows the expression of hedgehog protein in human tumors derived from salivary, esophageal, pancreatic, thyroid, colon, endometrial, kidney and prostate tissue. Hedgehog protein expression was examined by immunohistochemistry using a polyclonal anti-hedgehog antibody.
Figure 31:
FIG. 31 shows increased expression of hedgehog protein in a sample of pancreatic tumor in comparison to hedgehog protein expression in normal pancreatic tissue. Hedgehog protein expression was measured by immunohistochemistry using a polyclonal anti-hedgehog antibody.

Expression of hedgehog protein was additionally observed in human tumors harvested from a range of tissues. FIGS. 30 and 31 demonstrate that hedgehog protein is detectable by immunohistochemistry in tumors derived from salivary esophageal, pancreatic, thyroid, colon, endometrial, kidney and prostate tissue.

These results indicate that hedgehog is expressed, at both the mRNA and protein level, in a wide range of both normal and hyperproliferative tissues. Further analysis is needed to ascertain, for a given tissue type, the differences in the level of hedgehog expression between normal tissue and hyperproliferative tissue. Such analysis will help provide a better understanding of the mechanistic role of increased hedgehog expression in hyperproliferative conditions including cancer.

METHODS: Q-RT-PCR: Samples were collected in Trizol (GIBCO-BRL) and RNA isolated according to the manufacturer's protocol. The RNA was then transcribed into first strand cDNA according to standard protocols, and amplified using an ABI Prism 7700 Sequence Detection System (TaqMan) from Perkin Elmer and gene-specific primers. The housekeeping gene GAPDH was used to normalize RNA concentration and PCR efficiency, and GAPDH primers were added to the same reactions. Since probes for both genes are labeled with different fluorophores, the specific signal and that of GAPDH can be detected in the same tube. Signal intensities were calculated using the algorithms provided in Sequence Detector v1.7, the software provided by the manufacturer.

Immunohistochemistry: Samples were harvested and processed for immunohistochemistry using standard methods. Samples were incubated overnight with a polyclonal anti-hedgehog primary antibody.

EXAMPLE 15

Antagonism of Hedgehog Signaling in Colon Cancer

The growth of tumors is a complex process that requires proliferation, angiogenesis, the inhibition of cell death, and many other complex interactions between the cancer cells and the surrounding tissue. An additional mechanism by which hedgehog signaling may influence tumor growth and progression is through the induction of factors that enhance proliferation, angiogenesis, and the inhibition of cell death. For example, sonic hedgehog has been shown to induce VEGF in fibroblasts. Thus, the use of hedgehog antagonists may prevent hedgehog signaling from inducing factors that promote tumor formation, and therefore inhibit tumor formation or progression.

Given the complex interplay which likely exists between tumor cells and the surrounding tissue, we have used two models to analyze the effects of hedgehog antagonists in inhibiting the proliferation, growth, differentiation and survival of hyperproliferative tissues. In the first model, mice are injected with a combination of hedgehog expressing cancer cells and fibroblasts, and the effects of hedgehog antagonists on the growth of this mixed-tumor are examined over time. In the second model, mice are injected with hedgehog expressing cancer cells which have not been previously combined with fibroblast cells. Without wishing to be bound by any particular theory, both models appear to recapitulate at least to some degree the complex interactions which occur during tumor formation. In the mixed tumor model, cancer cells and fibroblast cells interact—much like cancer cells and stromal cells interact during the development of many forms of cancer. In the second model however, it appears that surrounding endogenous cells invade and interact with the injected hedgehog expressing cancer cells similarly recapitulating the interactions which occur in both the mixed-tumor model and during the development of many forms of cancer. Accordingly, results obtained using either model help to address the use of hedgehog antagonists in inhibiting the proliferation, growth, differentiation and survival of hyperproliferative cells.

Model I: Mixed Tumor Model

Figure 32:
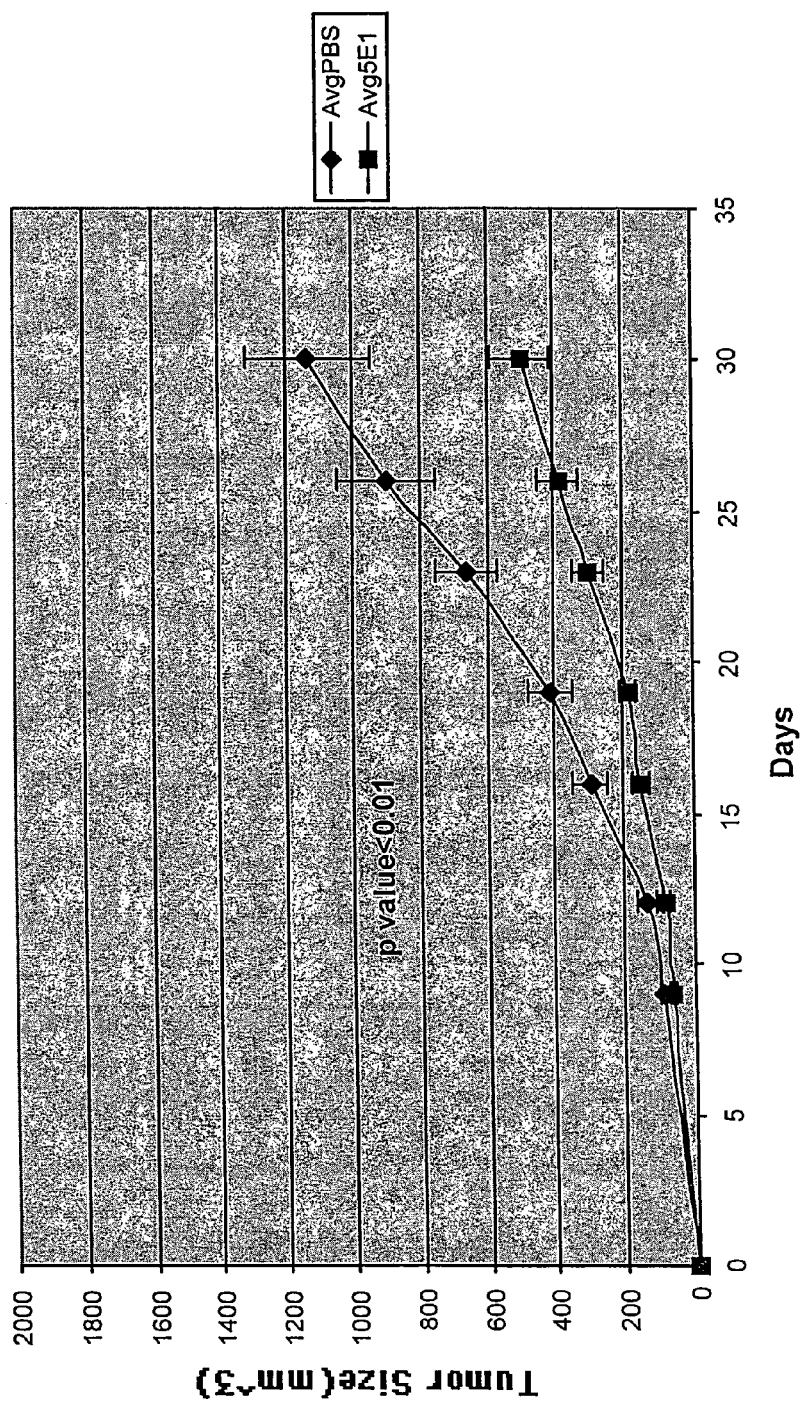
FIG. 32 shows that the Shh blocking antibody 5E1 decreases tumor size when administered to mice injected with a combination of the Shh expressing colon cancer cell line HT-29 and fibroblasts.
Figure 33:
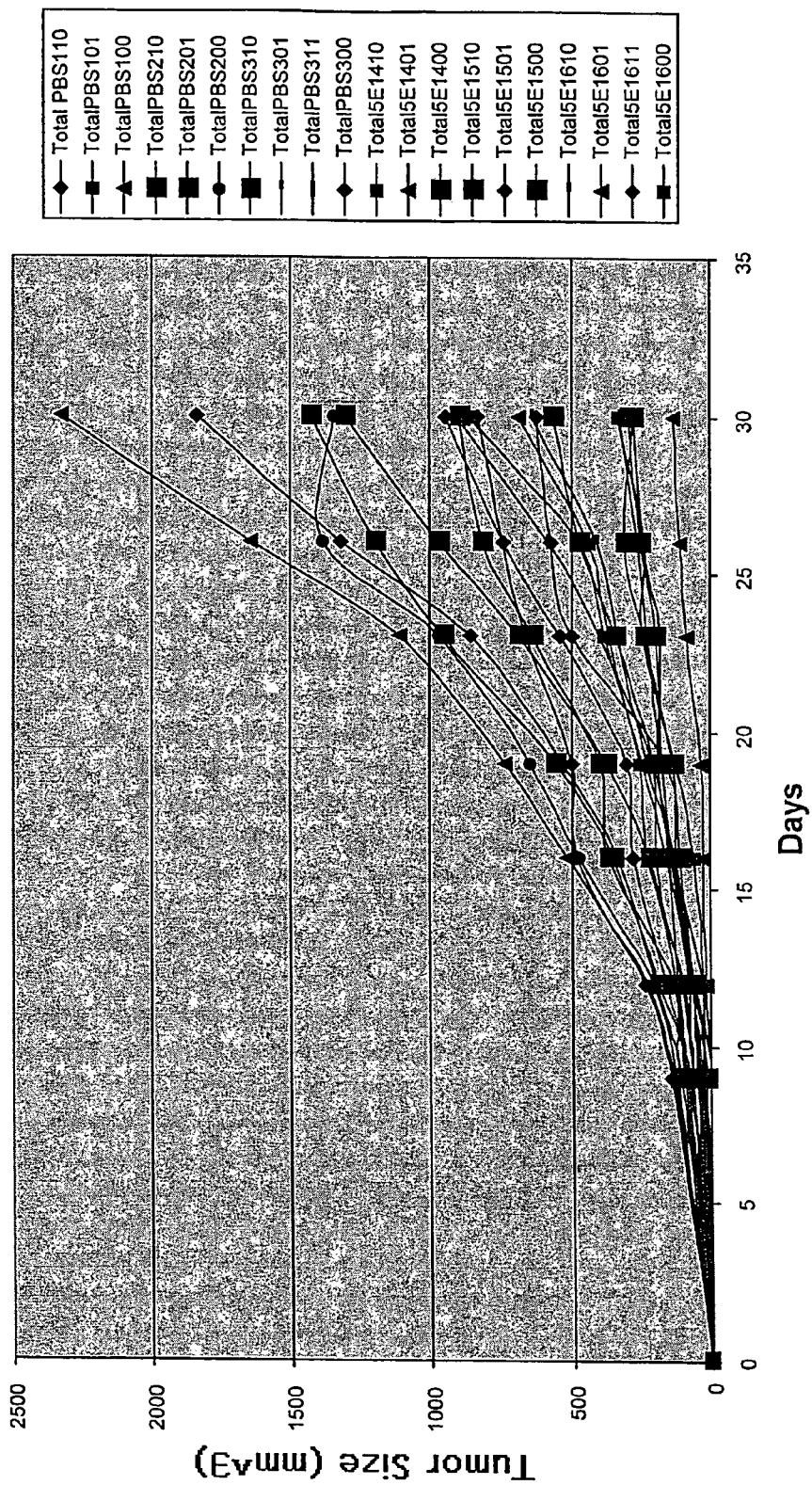
FIG. 33 shows that the Shh blocking antibody 5E1 decreases tumor size when administered to mice injected with a combination of the Shh expressing colon cancer cell line HT-29 and fibroblasts.

To help address this model, the ability of the antagonistic hedgehog antibody 5E1 to inhibit tumor growth in mice injected with a combination of hedgehog expressing colon cancer cells and fibroblasts was investigated. Two experiments were performed to assess the effects of 5E1 treatment on tumor size in mice injected with hedgehog expressing colon cancer cells. In the first experiment, treatment with 5E1, or PBS control, was initiated on the same day as injection with the tumor cells. The results are summarized in FIGS. 32 and 33, and demonstrate that treatment with 5E1 significantly decreases tumor size, weight, and rate of growth in comparison to that of mice treated with PBS (FIGS. 32 and 33). The experiment was performed using two separate colon cancer cell lines with similar affects.

Figure 34:
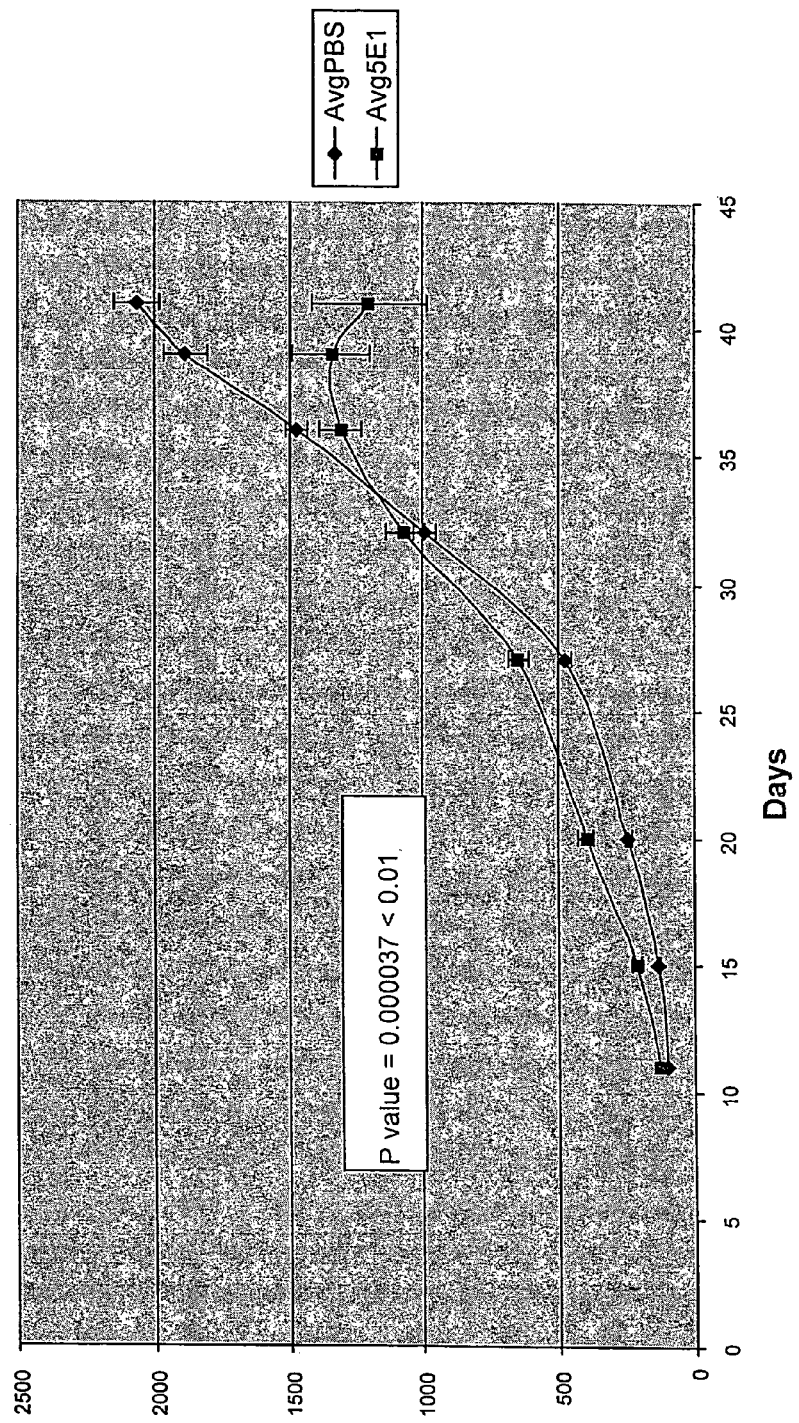
FIG. 34 shows that delayed administration of the Shh blocking antibody 5E1 decreases tumor size when administered to mice injected with a combination of the Shh expressing colon cancer cell line HT-29 and fibroblasts.
Figure 35:
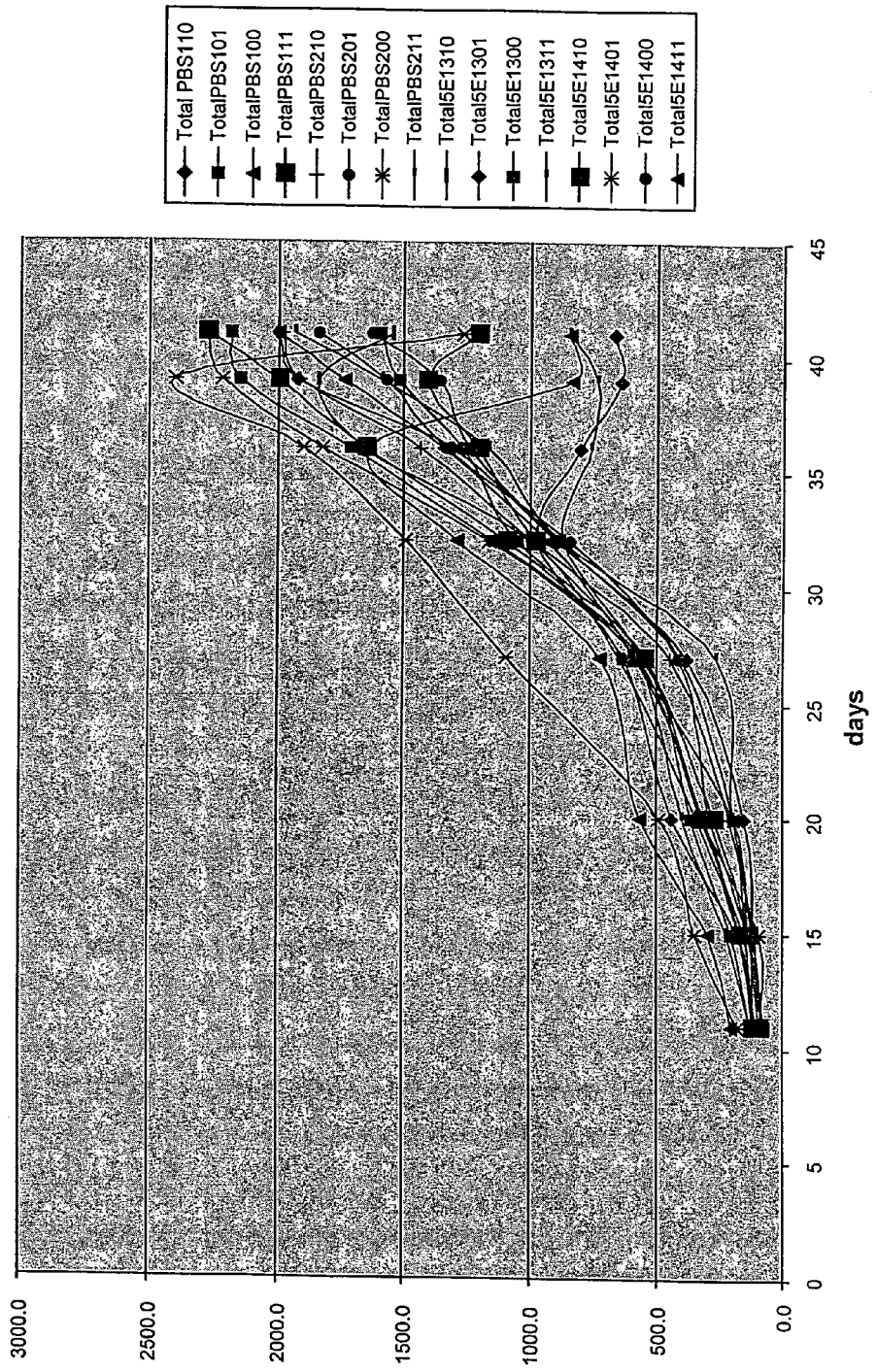
FIG. 35 shows that delayed administration of the Shh blocking antibody 5E1 decreases tumor size when administered to mice injected with a combination of the Shh expressing colon cancer cell line HT-29 and fibroblasts.

In the second experiment, treatment with 5E1 was delayed until the eleventh day of tumor growth. The results are summarized in FIGS. 34 and 35, and demonstrate that treatment with 5E1 significantly decreases the size and rate of growth of the tumor when compared to control mice (FIGS. 34 and 35). The experiment was performed using two separate colon cancer cell lines with similar affects.

Figure 36:
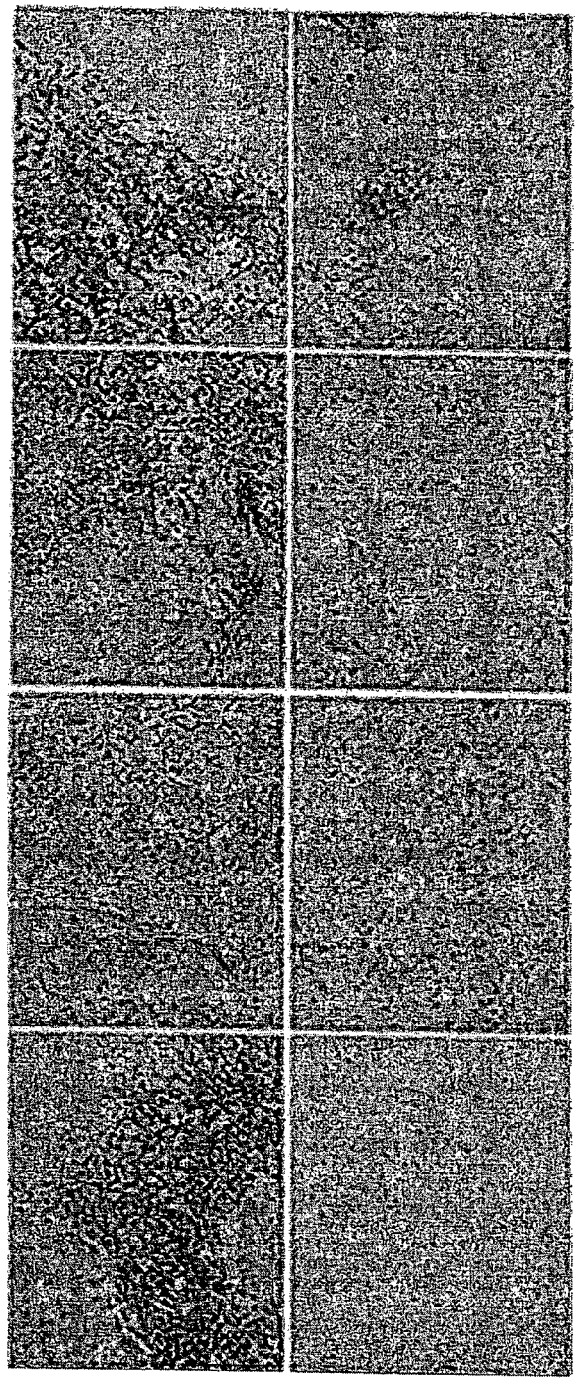
FIG. 36 shows that administration of the Shh blocking antibody 5E1 induces apoptosis in HT-29/fibroblast mixed tumors.

To further understand the mechanism by which administration of a hedgehog antagonist inhibits the growth of tumors in vivo, TUNEL analysis was performed on mixed tumors treated with either 5E1 or with the PBS control. FIG. 36 demonstrates that at least a portion of the cells in the HT-29/fibroblast mixed tumor die apoptotically following administration of the hedgehog antagonist 5E1. This result demonstrates that treatment of these hyperproliferative cells with a hedgehog antagonist inhibits the proliferation, growth and survival of the mixed tumor cells in vivo, and that at least some of this effect is due to the apoptotic death of cells in the mixed tumor following treatment.

These results demonstrate the utility of hedgehog antagonists in the inhibition of proliferation and growth of cancer cells. Additionally, this model provides an in vivo method for easily evaluating the efficacy of candidate hedgehog antagonists.

METHODS: Experiment 1. Twenty nude mice were injected subcutaneously with a combination of $10^6$ HT-29 cells (a Shh expressing colon cancer cell line) and $10^6$ 10T ½ cells (a fibroblast cell line) in a volume of 100 µl. The mice were randomized into two groups. Group A was treated with PBS, and group B was treated with 5E1. The treatments were initiated on the same day as injection of the tumor cells. Treatment was administered IP, 3 times/week over a period of thirty days, and at a dose of 6 mg/kg. Additionally, this experiment was carried out under an identical protocol using another Shh expressing colon cancer cell line (Colo205) with similar results.

Experiment 2—delayed administration. Twenty nude mice were injected subcutaneously with a combination of $10^6$ HT-29 cells (a Shh expressing colon cancer cell line) and $10^6$ 10T ½ cells (a fibroblast cell line) in a volume of 100 µl. The mice were randomized into two groups. Group A was treated with PBS, and group B was treated with 5E1. Treatment was initiated after the tumor had grown to day 11. Such tumors had a volume of approximately 90-210 $mm^3$. Treatment was administered IP, 3 times/week over a period of twenty-nine days (until day 40 of total tumor growth), and at a dose of 6 mg/kg. Additionally, this experiment was carried out under an identical protocol using another Shh expressing colon cancer cell line (Colo205) with similar results.

Model II

Figure 37:
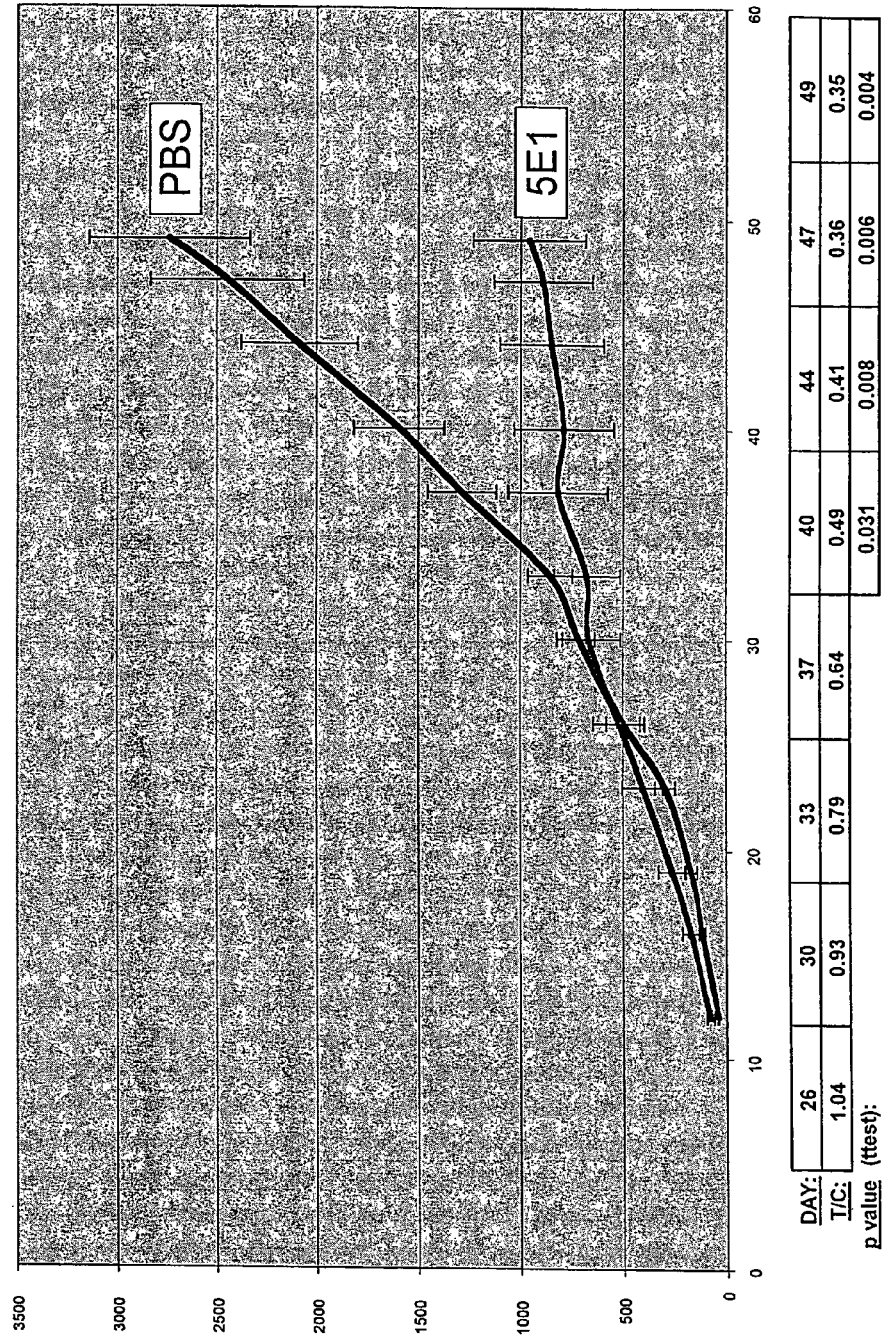
FIG. 37 shows that delayed administration of the Shh blocking antibody 5E1 decreases tumor size when administered to mice injected with the Shh expressing colon cancer cell line HT-29.
Figure 38:
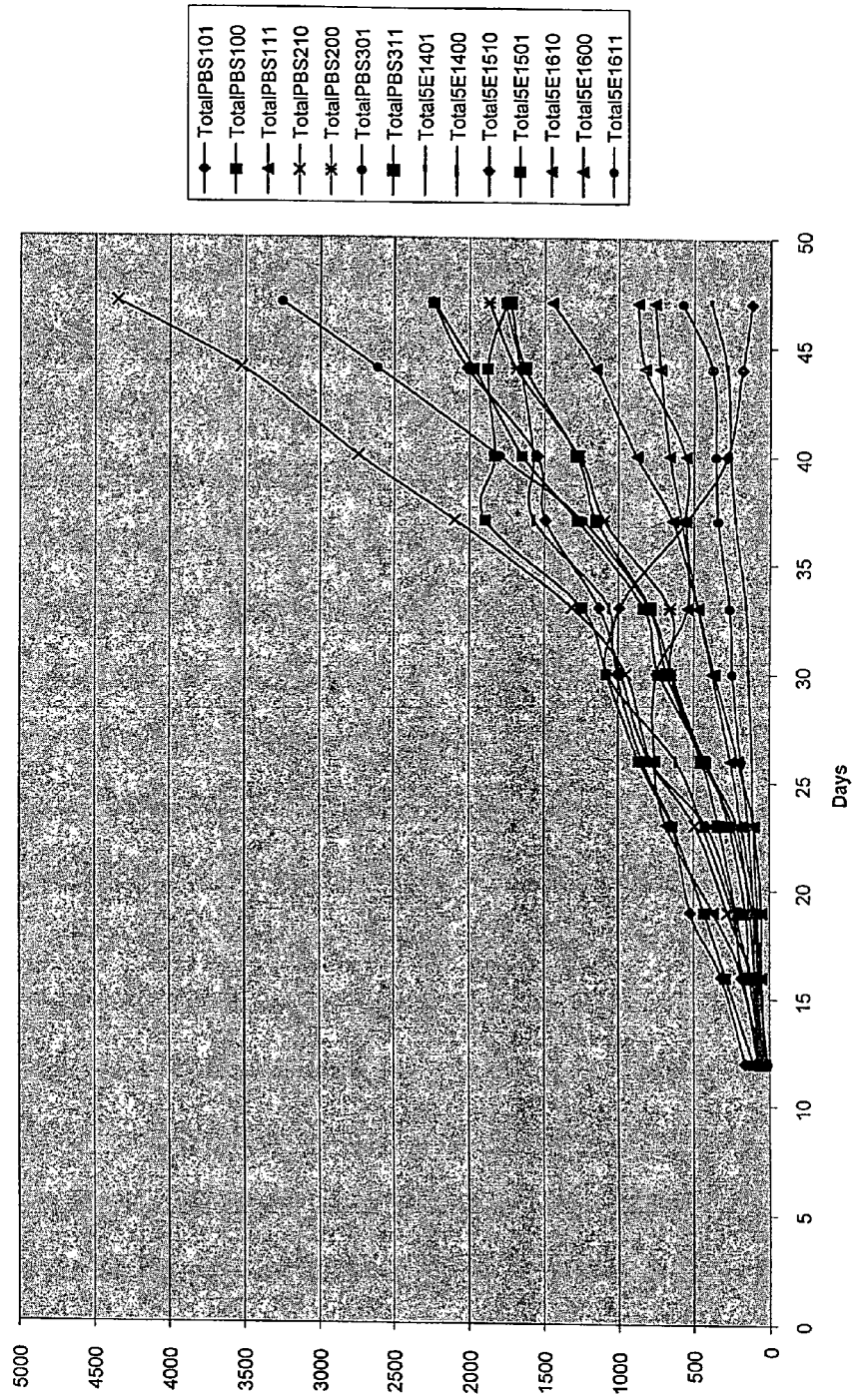
FIG. 38 shows that delayed administration of the Shh blocking antibody 5E1 decreases tumor size when administered to mice injected with the Shh expressing colon cancer cell line HT-29.
Figure 39:
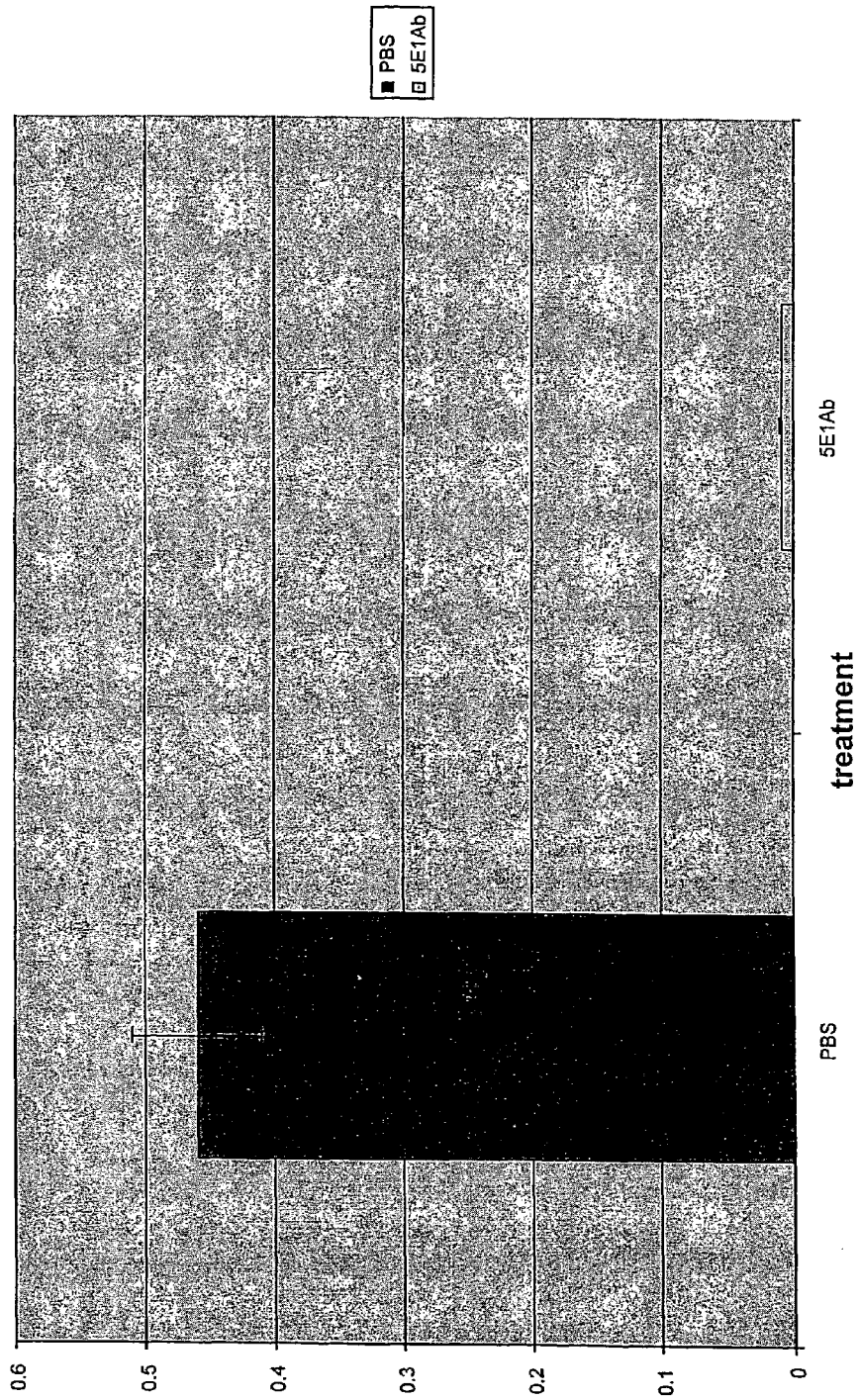
FIG. 39 shows that delayed administration of the Shh blocking antibody 5E1 to mice injected with the Shh expressing colon cancer cell line HT-29 decreases expression of gli-1 mRNA.

Similar experiments were conducted to assess the efficacy of a hedgehog antagonist in decreasing the growth, proliferation and survival of tumors derived from the transplantation of HT-29 cells alone. Hedgehog expressing HT-29 colon cancer cells were injected subcutaneously into nude mice as described in detail above. FIGS. 37 and 38 show that delayed administration of the hedgehog antagonist, 5E1, significantly reduces the growth of such tumors in vivo when compared to tumors treated with the PBS control. Consistant with these results, treatment with 5E1 also significantly reduces the expression of gli-1 in these tumors when compared to tumors treated with the PBS control (FIG. 39).

The results obtained using the two in vivo models described in detail above demonstrate that the antagonism of hedgehog signaling can significantly inhibit the growth, proliferation, and survival of hedgehog expressing tumors.

METHODS: Nude mice were injected subcutaneously with $10^6$ HT-29 cells (a Shh expressing colon cancer cell line) in a volume of 100 µl. The mice were randomized into two groups. Group A was treated with PBS, and group B was treated with 5E1. Treatment was initiated after the tumor had grown to day 11. Treatment was administered IP, 3 times/week over a period of fifty days, and at a dose of 6 mg/kg. Tumor volumes were measured over time. Additionally, expression of gli-1 mRNA was analyzed by Q-RT-PCR in PBS treated versus 5E1 treated tumors.

EXAMPLE 16

Antagonism of Hedgehog Signaling in Pancreatic Cancer

We had previously demonstrated that hedgehog mRNA and protein are expressed in several pancreatic cancer cell lines, as well as in primary human pancreatic tissue samples. Given the existence of hedgehog expressing pancreatic cancer cell lines, we examined the ability of antagonism of hedgehog signaling to decrease growth, proliferation, and survival of pancreatic cancel cells in xenografts in nude mice. Similar to the results observed with xenografts of hedgehog expressing bladder, prostate and colon cancer cell lines, administration of a hedgehog antagonist decrease the size and survival of tumors generated by xenografts of hedgehog expressing pancreatic cancer cells.

SW1990 Xenograft

SW-1990 is a hedgehog expressing pancreatic ductal adenocarcinoma cell line. To assess the potential efficacy of administration of hedgehog antagonists to treat pancreatic tumors, tumors were generated in nude mice by subcutaneous injection of SW-1990 cells. In these experiments, SW-1990 cells were injected in the absence of fibroblasts. Animals that received the SW-1990 cells were divided into two groups, and immediately began receiving treatment with either the hedgehog blocking antibody 5E1 or PBS. Animals receiving 5E1 received a dose of 2 mg/kg, intraveneously, once per week.

The effects of treatment with the hedgehog antagonist 5E1 were evaluated by measuring tumor volume and weight, as well as by visual inspection of the tumors. Interestingly, tumor volume was variable due to inflammation, and thus visual analysis and tumor weight appear to be a more accurate measure of the effects of hedgehog antagonism on these tumors.

Figure 40:
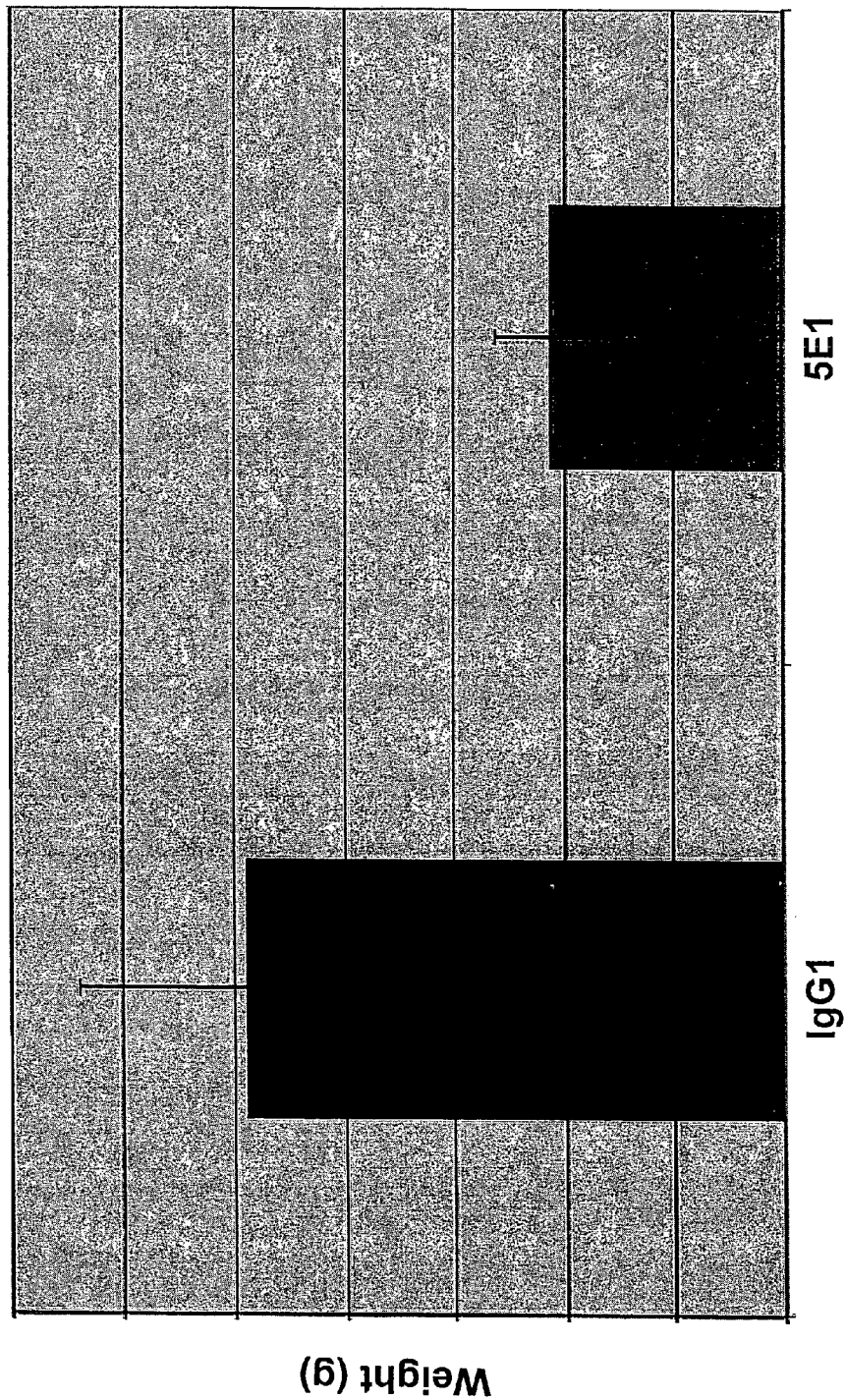
FIG. 40 shows that administration of the Shh blocking antibody 5E1 to mice injected with the hedgehog expressing pancreatic cancer cell line SW 1990 decreases tumor weight.
Figure 41:
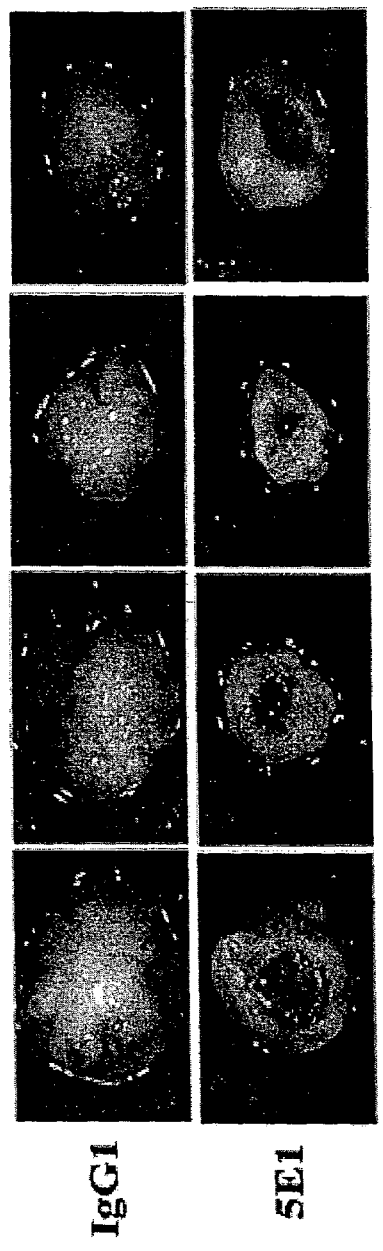
FIG. 41 shows that administration of the Shh blocking antibody 5E1 to mice injected with the hedgehog expressing pancreatic cancer cell line SW1990 decreases tumor size, and results in extensive domains of necrosis within said tumors.
Figure 42:
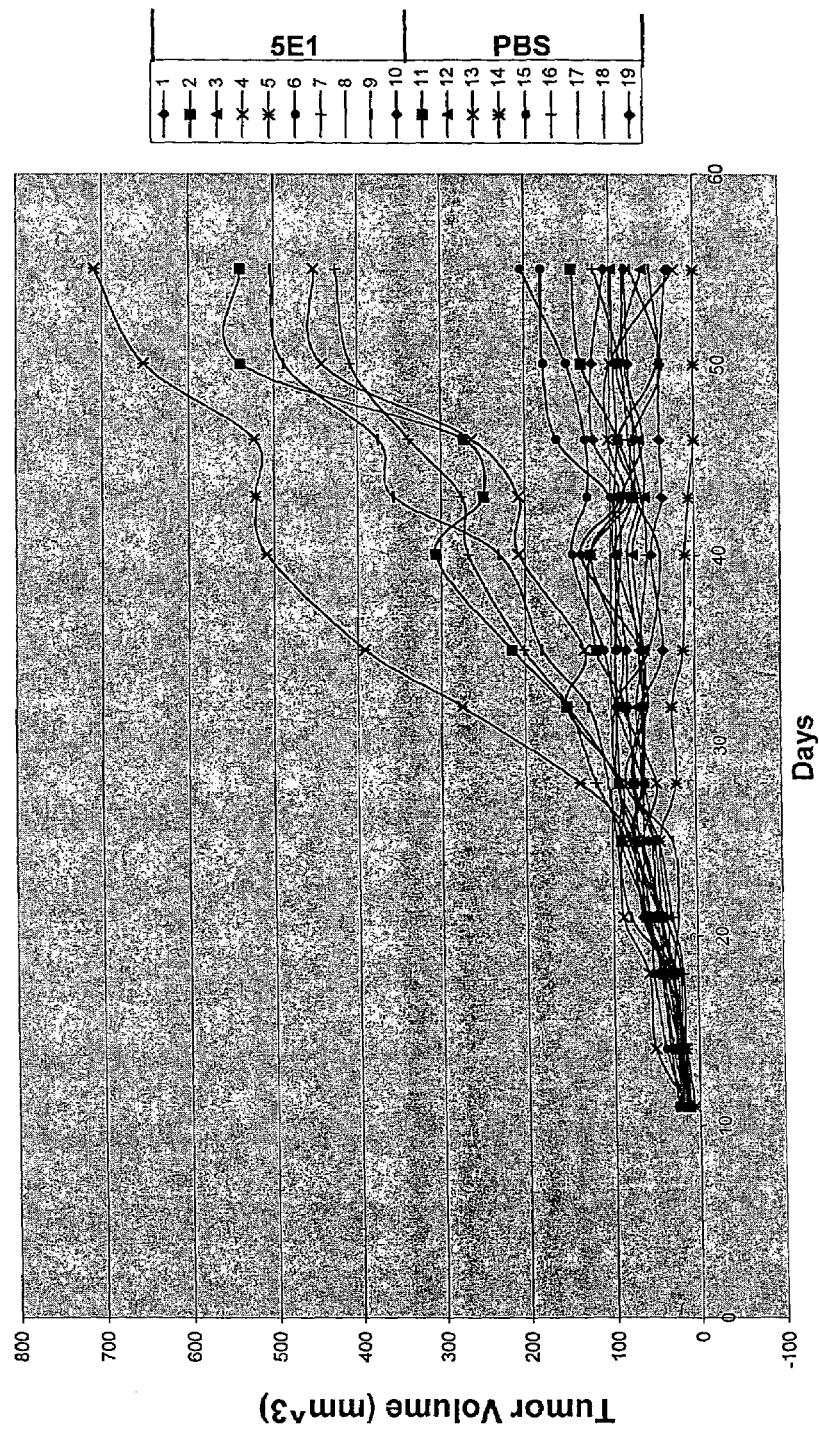
FIG. 42 shows that administration of the Shh blocking antibody 5E1 to mice injected with the hedgehog expressing pancreatic cancer cell line SW 1990 decreases tumor volume.

FIG. 40 demonstrates that administration of the blocking antibody 5E1 results in a significant decrease in the weigh of SW1990 xenograft tumors. The effects of 5E1 treatment are most dramatically related through visual inspection of the tumors. FIG. 41 shows that 5E1 treated tumors are smaller than control tumors, and that the 5E1 treated tumors contain extensive regions of necrosis. Although volume of SW1990 xenograft tumors was variable, owing to inflammation, FIG. 42 indicates the overall trend of decreased volume of xenograft tumors following administration of the hedgehog antagonist 5E1.

CF PAC Xenograft

To further confirm the results demonstrating that inhibition of hedgehog signaling has efficacy in inhibiting growth, proliferation and survival of hedgehog expressing pancreatic tumors, similar experiments were conducted with another hedgehog expressing pancreatic tumor cell line, CF PAC. Like SW1990, CF PAC is a hedgehog expressing pancreatic ductal adenocarcinoma cell line. Experiments were performed using similar methods for generating SW 1990 xenografts, and for testing the efficacy of the hedgehog antagonist 5E1 in said xenografts. The only difference in the two experiments is that 5E1 treatment was delayed until approximately 11 days following administration of CF-PAC cells The effects of treatment with the hedgehog antagonist 5E1 were evaluated by measuring tumor volume and weight. Interestingly, tumor volume was variable due to inflammation, and thus visual analysis and tumor weight appear to be a more accurate measure of the effects of hedgehog antagonism on these tumors.

Figure 43:
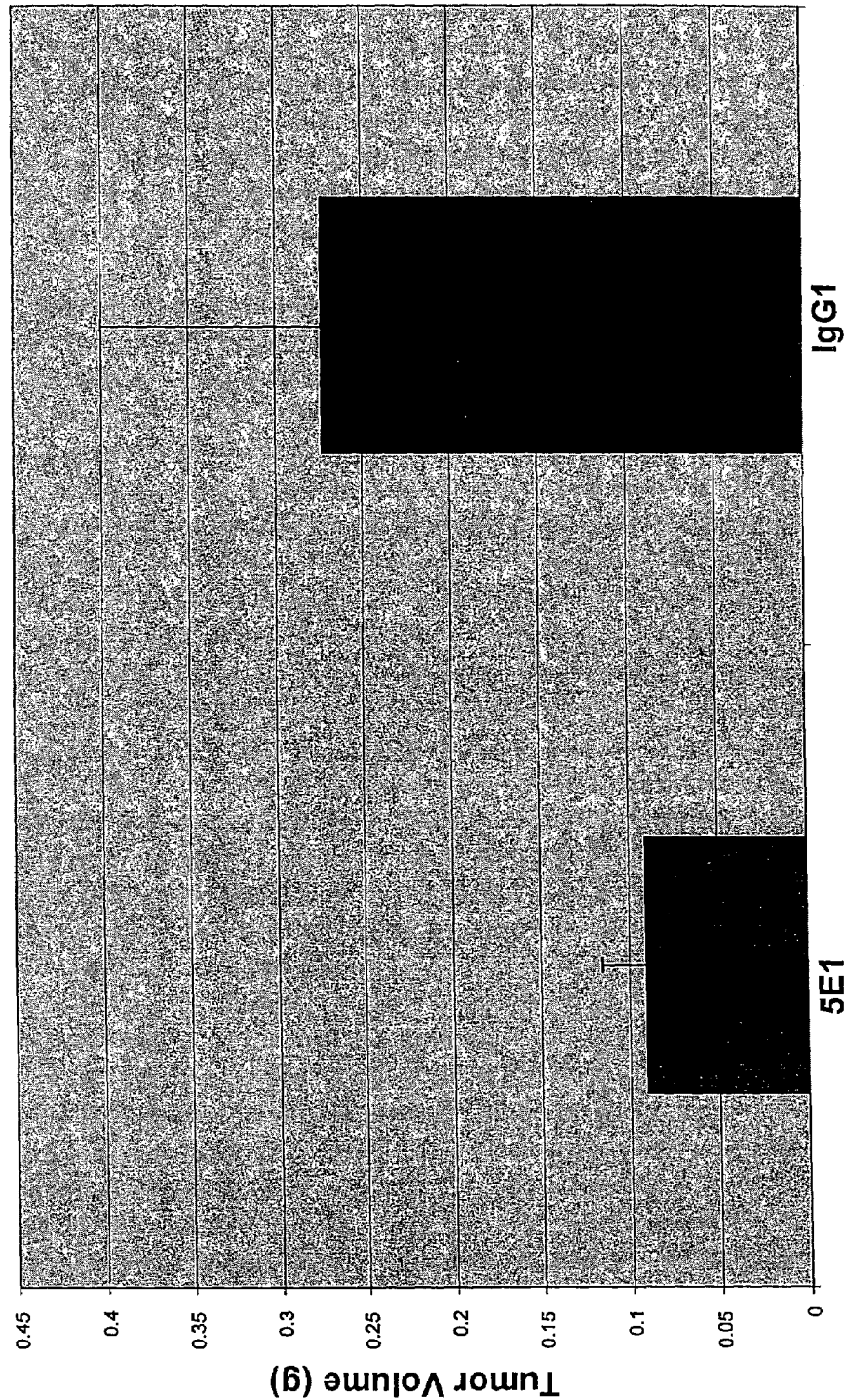
FIG. 43 shows that administration of the Shh blocking antibody 5E1 to mice injected with the hedgehog expressing pancreatic cancer cell line CF PAC decreases tumor weight.
Figure 44:
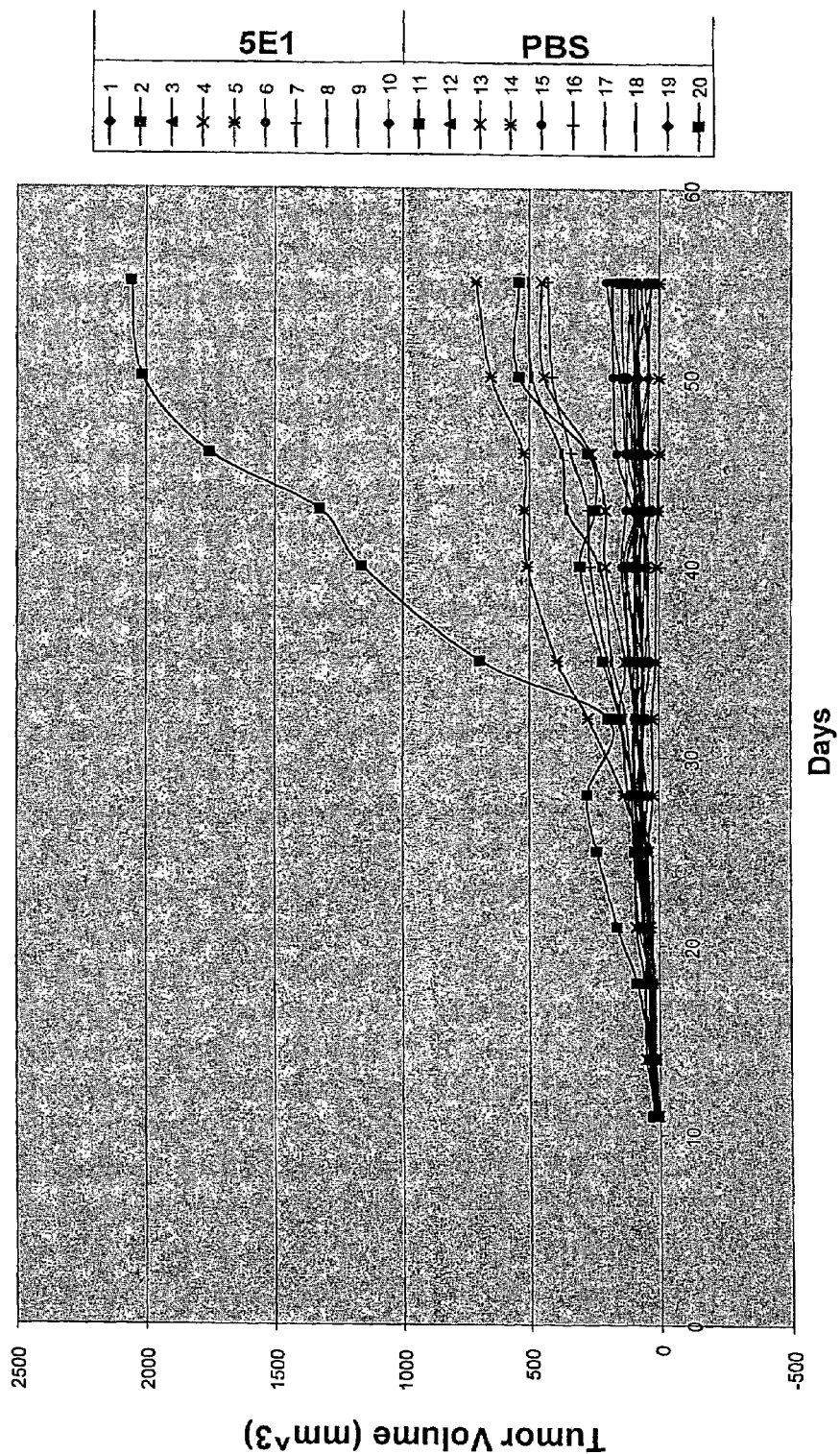
FIG. 44 shows that administration of the Shh blocking antibody 5E1 to mice injected with the hedgehog expressing pancreatic cancer cell line CF PAC decreases tumor volume.

FIG. 43 demonstrates that administration of the blocking antibody 5E1 results in a significant decrease in the weight of CF PAC xenograft tumors. Although the volume of CF PAC xenograft tumors was variable, owing to inflammation, FIG. 44 indicates the overall trend of decreased volume of xenograft tumors following administration of the hedgehog antagonist 5E1.

EXAMPLE 17

Non-Hedgehog Expressing Cancer Cell Line

Efficacy of antagonism of hedgehog signaling in regulating the growth, proliferation and survival of hyperproliferative cells was examined using a cancer cell line which does not express hedgehog. Without being bound by any particular theory, it is possible that the antagonism of hedgehog signaling is most effective in regulating cell growth, proliferation and survival in cells in which hedgehog signaling is already hyper-activated. Such cells would include, for example, cells comprising a mutation in a component of the hedgehog signaling pathway wherein the mutation results in at least one of gain-of-function of an activator of hedgehog signaling or loss-of-function of a repressor of hedgehog signaling (e.g, patched).

Figure 45:
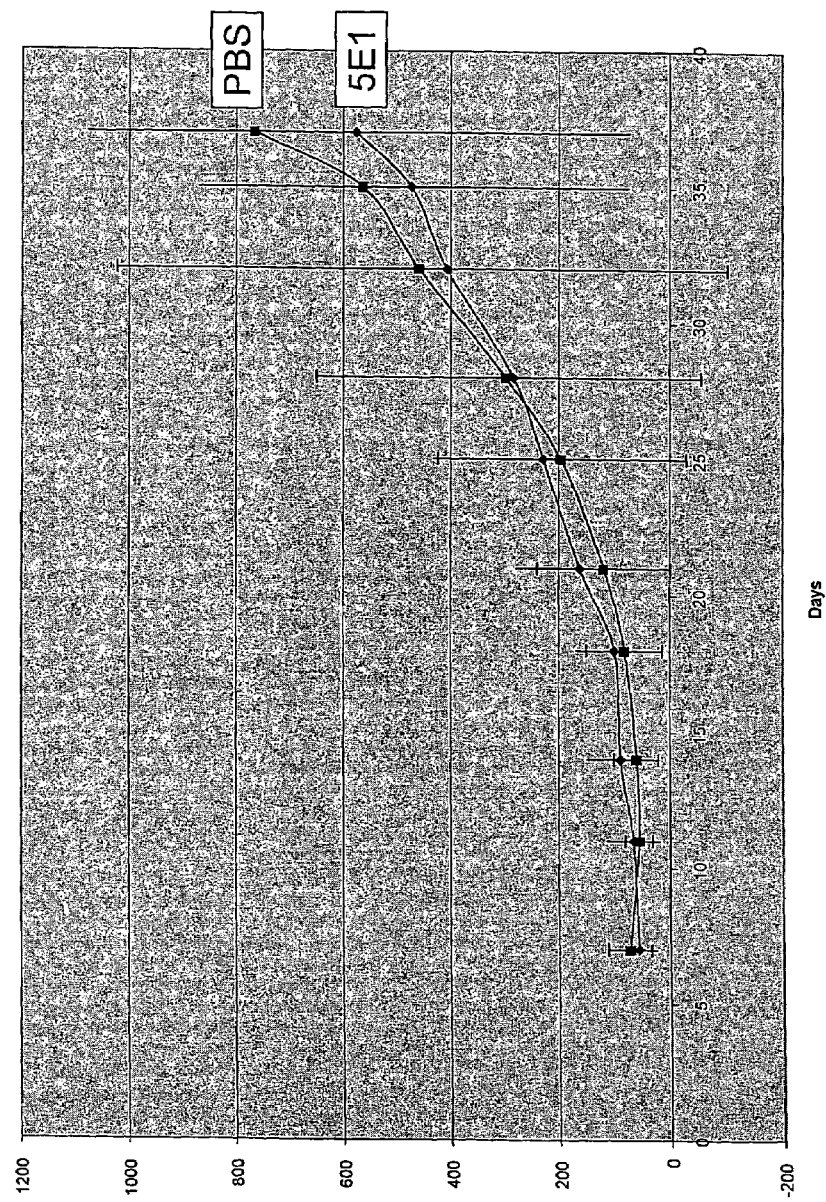
FIG. 45 shows that administration of the Shh blocking antibody 5E1 to mice injected with the non-hedgehog expressing colon cancer cell line SW480 has no effect on tumor volume.

SW-480 is a colon adenocarcinoma cell line which does not express hedgehog. SW-480 cells were administered subcutaneously to nude mice to generate xenografts, as previously described. Approximately seven days after administration of the SW-480 cells, treatment with either 5E1 or PBS control was initiated (delayed administration). In 5E1 treated animals, administration was at a dose of 2 mg/kg, intravenously, once per week. Tumor volumes were measured regularly throughout treatment. FIG. 45 demonstrates that administration of 5E1 appears to have no effect on tumor volume in SW-480 xenografts.

The results of these experiments further underscore that unregulated hedgehog signaling can result in hyper-proliferation and/or inappropriate cell survival. These results demonstrate the uility of inhibition of inappropriate hedgehog signaling as a method of inhibiting inappropriate cell proliferation, growth and survival. Examples of conditions which can be treated by these methods include, but are not limited to, various forms of cancer.

Additionally, the observation that hedgehog antagonism is most effective in regulating cell proliferation, growth and survival in cells which express hedgehog, or cells in which the hedgehog signaling pathway is hyperactivated, suggest diagnostic methods for predicting which conditions and which patients (e.g., which forms of cancer) are most likely to respond to treatment regimens which include a hedgehog antagonist.

EXAMPLE 18

Drug Screens

The foregoing examples present both in vitro and in vivo models for examining the effects of hedgehog antagonist on cell proliferation. The models provide assays for testing a range of antagonistic agents for the ability to inhibit cell growth and proliferation. Such screens can be used in initial assays to identify lead compounds, and can also be used to evaluate the relative efficacies of candidate compounds.

Antagonistic agents that can be analyzed in this way include small molecules, blocking antibodies, antisense oligonucleotides, and polypeptides. These agents may interfere with hedgehog signaling at any point along the signal transduction pathway. For example, preferred agents may interact with hedgehog, patched-1, or smoothened. Additional preferred agents may interact with an intracellular component of the hedgehog pathway including gli-1, gli-2, or gli-3.

The in vitro and in vivo methods described above are not specific for the cancer cell lines explicitly described herein. Any cell type or cell line could be similarly tested, and these methods could be easily used to assess the ability of hedgehog antagonists to inhibit tumor growth and proliferation in other types of cancer cells. Additionally, the in vitro assay could be employed to analyze hedgehog signaling and the ability of hedgehog antagonists to block hedgehog signaling in other non-cancerous hyperproliferative cell types. For example, hyperproliferative conditions include many other classes of disorders including skin maladies such as psoriasis. The effects of candidate hedgehog antagonists on these cell types can be easily assessed using the methods described here.

EXAMPLE 19

Production and Expression of HH-Ig Fusions

Materials and Methods

Construction of pUB55, Expression Plasmid for Sonic Hedgehog in *Pichia pastoris*:

pUB55 contains the N-terminal domain of human Sonic Hedgehog (SEQ ID NO: 21 in Table 4) with the alpha factor PrePro region as the secretion signal. pUB55 was constructed in pCCM73, a derivative of pPIC9 (obtained from Invitrogen, San Diego, Calif.) with the Kanamycin gene (HincII-HincII fragment) of pUC4-K inserted at the Sph1 site of pPIC9. The human Sonic hedgehog coding sequence from Ear1-Not1 was obtained from pEAG543 which has a stop codon and Not 1 site engineered following Gly197 in the coding sequence.

Plasmid pCCM73 was cut with XhoI and NotI and was ligated with the Ear1-Not1 fragment of pEAG543 (containing the Sonic Hedgehog coding sequence, Table 4) and oligonucleotides [5' TCG AGA AAA GAT GCG GAC CGG GCA GGG GGT 3': SEQ ID NO: 36 and 5'CGA ACC CCC TGC CCG GTC CGC ATC TTT TC 3': SEQ ID NO: 37] that form a XhoI-EarI fragment and create the appropriate coding sequence for placing Sonic hedgehog adjacent to the alpha factor leader sequence in frame.

Expression of Desert Hedgehog in *Pichia pastoris* and Construction of KEX2 Site Mutations:

The Desert Hedgehog coding region in plasmid pEAG680 was modified to incorporate a BsrGI and an XmaI site site using the Stratagene QuikChange mutagenesis kit.

Expression of Indian Hedgehog in *Pichia pastoris* and Construction of KEX2 Site Mutattions:

Plasmid pEAG657 is pBluescript with the Indian Hedgehog coding sequence with a stop codon following codon GlyXXX. pEAG658 is pBluescript with the Indian Hedgehog coding sequence and a Sall site engineered within residues suitable for fusing the Indian Hedgehog coding sequence (SEQ ID NO: 22) with Fc immunoglobulin coding sequences (SEQ ID NOS: 28-30) at the hinge region of immunoglobulins. To facilitate subsequent manipulations, SpeI and XmaI sites were introduced to pEAG658 by site-directed mutagenesis.

Table: DNA sequences of Hedgehog N-terminal domains and Immunoglobulin Fc

| Regions | Sequence |
| --- | --- |
| Human Sonic Hedgehog N-terminal domain | SEQ ID NO: 21 |
| Human Indian Hedgehog N-terminal domain | SEQ ID NO: 22 |
| Human Desert Hedgehog N-terminal domain | SEQ ID NO: 27 |
| Fc region of human IgG1 - with Asn-Gln glycosylation site mutation | SEQ ID NO: 28 |
| Fc region of murine IgG1 - with Asn-Gln glycosylation site mutation | SEQ ID NO: 29 |
| Fc region of murine IgG2a - with Asn-Gln glycosylation site mutation | SEQ ID NO: 30 |

Table: Plasmid DNA sequences

| | |
| --- | --- |
| pUB 55 | SEQ ID NO: 31 |
| pUB 114 | SEQ ID NO: 32 |
| pUB 115 | SEQ ID NO: 33 |
| pUB 116 | SEQ ID NO: 34 |
| pEAG657 | SEQ ID NO: 35 |

Construction of Hedgehog-Ig Fusion Proteins

Shh-Fc(muIgG1) plasmid pUB114 (SEQ ID NO: 32), has the wild-type SHH domain (SEQ ID NO: 21 or 23) fused to the $CH_2$ and $CH_3$ regions of murine IgGI (SEQ ID NO: 29).

The Fc region in pUB114 contains a glycosylation site mutation [Asn297Gln]. Plasmid pUB55 (SEQ ID NO: 31) and pUB 114 plasmids are identical outside of the region coding for the Fc domain fused to SHH. Plasmids identical to pUB 114, but containing the human IgGI or murine IgG2a Fc region are pUB 115 (SEQ ID NO: 33) and pUB 116 (SEQ ID NO: 34), respectively.

For construction of yeast strains expressing protein, plasmids were digested with Stu1 and transformed into *Pichia pastoris* GS115 by electroporation in 1M Sorbitol (Invitrogen) or by a Li salt transformation procedure (Frozen EZ Yeast Transformation kit, Zymo Research, Orange, Calif.). His+transformants were selected on MD agar. Colonies were purified on YPD agar and cultured for protein expression in 5 ml BMMY (2% Methanol) medium. BMMY culture supernatants were harvested at 1 or 2 days (1-day harvests were concentrated by TCA precipitation) and were analyzed by SDS-PAGE and Coomassie blue staining to distinguish clipped and unclipped SHE Protein Purification Large scale preparations of protein for purification were prepared as follows: An inoculum in BMGY (late log to stationary phase) was added to 1 L BMGY in a Fernbach flask and incubated at 150 rpm for 2-3 days. The stationary phase BMGY culture was centrifuged and the cell pellet from 1 L was resuspended in BMMY(2% Methanol) and incubated in a Fernbach flask at 30 C for 2-3 days. Pepstatin A (44 microM) was added to BMMY medium for expression of SHH-Fc fusion proteins.

A. Purification of Hedgehog-Ig Fusion Protein Constructs

*Pichia* cells were removed from the conditioned medium by centrifugation before application to Protein A Fast Flow® (Pharmacia). Protein from constructs utilizing human IgGl (SEQ ID NO: 28) or murine IgG2A sequences (SEQ ID NO: 30) were applied directly to the Protein A. Constructs utilizing murine IgG 1 sequences were diluted ten-fold with water to reduce the salt concentration, re-concentrated using a 3K cutoff spiral filter (Amicon) and the pH adjusted with the addition of sodium borate buffer, pH 8.5 to a final concentration of 50 mM.

HHIg was eluted with 25 mM sodium phosphate, pH 2.8, and the fractions collected into tubes containing 0.1 volume of 0.5 M sodium phosphate pH 6 to readjust the pH. The Protein A eluant was then diluted eight-fold with 0.5 mM sodium phosphate, pH 6 and applied to a CM-Poros® column (Perseptive Biosystems) equilibrated with 50 mM sodium phosphate, pH 6.0. Elution with a gradient of 0-0.8 M NaCl separated two HHIg peaks.

The first is "one-armed" protein in which one of the HHIg polypeptides of the dimer is proteolytically cleaved at a sequence near the hinge and therefore this dimer contains only one HH N-terminal domain. The second peak is the dimer with two full-length HHIg chains. The peaks were pooled separately, reduced with 10 mM DTT and dialyzed against 5 mM sodium phosphate, pH 5.5, 150 mM NaCl and 0.5 mM DTT. No DTT was used when the N-terminal cysteine of the protein was replaced with other amino acids. These two purification steps achieve >95% purity. Purity was determined by SDS-PAGE on 4-20% gradient gels (Novex) stained with Coomassie Blue. Identity was confirmed by mass spectrometry, and potency was analyzed using a cell-based bioactivity assay (see above).

Mass Spectrometry

The molecular masses of the purified proteins were determined by electrospray ionization mass spectroscopy (ESI-MS) on a Micromass Quattro II triple quadrupole mass spectrometer. Samples were desalted using an on-line Michrom Ultrafast Microprotein Analyzer system with a Reliasil© C4 column (1 mm×5 cm). All electrospray mass spectral data were processed using the Micromass MassLynx data system.

REFERENCES

Apelqvist A, Ahlgren U, Edlund H. Sonic hedgehog directs specialised mesoderm differentiation in the intestine and pancreas. Curr Biol. October 1, 1997;7(10):801-4.

Asahara, T, Chen D, Tomono, T, Fujikawa, K, Kearney, M, Magner, M, Yancopoulos, G D and Isner, J M. Tie2 receptor ligands, angiopoietin-1 and angiopoietin-2, modulate VEGF-Induced postnatal neovascularization. Circ. Res. 1997 83: 233-240.

Ballara S C, Miotla J M, Paleolog E M. New vessels, new approaches: angiogenesis as a therapeutic target in musculoskeletal disorders. Int J Exp Pathol. October 1999; 80(5): 235-50.

Banai S, Jaklitsch M T, Shou M, Lazarous D F, Scheinowitz M, Biro S, Epstein S E, Unger E F. Angiogenic-induced enhancement of collateral blood flow to ischemic myocardium by vascular endothelial growth factor in dogs. Circulation. May 1994; 89(5):2183-9

Battler A, Scheinowitz M, Bor A, Hasdai D, Vered Z, Di Segni E, Varda-Bloom N, Nass D, Engelberg S, Eldar M, et al. Intracoronary injection of basic fibroblast growth factor enhances angiogenesis in infarcted swine myocardium. J Am Coll Cardiol. December 1993; 22(7):2001-6.

Beck L Jr, D'Amore P A. Vascular development: cellular and molecular regulation. FASEB J. April 1997; 11(5):365-73

Bitgood M J, McMahon A P. Hedgehog and Bmp genes are coexpressed at many diverse sites of cell-cell interaction in the mouse embryo. Dev Biol. November 1995; 172(1): 126-38

Bitgood M J, Shen L, McMahon A P. (1996) Sertoli cell signaling by Desert hedgehog regulates the male germline. Curr Biol. 6(3):298-304.

Bhushan M, McLaughlin B, Weiss J B, Griffiths C E. Levels of endothelial cell stimulating angiogenesis factor and vascular endothelial growth factor are elevated in psoriasis. Br J Dermatol. December 1999; 141(6):1054-60.

Buschmann 1, Schaper W. The pathophysiology of the collateral circulation (arteriogenesis). J Pathol. February 2000; 190(3):338-42.

Carpenter D, Stone D M, Brush J, Ryan A, Armanini M, Frantz G, Rosenthal A, de Sauvage F J. Characterization of two patched receptors for the vertebrate hedgehog protein family. Proc Natl Acad Sci USA. Nov. 10, 1998;95(23): 13630-4.

Chiang C, Litingtung Y, Lee E, Young K E, Corden J L, Westphal H, Beachy P A. cyclopia and defective axial patterning in mice lacking sonic hedgehog gene function. Nature 1996; 383:407-413.

Cherrington J M, Strawn L M, Shawver L K. New paradigms for the treatment of cancer: the role of anti-angiogenesis agents. Adv Cancer Res. 2000;79: 1-38.

Couffinhal T, Silver M, Kearney M, Sullivan A, Witzenbichler B, Magner M, Annex B, Peters K, Isner J M. Impaired collateral vessel development associated with reduced expression of vascular endothelial growth factor in ApoE−/− mice. Circulation. 1999; 99: 3188-3198.

D'Amato R J, Adamis A P. Angiogenesis inhibition in age-related macular degeneration. Ophthalmology. September 1995;102(9):1261-2.

Ding Q, Fukami Si, Meng X, Nishizaki Y, Zhang X, Sasaki H, Dlugosz A, Nakafuku M, Hui Cc. Mouse suppressor of fused is a negative regulator of sonic hedgehog signaling and alters the subcellular distribution of Gli 1. Curr Biol. Oct. 7, 1999;9(19):1119-22.

Dockter J L. Sclerotome induction and differentiation. Curr Top Dev Biol. 2000 48:77-127.

Dodd J, Jessell T M, Placzek M. The when and where of floor plate induction. Science 1998 282(5394):1654-7.

Ericson J, Muhr J, Jessell T M, Edlund T. Sonic hedgehog: a common signal for ventral patterning along the rostrocaudal axis of the neural tube. Int J Dev Biol. 1995 39(5):809-16.

Ericson J, Briscoe J, Rashbass P, van Heyningen V, Jessell T M. Graded sonic hedgehog signaling and the specification of cell fate in the ventral neural tube. Cold Spring Harb Symp Quant Biol. 1997 62:451-66

Engler D A. Use of vascular endothelial growth factor for therapeutic angiogenesis. Circulation. Oct. 1, 1996;94(7): 1496-8.

Fan H, Villegas C, Chan A K, Wright J A. Myc-epitope tagged proteins detected with the 9E10 antibody in immunofluorescence and immunoprecipitation assays but not in western blot analysis. Biochem Cell Biol. 1998;76(1):125-8.

Folkman J, Shing Y. Angiogenesis. J Biol Chem. Jun. 5, 1992;267(16):10931-4

Fong T A, Shawver L K, Sun L, Tang C, App H, Powell T J, Kim Y H, Schreck R, Wang X, Risau W, Ullrich A, Hirth K P, McMahon G. SU5416 is a potent and selective inhibitor of the vascular endothelial growth factor receptor (Flk-1/KDR) that inhibits tyrosine kinase catalysis, tumor vascularization, and growth of multiple tumor types. Cancer Res. Jan. 1, 1999;59(1):99-106.

Goodrich L V, Milenkovic L, Higgins K M, Scott M P. Altered neural cell fate and medulloblastoma in mouse patched mutants. Science 1997;277(5329): 1109-1113.

Hammerschmidt M, Brook A, McMahon A P. The world according to hedgehog. Trends Genet. January 1997;13(1): 14-21.

Harada K, Grossman W, Friedman M, Edelman E R, Prasad P V, Keighley C S, Manning W J, Sellke F W, Simons M. Basic fibroblast growth factor improves myocardial function in chronically ischemic porcine hearts. J Clin Invest. August 1994; 94(2):623-30.

Hynes M, Ye W, Wang K, Stone D, Murone M, Sauvage Fd, Rosenthal A. The seven-transmembrane receptor smoothened cell-autonomously induces multiple ventral cell types. Nat Neurosci. January 2000;3(1):41-6.

Ingham P W. Signalling by hedgehog family proteins in Drosophila and vertebrate development. Curr Opin Genet Dev. 1995; 5:492-8.

Isner J M, Walsh K, Symes J, Pieczek A, Takeshita S, Lowry J, Rosenfield K, Weir L, Brogi E, Jurayj D. Arterial gene transfer for therapeutic angiogenesis in patients with peripheral artery disease. Hum Gene Ther. May 20, 1996;7 (8):959-88

Iwamoto M, Enomoto-Iwamoto M, Kurisu K. Actions of hedgehog proteins on skeletal cells. Crit Rev Oral Biol Med. 1999; 10:477-486.

Jensen A M, Wallace V A. Expression of Sonic hedgehog and its putative role as a precursor cell mitogen in the developing mouse retina. Development. January 1997; 124(2): 363-71.

Johnson R L, Tabin C J. Molecular models for vertebrate limb development. Cell. 1997; 90(6):979-90.

Karasek M A. Progress in our understanding of the biology of psoriasis. Cutis. November 1999; 64(5):319-22.

Karp S J, Schipani E, St-Jacques B, Hunzelman J, Kronenberg H, McMahon A P. Indian hedgehog coordinates endochondral bone growth and morphogenesis via parathyroid hormone related-protein-dependent and -independent pathways. Development. 2000; 127(3):543-8.

Kenyon, B M, Voest, E E, Chen C C. Flynn, E., Folkman, J and D'Amato, R J. A model of angiogenesis in the mouse cornea. Investigative Ophthalmology&Visual Science 1996; 37: 1625-1632.

Klagsbrun M, D'Amore P A. Regulators of angiogenesis. Annu Rev Physiol. 1991;53:217-39

Klohs W D, Hamby J M Antiangiogenic agents. Curr Opin Biotechnol. December 1999; 10(6):544-9.

Kornowski R, Hong M K, Leon M B. Comparison between left ventricular electromechanical mapping and radionuclide perfusion imaging for detection of myocardial viability. Circulation. Nov. 3, 1998;98(18):1837-41.

Kornowski R, Fuchs S, Leon M B, Epstein S E. Delivery strategies to achieve therapeutic myocardial angiogenesis. Circulation. Feb. 1, 2000;101(4):454-8.

Laham R J, Rezaee M, Post M, Novicki D, Sellke F W, Pearlman J D, Simons M, Hung D. Intrapericardial delivery of fibroblast growth factor-2 induces neovascularization in a porcine model of chronic myocardial ischemia. J Pharmacol Exp Ther. February 2000;292(2):795-802.

Landau C, Jacobs A K, Haudenschild C C. Intrapericardial basic fibroblast growth factor induces myocardial angiogenesis in a rabbit model of chronic ischemia. Am Heart J. May 1995; 129(5):924-31.

Lazarous D F, Shou M, Scheinowitz M, Hodge E, Thirumurti V, Kitsiou A N, Stiber J A, Lobo A D, Hunsberger S, Guetta E, Epstein S E, Unger E F. Comparative effects of basic fibroblast growth factor and vascular endothelial growth factor on coronary collateral development and the arterial response to injury. Circulation. Sep. 1, 1996; 94(5): 1074-82

Lemire J M, Covin C W, Whit S, Giacelli C M, Schwartz S M. Characterization of cloned aortic smooth muscle cells from young rats. Am. J. Pathol. 1994; 144:1068-1081.

Litingtung Y, Lei L, Westphal H, Chiang C. Sonic hedgehog is essential to foregut development. Nat Genet. 1998; 20(1):58-61. 119

Magovem C J, Mack C A, Zhang J, Rosengart T K, Isom O W, Crystal R G. Regional angiogenesis induced in nonischemic tissue by an adenoviral vector expressing vascular endothelial growth factor. Hum Gene Ther. Jan. 10, 1997;8 (2):215-27.

Majesky M W. A little VEGF goes a long way. Therapeutic angiogenesis by direct injection of vascular endothelial growth factor-encoding plasmid DNA. Circulation. Dec. 15, 1996;94(12):3062-4.

Mesri E A, Federoff H J, Brownlee M. Expression of vascular endothelial growth factor from a defective herpes simplex virus type 1 amplicon vector induces angiogenesis in mice. Circ Res. February 1995;76(2):161-7.

Motoyama J, Heng H, Crackower M A, Takabatake T, Takeshima K, Tsui L C, Hui C. Overlapping and non-overlapping Ptch2 expression with Shh during mouse embryogenesis. Mech Dev. November 1998;78(1-2):81-4.

Murone M, Rosenthal A, de Sauvage F J. Hedgehog signal transduction: from flies to vertebrates. Exp Cell Res. Nov. 25, 1999a;253(1):25-33

Murone M, Rosenthal A, de Sauvage F J. Sonic hedgehog signaling by the patched-smoothened receptor complex. Curr Biol. Jan. 28, 1999b;9(2):76-84.

Ozaki H, Seo M S, Ozaki K, Yamada H, Yamada E, Okamoto N, Hofmann F, Wood J M, Campochiaro P A. Blockade of vascular endothelial cell growth factor receptor signaling is sufficient to completely prevent retinal neovascularization. Am J Pathol. February 2000;156(2):697-707.

Parmantier E, Lynn B, Lawson D, Turmaine M, Namini S S, Chakrabarti L, McMahon A P, Jessen K R, Mirsky R. Schwann cell-derived Desert hedgehog controls the development of peripheral nerve sheaths. Neuron 1999; 23(4):713-24.

Passaniti, A, Taylor, R M, Pili, R, Guo, Y, Long, P V, Haney, F A, Pauly, R R, Grant, D S and Martin, G R. A simple, quantitative method for assessing angiogenesis and antiangiogenic agents using reconstituted basement membrane, heparin, and fibroblast growth factor. Lab. Invest. 1992 67: 519-528.

Peacock D J, Banquerigo M L, Brahn E. A novel angiogenesis inhibitor suppresses rat adjuvant arthritis. Cell Immunol. February 1995;160(2):178-84.

Pearlman J D, Hibberd M G, Chuang M L, Harada K, Lopez J J, Gladstone S R, Friedman M, Sellke F W, Simons M. Magnetic resonance mapping demonstrates benefits of VEGF-induced myocardial angiogenesis. Nat Med. October 1995;1(10): 1085-9.

Pearse R V 2nd, Collier L S, Scott M P, Tabin C J. Vertebrate homologs of Drosophila suppressor of fused interact with the gli family of transcriptional regulators. Dev Biol. Aug. 15, 1999;212(2):323-36.

Pepinsky R B, Zeng C, Wen D, Rayhorn P, Baker D P, Williams K P, Bixler S A, Ambrose C M, Garber E A, Miatkowski K, Taylor, F R, Wang E A, Galdes A. Identification of a palmitic acid-modified form of human Sonic hedgehog. J Biol Chem 1998 273(22):14037-45.

Pepinsky R B, Rayhorn P, Day E S, Dergay A, Williams K P, Galdes A, Taylor F R, Boriack-Sjodin A, Garber E A. Mapping sonic hedgehog-receptor interactions by steric interference. J. Biol. Chem. 2000 275:10995-11001.

Perrimon N. Hedgehog and beyond. Cell 1995; 80(4):517-20

Rivard A, Isner J M. Angiogenesis and vasculogenesis in treatment of cardiovascular disease. Mol Med. July 1998;4(7):429-40.

Rivard A, Fabre J E, Silver M, Chen D, Murohara T, Kearney M, Magner M, Asahara T, Isner J M. Age-dependent impairment of angiogenesis. Circulation. Jan. 5-12, 1999; 99(1):111-20.

Rothman A, Kulik, T J, Taubman, M B, Berk, B C, Smith C W J, nadal-Ginard, B. Development and characterization of a cloned rat pulmonary arterial smooth muscle cell line that maintains differentiated propoerties through multiple subcultures. Circulation. 1992; 86:1977-1986.

Sato N, Leopold P L, Crystal R G. Induction of the hair growth phase in postnatal mice by localized transient expression of Sonic hedgehog. J Clin Invest. October 1999; 104(7): 855-64.

Schratzberger P, Schratzberger G, Silver M, Curry C, Kearney M, Magner M, Alroy J, Adelman L S, Weinberg D H, Ropper A H, Isner J M. Favorable effect of VEGF gene transfer on ischemic peripheral neuropathy. -Nat Med. April 2000;6(4):405-13.

Shou M, Thirumurti V, Rajanayagam S, Lazarous D F, Hodge E, Stiber J A, Pettiford M, Elliott E, Shah S M, Unger E F. Effect of basic fibroblast growth factor on myocardial angiogenesis in dogs with mature collateral vessels. J Am Coll Cardiol. April 1997; 29(5): 1102-6.

St-Jacques B, Dassule H R, Karavanova I, Botchkarev V A, Li J, Danielian P S, McMahon J A, Lewis P M, Paus R, McMahon A P. Sonic hedgehog signaling is essential for hair development. Curr Biol. 1998; 8(19): 1058-68

St-Jacques B, Hammerschmidt M, McMahon A P. Indian hedgehog signaling regulates proliferation and differentiation of chondrocytes and is essential for bone formation. Genes Dev. 1999; 13(16):2072-86.

Stone D M, Murone M, Luoh S, Ye W, Armanini M P, Gurney A, Phillips H, Brush J, Goddard A, de Sauvage, F J, Rosenthal A. Characterization of the human suppressor of fused, a negative regulator of the zinc-finger transcription factor Gli. J Cell Sci. December 1999; 112 (Pt 23):4437-48.

Storgard C M, Stupack D G, Jonczyk A, Goodman S L, Fox R I, Cheresh D A. Decreased angiogenesis and arthritic disease in rabbits treated with an alphavbeta3 antagonist. J Clin Invest. January 1999;103(1):47-54.

Takeshita S, Pu L Q, Stein L A, Sniderman A D, Bunting S, Ferrara N, Isner J M, Symes J F. Intramuscular administration of vascular endothelial growth factor induces dose-dependent collateral artery augmentation in a rabbit model of chronic limb ischemia. Circulation. November 1994;90(5 Pt 2):II228-34.

Takeshita S, Weir L, Chen D, Zheng L P, Riessen R, Bauters C, Symes J F, Ferrara N, Isner J M. Therapeutic angiogenesis following arterial gene transfer of vascular endothelial growth factor in a rabbit model of hindlimb ischemia. Biochem Biophys Res Commun. Oct. 14, 1996;227(2):628-35.

Taylor F R, Wen D, Garber E A, Baker D P, Arduini R M, Williams K P, Weinreb P H, Rayhom P, Hronowski X, Whitty A, Day E S, Boriack-Sjodin A, Shapiro R, and Pepinsky R B. Enhanced potency of human sonic hedgehog by hydrophobic modification. Manuscript in prep.

Traiffort E, Charytoniuk D A, Faure H, Ruat M. Regional distribution of Sonic Hedgehog, patched, and smoothened mRNA in the adult rat brain. J Neurochem. March 1998; 70(3): 1327-30.

Traiffort E, Charytoniuk D, Watroba L, Faure H, Sales N, Ruat M. Discrete localizations of hedgehog signalling components in the developing and adult rat nervous system. Eur J Neurosci. September 1999;11(9):3199-214

Unger E F, Banai S, Shou M, Lazarous D F, Jaklitsch M T, Scheinowitz M, Correa R, Klingbeil C, Epstein S E. Basic fibroblast growth factor enhances myocardial collateral flow in a canine model. Am J Physiol. April 1994;266(4 Pt 2):H1588-95.

Vale P R, Losordo D W, Tkebuchava T, Chen D, Milliken C E, Isner J M. Catheter-based myocardial gene transfer utilizing nonfluoroscopic electromechanical left ventricular mapping. J Am Coll Cardiol. July 1999;34(1):246-54.

Valentini R P, Brookhiser W T, Park J, Yang T, Briggs J, Dressler G, Holzman L B. Post-translational processing and renal expression of mouse Indian hedgehog. J Biol Chem. Mar. 28, 1997;272(13):8466-73.

Walsh D A. Angiogenesis and arthritis. Rheumatology (Oxford). February 1999; 38(2): 103-12.

Wang L C, Liu Z Y, Gambardella L, Delacour A, Shapiro R, Yang J, Sizing I, Rayhom P, Garber E A, Benjamin C D, Williams K P, Taylor F R, Barrandon Y, Ling L, Burkly L C. Conditional Disruption of Hedgehog Signaling Pathway Defines its Critical Role in Hair Development and Regeneration. J Invest Dermatol. May 2000;114(5):901-908.

Wood J M, Bold G, Buchdunger E, Cozens R, Ferrari S, Frei J, Hofmann F, Mestan J, Mett H, O'Reilly T, Persohn E, Rosel J, Schnell C, Stover D, Theuer A, Towbin H, Wenger F, Woods-Cook K, Menrad A, Siemeister G, Schimer M, Thierauch K H, Schneider M R, Drevs J, Martiny-Baron G, Totzke F. PTK787/ZK 222584, a novel and potent inhibitor of vascular endothelial growth factor receptor tyrosine kinases, impairs vascular endothelial growth factor-induced responses and tumor growth after oral administration. Cancer Res. Apr. 15, 2000;60(8):2178-89.

Yancopoulos G D, Klagsbrun M, Folkman J. Vasculogenesis, angiogenesis, and growth factors: ephrins enter the fray at the border. Cell. May 29, 1998;93(5):661-4.

Yanagisawa-Miwa A, Uchida Y, Nakamura F, Tomaru T, Kido H, Kamijo T, Sugimoto T, Kaji K, Utsuyama M, Kurashima C, et al. Salvage of infarcted myocardium by angiogenic action of basic fibroblast growth factor. Science. Sep. 4, 1992; 257(5075):1401-3.

Zhu Z, Witte L. Inhibition of tumor growth and metastasis by targeting tumor-associated angiogenesis with antagonists to the receptors of vascular endothelial growth factor. Invest New Drugs. 1999; 17(3): 195-212.

All publications, patents and patent applications are herein incorporated by reference in their entirety to the same extent as if each individual publication, patent or patent application was specifically and individually indicated to be incorporated by reference in its entirety.

EQUIVALENTS

Those skilled in the art will recognize, or be able to ascertain using no more than routine experimentation, many equivalents to the specific embodiments of the invention described herein.

We claim:

1. A method for treating an endometrial or liver tumor in a patient in need thereof, comprising assaying whether said tumor expresses at least one of a Sonic hedgehog gene or a gli-1 gene and administering to said patient an amount of a hedgehog antagonist sufficient to decrease at least one of the growth, proliferation or survival of the tumor, wherein the tumor expresses at least one of a Sonic hedgehog gene or a gli-1 gene, and wherein the hedgehog antagonist is a hedgehog antibody that binds to Sonic hedgehog protein and inhibits hedgehog signaling.

2. The method of claim 1, wherein said hedgehog antagonist is administered as part of a cancer treatment regimen.

3. A method of inhibiting at least one of growth, proliferation or survival of an endometrial or liver cancer or tumor cell, comprising
   (a) assaying whether said cell expresses a Sonic hedgehog gene, and
   (b) contacting said cell which expresses said Sonic hedgehog gene with an effective amount of a hedgehog antagonist;
   wherein contacting said cell with said hedgehog antagonist decreases at least one of cell growth, proliferation or survival, and wherein the hedgehog antagonist is a hedgehog antibody that binds to Sonic hedgehog protein and inhibits hedgehog signaling.

4. The method of claim 1 or 3, wherein said hedgehog antibody is a monoclonal antibody.

5. The method of claim 4, wherein said monoclonal antibody is selected from 5E1 or an antigen-binding fragment thereof.

6. A method of inhibiting at least one of cell growth, proliferation or survival of an endometrial or liver cancer or tumor cell in a patient in need thereof, comprising
   (a) assaying whether the cell expresses a Sonic hedgehog gene, and
   (b) administering to said patient an effective amount of a hedgehog antibody, which hedgehog antibody binds to Sonic hedgehog protein and specifically antagonizes hedgehog signaling in both the tumor cell and in an adjacent non-tumor stromal cell;
   wherein administering said hedgehog antibody decreases at least one of cell growth, proliferation or survival.

7. The method of claim 6, wherein said hedgehog antibody which specifically antagonizes hedgehog signaling is a monoclonal antibody.

8. The method of claim 7, wherein said monoclonal antibody is 51 or an antigen-binding fragment thereof.

9. The method of claim 6, wherein said hedgehog antibody which antagonizes hedgehog signaling is formulated in a pharmaceutically acceptable carrier.

10. The method of claim 9, wherein said hedgehog antibody is administered as part of a cancer treatment regimen.

11. A method of inhibiting at least one of cell growth, proliferation or survival of an endometrial or liver cancer or tumor cell, comprising
    (a) assaying whether said cell expresses a Sonic hedgehog gene, and
    (b) contacting said cell which expresses said Sonic hedgehog gene with an effective amount of a hedgehog antibody that binds to Sonic hedgehog protein and inhibits hedgehog signaling, which hedgehog antibody is 5E1, a humanized antibody thereof, or an antigen-binding fragment thereof;
    wherein contacting said cell with said hedgehog antibody decreases at least one of cell growth, proliferation or survival.

12. The method of claim 11, wherein said hedgehog antibody which antagonizes hedgehog signaling is formulated in a pharmaceutically acceptable carrier.

13. The method of claim 11, wherein said hedgehog antibody is administered as part of a cancer treatment regimen.

14. A method for treating a liver tumor in a patient in need thereof comprising administering to said patient an amount of a hedgehog antagonist effective to decrease at least one of the growth, proliferation or survival of said tumor, wherein the hedgehog antagonist is a hedgehog antibody that binds to Sonic hedgehog protein and inhibits hedgehog signaling, and wherein the liver tumor expresses Sonic hedgehog.

15. The method of claim 14, wherein said hedgehog antagonist is administered as part of a cancer treatment regimen.

16. The method of claim 14, wherein said hedgehog antibody comprises a monoclonal antibody.

17. The method of claim 16, wherein said monoclonal antibody comprises 5E1 or an antigen-binding fragment thereof.

18. The method of claim 14, wherein said hedgehog antagonist is formulated in a pharmaceutically acceptable carrier.

19. The method of claim 1, wherein said tumor is an endometrial tumor.

20. The method of claim 1, wherein said tumor is a liver tumor.

21. The method of claim 3, wherein said cell is an endometrial cancer or tumor cell.

22. The method of claim 3, wherein said cell is a liver cancer or tumor cell.

23. The method of claim 6, wherein said cell is an endometrial cancer or tumor cell.

24. The method of claim 6, wherein said cell is a liver cancer or tumor cell.

25. The method of claim 11, wherein said cell is an endometrial cancer or tumor cell.

26. The method of claim 11, wherein said cell is a liver cancer or tumor cell.

27. A method for treating an endometrial or liver tumor in a patient, comprising assaying whether said tumor expresses a Sonic hedgehog protein, and administering to said patient an amount of a hedgehog antibody that binds to Sonic hedgehog protein and inhibits hedgehog signaling sufficient to decrease at least one of the growth, proliferation or survival of the tumor, wherein the tumor expresses a Sonic hedgehog protein.

28. The method of claim 27, wherein said hedgehog antibody is administered as part of a cancer treatment regimen.

29. A method of inhibiting at least one of growth, proliferation or survival of an endometrial or liver cancer or tumor cell, comprising
(a) assaying whether said cell expresses a Sonic hedgehog protein, and
(b) contacting said cell which expresses said Sonic hedgehog protein with an effective amount of a hedgehog antibody that binds to Sonic hedgehog protein and inhibits hedgehog signaling;
wherein contacting said cell with said hedgehog antibody decreases at least one of cell growth, proliferation or survival.

30. The method of claim 27, wherein said tumor is an endometrial tumor.

31. The method of claim 27, wherein said tumor is a liver tumor.

32. The method of claim 29, wherein said cancer or tumor cell is an endometrial cancer or tumor cell.

33. The method of claim 29, wherein said cancer or tumor cell is a liver cancer or tumor cell.

34. The method of claim 1, wherein the hedgehog antibody is a humanized antibody.

35. The method of claim 3, wherein the hedgehog antibody is a humanized antibody.

36. The method of claim 6, wherein the hedgehog antibody is a humanized antibody.

37. The method of claim 11, wherein the hedgehog antibody is a humanized antibody.

38. The method of claim 14, wherein the hedgehog antibody is a humanized antibody.

39. The method of claim 27, wherein the hedgehog antibody is a humanized antibody.

40. The method of claim 29, wherein the hedgehog antibody is a humanized antibody.

41. The method of claim 1, wherein the hedgehog antibody is a human antibody.

42. The method of claim 3, wherein the hedgehog antibody is a human antibody.

43. The method of claim 6, wherein the hedgehog antibody is a human antibody.

44. The method of claim 11, wherein the hedgehog antibody is a human antibody.

45. The method of claim 14, wherein the hedgehog antibody is a human antibody.

46. The method of claim 27, wherein the hedgehog antibody is a human antibody.

47. The method of claim 29, wherein the hedgehog antibody is a human antibody.

48. A method for treating an endometrial or liver tumor in a patient in need thereof, comprising assaying whether said tumor expresses at least one of a Sonic hedgehog gene or a gli-1 gene and administering to said patient an amount of a hedgehog antagonist sufficient to decrease at least one of the growth, proliferation or survival of the tumor, wherein the tumor expresses at least one of a Sonic hedgehog gene or a gli-1 gene, and wherein the hedgehog antagonist is a hedgehog antibody that binds to Sonic hedgehog protein and inhibits hedgehog signaling and is selected from 5E1 or an antigen-binding fragment thereof.

49. A method of inhibiting at least one of growth, proliferation or survival of an endometrial or liver cancer or tumor cell, comprising
(a) assaying whether said cell expresses a Sonic hedgehog gene, and
(b) contacting said cell which expresses said Sonic hedgehog gene with an effective amount of a hedgehog antagonist;
wherein contacting said cell with said hedgehog antagonist decreases at least one of cell growth, proliferation or survival, and wherein the hedgehog antagonist is a hedgehog antibody that binds to Sonic hedgehog protein and inhibits hedgehog signaling and is selected from 5E1 or an antigen-binding fragment thereof.

50. The method of claim 48, wherein said hedgehog antagonist is administered as part of a cancer treatment regimen.

51. A method for treating a liver tumor in a patient in need thereof, comprising administering to said patient an amount of a hedgehog antagonist effective to decrease at least one of the growth, proliferation or survival of said tumor, wherein the liver tumor expresses Sonic hedgehog and the hedgehog antagonist is a hedgehog antibody that binds to Sonic hedgehog protein and inhibits hedgehog signaling and is selected from 5E1 or an antigen-binding fragment thereof.

52. The method of claim 51, wherein said hedgehog antagonist is administered as part of a cancer treatment regimen.

53. The method of claim 48, wherein the hedgehog antibody is a humanized antibody.

54. The method of claim 48, wherein the hedgehog antibody is a human antibody.

55. The method of claim 49, wherein the hedgehog antibody is a humanized antibody.

56. The method of claim 49, wherein the hedgehog antibody is a human antibody.

57. The method of claim 51, wherein the hedgehog antibody is a humanized antibody.

58. The method of claim 51, wherein the hedgehog antibody is a human antibody.

59. A method for treating an endometrial or liver tumor in a patient, comprising assaying whether said tumor expresses a Sonic hedgehog protein, and administering to said patient an amount of a hedgehog antibody that binds to Sonic hedgehog protein and inhibits hedgehog signaling sufficient to decrease at least one of the growth, proliferation or survival of the tumor, which hedgehog antibody is selected from 5E1 or an antigen-binding fragment thereof, wherein the tumor expresses a Sonic hedgehog protein.

60. The method of claim 59, wherein the hedgehog antibody is a humanized antibody.

61. The method of claim 59, wherein the hedgehog antibody is a human antibody.

62. The method of claim 48, wherein the method is a method for treating an endometrial tumor.

63. The method of claim 48, wherein the method is a method for treating a liver tum or.

64. The method of claim 49, wherein the method is a method for treating an endometrial cancer or tumor cell.

65. The method of claim 49, wherein the method is a method for treating a liver cancer or tumor cell.

66. The method of claim 59, wherein the method is a method for treating an endometrial tumor in a patient.

67. The method of claim 59, wherein the method is a method for treating a liver tumor in a patient.

68. The method of claim 14, wherein the liver tumor expresses a Sonic hedgehog gene.

69. The method of claim 14, wherein the liver tumor expresses a Sonic hedgehog protein.

* * * * *

UNITED STATES PATENT AND TRADEMARK OFFICE
CERTIFICATE OF CORRECTION

PATENT NO. : 7,498,304 B2
APPLICATION NO. : 10/652686
DATED : March 3, 2009
INVENTOR(S) : Kotkow et al.

It is certified that error appears in the above-identified patent and that said Letters Patent is hereby corrected as shown below:

On the title page,

[*] Notice: Subject to any disclaimer, the term of this patent is extended or adjusted under 35 USC 154(b) by 611 days.

Delete the phrase "by 611 days" and insert -- by 659 days --

Signed and Sealed this

Twentieth Day of April, 2010

David J. Kappos
*Director of the United States Patent and Trademark Office*

SEQUENCE LISTING

<160> NUMBER OF SEQ ID NOS: 48

<210> SEQ ID NO 1
<211> LENGTH: 1277
<212> TYPE: DNA
<213> ORGANISM: Gallus gallus

<400> SEQUENCE: 1

```
atggtcgaaa tgctgctgtt gacaagaatt ctcttggtgg gcttcatctg cgctcttta      60 gtctcctctg ggctgacttg tggaccaggc aggggcattg gaaaaaggag gcaccccaaa    120
aagctgaccc cgttagccta taagcagttt attcccaatg tggcagagaa gaccctaggg    180
gccagtggaa gatatgaagg gaagatcaca agaaactccg agagatttaa agaactaacc    240
ccaaattaca accctgacat tatttttaag gatgaagaga cacgggagc tgacagactg    300 atgactcagc gctgcaagga caagctgaat gccctggcga tctcggtgat gaaccagtgg    360
cccggggtga agctgcgggt gaccgagggc tgggacgagg atggccatca ctccgaggaa    420
tcgctgcact acgagggtcg cgccgtggac atcaccacgt cggatcggga ccgcagcaag    480
tacggaatgc tggcccgcct cgccgtcgag gccggcttcg actgggtcta ctacgagtcc    540
aaggcgcaca tccactgctc cgtcaaagca gaaaactcag tggcagcgaa atcaggaggc    600
tgcttccctg gctcagccac agtgcacctg gagcatggag gcaccaagct ggtgaaggac    660
ctgagccctg ggaccgcgt gctggctgct gacgcggacg gccggctgct ctacagtgac    720
ttcctcacct tcctcgaccg gatggacagc tcccgaaagc tcttctacgt catcgagacg    780
cggcagcccc gggcccggct gctactgacg gcggcccacc tgctctttgt ggcccccag    840 cacaaccagt cggaggccac agggtccacc agtggccagg cgctcttcgc cagcaacgtg    900
aagcctggcc aacgtgtcta tgtgctgggc gagggcgggc agcagctgct gccggcgtct    960
gtccacagcg tctcattgcg ggaggaggcg tccggagcct acgcccact caccgcccag   1020 ggcaccatcc tcatcaaccg ggtgttggcc tcctgctacg ccgtcatcga ggagcacagt   1080
tgggcccatt gggccttcgc accattccgc ttggctcagg ggctgctggc cgccctctgc   1140
ccagatgggg ccatccctac tgccgccacc accaccactg gcatccattg gtactcacgg   1200
ctcctctacc gcatcggcag ctgggtgctg gatggtgacg cgctgcatcc gctgggcatg   1260
gtggcaccgg ccagctg                                                  1277
```

<210> SEQ ID NO 2
<211> LENGTH: 1190
<212> TYPE: DNA
<213> ORGANISM: Mus musculus

<400> SEQUENCE: 2

```
atggctctgc cggccagtct gttgcccctg tgctgcttgg cactcttggc actatctgcc    60
cagagctgcg ggccgggccg aggaccggtt ggccggcggc gttatgtgcg caagcaactt   120
gtgcctctgc tatacaagca gtttgtgccc agtatgcccg agcggaccct gggcgcgagt   180
gggccagcgg aggggagggt aacaaggggg tcggagcgct tccgggacct cgtacccaac   240
tacaaccccg acataatctt caaggatgag gagaacagcg cgcagaccg cctgatgaca   300
gagcgttgca aagagcgggt gaacgctcta gccatcgcgg tgatgaacat gtggcccgga   360
gtacgcctac gtgtgactga aggctgggac gaggacggcc accacgcaca ggattcactc   420
cactacgaag gccgtgcctt ggacatcacc acgtctgacc gtgaccgtaa taagtatggt   480
ttgttggcgc gcctagctgt ggaagccgga ttcgactggg tctactacga gtcccgcaac   540
cacatccacg tatcggtcaa agctgataac tcactggcgg tccgagccgg aggctgcttt   600
ccgggaaatg ccacggtgcg cttgcggagc ggcgaacgga aggggctgag ggaactacat   660
cgtggtgact gggtactggc cgctgatgca gcgggccgag tggtacccac gccagtgctg   720
ctcttcctgg accgggatct gcagcgccgc gcctcgttcg tggctgtgga gaccgagcgg   780
cctccgcgca aactgttgct cacaccctgg catctggtgt tcgctgctcg cgggccagcg   840
cctgctccag gtgactttgc accggtgttc gcgcgccgct acgtgctggc gactcggtg   900
ctggctcccg gcgggacgc gctccagccg gcgcgcgtag cccgcgtggc gcgcgaggaa   960
gccgtgggcg tgttcgcacc gctcactgcg cacgggacgc tgctggtcaa cgacgtcctc  1020
gcctcctgct acgcggttct agagagtcac cagtgggccc accgcgcctt cgccccttg  1080
cggctgctgc acgcgctcgg ggctctgctc cctgggggtg cagtccagcc gactggcatg  1140
cattggtact ctcgcctcct ttaccgcttg gccgaggagt taatgggctg              1190
```

<210> SEQ ID NO 3
<211> LENGTH: 1281
<212> TYPE: DNA
<213> ORGANISM: Mus musculus

<400> SEQUENCE: 3

```
atgtctcccg cctggctccg gccccgactg cggttctgtc tgttcctgct gctgctgctt    60
ctggtgccgg cggcgcgggg ctgcgggccg ggccgggtgg tgggcagccg ccggaggccg   120
cctcgcaagc tcgtgcctct tgcctacaag cagttcagcc ccaacgtgcc ggagaagacc   180
ctgggcgcca gcgggcgcta cgaaggcaag atcgcgcgca gctctgagcg cttcaaagag   240
ctcaccccca actacaatcc cgacatcatc ttcaaggacg aggagaacac gggtgccgac   300
cgcctcatga cccagcgctg caaggaccgt ctgaactcac tggccatctc tgtcatgaac   360
cagtggcctg tgtgaaaact gcgggtgacc gaaggccggg atgaagatgg ccatcactca   420
gaggagtctt tacactatga gggccgcgcg gtggatatca ccacctcaga ccgtgaccga   480
aataagtatg gactgctggc gcgcttagca gtggaggccg gcttcgactg ggtgtattac   540
gagtccaagg cccacgtgca ttgctctgtc aagtctgagc attcggccgc tgccaagaca   600
ggtggctgct tcctgccgg agcccaggtg cgcctagaga acggggagcg tgtggccctg   660
tcagctgtaa agccaggaga ccgggtgctg ccatgggggg aggatgggac ccccaccttc   720
agtgatgtgc ttatttttcct ggaccgcgag ccaaaccggc tgagagcttt ccaggtcatc   780
gagactcagg atcctccgcg tcggctggcg ctcacgcctg cccacctgct cttcattgcg   840
gacaatcata cagaaccagc agcccactc cgggccacat ttgccagcca tgtgcaacca   900
```

```
ggccaatatg tgctggtatc aggggtacca ggcctccagc ctgctcgggt ggcagctgtc      960
tccacccacg tggcccttgg gtcctatgct cctctcacaa ggcatgggac acttgtggtg     1020
gaggatgtgg tggcctcctg ctttgcagct gtggctgacc accatctggc tcagttggcc     1080
ttctggcccc tgcgactgtt tcccagtttg gcatggggca gctggacccc aagtgagggt     1140
gttcactcct accctcagat gctctaccgc ctggggcgtc tcttgctaga agagagcacc     1200
ttccatccac tgggcatgtc tggggcagga agctgaaggg actctaacca ctgccctcct     1260
ggaactgctg tgcgtggatc c                                               1281

<210> SEQ ID NO 4
<211> LENGTH: 1313
<212> TYPE: DNA
<213> ORGANISM: Mus musculus

<400> SEQUENCE: 4
atgctgctgc tgctggccag atgttttctg gtgatccttg cttcctcgct gctggtgtgc      60
cccgggctgg cctgtgggcc cggcaggggg tttggaaaga ggcggcaccc caaaaagctg     120
acccctttag cctacaagca gtttattccc aacgtagccg agaagaccct aggggccagc     180
ggcagatatg aagggaagat cacaagaaac tccgaacgat ttaaggaact cacccccaat     240
tacaaccccg acatcatatt taaggatgag gaaaacacgg gagcagaccg gctgatgact     300
cagaggtgca agacaagtt aaatgccttg gccatctctg tgatgaacca gtggcctgga     360
gtgaggctgc gagtgaccga gggctgggat gaggacggcc atcattcaga ggagtctcta     420
cactatgagg gtcgagcagt ggacatcacc acgtccgacc gggaccgcag caagtacggc     480
atgctggctc gcctggctgt ggaagcaggt ttcgactggg tctactatga atccaaagct     540
cacatccact gttctgtgaa agcagagaac tccgtggcgg ccaaatccgg cggctgtttc     600
ccgggatccg ccaccgtgca cctggagcag ggcggcacca agctggtgaa ggacttacgt     660
cccggagacc gcgtgctggc ggctgacgac cagggccggc tgctgtacag cgacttcctc     720
accttcctgg accgcgacga aggcgccaag aaggtcttct acgtgatcga gacgctggag     780
ccgcgcgagc gcctgctgct caccgccgcg cacctgctct tcgtggcgcc gcacaacgac     840
tcggggccca cgcccgggcc aagcgcgctc tttgccagcc gcgtgcgccc cgggcagcgc     900
gtgtacgtgg tggctgaacg cggcgggac cgccggctgc tgcccgccgc ggtgcacagc     960
gtgacgctgc gagaggagga ggcgggcgcg tacgcgccgc tcacggcgca cggcaccatt    1020
ctcatcaacc gggtgctcgc ctcgtgctac gctgtcatcg aggagcacag ctgggcacac    1080
cgggccttcg cgccttttccg cctgcgcac gcgctgctgg ccgcgctggc acccgcccgc    1140
acggacggcg gggcggggg cagcatccct gcagcgcaat ctgcaacgga agcgagggc     1200 gcggagccga ctgcgggcat ccactggtac tcgcagctgc tctaccacat tggcacctgg    1260
ctgttggaca gcgagaccat gcatcccttg ggaatggcgg tcaagtccag ctg          1313

<210> SEQ ID NO 5
<211> LENGTH: 1256
<212> TYPE: DNA
<213> ORGANISM: Brachydanio rerio

<400> SEQUENCE: 5
atgcggcttt tgacgagagt gctgctggtg tctcttctca ctctgtcctt ggtggtgtcc      60
ggactggcct gcgtcctgg cagaggctac ggcagaagaa gacatccgaa gaagctgaca     120
cctctcgcct acaagcagtt catacctaat gtcgcggaga agaccttagg ggccagcggc     180
```

| | |
|---|---|
| agatacgagg gcaagataac gcgcaattcg gagagattta agaacttac tccaaattac | 240 |
| aatcccgaca ttatctttaa ggatgaggag aacacgggag cggacaggct catgacacag | 300 |
| agatgcaaag acaagctgaa ctcgctggcc atctctgtaa tgaaccactg gccagggggtt | 360 |
| aagctgcgtg tgacagaggg ctgggatgag acggtcacc attttgaaga atcactccac | 420 |
| tacgagggaa gagctgttga tattaccacc tctgaccgag acaagagcaa atacgggaca | 480 |
| ctgtctcgcc tagctgtgga ggctggattt gactgggtct attacgagtc caaagcccac | 540 |
| attcattgct ctgtcaaagc agaaaattcg gttgctgcga atctgggggg ctgtttccca | 600 |
| ggttcggctc tggtctcgct ccaggacgga ggacagaagg ccgtgaagga cctgaacccc | 660 |
| ggagacaagg tgctggcggc agacagcgcg ggaaacctgg tgttcagcga cttcatcatg | 720 |
| ttcacagacc gagactccac gacgcgacgt gtgttttacg tcatagaaac gcaagaaccc | 780 |
| gttgaaaaga tcaccctcac cgccgctcac ctccttttttg tcctcgacaa ctcaacggaa | 840 |
| gatctccaca ccatgaccgc cgcgtatgcc agcagtgtca gagccggaca aaaggtgatg | 900 |
| gttgttgatg atagcggtca gcttaaatct gtcatcgtgc agcggatata cacggaggag | 960 |
| cagcggggct cgttcgcacc agtgactgca catgggacca ttgtggtcga cagaatactg | 1020 |
| gcgtcctgtt acgccgtaat agaggaccag gggcttgcgc attttggcctt cgcgcccgcc | 1080 |
| aggctctatt attacgtgtc atcattcctg tcccccaaaa ctccagcagt cggtccaatg | 1140 |
| cgactttaca acaggagggg gtccactggt actccaggct cctgtcatca aatgggaacg | 1200 |
| tggcttttgg acagcaacat gcttcatcct ttggggatgt cagtaaactc aagctg | 1256 |

<210> SEQ ID NO 6
<211> LENGTH: 1425
<212> TYPE: DNA
<213> ORGANISM: Homo sapiens
<220> FEATURE:
<221> NAME/KEY: modified_base
<222> LOCATION: (1387...1389)
<223> OTHER INFORMATION: n=a, c, g, or t

<400> SEQUENCE: 6

| | |
|---|---|
| atgctgctgc tggcgagatg tctgctgcta gtcctcgtct cctcgctgct ggtatgctcg | 60 |
| ggactggcgt gcggaccggg cagggggttc gggaagagga ggcaccccaa aaagctgacc | 120 |
| cctttagcct acaagcagtt tatccccaat gtggccgaga agaccctagg cgccagcgga | 180 |
| aggtatgaag ggaagatctc cagaaactcc gagcgattta aggaactcac ccccaattac | 240 |
| aaccccgaca tcatatttaa ggatgaagaa acaccggag cggacaggct gatgactcag | 300 |
| aggtgtaagg acaagttgaa cgctttggcc atctcggtga tgaaccagtg gccaggagtg | 360 |
| aaactgcggg tgaccgaggg ctgggacgaa gatggccacc actcagagga gtctctgcac | 420 |
| tacgagggcc gcgcagtgga catcaccacg tctgaccgcg accgcagcaa gtacggcatg | 480 |
| ctggcccgcc tggcggtgga ggccggcttc gactgggtgt actacgagtc caaggcacat | 540 |
| atccactgct cggtgaaagc agagaactcg gtggcggcca atcgggagg ctgcttcccg | 600 |
| ggctcggcca cggtgcacct ggagcagggc ggcaccaagc tggtgaagga cctgagcccc | 660 |
| ggggaccgcg tgctggcggc ggacgaccag ggccggctgc tctacagcga cttcctcact | 720 |
| ttcctggacc gcgacgacgg cgccaagaag gtcttctacg tgatcgagac gcgggagccg | 780 |
| cgcgagcgcc tgctgctcac cgccgcgcac ctgctctttg tggcgccgca caacgactcg | 840 |
| gccaccgggg agcccgaggc gtcctcgggc tcggggccgc cttccggggg cgcactgggg | 900 |

```
cctcgggcgc tgttcgccag ccgcgtgcgc ccgggccagc gcgtgtacgt ggtggccgag    960
cgtgacgggg accgccggct cctgcccgcc gctgtgcaca gcgtgaccct aagcgaggag   1020
gccgcgggcg cctacgcgcc gctcacggcc cagggcacca ttctcatcaa ccgggtgctg   1080
gcctcgtgct acgcggtcat cgaggagcac agctgggcgc accgggcctt cgcgcccttc   1140
cgcctggcgc acgcgctcct ggctgcactg gcgcccgcgc gcacggaccg cggcggggac   1200
agcggcggcg gggaccgcgg gggcggcggc ggcagagtag ccctaaccgc tccaggtgct   1260
gccgacgctc cgggtgcggg ggccaccgcg ggcatccact ggtactcgca gctgctctac   1320
caaataggca cctggctcct ggacagcgag gccctgcacc cgctgggcat ggcggtcaag   1380
tccagcnnna gccggggggc cggggagggg gcgcgggagg gggcc                  1425
```

<210> SEQ ID NO 7
<211> LENGTH: 1622
<212> TYPE: DNA
<213> ORGANISM: Homo sapiens

<400> SEQUENCE: 7

```
catcagccca ccaggagacc tcgcccgccg ctcccccggg ctccccggcc atgtctcccg     60
cccggctccg gccccgactg cacttctgcc tggtcctgtt gctgctgctg gtggtgcccg    120
cggcatgggg ctgcgggccg ggtcgggtgg tgggcagccg ccggcgaccg ccacgcaaac    180
tcgtgccgct cgcctacaag cagttcagcc ccaatgtgcc cgagaagacc ctgggcgcca    240
gcggacgcta tgaaggcaag atcgctcgca gctccgagcg cttcaaggag ctcacccccca   300 attacaatcc agacatcatc ttcaaggacg aggagaacac aggcgccgac cgcctcatga    360
cccagcgctg caaggaccgc ctgaactcgc tggctatctc ggtgatgaac cagtggcccg    420
gtgtgaagct gcgggtgacc gagggctggg acgaggacgg ccaccactca gaggagtccc    480
tgcattatga gggccgcgcg gtggacatca ccacatcaga ccgcgaccgc aataagtatg    540
gactgctggc gcgcttggca gtggaggccg gctttgactg ggtgtattac gagtcaaagg    600
cccacgtgca ttgctccgtc aagtccgagc actcggccgc agccaagacg gcggctgct    660 tccctgccgg agcccaggta cgcctggaga gtggggcgcg tgtggccttg tcagccgtga    720
ggccgggaga ccgtgtgctg gccatggggg aggatgggag ccccaccttc agcgatgtgc    780
tcattttcct ggaccgcgag ccccacaggc tgagagcctt ccaggtcatc gagactcagg    840
accccccacg ccgcctggca ctcacacccg ctcacctgct ctttacggct gacaatcaca    900
cggagccggc agcccgcttc cgggccacat ttgccagcca cgtgcagcct ggccagtacg    960
tgctggtggc tggggtgcca ggcctgcagc ctgcccgcgt ggcagctgtc tctacacacg   1020
tggccctcgg ggcctacgcc ccgctcacaa agcatggac actggtggtg gaggatgtgg   1080
tggcatcctg cttcgcggcc gtggctgacc accacctggc tcagttggcc ttctggcccc   1140
tgagactctt tcacagcttg gcatgggca gctggacccc gggggagggt gtgcattggt   1200 accccccagct gctctaccgc ctggggcgtc tcctgctaga agagggcagc ttccacccac   1260
tgggcatgtc cggggcaggg agctgaaagg actccaccgc tgccctcctg gaactgctgt   1320
actgggtcca gaagcctctc agcaggagg gagctggccc tggaagggac ctgagctggg    1380
ggacactggc tcctgccatc tcctctgcca tgaagataca ccattgagac ttgactgggc   1440
aacaccagcg tccccaccc gcgtcgtggt gtagtcatag agctgcaagc tgagctggcg   1500
aggggatggt tgttgacccc tctctcctag agaccttgag gctggcacgg cgactcccaa   1560
ctcagcctgc tctcactacg agttttcata ctctgcctcc cccattggga gggcccattc   1620
```

| | |
|---|---:|
| cc | 1622 |

<210> SEQ ID NO 8
<211> LENGTH: 1191
<212> TYPE: DNA
<213> ORGANISM: Homo sapiens

<400> SEQUENCE: 8

| | |
|---|---:|
| atggctctcc tgaccaatct actgcccttg tgctgcttgg cacttctggc gctgccagcc | 60 |
| cagagctgcg ggccgggccg ggggccggtt ggccggcgcc gctatgcgcg caagcagctc | 120 |
| gtgccgctac tctacaagca atttgtgccc ggcgtgccag agcggaccct gggcgccagt | 180 |
| gggccagcgg aggggagggt ggcaaggggc tccgagcgct tccggaccct cgtgcccaac | 240 |
| tacaaccccg acatcatctt caaggatgag agaacagtg gagccgaccg cctgatgacc | 300 |
| gagcgttgca aggagagggt gaacgctttg gccattgccg tgatgaacat gtggcccgga | 360 |
| gtgcgcctac gagtgactga gggctgggac gaggacggcc accacgctca ggattcactc | 420 |
| cactacgaag gccgtgcttt ggacatcact acgtctgacc gcgaccgcaa caagtatggg | 480 |
| ttgctggcgc gcctcgcagt ggaagccggc ttcgactggg tctactacga gtcccgcaac | 540 |
| cacgtccacg tgtcggtcaa agctgataac tcactggcgg tccgggcggg cggctgcttt | 600 |
| ccgggaaatg caactgtgcg cctgtggagc ggcgagcgga aagggctgcg ggaactgcac | 660 |
| cgcggagact gggttttggc ggccgatgcg tcaggccggg tggtgcccac gccggtgctg | 720 |
| ctcttcctgg accgggactt gcagcgccgg gcttcatttg tggctgtgga gaccgagtgg | 780 |
| cctccacgca aactgttgct cacgccctgg cacctggtgt ttgccgctcg agggccggcg | 840 |
| cccgcgccag gcgactttgc accggtgttc gcgcgccggc tacgcgctgg ggactcggtg | 900 |
| ctggcgcccg gcggggatgc gcttcggcca gcgcgcgtgg cccgtgtggc gcggaggaa | 960 |
| gccgtgggcg tgttcgcgcc gctcaccgcg cacgggacgc tgctggtgaa cgatgtcctg | 1020 |
| gcctcttgct acgcggttct ggagagtcac cagtgggcgc accgcgcttt tgccccctta | 1080 |
| agactgctgc acgcgctagg ggcgctgctc cccggcgggg ccgtccagcc gactggcatg | 1140 |
| cattggtact ctcggctcct ctaccgctta gcggaggagc tactgggctg a | 1191 |

<210> SEQ ID NO 9
<211> LENGTH: 1251
<212> TYPE: DNA
<213> ORGANISM: Brachydanio rerio

<400> SEQUENCE: 9

| | |
|---|---:|
| atggacgtaa ggctgcatct gaagcaattt gctttactgt gttttatcag cttgcttctg | 60 |
| acgccttgtg gattagcctg tggtcctggt agaggttatg gaaaacgaag acacccaaag | 120 |
| aaattaaccc cgttggctta caagcaattc atccccaacg ttgctgagaa acgcttgga | 180 |
| gccagcggca aatacgaagg caaaatcaca aggaattcag agagatttaa agagctgatt | 240 |
| ccgaattata tcccgatat catctttaag gacgaggaaa acacaaacgc tgacaggctg | 300 |
| atgaccaagc gctgtaagga caagttaaat tcgttggcca tatccgtcat gaaccactgg | 360 |
| cccgcgtga aactgcgcgt cactgaaggc tgggatgagg atggtcacca tttagaagaa | 420 |
| tctttgcact atgagggacg ggcagtggac atcactacct cagacaggga taaaagcaag | 480 |
| tatgggatgc tatccaggct tgcagtggag gcaggattcg actgggtcta ttatgaatct | 540 |
| aaagcccaca tacactgctc tgtcaaagca gaaaattcag tggctgctaa atcaggagga | 600 |

```
tgttttcctg ggtctgggac ggtgacactt ggtgatggga cgaggaaacc catcaaagat    660
cttaaagtgg gcgaccgggt tttggctgca cgagaagg gaaatgtctt aataagcgac    720
tttattatgt ttatagacca cgatccgaca acgagaaggc aattcatcgt catcgagacg    780
tcagaacctt tcaccaagct caccctcact gccgcgcacc tagttttcgt tggaaactct    840
tcagcagctt cgggtataac agcaacattt gccagcaacg tgaagcctgg agatacagtt    900
ttagtgtggg aagacacatg cgagagcctc aagagcgtta cagtgaaaag gatttacact    960
gaggagcacg agggctcttt tgcgccagtc accgcgcacg gaaccataat agtggatcag   1020
gtgttggcat cgtgctacgc ggtcattgag aaccacaaat gggcacattg gcttttgcg   1080 ccggtcaggt tgtgtcacaa gctgatgacg tggctttttc cggctcgtga atcaaacgtc   1140
aattttcagg aggatggtat ccactggtac tcaaatatgc tgtttcacat cggctcttgg   1200
ctgctggaca gagactcttt ccatccactc gggatttac acttaagttg a          1251
```

<210> SEQ ID NO 10
<211> LENGTH: 425
<212> TYPE: PRT
<213> ORGANISM: Gallus gallus

<400> SEQUENCE: 10

```
Met Val Glu Met Leu Leu Thr Arg Ile Leu Leu Val Gly Phe Ile
 1               5                  10                  15

Cys Ala Leu Leu Val Ser Ser Gly Leu Thr Cys Gly Pro Gly Arg Gly
                20                  25                  30

Ile Gly Lys Arg Arg His Pro Lys Lys Leu Thr Pro Leu Ala Tyr Lys
            35                  40                  45

Gln Phe Ile Pro Asn Val Ala Glu Lys Thr Leu Gly Ala Ser Gly Arg
        50                  55                  60

Tyr Glu Gly Lys Ile Thr Arg Asn Ser Glu Arg Phe Lys Glu Leu Thr
 65                  70                  75                  80

Pro Asn Tyr Asn Pro Asp Ile Ile Phe Lys Asp Glu Glu Asn Thr Gly
                85                  90                  95

Ala Asp Arg Leu Met Thr Gln Arg Cys Lys Asp Lys Leu Asn Ala Leu
            100                 105                 110

Ala Ile Ser Val Met Asn Gln Trp Pro Gly Val Lys Leu Arg Val Thr
        115                 120                 125

Glu Gly Trp Asp Glu Asp Gly His His Ser Glu Glu Ser Leu His Tyr
130                 135                 140

Glu Gly Arg Ala Val Asp Ile Thr Thr Ser Asp Arg Asp Arg Ser Lys
145                 150                 155                 160

Tyr Gly Met Leu Ala Arg Leu Ala Val Glu Ala Gly Phe Asp Trp Val
                165                 170                 175

Tyr Tyr Glu Ser Lys Ala His Ile His Cys Ser Val Lys Ala Glu Asn
            180                 185                 190

Ser Val Ala Ala Lys Ser Gly Gly Cys Phe Pro Gly Ser Ala Thr Val
        195                 200                 205

His Leu Glu His Gly Gly Thr Lys Leu Val Lys Asp Leu Ser Pro Gly
    210                 215                 220

Asp Arg Val Leu Ala Ala Asp Ala Asp Gly Arg Leu Leu Tyr Ser Asp
225                 230                 235                 240

Phe Leu Thr Phe Leu Asp Arg Met Asp Ser Ser Arg Lys Leu Phe Tyr
                245                 250                 255

Val Ile Glu Thr Arg Gln Pro Arg Ala Arg Leu Leu Leu Thr Ala Ala
```

-continued

```
                260                 265                 270
His Leu Leu Phe Val Ala Pro Gln His Asn Gln Ser Glu Ala Thr Gly
            275                 280                 285
Ser Thr Ser Gly Gln Ala Leu Phe Ala Ser Asn Val Lys Pro Gly Gln
        290                 295                 300
Arg Val Tyr Val Leu Gly Glu Gly Gln Gln Leu Leu Pro Ala Ser
305                 310                 315                 320
Val His Ser Val Ser Leu Arg Glu Glu Ala Ser Gly Ala Tyr Ala Pro
                325                 330                 335
Leu Thr Ala Gln Gly Thr Ile Leu Ile Asn Arg Val Leu Ala Ser Cys
            340                 345                 350
Tyr Ala Val Ile Glu Glu His Ser Trp Ala His Trp Ala Phe Ala Pro
        355                 360                 365
Phe Arg Leu Ala Gln Gly Leu Leu Ala Ala Leu Cys Pro Asp Gly Ala
    370                 375                 380
Ile Pro Thr Ala Ala Thr Thr Thr Gly Ile His Trp Tyr Ser Arg
385                 390                 395                 400
Leu Leu Tyr Arg Ile Gly Ser Trp Val Leu Asp Gly Asp Ala Leu His
                405                 410                 415
Pro Leu Gly Met Val Ala Pro Ala Ser
            420                 425

<210> SEQ ID NO 11
<211> LENGTH: 396
<212> TYPE: PRT
<213> ORGANISM: Mus musculus

<400> SEQUENCE: 11

Met Ala Leu Pro Ala Ser Leu Leu Pro Leu Cys Cys Leu Ala Leu Leu
1               5                   10                  15
Ala Leu Ser Ala Gln Ser Cys Gly Pro Gly Arg Gly Pro Val Gly Arg
            20                  25                  30
Arg Arg Tyr Val Arg Lys Gln Leu Val Pro Leu Leu Tyr Lys Gln Phe
        35                  40                  45
Val Pro Ser Met Pro Glu Arg Thr Leu Gly Ala Ser Gly Pro Ala Glu
    50                  55                  60
Gly Arg Val Thr Arg Gly Ser Glu Arg Phe Arg Asp Leu Val Pro Asn
65                  70                  75                  80
Tyr Asn Pro Asp Ile Ile Phe Lys Asp Glu Glu Asn Ser Gly Ala Asp
                85                  90                  95
Arg Leu Met Thr Glu Arg Cys Lys Glu Arg Val Asn Ala Leu Ala Ile
            100                 105                 110
Ala Val Met Asn Met Trp Pro Gly Val Arg Leu Arg Val Thr Glu Gly
        115                 120                 125
Trp Asp Glu Asp Gly His His Ala Gln Asp Ser Leu His Tyr Glu Gly
    130                 135                 140
Arg Ala Leu Asp Ile Thr Thr Ser Asp Arg Asp Arg Asn Lys Tyr Gly
145                 150                 155                 160
Leu Leu Ala Arg Leu Ala Val Glu Ala Gly Phe Asp Trp Val Tyr Tyr
                165                 170                 175
Glu Ser Arg Asn His Ile His Val Ser Val Lys Ala Asp Asn Ser Leu
            180                 185                 190
Ala Val Arg Ala Gly Gly Cys Phe Pro Gly Asn Ala Thr Val Arg Leu
        195                 200                 205
```

```
Arg Ser Gly Glu Arg Lys Gly Leu Arg Glu Leu His Arg Gly Asp Trp
    210                 215                 220

Val Leu Ala Ala Asp Ala Ala Gly Arg Val Val Pro Thr Pro Val Leu
225                 230                 235                 240

Leu Phe Leu Asp Arg Asp Leu Gln Arg Arg Ala Ser Phe Val Ala Val
                245                 250                 255

Glu Thr Glu Arg Pro Pro Arg Lys Leu Leu Thr Pro Trp His Leu
            260                 265                 270

Val Phe Ala Ala Arg Gly Pro Ala Pro Ala Pro Gly Asp Phe Ala Pro
            275                 280                 285

Val Phe Ala Arg Arg Leu Arg Ala Gly Asp Ser Val Leu Ala Pro Gly
    290                 295                 300

Gly Asp Ala Leu Gln Pro Ala Arg Val Ala Arg Val Ala Arg Glu Glu
305                 310                 315                 320

Ala Val Gly Val Phe Ala Pro Leu Thr Ala His Gly Thr Leu Leu Val
                325                 330                 335

Asn Asp Val Leu Ala Ser Cys Tyr Ala Val Leu Glu Ser His Gln Trp
                340                 345                 350

Ala His Arg Ala Phe Ala Pro Leu Arg Leu Leu His Ala Leu Gly Ala
            355                 360                 365

Leu Leu Pro Gly Gly Ala Val Gln Pro Thr Gly Met His Trp Tyr Ser
370                 375                 380

Arg Leu Leu Tyr Arg Leu Ala Glu Glu Leu Met Gly
385                 390                 395

<210> SEQ ID NO 12
<211> LENGTH: 411
<212> TYPE: PRT
<213> ORGANISM: Mus musculus

<400> SEQUENCE: 12

Met Ser Pro Ala Trp Leu Arg Pro Arg Leu Arg Phe Cys Leu Phe Leu
1               5                   10                  15

Leu Leu Leu Leu Leu Val Pro Ala Ala Arg Gly Cys Gly Pro Gly Arg
                20                  25                  30

Val Val Gly Ser Arg Arg Arg Pro Pro Arg Lys Leu Val Pro Leu Ala
            35                  40                  45

Tyr Lys Gln Phe Ser Pro Asn Val Pro Glu Lys Thr Leu Gly Ala Ser
    50                  55                  60

Gly Arg Tyr Glu Gly Lys Ile Ala Arg Ser Ser Glu Arg Phe Lys Glu
65                  70                  75                  80

Leu Thr Pro Asn Tyr Asn Pro Asp Ile Ile Phe Lys Asp Glu Glu Asn
                85                  90                  95

Thr Gly Ala Asp Arg Leu Met Thr Gln Arg Cys Lys Asp Arg Leu Asn
            100                 105                 110

Ser Leu Ala Ile Ser Val Met Asn Gln Trp Pro Gly Val Lys Leu Arg
    115                 120                 125

Val Thr Glu Gly Arg Asp Glu Asp Gly His His Ser Glu Glu Ser Leu
130                 135                 140

His Tyr Glu Gly Arg Ala Val Asp Ile Thr Thr Ser Asp Arg Asp Arg
145                 150                 155                 160

Asn Lys Tyr Gly Leu Leu Ala Arg Leu Ala Val Glu Ala Gly Phe Asp
                165                 170                 175

Trp Val Tyr Tyr Glu Ser Lys Ala His Val His Cys Ser Val Lys Ser
            180                 185                 190
```

```
Glu His Ser Ala Ala Ala Lys Thr Gly Gly Cys Phe Pro Ala Gly Ala
            195                 200                 205

Gln Val Arg Leu Glu Asn Gly Glu Arg Val Ala Leu Ser Ala Val Lys
        210                 215                 220

Pro Gly Asp Arg Val Leu Ala Met Gly Glu Asp Gly Thr Pro Thr Phe
225                 230                 235                 240

Ser Asp Val Leu Ile Phe Leu Asp Arg Glu Pro Asn Arg Leu Arg Ala
                245                 250                 255

Phe Gln Val Ile Glu Thr Gln Asp Pro Pro Arg Arg Leu Ala Leu Thr
            260                 265                 270

Pro Ala His Leu Leu Phe Ile Ala Asp Asn His Thr Glu Pro Ala Ala
        275                 280                 285

His Phe Arg Ala Thr Phe Ala Ser His Val Gln Pro Gly Gln Tyr Val
        290                 295                 300

Leu Val Ser Gly Val Pro Gly Leu Gln Pro Ala Arg Val Ala Ala Val
305                 310                 315                 320

Ser Thr His Val Ala Leu Gly Ser Tyr Ala Pro Leu Thr Arg His Gly
                325                 330                 335

Thr Leu Val Val Glu Asp Val Val Ala Ser Cys Phe Ala Ala Val Ala
            340                 345                 350

Asp His His Leu Ala Gln Leu Ala Phe Trp Pro Leu Arg Leu Phe Pro
        355                 360                 365

Ser Leu Ala Trp Gly Ser Trp Thr Pro Ser Glu Gly Val His Ser Tyr
370                 375                 380

Pro Gln Met Leu Tyr Arg Leu Gly Arg Leu Leu Glu Glu Ser Thr
385                 390                 395                 400

Phe His Pro Leu Gly Met Ser Gly Ala Gly Ser
                405                 410

<210> SEQ ID NO 13
<211> LENGTH: 437
<212> TYPE: PRT
<213> ORGANISM: Mus musculus

<400> SEQUENCE: 13

Met Leu Leu Leu Leu Ala Arg Cys Phe Leu Val Ile Leu Ala Ser Ser
1               5                   10                  15

Leu Leu Val Cys Pro Gly Leu Ala Cys Gly Pro Gly Arg Gly Phe Gly
            20                  25                  30

Lys Arg Arg His Pro Lys Lys Leu Thr Pro Leu Ala Tyr Lys Gln Phe
        35                  40                  45

Ile Pro Asn Val Ala Glu Lys Thr Leu Gly Ala Ser Gly Arg Tyr Glu
    50                  55                  60

Gly Lys Ile Thr Arg Asn Ser Glu Arg Phe Lys Glu Leu Thr Pro Asn
65                  70                  75                  80

Tyr Asn Pro Asp Ile Ile Phe Lys Asp Glu Glu Asn Thr Gly Ala Asp
                85                  90                  95

Arg Leu Met Thr Gln Arg Cys Lys Asp Lys Leu Asn Ala Leu Ala Ile
            100                 105                 110

Ser Val Met Asn Gln Trp Pro Gly Val Arg Leu Arg Val Thr Glu Gly
        115                 120                 125

Trp Asp Glu Asp Gly His His Ser Glu Glu Ser Leu His Tyr Glu Gly
    130                 135                 140

Arg Ala Val Asp Ile Thr Thr Ser Asp Arg Asp Arg Ser Lys Tyr Gly
```

```
                145                 150                 155                 160
Met Leu Ala Arg Leu Ala Val Glu Ala Gly Phe Asp Trp Val Tyr Tyr
                    165                 170                 175
Glu Ser Lys Ala His Ile His Cys Ser Val Lys Ala Glu Asn Ser Val
                    180                 185                 190
Ala Ala Lys Ser Gly Gly Cys Phe Pro Gly Ser Ala Thr Val His Leu
                    195                 200                 205
Glu Gln Gly Gly Thr Lys Leu Val Lys Asp Leu Arg Pro Gly Asp Arg
                    210                 215                 220
Val Leu Ala Ala Asp Asp Gln Gly Arg Leu Leu Tyr Ser Asp Phe Leu
225                 230                 235                 240
Thr Phe Leu Asp Arg Asp Glu Gly Ala Lys Lys Val Phe Tyr Val Ile
                    245                 250                 255
Glu Thr Leu Glu Pro Arg Glu Arg Leu Leu Thr Ala Ala His Leu
                    260                 265                 270
Leu Phe Val Ala Pro His Asn Asp Ser Gly Pro Thr Pro Gly Pro Ser
                    275                 280                 285
Ala Leu Phe Ala Ser Arg Val Arg Pro Gly Gln Arg Val Tyr Val Val
                    290                 295                 300
Ala Glu Arg Gly Gly Asp Arg Arg Leu Leu Pro Ala Ala Val His Ser
305                 310                 315                 320
Val Thr Leu Arg Glu Glu Ala Gly Ala Tyr Ala Pro Leu Thr Ala
                    325                 330                 335
His Gly Thr Ile Leu Ile Asn Arg Val Leu Ala Ser Cys Tyr Ala Val
                    340                 345                 350
Ile Glu Glu His Ser Trp Ala His Arg Ala Phe Ala Pro Phe Arg Leu
                    355                 360                 365
Ala His Ala Leu Leu Ala Ala Leu Ala Pro Ala Arg Thr Asp Gly Gly
                    370                 375                 380
Gly Gly Gly Ser Ile Pro Ala Ala Gln Ser Ala Thr Glu Ala Arg Gly
385                 390                 395                 400
Ala Glu Pro Thr Ala Gly Ile His Trp Tyr Ser Gln Leu Leu Tyr His
                    405                 410                 415
Ile Gly Thr Trp Leu Leu Asp Ser Glu Thr Met His Pro Leu Gly Met
                    420                 425                 430
Ala Val Lys Ser Ser
        435

<210> SEQ ID NO 14
<211> LENGTH: 418
<212> TYPE: PRT
<213> ORGANISM: Brachydanio rerio

<400> SEQUENCE: 14

Met Arg Leu Leu Thr Arg Val Leu Leu Val Ser Leu Leu Thr Leu Ser
1               5                   10                  15
Leu Val Val Ser Gly Leu Ala Cys Gly Pro Gly Arg Gly Tyr Gly Arg
                    20                  25                  30
Arg Arg His Pro Lys Lys Leu Thr Pro Leu Ala Tyr Lys Gln Phe Ile
                    35                  40                  45
Pro Asn Val Ala Glu Lys Thr Leu Gly Ala Ser Gly Arg Tyr Glu Gly
            50                  55                  60
Lys Ile Thr Arg Asn Ser Glu Arg Phe Lys Glu Leu Thr Pro Asn Tyr
65              70                  75                  80
```

```
Asn Pro Asp Ile Ile Phe Lys Asp Glu Glu Asn Thr Gly Ala Asp Arg
             85                  90                  95

Leu Met Thr Gln Arg Cys Lys Asp Lys Leu Asn Ser Leu Ala Ile Ser
            100                 105                 110

Val Met Asn His Trp Pro Gly Val Lys Leu Arg Val Thr Glu Gly Trp
        115                 120                 125

Asp Glu Asp Gly His His Phe Glu Glu Ser Leu His Tyr Glu Gly Arg
    130                 135                 140

Ala Val Asp Ile Thr Thr Ser Asp Arg Asp Lys Ser Lys Tyr Gly Thr
145                 150                 155                 160

Leu Ser Arg Leu Ala Val Glu Ala Gly Phe Asp Trp Val Tyr Tyr Glu
                165                 170                 175

Ser Lys Ala His Ile His Cys Ser Val Lys Ala Glu Asn Ser Val Ala
            180                 185                 190

Ala Lys Ser Gly Gly Cys Phe Pro Gly Ser Ala Leu Val Ser Leu Gln
        195                 200                 205

Asp Gly Gly Gln Lys Ala Val Lys Asp Leu Asn Pro Gly Asp Lys Val
    210                 215                 220

Leu Ala Ala Asp Ser Ala Gly Asn Leu Val Phe Ser Asp Phe Ile Met
225                 230                 235                 240

Phe Thr Asp Arg Asp Ser Thr Thr Arg Arg Val Phe Tyr Val Ile Glu
                245                 250                 255

Thr Gln Glu Pro Val Glu Lys Ile Thr Leu Thr Ala Ala His Leu Leu
            260                 265                 270

Phe Val Leu Asp Asn Ser Thr Glu Asp Leu His Thr Met Thr Ala Ala
        275                 280                 285

Tyr Ala Ser Ser Val Arg Ala Gly Gln Lys Val Met Val Val Asp Asp
    290                 295                 300

Ser Gly Gln Leu Lys Ser Val Ile Val Gln Arg Ile Tyr Thr Glu Glu
305                 310                 315                 320

Gln Arg Gly Ser Phe Ala Pro Val Thr Ala His Gly Thr Ile Val Val
                325                 330                 335

Asp Arg Ile Leu Ala Ser Cys Tyr Ala Val Ile Glu Asp Gln Gly Leu
            340                 345                 350

Ala His Leu Ala Phe Ala Pro Ala Arg Leu Tyr Tyr Tyr Val Ser Ser
        355                 360                 365

Phe Leu Ser Pro Lys Thr Pro Ala Val Gly Pro Met Arg Leu Tyr Asn
    370                 375                 380

Arg Arg Gly Ser Thr Gly Thr Pro Gly Ser Cys His Gln Met Gly Thr
385                 390                 395                 400

Trp Leu Leu Asp Ser Asn Met Leu His Pro Leu Gly Met Ser Val Asn
                405                 410                 415

Ser Ser

<210> SEQ ID NO 15
<211> LENGTH: 475
<212> TYPE: PRT
<213> ORGANISM: Homo sapiens
<220> FEATURE:
<221> NAME/KEY: SITE
<222> LOCATION: (463)
<223> OTHER INFORMATION: Xaa=unknown amino acid residue

<400> SEQUENCE: 15

Met Leu Leu Leu Ala Arg Cys Leu Leu Leu Val Leu Val Ser Ser Leu
  1               5                  10                  15
```

-continued

Leu Val Cys Ser Gly Leu Ala Cys Gly Pro Gly Arg Gly Phe Gly Lys
            20                  25                  30

Arg Arg His Pro Lys Lys Leu Thr Pro Leu Ala Tyr Lys Gln Phe Ile
        35                  40                  45

Pro Asn Val Ala Glu Lys Thr Leu Gly Ala Ser Gly Arg Tyr Glu Gly
    50                  55                  60

Lys Ile Ser Arg Asn Ser Glu Arg Phe Lys Glu Leu Thr Pro Asn Tyr
65                  70                  75                  80

Asn Pro Asp Ile Ile Phe Lys Asp Glu Glu Asn Thr Gly Ala Asp Arg
                85                  90                  95

Leu Met Thr Gln Arg Cys Lys Asp Lys Leu Asn Ala Leu Ala Ile Ser
            100                 105                 110

Val Met Asn Gln Trp Pro Gly Val Lys Leu Arg Val Thr Glu Gly Trp
        115                 120                 125

Asp Glu Asp Gly His His Ser Glu Glu Ser Leu His Tyr Glu Gly Arg
    130                 135                 140

Ala Val Asp Ile Thr Thr Ser Asp Arg Asp Arg Ser Lys Tyr Gly Met
145                 150                 155                 160

Leu Ala Arg Leu Ala Val Glu Ala Gly Phe Asp Trp Val Tyr Tyr Glu
                165                 170                 175

Ser Lys Ala His Ile His Cys Ser Val Lys Ala Glu Asn Ser Val Ala
            180                 185                 190

Ala Lys Ser Gly Gly Cys Phe Pro Gly Ser Ala Thr Val His Leu Glu
        195                 200                 205

Gln Gly Gly Thr Lys Leu Val Lys Asp Leu Ser Pro Gly Asp Arg Val
    210                 215                 220

Leu Ala Ala Asp Asp Gln Gly Arg Leu Leu Tyr Ser Asp Phe Leu Thr
225                 230                 235                 240

Phe Leu Asp Arg Asp Asp Gly Ala Lys Lys Val Phe Tyr Val Ile Glu
                245                 250                 255

Thr Arg Glu Pro Arg Glu Arg Leu Leu Leu Thr Ala Ala His Leu Leu
            260                 265                 270

Phe Val Ala Pro His Asn Asp Ser Ala Thr Gly Glu Pro Glu Ala Ser
        275                 280                 285

Ser Gly Ser Gly Pro Pro Ser Gly Gly Ala Leu Gly Pro Arg Ala Leu
    290                 295                 300

Phe Ala Ser Arg Val Arg Pro Gly Gln Arg Val Tyr Val Val Ala Glu
305                 310                 315                 320

Arg Asp Gly Asp Arg Arg Leu Leu Pro Ala Ala Val His Ser Val Thr
                325                 330                 335

Leu Ser Glu Glu Ala Ala Gly Ala Tyr Ala Pro Leu Thr Ala Gln Gly
            340                 345                 350

Thr Ile Leu Ile Asn Arg Val Leu Ala Ser Cys Tyr Ala Val Ile Glu
        355                 360                 365

Glu His Ser Trp Ala His Arg Ala Phe Ala Pro Phe Arg Leu Ala His
    370                 375                 380

Ala Leu Leu Ala Ala Leu Ala Pro Ala Arg Thr Asp Arg Gly Gly Asp
385                 390                 395                 400

Ser Gly Gly Gly Asp Arg Gly Gly Gly Gly Arg Val Ala Leu Thr
                405                 410                 415

Ala Pro Gly Ala Ala Asp Ala Pro Gly Ala Gly Ala Thr Ala Gly Ile
            420                 425                 430

His Trp Tyr Ser Gln Leu Leu Tyr Gln Ile Gly Thr Trp Leu Leu Asp
                435                 440                 445

Ser Glu Ala Leu His Pro Leu Gly Met Ala Val Lys Ser Ser Xaa Ser
    450                 455                 460

Arg Gly Ala Gly Gly Ala Arg Glu Gly Ala
465                 470                 475

<210> SEQ ID NO 16
<211> LENGTH: 411
<212> TYPE: PRT
<213> ORGANISM: Homo sapiens

<400> SEQUENCE: 16

Met Ser Pro Ala Arg Leu Arg Pro Arg Leu His Phe Cys Leu Val Leu
  1               5                  10                  15

Leu Leu Leu Leu Val Pro Ala Ala Trp Gly Cys Gly Pro Gly Arg
             20                  25                  30

Val Val Gly Ser Arg Arg Arg Pro Arg Lys Leu Val Pro Leu Ala
         35                  40                  45

Tyr Lys Gln Phe Ser Pro Asn Val Pro Glu Lys Thr Leu Gly Ala Ser
     50                  55                  60

Gly Arg Tyr Glu Gly Lys Ile Ala Arg Ser Ser Glu Arg Phe Lys Glu
 65                  70                  75                  80

Leu Thr Pro Asn Tyr Asn Pro Asp Ile Ile Phe Lys Asp Glu Glu Asn
                 85                  90                  95

Thr Gly Ala Asp Arg Leu Met Thr Gln Arg Cys Lys Asp Arg Leu Asn
            100                 105                 110

Ser Leu Ala Ile Ser Val Met Asn Gln Trp Pro Gly Val Lys Leu Arg
        115                 120                 125

Val Thr Glu Gly Trp Asp Glu Asp Gly His His Ser Glu Glu Ser Leu
    130                 135                 140

His Tyr Glu Gly Arg Ala Val Asp Ile Thr Thr Ser Asp Arg Asp Arg
145                 150                 155                 160

Asn Lys Tyr Gly Leu Leu Ala Arg Leu Ala Val Glu Ala Gly Phe Asp
                165                 170                 175

Trp Val Tyr Tyr Glu Ser Lys Ala His Val His Cys Ser Val Lys Ser
            180                 185                 190

Glu His Ser Ala Ala Ala Lys Thr Gly Gly Cys Phe Pro Ala Gly Ala
        195                 200                 205

Gln Val Arg Leu Glu Ser Gly Ala Arg Val Ala Leu Ser Ala Val Arg
    210                 215                 220

Pro Gly Asp Arg Val Leu Ala Met Gly Glu Asp Gly Ser Pro Thr Phe
225                 230                 235                 240

Ser Asp Val Leu Ile Phe Leu Asp Arg Glu Pro His Arg Leu Arg Ala
                245                 250                 255

Phe Gln Val Ile Glu Thr Gln Asp Pro Pro Arg Arg Leu Ala Leu Thr
            260                 265                 270

Pro Ala His Leu Leu Phe Thr Ala Asp Asn His Thr Glu Pro Ala Ala
        275                 280                 285

Arg Phe Arg Ala Thr Phe Ala Ser His Val Gln Pro Gly Gln Tyr Val
    290                 295                 300

Leu Val Ala Gly Val Pro Gly Leu Gln Pro Ala Arg Val Ala Ala Val
305                 310                 315                 320

Ser Thr His Val Ala Leu Gly Ala Tyr Ala Pro Leu Thr Lys His Gly
                325                 330                 335

```
Thr Leu Val Val Glu Asp Val Val Ala Ser Cys Phe Ala Ala Val Ala
                340                 345                 350

Asp His His Leu Ala Gln Leu Ala Phe Trp Pro Leu Arg Leu Phe His
            355                 360                 365

Ser Leu Ala Trp Gly Ser Trp Thr Pro Gly Glu Gly Val His Trp Tyr
    370                 375                 380

Pro Gln Leu Leu Tyr Arg Leu Gly Arg Leu Leu Glu Glu Gly Ser
385                 390                 395                 400

Phe His Pro Leu Gly Met Ser Gly Ala Gly Ser
                405                 410

<210> SEQ ID NO 17
<211> LENGTH: 396
<212> TYPE: PRT
<213> ORGANISM: Homo sapiens

<400> SEQUENCE: 17

Met Ala Leu Leu Thr Asn Leu Pro Leu Cys Cys Leu Ala Leu Leu
  1               5                  10                  15

Ala Leu Pro Ala Gln Ser Cys Gly Pro Gly Arg Gly Pro Val Gly Arg
             20                  25                  30

Arg Arg Tyr Ala Arg Lys Gln Leu Val Pro Leu Leu Tyr Lys Gln Phe
         35                  40                  45

Val Pro Gly Val Pro Glu Arg Thr Leu Gly Ala Ser Gly Pro Ala Glu
 50                  55                  60

Gly Arg Val Ala Arg Gly Ser Glu Arg Phe Arg Asp Leu Val Pro Asn
 65                  70                  75                  80

Tyr Asn Pro Asp Ile Ile Phe Lys Asp Glu Glu Asn Ser Gly Ala Asp
                 85                  90                  95

Arg Leu Met Thr Glu Arg Cys Lys Glu Arg Val Asn Ala Leu Ala Ile
            100                 105                 110

Ala Val Met Asn Met Trp Pro Gly Val Arg Leu Arg Val Thr Glu Gly
        115                 120                 125

Trp Asp Glu Asp Gly His His Ala Gln Asp Ser Leu His Tyr Glu Gly
    130                 135                 140

Arg Ala Leu Asp Ile Thr Thr Ser Asp Arg Asp Arg Asn Lys Tyr Gly
145                 150                 155                 160

Leu Leu Ala Arg Leu Ala Val Glu Ala Gly Phe Asp Trp Val Tyr Tyr
                165                 170                 175

Glu Ser Arg Asn His Val His Val Ser Val Lys Ala Asp Asn Ser Leu
            180                 185                 190

Ala Val Arg Ala Gly Gly Cys Phe Pro Gly Asn Ala Thr Val Arg Leu
        195                 200                 205

Trp Ser Gly Glu Arg Lys Gly Leu Arg Glu Leu His Arg Gly Asp Trp
    210                 215                 220

Val Leu Ala Ala Asp Ala Ser Gly Arg Val Val Pro Thr Pro Val Leu
225                 230                 235                 240

Leu Phe Leu Asp Arg Asp Leu Gln Arg Arg Ala Ser Phe Val Ala Val
                245                 250                 255

Glu Thr Glu Trp Pro Pro Arg Lys Leu Leu Leu Thr Pro Trp His Leu
            260                 265                 270

Val Phe Ala Ala Arg Gly Pro Ala Pro Ala Pro Gly Asp Phe Ala Pro
        275                 280                 285

Val Phe Ala Arg Arg Leu Arg Ala Gly Asp Ser Val Leu Ala Pro Gly
```

```
                290                 295                 300
Gly Asp Ala Leu Arg Pro Ala Arg Val Ala Arg Val Ala Arg Glu Glu
305                 310                 315                 320

Ala Val Gly Val Phe Ala Pro Leu Thr Ala His Gly Thr Leu Leu Val
                325                 330                 335

Asn Asp Val Leu Ala Ser Cys Tyr Ala Val Leu Glu Ser His Gln Trp
            340                 345                 350

Ala His Arg Ala Phe Ala Pro Leu Arg Leu Leu His Ala Leu Gly Ala
        355                 360                 365

Leu Leu Pro Gly Gly Ala Val Gln Pro Thr Gly Met His Trp Tyr Ser
370                 375                 380

Arg Leu Leu Tyr Arg Leu Ala Glu Glu Leu Leu Gly
385                 390                 395

<210> SEQ ID NO 18
<211> LENGTH: 416
<212> TYPE: PRT
<213> ORGANISM: Brachydanio rerio

<400> SEQUENCE: 18

Met Asp Val Arg Leu His Leu Lys Gln Phe Ala Leu Leu Cys Phe Ile
1               5                   10                  15

Ser Leu Leu Leu Thr Pro Cys Gly Leu Ala Cys Gly Pro Gly Arg Gly
                20                  25                  30

Tyr Gly Lys Arg Arg His Pro Lys Lys Leu Thr Pro Leu Ala Tyr Lys
            35                  40                  45

Gln Phe Ile Pro Asn Val Ala Glu Lys Thr Leu Gly Ala Ser Gly Lys
        50                  55                  60

Tyr Glu Gly Lys Ile Thr Arg Asn Ser Glu Arg Phe Lys Glu Leu Ile
65                  70                  75                  80

Pro Asn Tyr Asn Pro Asp Ile Ile Phe Lys Asp Glu Glu Asn Thr Asn
                85                  90                  95

Ala Asp Arg Leu Met Thr Lys Arg Cys Lys Asp Lys Leu Asn Ser Leu
            100                 105                 110

Ala Ile Ser Val Met Asn His Trp Pro Gly Val Lys Leu Arg Val Thr
        115                 120                 125

Glu Gly Trp Asp Glu Asp Gly His His Leu Glu Ser Leu His Tyr
130                 135                 140

Glu Gly Arg Ala Val Asp Ile Thr Thr Ser Asp Arg Asp Lys Ser Lys
145                 150                 155                 160

Tyr Gly Met Leu Ser Arg Leu Ala Val Glu Ala Gly Phe Asp Trp Val
                165                 170                 175

Tyr Tyr Glu Ser Lys Ala His Ile His Cys Ser Val Lys Ala Glu Asn
            180                 185                 190

Ser Val Ala Ala Lys Ser Gly Gly Cys Phe Pro Gly Ser Gly Thr Val
        195                 200                 205

Thr Leu Gly Asp Gly Thr Arg Lys Pro Ile Lys Asp Leu Lys Val Gly
    210                 215                 220

Asp Arg Val Leu Ala Ala Asp Glu Lys Gly Asn Val Leu Ile Ser Asp
225                 230                 235                 240

Phe Ile Met Phe Ile Asp His Asp Pro Thr Thr Arg Arg Gln Phe Ile
                245                 250                 255

Val Ile Glu Thr Ser Glu Pro Phe Thr Lys Leu Thr Leu Thr Ala Ala
            260                 265                 270
```

-continued

```
His Leu Val Phe Val Gly Asn Ser Ser Ala Ala Ser Gly Ile Thr Ala
        275                 280                 285

Thr Phe Ala Ser Asn Val Lys Pro Gly Asp Thr Val Leu Val Trp Glu
        290                 295                 300

Asp Thr Cys Glu Ser Leu Lys Ser Val Thr Val Lys Arg Ile Tyr Thr
305                 310                 315                 320

Glu Glu His Glu Gly Ser Phe Ala Pro Val Thr Ala His Gly Thr Ile
                325                 330                 335

Ile Val Asp Gln Val Leu Ala Ser Cys Tyr Ala Val Ile Glu Asn His
            340                 345                 350

Lys Trp Ala His Trp Ala Phe Ala Pro Val Arg Leu Cys His Lys Leu
        355                 360                 365

Met Thr Trp Leu Phe Pro Ala Arg Glu Ser Asn Val Asn Phe Gln Glu
    370                 375                 380

Asp Gly Ile His Trp Tyr Ser Asn Met Leu Phe His Ile Gly Ser Trp
385                 390                 395                 400

Leu Leu Asp Arg Asp Ser Phe His Pro Leu Gly Ile Leu His Leu Ser
                405                 410                 415
```

<210> SEQ ID NO 19
<211> LENGTH: 1416
<212> TYPE: DNA
<213> ORGANISM: Drosophila melanogaster
<220> FEATURE:
<221> NAME/KEY: CDS
<222> LOCATION: (1)..(1413)

<400> SEQUENCE: 19

```
atg gat aac cac agc tca gtg cct tgg gcc agt gcc gcc agt gtc acc      48
Met Asp Asn His Ser Ser Val Pro Trp Ala Ser Ala Ala Ser Val Thr
 1               5                  10                  15 tgt ctc tcc ctg gga tgc caa atg cca cag ttc cag ttc cag ttc cag      96
Cys Leu Ser Leu Gly Cys Gln Met Pro Gln Phe Gln Phe Gln Phe Gln
            20                  25                  30 ctc caa atc cgc agc gag ctc cat ctc cgc aag ccc gca aga aga acg     144
Leu Gln Ile Arg Ser Glu Leu His Leu Arg Lys Pro Ala Arg Arg Thr
        35                  40                  45 caa acg atg cgc cac att gcg cat acg cag cgt tgc ctc agc agg ctg     192
Gln Thr Met Arg His Ile Ala His Thr Gln Arg Cys Leu Ser Arg Leu
    50                  55                  60 acc tct ctg gtg gcc ctg ctg ctg atc gtc ttg ccg atg gtc ttt agc     240
Thr Ser Leu Val Ala Leu Leu Leu Ile Val Leu Pro Met Val Phe Ser
 65                  70                  75                  80 ccg gct cac agc tgc ggt cct ggc cga gga ttg ggt cgt cat agg gcg     288
Pro Ala His Ser Cys Gly Pro Gly Arg Gly Leu Gly Arg His Arg Ala
                85                  90                  95 cgc aac ctg tat ccg ctg gtc ctc aag cag aca att ccc aat cta tcc     336
Arg Asn Leu Tyr Pro Leu Val Leu Lys Gln Thr Ile Pro Asn Leu Ser
            100                 105                 110 gag tac acg aac agc gcc tcc gga cct ctg gag ggt gtg atc cgt cgg     384
Glu Tyr Thr Asn Ser Ala Ser Gly Pro Leu Glu Gly Val Ile Arg Arg
        115                 120                 125 gat tcg ccc aaa ttc aag gac ctc gtg ccc aac tac aac agg gac atc     432
Asp Ser Pro Lys Phe Lys Asp Leu Val Pro Asn Tyr Asn Arg Asp Ile
    130                 135                 140 ctt ttc cgt gac gag gaa ggc acc gga gcg gat ggc ttg atg agc aag     480
Leu Phe Arg Asp Glu Glu Gly Thr Gly Ala Asp Gly Leu Met Ser Lys
145                 150                 155                 160 cgc tgc aag gag aag cta aac gtg ctg gcc tac tcg gtg atg aac gaa     528
```

```
         Arg Cys Lys Glu Lys Leu Asn Val Leu Ala Tyr Ser Val Met Asn Glu
                         165                 170                 175 tgg ccc ggc atc cgg ctg ctc gtc acc gag agc tgg gac gag gac tac         576
Trp Pro Gly Ile Arg Leu Leu Val Thr Glu Ser Trp Asp Glu Asp Tyr
                180                 185                 190 cat cac ggc cag gag tcg ctc cac tac gag ggc cga gcg gtg acc att         624
His His Gly Gln Glu Ser Leu His Tyr Glu Gly Arg Ala Val Thr Ile
                195                 200                 205 gcc acc tcc gat cgc gac cag tcc aaa tac ggc atg ctc gct cgc ctg         672
Ala Thr Ser Asp Arg Asp Gln Ser Lys Tyr Gly Met Leu Ala Arg Leu
        210                 215                 220 gcc gtc gag gct gga ttc gat tgg gtc tcc tac gtc agc agg cgc cac         720
Ala Val Glu Ala Gly Phe Asp Trp Val Ser Tyr Val Ser Arg Arg His
225                 230                 235                 240 atc tac tgc tcc gtc aag tca gat tcg tcg atc agt tcc cac gtg cac         768
Ile Tyr Cys Ser Val Lys Ser Asp Ser Ser Ile Ser Ser His Val His
                245                 250                 255 ggc tgc ttc acg ccg gag agc aca gcg ctg ctg gag agt gga gtc cgg         816
Gly Cys Phe Thr Pro Glu Ser Thr Ala Leu Leu Glu Ser Gly Val Arg
                260                 265                 270 aag ccg ctc ggc gag ctc tct atc gga gat cgt gtt ttg agc atg acc         864
Lys Pro Leu Gly Glu Leu Ser Ile Gly Asp Arg Val Leu Ser Met Thr
                275                 280                 285 gcc aac gga cag gcc gtc tac agc gaa gtg atc ctc ttc atg gac cgc         912
Ala Asn Gly Gln Ala Val Tyr Ser Glu Val Ile Leu Phe Met Asp Arg
        290                 295                 300 aac ctc gag cag atg caa aac ttt gtg cag ctg cac acg gac ggt gga         960
Asn Leu Glu Gln Met Gln Asn Phe Val Gln Leu His Thr Asp Gly Gly
305                 310                 315                 320 gca gtg ctc acg gtg acg ccg gct cac ctg gtt agc gtt tgg cag ccg        1008
Ala Val Leu Thr Val Thr Pro Ala His Leu Val Ser Val Trp Gln Pro
                325                 330                 335 gag agc cag aag ctc acg ttt gtg ttt gcg cat cgc atc gag gag aag        1056
Glu Ser Gln Lys Leu Thr Phe Val Phe Ala His Arg Ile Glu Glu Lys
                340                 345                 350 aac cag gtg ctc gta cgg gat gtg gag acg ggc gag ctg agg ccc cag        1104
Asn Gln Val Leu Val Arg Asp Val Glu Thr Gly Glu Leu Arg Pro Gln
                355                 360                 365 cga gtg gtc aag ttg ggc agt gtg cgc agt aag ggc gtg gtc gcg ccg        1152
Arg Val Val Lys Leu Gly Ser Val Arg Ser Lys Gly Val Val Ala Pro
        370                 375                 380 ctg acc cgc gag ggc acc att gtg gtc aac tcg gtg gcc gcc agt tgc        1200
Leu Thr Arg Glu Gly Thr Ile Val Val Asn Ser Val Ala Ala Ser Cys
385                 390                 395                 400 tat gcg gtg atc aac agt cag tcg ctg gcc cac tgg gga ctg gct ccc        1248
Tyr Ala Val Ile Asn Ser Gln Ser Leu Ala His Trp Gly Leu Ala Pro
                405                 410                 415 atg cgc ctg ctg tcc acg ctg gag gcg tgg ctg ccc gcc aag gag cag        1296
Met Arg Leu Leu Ser Thr Leu Glu Ala Trp Leu Pro Ala Lys Glu Gln
                420                 425                 430 ttg cac agt tcg ccg aag gtg gtg agc tcg gcg cag cag cag aat ggc        1344
Leu His Ser Ser Pro Lys Val Val Ser Ser Ala Gln Gln Gln Asn Gly
                435                 440                 445 atc cat tgg tat gcc aat gcg ctc tac aag gtc aag gac tac gtg ctg        1392
Ile His Trp Tyr Ala Asn Ala Leu Tyr Lys Val Lys Asp Tyr Val Leu
        450                 455                 460 ccg cag agc tgg cgc cac gat tga                                        1416
Pro Gln Ser Trp Arg His Asp
465                 470
```

<210> SEQ ID NO 20
<211> LENGTH: 471
<212> TYPE: PRT
<213> ORGANISM: Drosophila melanogaster

<400> SEQUENCE: 20

```
Met Asp Asn His Ser Ser Val Pro Trp Ala Ser Ala Ser Val Thr
  1               5                  10                  15

Cys Leu Ser Leu Gly Cys Gln Met Pro Gln Phe Gln Phe Gln Phe Gln
                 20                  25                  30

Leu Gln Ile Arg Ser Glu Leu His Leu Arg Lys Pro Ala Arg Arg Thr
             35                  40                  45

Gln Thr Met Arg His Ile Ala His Thr Gln Arg Cys Leu Ser Arg Leu
         50                  55                  60

Thr Ser Leu Val Ala Leu Leu Ile Val Leu Pro Met Val Phe Ser
 65                  70                  75                  80

Pro Ala His Ser Cys Gly Pro Gly Arg Gly Leu Gly Arg His Arg Ala
                 85                  90                  95

Arg Asn Leu Tyr Pro Leu Val Leu Lys Gln Thr Ile Pro Asn Leu Ser
            100                 105                 110

Glu Tyr Thr Asn Ser Ala Ser Gly Pro Leu Glu Gly Val Ile Arg Arg
        115                 120                 125

Asp Ser Pro Lys Phe Lys Asp Leu Val Pro Asn Tyr Asn Arg Asp Ile
    130                 135                 140

Leu Phe Arg Asp Glu Glu Gly Thr Gly Ala Asp Gly Leu Met Ser Lys
145                 150                 155                 160

Arg Cys Lys Glu Lys Leu Asn Val Leu Ala Tyr Ser Val Met Asn Glu
                165                 170                 175

Trp Pro Gly Ile Arg Leu Leu Val Thr Glu Ser Trp Asp Glu Asp Tyr
            180                 185                 190

His His Gly Gln Glu Ser Leu His Tyr Glu Gly Arg Ala Val Thr Ile
        195                 200                 205

Ala Thr Ser Asp Arg Asp Gln Ser Lys Tyr Gly Met Leu Ala Arg Leu
    210                 215                 220

Ala Val Glu Ala Gly Phe Asp Trp Val Ser Tyr Val Ser Arg Arg His
225                 230                 235                 240

Ile Tyr Cys Ser Val Lys Ser Asp Ser Ser Ile Ser Ser His Val His
                245                 250                 255

Gly Cys Phe Thr Pro Glu Ser Thr Ala Leu Leu Glu Ser Gly Val Arg
            260                 265                 270

Lys Pro Leu Gly Glu Leu Ser Ile Gly Asp Arg Val Leu Ser Met Thr
        275                 280                 285

Ala Asn Gly Gln Ala Val Tyr Ser Glu Val Ile Leu Phe Met Asp Arg
    290                 295                 300

Asn Leu Glu Gln Met Gln Asn Phe Val Gln Leu His Thr Asp Gly Gly
305                 310                 315                 320

Ala Val Leu Thr Val Thr Pro Ala His Leu Val Ser Val Trp Gln Pro
                325                 330                 335

Glu Ser Gln Lys Leu Thr Phe Val Phe Ala His Arg Ile Glu Glu Lys
            340                 345                 350

Asn Gln Val Leu Val Arg Asp Val Glu Thr Gly Glu Leu Arg Pro Gln
        355                 360                 365

Arg Val Val Lys Leu Gly Ser Val Arg Ser Lys Gly Val Val Ala Pro
    370                 375                 380
```

```
Leu Thr Arg Glu Gly Thr Ile Val Val Asn Ser Val Ala Ala Ser Cys
385                 390                 395                 400

Tyr Ala Val Ile Asn Ser Gln Ser Leu Ala His Trp Gly Leu Ala Pro
                405                 410                 415

Met Arg Leu Leu Ser Thr Leu Glu Ala Trp Leu Pro Ala Lys Glu Gln
                420                 425                 430

Leu His Ser Ser Pro Lys Val Val Ser Ser Ala Gln Gln Gln Asn Gly
                435                 440                 445

Ile His Trp Tyr Ala Asn Ala Leu Tyr Lys Val Lys Asp Tyr Val Leu
        450                 455                 460

Pro Gln Ser Trp Arg His Asp
465                 470

<210> SEQ ID NO 21
<211> LENGTH: 522
<212> TYPE: DNA
<213> ORGANISM: Homo sapiens

<400> SEQUENCE: 21
tgcggaccgg gcaggggagtt cgggaagagg aggcacccca aaaagctgac ccctttagcc      60
tacaagcagt ttatccccaa tgtggccgag aagaccctag gcgccagcgg aaggtatgaa     120
gggaagatct ccagaaactc cgagcgattt aaggaactca cccccaatta caaccccgac     180
atcatattta aggatgaaga aaacaccgga gcggacaggc tgatgactca gaggtgtaag     240
gacaagttga acgctttggc catctcggtg atgaaccagt ggccaggagt gaaactgcgg     300
gtgaccgagg gctgggacga agatggccac cactcagagg agtctctgca ctacgagggc     360
cgcgcagtgg acatcaccac gtctgaccgc gaccgcagca gtacggcat gctggcccgc     420 ctggcggtgg aggccggctt cgactgggtg tactacgagt ccaaggcaca tatccactgc     480
tcggtgaaag cagagaactc ggtggcggcc aaatcgggag gc                       522

<210> SEQ ID NO 22
<211> LENGTH: 525
<212> TYPE: DNA
<213> ORGANISM: Homo sapiens

<400> SEQUENCE: 22
tgcgggccgg gtcgggtggt gggcagccgc cggcgaccgc cacgcaaact cgtgccgctc      60
gcctacaagc agttcagccc caatgtgccc gagaagaccc tgggcgccag cggacgctat     120
gaaggcaaga tcgctcgcag ctccgagcgc ttcaaggagc tcacccccaa ttacaatcca     180
gacatcatct tcaaggacga ggagaacaca ggcgccgacc gcctcatgac ccagcgctgc     240
aaggaccgcc tgaactcgct ggctatctcg gtgatgaacc agtggccacgg tgtgaagctg     300 cgggtgaccg agggctggga cgaggacggc caccactcag aggagtccct gcattatgag     360
ggccgcgcgg tggacatcac cacatcagac cgcgaccgca ataagtatgg actgctggcg     420
cgcttggcag tggaggccgg ctttgactgg gtgtattacg agtcaaaggc ccacgtgcat     480
tgctccgtca agtccgagca ctcggccgca gccaagacgg gcggc                     525

<210> SEQ ID NO 23
<211> LENGTH: 175
<212> TYPE: PRT
<213> ORGANISM: Homo sapiens

<400> SEQUENCE: 23
```

```
Cys Gly Pro Gly Arg Val Val Gly Ser Arg Arg Pro Pro Arg Lys
  1               5                  10                 15

Leu Val Pro Leu Ala Tyr Lys Gln Phe Ser Pro Asn Val Pro Glu Lys
             20                  25                  30

Thr Leu Gly Ala Ser Gly Arg Tyr Glu Gly Lys Ile Ala Arg Ser Ser
             35                  40                  45

Glu Arg Phe Lys Glu Leu Thr Pro Asn Tyr Asn Pro Asp Ile Ile Phe
 50                  55                  60

Lys Asp Glu Glu Asn Thr Gly Ala Asp Arg Leu Met Thr Gln Arg Cys
 65                  70                  75                  80

Lys Asp Arg Leu Asn Ser Leu Ala Ile Ser Val Met Asn Gln Trp Pro
             85                  90                  95

Gly Val Lys Leu Arg Val Thr Glu Gly Trp Asp Glu Asp Gly His His
            100                 105                 110

Ser Glu Glu Ser Leu His Tyr Glu Gly Arg Ala Val Asp Ile Thr Thr
            115                 120                 125

Ser Asp Arg Asp Arg Asn Lys Tyr Gly Leu Leu Ala Arg Leu Ala Val
130                 135                 140

Glu Ala Gly Phe Asp Trp Val Tyr Tyr Glu Ser Lys Ala His Val His
145                 150                 155                 160

Cys Ser Val Lys Ser Glu His Ser Ala Ala Lys Thr Gly Gly
            165                 170                 175
```

<210> SEQ ID NO 24
<211> LENGTH: 174
<212> TYPE: PRT
<213> ORGANISM: Homo sapiens

<400> SEQUENCE: 24

```
Cys Gly Pro Gly Arg Gly Phe Gly Lys Arg Arg His Pro Lys Lys Leu
  1               5                  10                  15

Thr Pro Leu Ala Tyr Lys Gln Phe Ile Pro Asn Val Ala Glu Lys Thr
             20                  25                  30

Leu Gly Ala Ser Gly Arg Tyr Glu Gly Lys Ile Ser Arg Asn Ser Glu
             35                  40                  45

Arg Phe Lys Glu Leu Thr Pro Asn Tyr Asn Pro Asp Ile Ile Phe Lys
 50                  55                  60

Asp Glu Glu Asn Thr Gly Ala Asp Arg Leu Met Thr Gln Arg Cys Lys
 65                  70                  75                  80

Asp Lys Leu Asn Ala Leu Ala Ile Ser Val Met Asn Gln Trp Pro Gly
             85                  90                  95

Val Lys Leu Arg Val Thr Glu Gly Trp Asp Glu Asp Gly His His Ser
            100                 105                 110

Glu Glu Ser Leu His Tyr Glu Gly Arg Ala Val Asp Ile Thr Thr Ser
            115                 120                 125

Asp Arg Asp Arg Ser Lys Tyr Gly Met Leu Ala Arg Leu Ala Val Glu
130                 135                 140

Ala Gly Phe Asp Trp Val Tyr Tyr Glu Ser Lys Ala His Ile His Cys
145                 150                 155                 160

Ser Val Lys Ala Glu Asn Ser Val Ala Ala Lys Ser Gly Gly
            165                 170
```

<210> SEQ ID NO 25
<211> LENGTH: 176
<212> TYPE: PRT
<213> ORGANISM: Homo sapiens

<400> SEQUENCE: 25

```
Cys Gly Pro Gly Arg Gly Pro Val Gly Arg Arg Tyr Ala Arg Lys
  1               5                  10                  15

Gln Leu Val Pro Leu Leu Tyr Lys Gln Phe Val Pro Gly Val Pro Glu
             20                  25                  30

Arg Thr Leu Gly Ala Ser Gly Pro Ala Glu Gly Arg Val Ala Arg Gly
         35                  40                  45

Ser Glu Arg Phe Arg Asp Leu Val Pro Asn Tyr Asn Pro Asp Ile Ile
 50                  55                  60

Phe Lys Asp Glu Glu Asn Ser Gly Ala Asp Arg Leu Met Thr Glu Arg
 65                  70                  75                  80

Cys Lys Glu Arg Val Asn Ala Leu Ala Ile Ala Val Met Asn Met Trp
                 85                  90                  95

Pro Gly Val Arg Leu Arg Val Thr Glu Gly Trp Asp Glu Asp Gly His
             100                 105                 110

His Ala Gln Asp Ser Leu His Tyr Glu Gly Arg Ala Leu Asp Ile Thr
         115                 120                 125

Thr Ser Asp Arg Asp Arg Asn Lys Tyr Gly Leu Leu Ala Arg Leu Ala
    130                 135                 140

Val Glu Ala Gly Phe Asp Trp Val Tyr Tyr Glu Ser Arg Asn His Val
145                 150                 155                 160

His Val Ser Val Lys Ala Asp Asn Ser Leu Ala Val Arg Ala Gly Gly
                165                 170                 175
```

<210> SEQ ID NO 26
<211> LENGTH: 175
<212> TYPE: PRT
<213> ORGANISM: Artificial Sequence
<220> FEATURE:
<223> OTHER INFORMATION: Description of Artificial Sequence: Consensus
      sequence
<220> FEATURE:
<221> NAME/KEY: SITE
<222> LOCATION: (1)
<223> OTHER INFORMATION: Xaa=Cys that may be modified, altered or
      substituted within another moiety or series of
      moieties as described herein
<220> FEATURE:
<221> NAME/KEY: SITE
<222> LOCATION: (6)
<223> OTHER INFORMATION: Xaa=Val or Gly
<220> FEATURE:
<221> NAME/KEY: SITE
<222> LOCATION: (7)
<223> OTHER INFORMATION: Xaa=Val, Glu or Pro
<220> FEATURE:
<221> NAME/KEY: SITE
<222> LOCATION: (8)
<223> OTHER INFORMATION: Xaa=Gly or Val
<220> FEATURE:
<221> NAME/KEY: SITE
<222> LOCATION: (9)
<223> OTHER INFORMATION: Xaa=Ser or Gly
<220> FEATURE:
<221> NAME/KEY: SITE
<222> LOCATION: (10)
<223> OTHER INFORMATION: Xaa=Arg or Lys
<220> FEATURE:
<221> NAME/KEY: SITE
<222> LOCATION: (13)
<223> OTHER INFORMATION: Xaa=Pro, His or Tyr
<220> FEATURE:
<221> NAME/KEY: SITE
<222> LOCATION: (14)
<223> OTHER INFORMATION: Xaa=Pro or Ala
<220> FEATURE:

-continued

```
<221> NAME/KEY: SITE
<222> LOCATION: (15)
<223> OTHER INFORMATION: Xaa=Arg or Lys
<220> FEATURE:
<221> NAME/KEY: SITE
<222> LOCATION: (17)
<223> OTHER INFORMATION: Xaa=any amino acid
<220> FEATURE:
<221> NAME/KEY: SITE
<222> LOCATION: (19)
<223> OTHER INFORMATION: Xaa=Val or Thr
<220> FEATURE:
<221> NAME/KEY: SITE
<222> LOCATION: (22)
<223> OTHER INFORMATION: Xaa=Ala or Leu
<220> FEATURE:
<221> NAME/KEY: SITE
<222> LOCATION: (27)
<223> OTHER INFORMATION: Xaa=Ser, Ile or Val
<220> FEATURE:
<221> NAME/KEY: SITE
<222> LOCATION: (29)
<223> OTHER INFORMATION: Xaa=Asn or Gly
<220> FEATURE:
<221> NAME/KEY: SITE
<222> LOCATION: (31)
<223> OTHER INFORMATION: Xaa=Pro ar Ala
<220> FEATURE:
<221> NAME/KEY: SITE
<222> LOCATION: (41)
<223> OTHER INFORMATION: Xaa=Tyr or Ala
<220> FEATURE:
<221> NAME/KEY: SITE
<222> LOCATION: (45)
<223> OTHER INFORMATION: Xaa=Ile or Val
<220> FEATURE:
<221> NAME/KEY: SITE
<222> LOCATION: (46)
<223> OTHER INFORMATION: Xaa=Ala or Ser
<220> FEATURE:
<221> NAME/KEY: SITE
<222> LOCATION: (48)
<223> OTHER INFORMATION: Xaa=Ser, Asn or Gly
<220> FEATURE:
<221> NAME/KEY: SITE
<222> LOCATION: (54)
<223> OTHER INFORMATION: Xaa=Glu or Asp
<220> FEATURE:
<221> NAME/KEY: SITE
<222> LOCATION: (56)
<223> OTHER INFORMATION: Xaa=Thr or Val
<220> FEATURE:
<221> NAME/KEY: SITE
<222> LOCATION: (71)
<223> OTHER INFORMATION: Xaa=Thr or Ser
<220> FEATURE:
<221> NAME/KEY: SITE
<222> LOCATION: (79)
<223> OTHER INFORMATION: Xaa=Gln or Glu
<220> FEATURE:
<221> NAME/KEY: SITE
<222> LOCATION: (83)
<223> OTHER INFORMATION: Xaa=Asp or Glu
<220> FEATURE:
<221> NAME/KEY: SITE
<222> LOCATION: (84)
<223> OTHER INFORMATION: Xaa=Arg or Lys
<220> FEATURE:
<221> NAME/KEY: SITE
<222> LOCATION: (85)
<223> OTHER INFORMATION: Xaa=Leu or Val
<220> FEATURE:
<221> NAME/KEY: SITE
<222> LOCATION: (91)
<223> OTHER INFORMATION: Xaa=Ser or Ala
<220> FEATURE:
<221> NAME/KEY: SITE
<222> LOCATION: (95)
<223> OTHER INFORMATION: Xaa=Gln or Met
```

```
<220> FEATURE:
<221> NAME/KEY: SITE
<222> LOCATION: (114)
<223> OTHER INFORMATION: Xaa=Ser or Ala
<220> FEATURE:
<221> NAME/KEY: SITE
<222> LOCATION: (115)
<223> OTHER INFORMATION: Xaa=Glu or Gln
<220> FEATURE:
<221> NAME/KEY: SITE
<222> LOCATION: (116)
<223> OTHER INFORMATION: Xaa=Glu or Asp
<220> FEATURE:
<221> NAME/KEY: SITE
<222> LOCATION: (135)
<223> OTHER INFORMATION: Xaa=Asn or Ser
<220> FEATURE:
<221> NAME/KEY: SITE
<222> LOCATION: (139)
<223> OTHER INFORMATION: Xaa=Leu or Met
<220> FEATURE:
<221> NAME/KEY: SITE
<222> LOCATION: (157)
<223> OTHER INFORMATION: Xaa=Lys or Arg
<220> FEATURE:
<221> NAME/KEY: SITE
<222> LOCATION: (158)
<223> OTHER INFORMATION: Xaa=Ala or Asn
<220> FEATURE:
<221> NAME/KEY: SITE
<222> LOCATION: (160)
<223> OTHER INFORMATION: Xaa=Val or Ile
<220> FEATURE:
<221> NAME/KEY: SITE
<222> LOCATION: (162)
<223> OTHER INFORMATION: Xaa=Cys or Val
<220> FEATURE:
<221> NAME/KEY: SITE
<222> LOCATION: (166)
<223> OTHER INFORMATION: Xaa=Ser or Ala
<220> FEATURE:
<221> NAME/KEY: SITE
<222> LOCATION: (167)
<223> OTHER INFORMATION: Xaa=Glu or Asp
<220> FEATURE:
<221> NAME/KEY: SITE
<222> LOCATION: (168)
<223> OTHER INFORMATION: Xaa=His or Asn
<220> FEATURE:
<221> NAME/KEY: SITE
<222> LOCATION: (169)
<223> OTHER INFORMATION: Xaa=Ala, Val or Leu
<220> FEATURE:
<221> NAME/KEY: SITE
<222> LOCATION: (172)
<223> OTHER INFORMATION: Xaa=Lys or Arg
<220> FEATURE:
<221> NAME/KEY: SITE
<222> LOCATION: (173)
<223> OTHER INFORMATION: Xaa=Thr, Ser or Ala

<400> SEQUENCE: 26

Xaa Gly Pro Gly Arg Xaa Xaa Xaa Xaa Arg Arg Xaa Xaa Xaa Lys
 1               5                  10                  15

Xaa Leu Xaa Pro Leu Xaa Tyr Lys Gln Phe Xaa Pro Xaa Val Xaa Glu
                20                  25                  30

Lys Thr Leu Gly Ala Ser Gly Arg Xaa Glu Gly Lys Xaa Xaa Arg Xaa
            35                  40                  45

Ser Glu Arg Phe Lys Xaa Leu Xaa Pro Asn Tyr Asn Pro Asp Ile Ile
        50                  55                  60

Phe Lys Asp Glu Glu Asn Xaa Gly Ala Asp Arg Leu Met Thr Xaa Arg
 65                 70                  75                  80

Cys Lys Xaa Xaa Xaa Asn Ser Leu Ala Ile Xaa Val Met Asn Xaa Trp
```

```
                85                  90                  95
Pro Gly Val Lys Leu Arg Val Thr Glu Gly Trp Asp Glu Asp Gly His
               100                 105                 110
His Xaa Xaa Xaa Ser Leu His Tyr Glu Gly Arg Ala Val Asp Ile Thr
               115                 120                 125
Thr Ser Asp Arg Asp Arg Xaa Lys Tyr Gly Xaa Leu Ala Arg Leu Ala
               130                 135                 140
Val Glu Ala Gly Phe Asp Trp Val Tyr Tyr Glu Ser Xaa Xaa His Xaa
145                 150                 155                 160
His Xaa Ser Val Lys Xaa Xaa Xaa Xaa Ala Ala Xaa Xaa Gly Gly
               165                 170                 175
```

<210> SEQ ID NO 27
<211> LENGTH: 528
<212> TYPE: DNA
<213> ORGANISM: Homo sapiens

<400> SEQUENCE: 27

| | | | | | | |
|---|---|---|---|---|---|---|
| tgcgggccgg | gccgggggcc | ggttggccgg | cgccgctatg | cgcgcaagca | gctcgtgccg | 60 |
| ctactctaca | agcaatttgt | gcccggcgtg | ccagagcgga | ccctgggcgc | cagtgggcca | 120 |
| gcggagggga | gggtggcaag | gggctccgag | cgcttccggg | acctcgtgcc | caactacaac | 180 |
| cccgacatca | tcttcaagga | tgaggagaac | agtggagccg | accgcctgat | gaccgagcgt | 240 |
| tgtaaggagc | gggtgaacgc | tttggccatt | gccgtgatga | acatgtggcc | cggagtgcgc | 300 |
| ctacgagtga | ctgagggctg | ggacgaggac | ggccaccacg | ctcaggattc | actccactac | 360 |
| gaaggccgtg | ctttggacat | cactacgtct | gaccgcgacc | gcaacaagta | tgggttgctg | 420 |
| gcgcgcctcg | cagtggaagc | cggcttcgac | tgggtctact | acgagtcccg | caaccacgtc | 480 |
| cacgtgtcgg | tcaaagctga | taactcactg | gcggtccggg | cgggcggc | | 528 |

<210> SEQ ID NO 28
<211> LENGTH: 684
<212> TYPE: DNA
<213> ORGANISM: Homo sapiens

<400> SEQUENCE: 28

| | | | | | | |
|---|---|---|---|---|---|---|
| gtcgacaaaa | ctcacacatg | cccaccgtgc | ccagcacctg | aactcctggg | gggaccgtca | 60 |
| gtcttcctct | tccccccaaa | acccaaggac | accctcatga | tctcccggac | ccctgaggtc | 120 |
| acatgcgtgg | tggtggacgt | gagccacgaa | gaccctgagg | tcaagttcaa | ctggtacgtg | 180 |
| gacggcgtgg | aggtgcataa | tgccaagaca | aagccgcggg | aggagcagta | ccagagcacg | 240 |
| taccgtgtgg | tcagcgtcct | caccgtcctg | caccaggact | ggctgaatgg | caaggagtac | 300 |
| aagtgcaagg | tctccaacaa | agccctccca | gcccccatcg | agaaaaccat | ctccaaagcc | 360 |
| aaagggcagc | cccgagaacc | acaggtgtac | accctgcccc | catcccggga | tgagctgacc | 420 |
| aagaaccagg | tcagcctgac | ctgcctggtc | aaaggcttct | atcccagcga | catcgccgtg | 480 |
| gagtgggaga | gcaatgggca | gccggagaac | aactacaaga | ccacgcctcc | cgtgttggac | 540 |
| tccgacggct | ccttcttcct | ctacagcaag | ctcaccgtgg | acaagagcag | gtggcagcag | 600 |
| gggaacgtct | tctcatgctc | cgtgatgcat | gaggctctgc | acaaccacta | cacgcagaag | 660 |
| agcctctccc | tgtctcccgg | gaaa | | | | 684 |

<210> SEQ ID NO 29
<211> LENGTH: 687
<212> TYPE: DNA

<213> ORGANISM: Homo sapiens

<400> SEQUENCE: 29

```
gtcgacgtgc ccagggattg tggttgtaag ccttgcatat gtacagtccc agaagtatca    60
tctgtcttca tcttccccccc aaagcccaag gatgtgctca ccattactct gactcctaag   120
gtcacgtgtg ttgtggtaga catcagcaag gatgatcccg aggtccagtt cagctggttt   180
gtagatgatg tggaggtgca cacagctcag acgcaaccac gggaagagca gttccaaagc   240
actttccgct cagtcagtga acttcccatc atgcaccagg actggctcaa tggcaaggag   300
ttcaaatgca gggtcaacag tgcagctttc cctgccccca tcgagaaaac catctccaaa   360
accaaaggca gaccgaaggc tccacaggtg taccattc cacctcccaa ggagcagatg      420
gccaaggata aagtcagtct gacctgcatg ataacagact tcttccctga agacattact   480
gtggagtggc agtggaatgg gcagccagcg agaactaca agaacactca gcccatcatg    540
gacacagatg gctcttactt cgtctacagc aagctcaatg tgcagaagag caactgggag   600
gcaggaaata ctttcacctg ctctgtgtta catgagggcc tgcacaacca ccatactgag   660
aagagcctct cccactctcc tggtaaa                                        687
```

<210> SEQ ID NO 30
<211> LENGTH: 702
<212> TYPE: DNA
<213> ORGANISM: Homo sapiens

<400> SEQUENCE: 30

```
gtcgacccca gagggcccac aatcaagccc tgtcctccat gcaaatgccc agcacctaac    60
ctcttgggtg gaccatccgt cttcatcttc cctccaaaga tcaaggatgt actcatgatc   120
tccctgagcc ccatagtcac atgtgtggtg gtggatgtga gcgaggatga cccagatgtc   180
cagatcagct ggtttgtgaa caacgtggaa gtacacacag ctcagacaca aacccataga   240
gaggattacc aaagtacact tcgggtggtc agtgccctcc ccatccagca ccaggactgg   300
atgagtggca aggagttcaa atgcaaggtc aacaacaaag acctcccagc gcccatcgag   360
agaaccatct caaacccaa agggtcagta agagctccac aggtatatgt cttgcctcca    420
ccagaagaag agatgactaa gaaacaggtc actctgacct gcatggtgac agacttcatg   480
cctgaagaca tttacgtgga gtggaccaac aacgggaaaa cagagctaaa ctacaagaac   540
actgaaccag tcctggactc tgatggttct tacttcatgt acagcaagct gagagtggaa   600
aagaagaact gggtggaaag aaatagctac tcctgttcag tggtccacga gggtctgcac   660
aatcaccaca cgactaagag cttctcccgg actccgggta aa                      702
```

<210> SEQ ID NO 31
<211> LENGTH: 9776
<212> TYPE: DNA
<213> ORGANISM: Plasmid P55

<400> SEQUENCE: 31

```
gatctaacat ccaaagacga aaggttgaat gaaacctttt tgccatccga catccacagg    60
tccattctca cacataagtg ccaaacgcaa caggagggga tacactagca gcagaccgtt   120
gcaaacgcag gacctccact cctcttctcc tcaacaccca cttttgccat cgaaaaacca   180
gcccagttat tgggcttgat tggagctcgc tcattccaat tccttctatt aggctactaa   240
caccatgact ttattagcct gtctatcctg gccccctgg cgaggttcat gtttgtttat    300
ttccgaatgc aacaagctcc gcattacacc cgaacatcac tccagatgag ggctttctga   360
```

```
gtgtggggtc aaatagtttc atgttcccca aatggcccaa aactgacagt ttaaacgctg      420
tcttggaacc taatatgaca aaagcgtgat ctcatccaag atgaactaag tttggttcgt      480
tgaaatgcta acggccagtt ggtcaaaaag aaacttccaa aagtcgccat accgtttgtc      540
ttgtttggta ttgattgacg aatgctcaaa ataatctca ttaatgctta gcgcagtctc       600
tctatcgctt ctgaaccccg gtgcacctgt gccgaaacgc aaatggggaa acacccgctt      660
tttggatgat tatgcattgt ctccacattg tatgcttcca agattctggt gggaatactg      720
ctgatagcct aacgttcatg atcaaaattt aactgttcta cccctactt gacagcaata       780 tataaacaga aggaagctgc cctgtcttaa acctttttt ttatcatcat tattagctta       840
ctttcataat tgcgactggt tccaattgac aagcttttga ttttaacgac ttttaacgac      900
aacttgagaa gatcaaaaaa caactaatta ttcgaaggat ccaaacgatg agatttcctt      960
caatttttac tgcagtttta ttcgcagcat cctccgcatt agctgctcca gtcaacacta     1020
caacagaaga tgaaacggca caaattccgg ctgaagctgt catcggttac tcagatttag     1080
aaggggattt cgatgttgct gttttgccat tttccaacag cacaaataac gggttattgt     1140
ttataaatac tactattgcc agcattgctg ctaaagaaga aggggtatct ctcgagaaaa     1200
gatgcggacc gggcaggggg ttcgggaaga ggaggcaccc caaaaagctg acccctttag     1260
cctacaagca gtttatcccc aatgtggccg agaagaccct aggcgccagc ggaaggtatg     1320
aagggaagat ctccagaaac tccgagcgat ttaaggaact cacccccaat tacaaccccg     1380
acatcatatt taaggatgaa gaaaacaccg gagcggacag gctgatgact cagaggtgta     1440
aggacaagtt gaacgctttg gccatctcgg tgatgaacca gtggccagga gtgaaactgc     1500
gggtgaccga gggctgggac gaagatggcc accactcaga ggagtctctg cactacgagg     1560
gccgcgcagt ggacatcacc acgtctgacc gcgaccgcag caagtacggc atgctggccc     1620
gcctggcggt ggaggccggc ttcgactggg tgtactacga gtccaaggca catatccact     1680
gctcggtgaa agcagagaac tcggtggcgg ccaaatcggg aggctgattc gcggccgcga     1740
attaattcgc cttagacatg actgttcctc agttcaagtt gggcacttac gagaagaccg     1800
gtcttgctag attctaatca agaggatgtc agaatgccat ttgcctgaga gatgcaggct     1860
tcatttttga tactttttta tttgtaacct atatagtata ggattttttt tgtcattttg     1920
tttcttctcg tacgagcttg ctcctgatca gcctatctcg cagctgatga atatcttgtg     1980
gtaggggttt gggaaaatca ttcgagtttg atgtttttct tggtatttcc cactcctctt     2040
cagagtacag aagattaagt gagaagttcg tttgtgcaag cttatcgata agctttaatg     2100
cggtagttta tcacagttaa attgctaacg cagtcaggca ccgtgtatga aatctaacaa     2160
tgcgctcatc gtcatcctcg gcaccgtcac cctggatgct gtaggcatag cttggttat      2220 gccggtactg ccgggcctct tgcgggatat cgtccattcc gacagcatcg ccagtcacta     2280
tggcgtgctg ctagcgctat atgcgttgat gcaatttcta tgcgcacccg ttctcggagc     2340
actgtccgac cgctttggcc gccgcccagt cctgctcgct tcgctacttg gagccactat     2400
cgactacgcg atcatggcga ccacacccgt cctgtggatc tatcgaatct aaatgtaagt     2460
taaaatctct aaataattaa ataagtccca gtttctccat acgaacctta acagcattgc     2520
ggtgagcatc tagaccttca acagcagcca gatccatcac tgcttggcca atatgtttca     2580
gtccctcagg agttacgtct tgtgaagtga tgaacttctg gaaggttgca gtgttaactc     2640
cgctgtattg acgggcatat ccgtacgttg gcaaagtgtg gttggtaccg gaggagtaat     2700
```

```
ctccacaact ctctggagag taggcaccaa caaacacaga tccagcgtgt tgtacttgat    2760
caacataaga agaagcattc tcgatttgca ggatcaagtg ttcaggagcg tactgattgg    2820
acatttccaa agcctgctcg taggttgcaa ccgatagggt tgtagagtgt gcaatacact    2880
tgcgtacaat ttcaacccett ggcaactgca cagcttggtt gtgaacagca tcttcaattc    2940
tggcaagctc cttgtctgtc atatcgacag ccaacagaat cacctgggaa tcaataccat    3000
gttcagcttg agcagaaggt ctgaggcaac gaaatctgga tcagcgtatt tatcagcaat    3060
aactagaact tcagaaggcc cagcaggcat gtcaatacta cacagggctg atgtgtcatt    3120
ttgaaccatc atcttggcag cagtaacgaa ctggtttcct ggaccaaata ttttgtcaca    3180
cttaggaaca gtttctgttc cgtaagccat agcagctact gcctgggcgc tcctgctag    3240 cacgatacac ttagcaccaa ccttgtgggc aacgtagatg acttctgggg taagggtacc    3300
atccttctta ggtggagatg caaaaacaat ttctttgcaa ccagcaactt tggcaggaac    3360
acccagcatc agggaagtgg aaggcagaat tgcggttcca ccaggaatat agaggccaac    3420
tttctcaata ggtcttgcaa aacgagagca gactacacca gggcaagtct caacttgcaa    3480
cgtctccgtt agttgagctt catggaattt cctgacgtta tctatagaga gatcaatggc    3540
tctcttaacg ttatctggca attgcataag ttcctctggg aaaggagctt ctaacacagg    3600
tgtcttcaaa gcgactccat caaacttggc agttagttct aaaagggctt tgtcaccatt    3660
ttgacgaaca ttgtcgacaa ttggtttgac taattccata atctgttccg ttttctggat    3720
aggacgacga agggcatctt caatttcttg tgaggaggcc ttagaaacgt caattttgca    3780
caattcaata cgaccttcag aagggacttc tttaggtttg gattcttctt taggttgttc    3840
cttggtgtat cctggcttgg catctccttt ccttctagtg acctttaggg acttcatatc    3900
caggtttctc tccacctcgt ccaacgtcac accgtacttg gcacatctaa ctaatgcaaa    3960
ataaaataag tcagcacatt cccaggctat atcttccttg gatttagctt ctgcaagttc    4020
atcagcttcc tccctaattt tagcgttcaa acaaaacttc gtcgtcaaat aaccgtttgg    4080
tataagaacc ttctggagca ttgctcttac gatcccacaa ggtgcttcca tggctctaag    4140 acccttttgat tggccaaaac aggaagtgcg ttccaagtga cagaaaccaa cacctgtttg    4200
ttcaaccaca aatttcaagc agtctccatc acaatccaat tcgatacccca gcaacttttg    4260 agttcgtcca gatgtagcac ctttatacca caaaccgtga cgacgagatt ggtagactcc    4320
agtttgtgtc cttatagcct ccggaataga cttttttggac gagtacacca ggcccaacga    4380
gtaattagaa gagtcagcca ccaaagtagt gaatagacca tcgggcggt cagtagtcaa    4440 agacgccaac aaaatttcac tgacagggaa cttttttgaca tcttcagaaa gttcgtattc    4500
agtagtcaat tgccgagcat caataatggg gattatacca gaagcaacag tggaagtcac    4560
atctaccaac tttgcggtct cagaaaaagc ataaacagtt ctactaccgc cattagtgaa    4620
acttttcaaa tcgcccagtg gagaagaaaa aggcacagcg atactagcat tagcgggcaa    4680
ggatgcaact ttatcaacca gggtcctata gataaaccta gcgcctggga tcatcctttg    4740
gacaactctt tctgccaaat ctaggtccaa aatcacttca ttgataccat tattgtacaa    4800
cttgagcaag ttgtcgatca gctcctcaaa ttggtcctct gtaacggatg actcaacttg    4860
cacattaact tgaagctcag tcgattgagt gaacttgatc aggttgtgca gctggtcagc    4920 agcatagga acacggctt ttcctaccaa actcaaggaa ttatcaaact ctgcaacact    4980
tgcgtatgca ggtagcaagg gaaatgtcat acttgaagtc ggacagtgag tgtagtcttg    5040
agaaattctg aagccgtatt tttattatca gtgagtcagt catcaggaga tcctctacgc    5100
```

```
cggacgcatc gtggccgacc tgcaggtcgg catcaccggc gccacaggtg cggttgctgg    5160
cgcctatatc gccgacatca ccgatgggga agatcgggct cgccacttcg ggctcatgag    5220
cgcttgtttc ggcgtgggta tggtggcagg ccccgtggcc gggggactgt tgggcgccat    5280
ctccttggac ctgcaggggg ggggggggaa agccacgttg tgtctcaaaa tctctgatgt    5340
tacattgcac aagataaaaa tatatcatca tgaacaataa aactgtctgc ttacataaac    5400
agtaatacaa ggggtgttat gagccatatt caacgggaaa cgtcttgctc aaggccgcga    5460
ttaaattcca acatggatgc tgatttatat gggtataaat gggctcgcga taatgtcggg    5520
caatcaggtg cgacaatcta tcgattgtat gggaagcccg atgcgccaga gttgtttctg    5580
aaacatggca aaggtagcgt tgccaatgat gttacagatg agatggtcag actaaactgg    5640
ctgacggaat ttatgcctct tccgaccatc aagcatttta tccgtactcc tgatgatgca    5700
tggttactca ccactgcgat ccccgggaaa acagcattcc aggtattaga agaatatcct    5760
gattcaggtg aaaatattgt tgatgcgctg gcagtgttcc tgcgccggtt gcattcgatt    5820
cctgtttgta attgtccttt taacagcgat cgcgtatttc gtctcgctca ggcgcaatca    5880
cgaatgaata acggtttggt tgatgcgagt gattttgatg acgagcgtaa tggctggcct    5940
gttgaacaag tctggaaaga aatgcataag cttttgccat tctcaccgga ttcagtcgtc    6000
actcatggtg atttctcact tgataacctt attttttgacg aggggaaatt aataggttgt    6060
attgatgttg gacgagtcgg aatcgcagac cgataccagg atcttgccat cctatggaac    6120
tgcctcggtg agttttctcc ttcattacag aaacggcttt ttcaaaaata tggtattgat    6180
aatcctgata tgaataaatt gcagtttcat ttgatgctcg atgagttttt ctaatcagaa    6240
ttggttaatt ggttgtaaca ctggcagagc attacgctga cttgacggga cggcggcttt    6300
gttgaataaa tcgaactttt gctgagttga aggatcagat cacgcatctt cccgacaacg    6360
cagaccgttc cgtggcaaag caaaagttca aaatcaccaa ctggtccacc tacaacaaag    6420
ctctcatcaa ccgtggctcc ctcactttct ggctggatga tggggcgatt caggcctggt    6480
atgagtcagc aacaccttct tcacgaggca gacctcagcg cccccccccc cctgcaggtc    6540
ccacggcggc ggtgctcaac ggcctcaacc tactactggg ctgcttccta atgcaggagt    6600
cgcataaggg agagcgtcga gtatctatga ttggaagtat gggaatggtg atacccgcat    6660
tcttcagtgt cttgaggtct cctatcagat tatgcccaac taaagcaacc ggaggaggag    6720
atttcatggt aaatttctct gacttttggt catcagtaga ctcgaactgt gagactatct    6780
cggttatgac agcagaaatg tccttcttgg agacagtaaa tgaagtccca ccaataaaga    6840
aatccttgtt atcaggaaca aacttcttgt ttcgaacttt ttcggtgcct tgaactataa    6900
aatgtagagt ggatatgtcg ggtaggaatg gagcgggcaa atgcttacct tctggacctt    6960
caagaggtat gtagggtttg tagatactga tgccaacttc agtgacaacg ttgctatttc    7020
gttcaaacca ttccgaatcc agagaaatca agttgtttg tctactattg atccaagcca    7080
gtgcggtctt gaaactgaca atagtgtgct cgtgttttga ggtcatcttt gtatgaataa    7140
atctagtctt tgatctaaat aatcttgacg agccaaggcg ataaataccc aaatctaaaa    7200
ctcttttaaa acgttaaaag gacaagtatg tctgcctgta ttaaacccca aatcagctcg    7260
tagtctgatc ctcatcaact tgaggggcac tatcttgttt tagagaaatt tgcggagatg    7320
cgatatcgag aaaaaggtac gctgatttta aacgtgaaat ttatctcaag atctctgcct    7380
cgcgcgtttc ggtgatgacg gtgaaaacct ctgacacatg cagctcccgg agacggtcac    7440
```

```
agcttgtctg taagcggatg ccgggagcag acaagcccgt cagggcgcgt cagcgggtgt   7500
tggcgggtgt cggggcgcag ccatgaccca gtcacgtagc gatagcggag tgtatactgg   7560
cttaactatg cggcatcaga gcagattgta ctgagagtgc accatatgcg gtgtgaaata   7620
ccgcacagat gcgtaaggag aaaataccgc atcaggcgct cttccgcttc ctcgctcact   7680
gactcgctgc gctcggtcgt tcggctgcgg cgagcggtat cagctcactc aaaggcggta   7740
atacggttat ccacagaatc aggggataac gcaggaaaga acatgtgagc aaaaggccag   7800
caaaaggcca ggaaccgtaa aaaggccgcg ttgctggcgt ttttccatag gctccgcccc   7860
cctgacgagc atcacaaaaa tcgacgctca agtcagaggt ggcgaaaccc gacaggacta   7920
taaagatacc aggcgtttcc ccctggaagc tccctcgtgc gctctcctgt tccgaccctg   7980
ccgcttaccg gatacctgtc cgcctttctc ccttcgggaa gcgtggcgct ttctcaatgc   8040
tcacgctgta ggtatctcag ttcggtgtag gtcgttcgct ccaagctggg ctgtgtgcac   8100
gaaccccccg ttcagcccga ccgctgcgcc ttatccggta actatcgtct tgagtccaac   8160
ccggtaagac acgacttatc gccactggca gcagccactg gtaacaggat tagcagagcg   8220
aggtatgtag gcggtgctac agagttcttg aagtggtggc ctaactacgg ctacactaga   8280
aggacagtat ttggtatctg cgctctgctg aagccagtta ccttcggaaa aagagttggt   8340
agctcttgat ccggcaaaca aaccaccgct ggtagcggtg gttttttttgt ttgcaagcag   8400
cagattacgc gcagaaaaaa aggatctcaa gaagatcctt tgatcttttc tacggggtct   8460
gacgctcagt ggaacgaaaa ctcacgttaa gggattttgg tcatgagatt atcaaaaagg   8520
atcttcacct agatcctttt aaattaaaaa tgaagtttta aatcaatcta agtatatat    8580
gagtaaactt ggtctgacag ttaccaatgc ttaatcagtg aggcacctat ctcagcgatc   8640
tgtctatttc gttcatccat agttgcctga ctccccgtcg tgtagataac tacgatacgg   8700
gagggcttac catctggccc cagtgctgca atgataccgc gagacccacg ctcaccggct   8760
ccagatttat cagcaataaa ccagccagcc ggaagggccg agcgcagaag tggtcctgca   8820
actttatccg cctccatcca gtctattaat tgttgccggg aagctagagt aagtagttcg   8880
ccagttaata gtttgcgcaa cgttgttgcc attgctgcag catcgtggt gtcacgctcg    8940
tcgtttggta tggcttcatt cagctccggt tcccaacgat caaggcgagt tacatgatcc   9000
cccatgttgt gcaaaaaagc ggttagctcc ttcggtcctc cgatcgttgt cagaagtaag   9060
ttggccgcag tgttatcact catggttatg gcagcactgc ataattctct tactgtcatg   9120
ccatccgtaa gatgcttttc tgtgactggt gagtactcaa ccaagtcatt ctgagaatag   9180
tgtatgcggc gaccgagttg ctcttgcccg gcgtcaacac gggataatac cgcgccacat   9240
agcagaactt taaaagtgct catcattgga aaacgttctt cggggcgaaa actctcaagg   9300
atcttaccgc tgttgagatc cagttcgatg taacccactc gtgcacccaa ctgatcttca   9360
gcatctttta ctttcaccag cgtttctggg tgagcaaaaa caggaaggca aaatgccgca   9420
aaaaagggaa taagggcgac acggaaatgt tgaatactca tactcttcct ttttcaatat   9480
tattgaagca tttatcaggg ttattgtctc atgagcggat acatatttga atgtatttag   9540
aaaaataaac aaatagdggt tccgcgcaca tttccccgaa aagtgccacc tgacgtctaa   9600
gaaaccatta ttatcatgac attaacctat aaaaataggc gtatcacgag gccctttcgt   9660
cttcaagaat taattctcat gtttgacagc ttatcatcga taagctgact catgttggta   9720
ttgtgaaata gacgcagatc gggaacactg aaaaataaca gttattattc gagatc       9776
```

<210> SEQ ID NO 32
<211> LENGTH: 10491
<212> TYPE: DNA
<213> ORGANISM: Plasmid pUB114

<400> SEQUENCE: 32

```
gatctaacat ccaaagacga aaggttgaat gaaaccttt tgccatccga catccacagg      60
tccattctca cacataagtg ccaaacgcaa caggagggga tacactagca gcagaccgtt    120
gcaaacgcag gacctccact cctcttctcc tcaacaccca cttttgccat cgaaaaacca    180
gcccagttat tgggcttgat tggagctcgc tcattccaat tccttctatt aggctactaa    240
caccatgact ttattagcct gtctatcctg gccccctgg cgaggttcat gtttgtttat     300
ttccgaatgc aacaagctcc gcattacacc cgaacatcac tccagatgag ggctttctga    360
gtgtgggtc aaatagtttc atgttcccca aatggcccaa aactgacagt ttaaacgctg     420
tcttggaacc taatatgaca aaagcgtgat ctcatccaag atgaactaag tttggttcgt    480
tgaaatgcta acggccagtt ggtcaaaaag aaacttccaa aagtcgccat accgtttgtc    540
ttgtttggta ttgattgacg aatgctcaaa ataatctca ttaatgctta gcgcagtctc     600
tctatcgctt ctgaacccg gtgcacctgt gccgaaacgc aaatggggaa acacccgctt    660
tttggatgat tatgcattgt ctccacattg tatgcttcca agattctggt gggaatactg    720
ctgatagcct aacgttcatg atcaaaattt aactgttcta accctactt gacagcaata     780
tataaacaga aggaagctgc cctgtcttaa acctttttt tatcatcatt attagcttac     840
tttcataatt gcgactggtt ccaattgaca agcttttgat tttaacgact tttaacgaca    900
acttgagaag atcaaaaaac aactaattat tcgaaggatc caaacgatga gatttccttc    960
aattttact gcagttttat tcgcagcatc ctccgcatta gctgctccag tcaacactac   1020
aacagaagat gaaacggcac aaattccggc tgaagctgtc atcggttact cagatttaga   1080
aggggatttc gatgttgctg ttttgccatt ttccaacagc acaataacg ggttattgtt    1140
tataaatact actattgcca gcattgctgc taaagaagaa ggggtatctc tcgagaaaag   1200
atgcggaccg gcaggggt tcgggaagag gaggcacccc aaaaagctga cccctttagc     1260
ctacaagcag tttatcccca atgtggccga aagaccta ggcgccagcg aaggtatga      1320
agggaagatc tccagaaact ccgagcgatt taaggaactc accccaatt acaaccccga    1380
catcatattt aaggatgaag aaaacaccgg agcggacagg ctgatgactc agaggtgtaa   1440
ggacaagttg aacgctttgg ccatctcggt gatgaaccag tggccaggag tgaaactgcg   1500
ggtgaccgag ggctgggacg aagatggcca ccactcagag gagtctctgc actacgaggg   1560
ccgcgcagtg gacatcacca cgtctgaccg cgaccgcagc aagtacggca tgctggcccg   1620
cctggcggtg gaggccggct cgactgggt gtactacgag tccaaggcac atatccactg   1680
ctcggtgaaa gcagagaact cggtggcggc caaatcggga ggcgtcgacg tgcccaggga   1740
ttgtggttgt aagccttgca tatgtacagt cccagaagta tcatctgtct tcatcttccc   1800
cccaaagccc aaggatgtgc tcaccattac tctgactcct aaggtcacgt gtgttgtggt   1860
agacatcagc aaggatgatc ccgaggtcca gttcagctgg tttgtagatg atgtggaggt   1920
gcacacagct cagacgcaac cacgggaaga gcagttccaa agcactttcc gctcagtcag   1980
tgaacttccc atcatgcacc aggactggct caatggcaag gagttcaaat gcagggtcaa   2040
cagtgcagct ttccctgccc ccatcgagaa aaccatctcc aaaaccaaag gcagaccgaa   2100
ggctccacag gtgtacacca ttccacctcc caaggagcag atggccaagg ataaagtcag   2160
```

```
tctgacctgc atgataacag acttcttccc tgaagacatt actgtggagt ggcagtggaa    2220
tgggcagcca gcggagaact acaagaacac tcagcccatc atggacacag atggctctta    2280
cttcgtctac agcaagctca atgtgcagaa gagcaactgg gaggcaggaa atactttcac    2340
ctgctctgtg ttacatgagg gcctgcacaa ccaccatact gagaagagcc tctcccactc    2400
tcctggtaaa tgatcccagt gtccttggag ccctctggtc ctacagcggc cgcgaattaa    2460
ttcgccttag acatgactgt tcctcagttc aagttgggca cttacgagaa gaccggtctt    2520
gctagattct aatcaagagg atgtcagaat gccatttgcc tgagagatgc aggcttcatt    2580
tttgatactt ttttatttgt aacctatata gtataggatt ttttttgtca ttttgtttct    2640
tctcgtacga gcttgctcct gatcagccta tctcgcagct gatgaatatc ttgtggtagg    2700
ggtttgggaa atcattcga gtttgatgtt tttcttggta tttcccactc ctcttcagag    2760
tacagaagat taagtgagaa gttcgtttgt gcaagcttat cgataagctt taatgcggta    2820
gtttatcaca gttaaattgc taacgcagtc aggcaccgtg tatgaaatct aacaatgcgc    2880
tcatcgtcat cctcggcacc gtcaccctgg atgctgtagg cataggcttg gttatgccgg    2940
tactgccggg cctcttgcgg gatatcgtcc attccgacag catcgccagt cactatggcg    3000
tgctgctagc gctatatgcg ttgatgcaat ttctatgcgc acccgttctc ggagcactgt    3060
ccgaccgctt tggccgccgc ccagtcctgc tcgcttcgct acttggagcc actatcgact    3120
acgcgatcat ggcgaccaca cccgtcctgt ggatctatcg aatctaaatg taagttaaaa    3180
tctctaaata attaaataag tcccagtttc tccatacgaa ccttaacagc attgcggtga    3240
gcatctagac cttcaacagc agccagatcc atcactgctt ggccaatatg tttcagtccc    3300
tcaggagtta cgtcttgtga agtgatgaac ttctggaagg ttgcagtgtt aactccgctg    3360
tattgacggg catatccgta cgttggcaaa gtgtggttgg taccggagga gtaatctcca    3420
caactctctg gagagtaggc accaacaaac acagatccag cgtgttgtac ttgatcaaca    3480
taagaagaag cattctcgat ttgcaggatc aagtgttcag gagcgtactg attggacatt    3540
tccaaagcct gctcgtaggt tgcaaccgat agggttgtag agtgtgcaat acacttgcgt    3600
acaatttcaa cccttggcaa ctgcacagct tggttgtgaa cagcatcttc aattctggca    3660
agctccttgt ctgtcatatc gacagccaac agaatcacct gggaatcaat accatgttca    3720
gcttgagcag aaggtctgag gcaacgaaat ctggatcagc gtatttatca gcaataacta    3780
gaacttcaga aggcccagca ggcatgtcaa tactacacag ggctgatgtg tcattttgaa    3840
ccatcatctt ggcagcagta acgaactggt ttcctggacc aaatattttg tcacacttag    3900
gaacagtttc tgttccgtaa gccatagcag ctactgcctg ggcgcctcct gctagcacga    3960
tacacttagc accaaccttg tgggcaacgt agatgacttc tggggtaagg gtaccatcct    4020
tcttaggtgg agatgcaaaa acaatttctt tgcaaccagc aactttggca ggaacaccca    4080
gcatcaggga agtggaaggc agaattgcgg ttccaccagg aatatagagg ccaacttcct    4140
caataggtct tgcaaaacga gagcagacta caccagggca agtctcaact tgcaacgtct    4200
ccgttagttg agcttcatgg aatttcctga cgttatctat agagagatca atggctctct    4260
taacgttatc tggcaattgc ataagttcct ctgggaaagg agcttctaac acaggtgtct    4320
tcaaagcgac tccatcaaac ttggcagtta gttctaaaag ggctttgtca ccattttgac    4380
gaacattgtc gacaattggt ttgactaatt ccataatctg ttccgttttc tggataggac    4440
gacgaagggc atcttcaatt tcttgtgagg aggcctagga aacgtcaatt ttgcacaatt    4500
caatacgacc ttcagaaggg acttctttag gtttggattc ttctttaggt tgttccttgg    4560
```

```
tgtatcctgg cttggcatct cctttccttc tagtgacctt tagggacttc atatccaggt    4620
ttctctccac ctcgtccaac gtcacaccgt acttggcaca tctaactaat gcaaaataaa    4680
ataagtcagc acattcccag gctatatctt ccttggattt agcttctgca agttcatcag    4740
cttcctccct aattttagcg ttcaaacaaa acttcgtcgt caaataaccg tttggtataa    4800
gaaccttctg gagcattgct cttacgatcc cacaaggtgc ttccatggct ctaagaccct    4860
ttgattggcc aaaacaggaa gtgcgttcca agtgacagaa accaacacct gtttgttcaa    4920
ccacaaattt caagcagtct ccatcacaat ccaattcgat acccagcaac tttttgagttc   4980
gtccagatgt agcacctta taccacaaac cgtgacgacg agattggtag actccagttt     5040
gtgtccttat agcctccgga atagactttt tggacgagta caccaggccc aacgagtaat    5100
tagaagagtc agccaccaaa gtagtgaata gaccatcggg gcggtcagta gtcaaagacg    5160
ccaacaaaat ttcactgaca gggaactttt tgacatcttc agaaagttcg tattcagtag    5220
tcaattgccg agcatcaata atggggatta taccagaagc aacagtggaa gtcacatcta    5280
ccaactttgc ggtctcagaa aaagcataaa cagttctact accgccatta gtgaaacttt    5340
tcaaatcgcc cagtggagaa gaaaaaggca cagcgatact agcattagcg ggcaaggatg    5400
caactttatc aaccagggtc ctatagataa ccctagcgcc tgggatcatc ctttggacaa    5460
ctctttctgc caaatctagg tccaaaatca cttcattgat accattattg tacaacttga    5520
gcaagttgtc gatcagctcc tcaaattggt cctctgtaac ggatgactca acttgcacat    5580
taacttgaag ctcagtcgat tgagtgaact tgatcaggtt gtgcagctgg tcagcagcat    5640
agggaaacac ggcttttcct accaaactca aggaattatc aaactctgca cacttgcgt     5700
atgcaggtag caagggaaat gtcatacttg aagtcggaca gtgagtgtag tcttgagaaa    5760
ttctgaagcc gtatttttat tatcagtgag tcagtcatca ggagatcctc tacgccggac    5820
gcatcgtggc cgacctgcag gtcggcatca ccggcgccac aggtgcggtt gctggcgcct    5880
atatcgccga catcaccgat ggggaagatc gggctcgcca cttcgggctc atgagcgctt    5940
gtttcggcgt gggtatggtg gcaggccccg tggccggggg actgttgggc gccatctcct    6000
tggacctgca ggggggggg gggaaagcca cgttgtgtct caaaatctct gatgttacat     6060
tgcacaagat aaaatatat catcatgaac aataaaactg tctgcttaca taaacagtaa     6120
tacaagggt gttatgagcc atattcaacg ggaaacgtct tgctcaaggc cgcgattaaa     6180
ttccaacatg gatgctgatt tatatgggta taaatgggct cgcgataatg tcgggcaatc    6240
aggtgcgaca atctatcgat tgtatgggaa gcccgatgcg ccagagttgt ttctgaaaca    6300
tggcaaaggt agcgttgcca atgatgttac agatgagatg gtcagactaa actggctgac    6360
ggaatttatg cctcttccga ccatcaagca ttttatccgt actcctgatg atgcatggtt    6420
actcaccact gcgatcccg ggaaaacagc attccaggta ttagaagaat atcctgattc      6480
aggtgaaaat attgttgatg cgctggcagt gttcctgcgc cggttgcatt cgattcctgt    6540
ttgtaattgt ccttttaaca gcgatcgcgt atttcgtctc gctcaggcgc aatcacgaat    6600
gaataacggt ttggttgatg cgagtgattt tgatgacgag cgtaatggct ggcctgttga    6660
acaagtctgg aaagaaatgc ataagctttt gccattctca ccggattcag tcgtcactca    6720
tggtgatttc tcacttgata accttatttt tgacgagggg aaattaatag gttgtattga    6780
tgttggacga gtcggaatcg cagaccgata ccaggatctt gccatcctat ggaactgcct    6840
cggtgagttt tctccttcat tacagaaacg gcttttcaa aaatatggta ttgataatcc      6900
```

```
tgatatgaat aaattgcagt ttcatttgat gctcgatgag ttttctaat cagaattggt    6960 taattggttg taacactggc agagcattac gctgacttga cgggacggcg gctttgttga    7020
ataaatcgaa cttttgctga gttgaaggat cagatcacgc atcttcccga caacgcagac    7080
cgttccgtgg caaagcaaaa gttcaaaatc accaactggt ccacctacaa caaagctctc    7140
atcaaccgtg gctccctcac tttctggctg gatgatgggg cgattcaggc ctggtatgag    7200
tcagcaacac cttcttcacg aggcagacct cagcgccccc cccccctgc aggtcccacg     7260 gcggcggtgc tcaacggcct caacctacta ctgggctgct tcctaatgca ggagtcgcat    7320
aagggagagc gtcgagtatc tatgattgga agtatgggaa tggtgatacc cgcattcttc    7380
agtgtcttga ggtctcctat cagattatgc ccaactaaag caaccggagg aggagatttc    7440
atggtaaatt tctctgactt ttggtcatca gtagactcga actgtgagac tatctcggtt    7500
atgacagcag aaatgtcctt cttggagaca gtaaatgaag tcccaccaat aaagaaatcc    7560
ttgttatcag gaacaaactt cttgtttcga acttttcgg tgccttgaac tataaaatgt      7620
agagtggata tgtcgggtag gaatggagcg ggcaaatgct taccttctgg accttcaaga    7680
ggtatgtagg gtttgtagat actgatgcca acttcagtga caacgttgct atttcgttca    7740
aaccattccg aatccagaga aatcaaagtt gtttgtctac tattgatcca agccagtgcg    7800
gtcttgaaac tgacaatagt gtgctcgtgt tttgaggtca tctttgtatg aataaatcta    7860
gtctttgatc taaataatct tgacgagcca aggcgataaa tacccaaatc taaaactctt    7920
ttaaaacgtt aaaaggacaa gtatgtctgc ctgtattaaa ccccaaatca gctcgtagtc    7980
tgatcctcat caacttgagg ggcactatct tgttttagag aaatttgcgg agatgcgata    8040
tcgagaaaaa ggtacgctga tttttaaacgt gaaatttatc tcaagatctc tgcctcgcgc    8100
gtttcggtga tgacggtgaa aacctctgac acatgcagct cccggagacg gtcacagctt    8160
gtctgtaagc ggatgccggg agcagacaag cccgtcaggg cgcgtcagcg ggtgttggcg    8220
ggtgtcgggg cgcagccatg acccagtcac gtagcgatag cggagtgtat actggcttaa    8280
ctatgcggca tcagagcaga ttgtactgag agtgcaccat atgcggtgtg aaataccgca    8340
cagatgcgta aggagaaaat accgcatcag gcgctcttcc gcttcctcgc tcactgactc    8400
gctgcgctcg gtcgttcggc tgcggcgagc ggtatcagct cactcaaagg cggtaatacg    8460
gttatccaca gaatcagggg ataacgcagg aaagaacatg tgagcaaaag gccagcaaaa    8520
ggccaggaac cgtaaaaagg ccgcgttgct ggcgtttttc cataggctcc gcccccctga    8580
cgagcatcac aaaaatcgac gctcaagtca gaggtggcga aacccgacag gactataaag    8640
ataccaggcg tttccccctg gaagctccct cgtgcgctct cctgttccga ccctgccgct    8700
taccggatac ctgtccgcct ttctcccttc gggaagcgtg gcgctttctc aatgctcacg    8760
ctgtaggtat ctcagttcgg tgtaggtcgt tcgctccaag ctgggctgtg tgcacgaacc    8820
ccccgttcag cccgaccgct gcgccttatc cggtaactat cgtcttgagt ccaacccggt    8880
aagacacgac ttatcgccac tggcagcagc cactggtaac aggattagca gagcgaggta    8940
tgtaggcggt gctacagagt tcttgaagtg gtggcctaac tacggctaca ctagaaggac    9000
agtatttggt atctgcgctc tgctgaagcc agttaccttc ggaaaaagag ttggtagctc    9060
ttgatccggc aaacaaacca ccgctggtag cggtggtttt tttgtttgca agcagcagat    9120
tacgcgcaga aaaaaaggat ctcaagaaga tcctttgatc ttttctacgg ggtctgacgc    9180
tcagtggaac gaaaactcac gttaagggat tttggtcatg agattatcaa aaaggatctt    9240
cacctagatc cttttaaatt aaaaatgaag ttttaaatca atctaaagta tatatgagta    9300
```

```
aacttggtct gacagttacc aatgcttaat cagtgaggca cctatctcag cgatctgtct    9360
atttcgttca tccatagttg cctgactccc cgtcgtgtag ataactacga tacgggaggg    9420
cttaccatct ggccccagtg ctgcaatgat accgcgagac ccacgctcac cggctccaga    9480
tttatcagca ataaaccagc cagccggaag ggccgagcgc agaagtggtc ctgcaacttt    9540
atccgcctcc atccagtcta ttaattgttg ccgggaagct agagtaagta gttcgccagt    9600
taatagtttg cgcaacgttg ttgccattgc tgcaggcatc gtggtgtcac gctcgtcgtt    9660
tggtatggct tcattcagct ccggttccca acgatcaagg cgagttacat gatccccat     9720
gttgtgcaaa aaagcggtta gctccttcgg tcctccgatc gttgtcagaa gtaagttggc    9780
cgcagtgtta tcactcatgg ttatggcagc actgcataat tctcttactg tcatgccatc    9840
cgtaagatgc ttttctgtga ctggtgagta ctcaaccaag tcattctgag aatagtgtat    9900
gcggcgaccg agttgctctt gcccggcgtc aacacgggaa ataccgcgc cacatagcag     9960
aactttaaaa gtgctcatca ttggaaaacg ttcttcgggg cgaaaactct caaggatctt   10020
accgctgttg agatccagtt cgatgtaacc cactcgtgca cccaactgat cttcagcatc   10080
ttttactttc accagcgttt ctgggtgagc aaaaacagga aggcaaaatg ccgcaaaaaa   10140
gggaataagg gcgacacgga aatgttgaat actcatactc ttccttttc aatattattg    10200
aagcatttat cagggttatt gtctcatgag cggatacata tttgaatgta tttagaaaaa   10260
taaacaaata ggggttccgc gcacatttcc ccgaaaagtg ccacctgacg tctaagaaac   10320
cattattatc atgacattaa cctataaaaa taggcgtatc acgaggccct ttcgtcttca   10380
agaattaatt ctcatgtttg acagcttatc atcgataagc tgactcatgt tggtattgtg   10440
aaatagcgc agatcgggaa cactgaaaaa taacagttat tattcgagat c             10491
```

<210> SEQ ID NO 33
<211> LENGTH: 10512
<212> TYPE: DNA
<213> ORGANISM: Plasmid pUB115

<400> SEQUENCE: 33

```
gatctaacat ccaaagacga aaggttgaat gaaacctttt tgccatccga catccacagg     60
tccattctca cacataagtg ccaaacgcaa caggagggga tacactagca gcagaccgtt    120
gcaaacgcag gacctccact cctcttctcc tcaacaccca cttttgccat cgaaaaacca    180
gcccagttat tgggcttgat tggagctcgc tcattccaat tccttctatt aggctactaa    240
caccatgact ttattagcct gtctatcctg gccccctgg cgaggttcat gtttgtttat     300
ttccgaatgc aacaagctcc gcattacacc cgaacatcac tccagatgag ggctttctga    360
gtgtggggtc aaatagtttc atgttcccca aatggcccaa aactgacagt taaacgctg     420
tcttggaacc taatatgaca aaagcgtgat ctcatccaag atgaactaag tttggttcgt    480
tgaaatgcta acggccagtt ggtcaaaaag aaacttccaa aagtcgccat accgtttgtc    540
ttgtttggta ttgattgacg aatgctcaaa ataatctca ttaatgctta gcgcagtctc    600
tctatcgctt ctgaaccccg gtgcacctgt gccgaaacgc aaatggggaa cacccgcctt    660
tttggatgat tatgcattgt ctccacattg tatgcttcca agattctggt gggaatactg    720
ctgatagcct aacgttcatg atcaaaattt aactgttcta cccctactt gacagcaata    780
tataaacaga aggaagctgc cctgtcttaa acctttttt ttatcatcat tattagctta    840
cttttcataat tgcgactggt tccaattgac aagcttttga ttttaacgac ttttaacgac   900
```

```
aacttgagaa gatcaaaaaa caactaatta ttcgaaggat ccaaacgatg agatttcctt      960
caatttttac tgcagtttta ttcgcagcat cctccgcatt agctgctcca gtcaacacta     1020
caacagaaga tgaaacggca caaattccgg ctgaagctgt catcggttac tcagatttag     1080
aaggggattt cgatgttgct gttttgccat tttccaacag cacaaataac gggttattgt     1140
ttataaatac tactattgcc agcattgctg ctaaagaaga aggggtatct ctcgagaaaa     1200
gatgcggacc gggcaggggg ttcgggaaga ggaggcaccc caaaaagctg accccttttag    1260
cctacaagca gtttatcccc aatgtggccg agaagaccct aggcgccagc ggaaggtatg     1320
aagggaagat ctccagaaac tccgagcgat ttaaggaact cacccccaat tacaaccccg     1380
acatcatatt taaggatgaa gaaaacaccg gagcggacag gctgatgact cagaggtgta     1440
aggacaagtt gaacgctttg ccatctcgg tgatgaacca gtggccagga gtgaaactgc      1500
gggtgaccga gggctgggac gaagatggcc accactcaga ggagtctctg cactacgagg     1560
gccgcgcagt ggacatcacc acgtctgacc gcgaccgcag caagtacggc atgctggccc     1620
gcctggcggt ggaggccggc ttcgactggg tgtactacga gtccaaggca catatccact     1680
gctcggtgaa agcagagaac tcggtggcgg ccaaatcggg aggcgtcgac cccagagggc     1740
ccacaatcaa gccctgtcct ccatgcaaat gcccagcacc taacctcttg ggtggaccat     1800
ccgtcttcat cttccctcca aagatcaagg atgtactcat gatctccctg agccccatag     1860
tcacatgtgt ggtggtggat gtgagcgagg atgacccaga tgtccagatc agctggtttg     1920
tgaacaacgt ggaagtacac acagctcaga cacaaaccca tagagaggat taccaaagta     1980
cacttcgggt ggtcagtgcc ctccccatcc agcaccagga ctggatgagt ggcaaggagt     2040
tcaaatgcaa ggtcaacaac aaagacctcc cagcgcccat cgagagaacc atctcaaaac     2100
ccaaagggtc agtaagagct ccacaggtat atgtcttgcc tccaccagaa gaagagatga     2160
ctaagaaaca ggtcactctg acctgcatgg tgacagactt catgcctgaa gacatttacg     2220
tggagtggac caacaacggg aaaacagagc taaactacaa gaacactgaa ccagtcctgg     2280
actctgatgg ttcttacttc atgtacagca agctgagagt ggaaaagaag aactgggtgg     2340
aaagaaatag ctactcctgt tcagtggtcc acgagggtct gcacaatcac cacacgacta     2400
agagcttctc ccggactccg ggtaaatgag ctcagatcga ttccatggat cctcacatcc     2460
caatccgcgg ccgcgaatta attcgcctta gacatgactg ttcctcagtt caagttgggc     2520
acttacgaga agaccggtct tgctagattc taatcaagag gatgtcagaa tgccatttgc     2580
ctgagagatg caggcttcat ttttgatact tttttatttg taacctatat agtataggat     2640
ttttttgtc attttgtttc ttctcgtacg agcttgctcc tgatcagcct atctcgcagc      2700
tgatgaatat cttgtggtag gggtttggga aaatcattcg agtttgatgt ttttcttggt     2760
atttcccact cctcttcaga gtacagaaga ttaagtgaga agttcgtttg tgcaagctta     2820
tcgataagct ttaatgcggt agtttatcac agttaaattg ctaacgcagt caggcaccgt     2880
gtatgaaatc taacaatgcg ctcatcgtca tcctcggcac cgtcaccctg gatgctgtag     2940
gcataggctt ggttatgccg gtactgccgg gcctcttgcg ggatatcgtc cattccgaca     3000
gcatcgccag tcactatggc gtgctgctag cgctatatgc gttgatgcaa tttctatgcg     3060
cacccgttct cggagcactg tccgaccgct ttggccgccg cccagtcctg ctcgcttcgc     3120
tacttggagc cactatcgac tacgcgatca tggcgaccac accgtcctg tggatctatc      3180
gaatctaaat gtaagttaaa atctctaaat aattaaataa gtcccagttt ctccatacga     3240
accttaacag cattgcggtg agcatctaga ccttcaacag cagccagatc catcactgct     3300
```

```
tggccaatat gtttcagtcc ctcaggagtt acgtcttgtg aagtgatgaa cttctggaag    3360
gttgcagtgt taactccgct gtattgacgg gcatatccgt acgttggcaa agtgtggttg    3420
gtaccggagg agtaatctcc acaactctct ggagagtagg caccaacaaa cacagatcca    3480
gcgtgttgta cttgatcaac ataagaagaa gcattctcga tttgcaggat caagtgttca    3540
ggagcgtact gattggacat ttccaaagcc tgctcgtagg ttgcaaccga tagggttgta    3600
gagtgtgcaa tacacttgcg tacaatttca acccttggca actgcacagc ttggttgtga    3660
acagcatctt caattctggc aagctccttg tctgtcatat cgacagccaa cagaatcacc    3720
tgggaatcaa taccatgttc agcttgagca gaaggtctga ggcaacgaaa tctggatcag    3780
cgtatttatc agcaataact agaacttcag aaggcccagc aggcatgtca atactacaca    3840
gggctgatgt gtcattttga accatcatct tggcagcagt aacgaactgg tttcctggac    3900
caaatatttt gtcacactta ggaacagttt ctgttccgta agccatagca gctactgcct    3960
gggcgcctcc tgctagcacg atacacttag caccaacctt gtgggcaacg tagatgactt    4020
ctggggtaag ggtaccatcc ttcttaggtg gagatgcaaa aacaatttct ttgcaaccag    4080
caactttggc aggaacaccc agcatcaggg aagtggaagg cagaattgcg gttccaccag    4140
gaatatagag gccaactttc tcaataggtc ttgcaaaacg agagcagact acaccagggc    4200
aagtctcaac ttgcaacgtc tccgttagtt gagcttcatg gaatttcctg acgttatcta    4260
tagagagatc aatggctctc ttaacgttat ctggcaattg cataagttcc tctgggaaag    4320
gagcttctaa cacaggtgtc ttcaaagcga ctccatcaaa cttggcagtt agttctaaaa    4380
gggctttgtc accattttga cgaacattgt cgacaattgg tttgactaat tccataatct    4440
gttccgtttt ctggatagga cgacgaaggg catcttcaat ttcttgtgag gaggccttag    4500
aaacgtcaat tttgcacaat tcaatacgac cttcagaagg gacttcttta ggtttggatt    4560
cttctttagg ttgttccttg gtgtatcctg gcttggcatc tcctttcctt ctagtgacct    4620
ttagggactt catatccagg tttctctcca cctcgtccaa cgtcacaccg tacttggcac    4680
atctaactaa tgcaaaataa aataagtcag cacattccca ggctatatct tccttggatt    4740
tagcttctgc aagttcatca gcttcctccc taattttagc gttcaaacaa aacttcgtcg    4800
tcaaataacc gtttggtata agaaccttct ggagcattgc tcttacgatc ccacaaggtg    4860
cttccatggc tctaagaccc tttgattggc caaaacagga agtgcgttcc aagtgacaga    4920
aaccaacacc tgtttgttca accacaaatt tcaagcagtc tccatcacaa tccaattcga    4980
tacccagcaa cttttgagtt cgtccagatg tagcaccttt ataccacaaa ccgtgacgac    5040
gagattggta gactccagtt tgtgtcctta tagcctccgg aatagacttt ttggacgagt    5100
acaccaggcc caacgagtaa ttagaagagt cagccaccaa agtagtgaat agaccatcgg    5160
ggcggtcagt agtcaaagac gccaacaaaa tttcactgac agggaacttt ttgacatctt    5220
cagaaagttc gtattcagta gtcaattgcc gagcatcaat aatggggatt ataccagaag    5280
caacagtgga agtcacatct accaactttg cggtctcaga aaaagcataa acagttctac    5340
taccgccatt agtgaaactt ttcaaatcgc ccagtggaga agaaaaaggc acagcgatac    5400
tagcattagc gggcaaggat gcaactttat caaccagggt cctatagata accctagcgc    5460
ctgggatcat cctttggaca actctttctg ccaaatctag gtccaaaatc acttcattga    5520
taccattatt gtacaacttg agcaagttgt cgatcagctc ctcaaattgg tcctctgtaa    5580
cggatgactc aacttgcaca ttaacttgaa gctcagtcga ttgagtgaac ttgatcaggt    5640
```

```
tgtgcagctg gtcagcagca tagggaaaca cggcttttcc taccaaactc aaggaattat    5700
caaactctgc aacacttgcg tatgcaggta gcaagggaaa tgtcatactt gaagtcggac    5760
agtgagtgta gtcttgagaa attctgaagc cgtattttta ttatcagtga gtcagtcatc    5820
aggagatcct ctacgccgga cgcatcgtgg ccgacctgca ggtcggcatc accggcgcca    5880
caggtgcggt tgctggcgcc tatatcgccg acatcaccga tggggaagat cgggctcgcc    5940
acttcgggct catgagcgct tgtttcggcg tgggtatggt ggcaggcccc gtggccgggg    6000
gactgttggg cgccatctcc ttggacctgc agggggggg ggggaaagcc acgttgtgtc    6060
tcaaaatctc tgatgttaca ttgcacaaga taaaaatata tcatcatgaa caataaaact    6120
gtctgcttac ataaacagta atacaagggg tgttatgagc catattcaac gggaaacgtc    6180
ttgctcaagg ccgcgattaa attccaacat ggatgctgat ttatatgggt ataaatgggc    6240
tcgcgataat gtcgggcaat caggtgcgac aatctatcga ttgtatggga agcccgatgc    6300
gccagagttg tttctgaaac atggcaaagg tagcgttgcc aatgatgtta cagatgagat    6360
ggtcagacta aactggctga cggaatttat gcctcttccg accatcaagc attttatccg    6420
tactcctgat gatgcatggt tactcaccac tgcgatcccc gggaaaacag cattccaggt    6480
attagaagaa tatcctgatt caggtgaaaa tattgttgat gcgctggcag tgttcctgcg    6540
ccggttgcat tcgattcctg tttgtaattg tccttttaac agcgatcgcg tatttcgtct    6600
cgctcaggcg caatcacgaa tgaataacgg tttggttgat gcgagtgatt ttgatgacga    6660
gcgtaatggc tggcctgttg aacaagtctg gaaagaaatg cataagcttt tgccattctc    6720
accggattca gtcgtcactc atggtgattt ctcacttgat aaccttattt ttgacgaggg    6780
gaaattaata ggttgtattg atgttggacg agtcggaatc gcagaccgat accaggatct    6840
tgccatccta tggaactgcc tcggtgagtt ttctccttca ttacagaaac ggcttttca    6900 aaaatatggt attgataatc ctgatatgaa taaattgcag tttcatttga tgctcgatga    6960 gttttttctaa tcagaattgg ttaattggtt gtaacactgg cagagcatta cgctgacttg    7020
acgggacggc ggctttgttg aataaatcga acttttgctg agttgaagga tcagatcacg    7080
catcttcccg acaacgcaga ccgttccgtg gcaaagcaaa agttcaaaat caccaactgg    7140
tccacctaca acaaagctct catcaaccgt ggctccctca ctttctggct ggatgatggg    7200
gcgattcagg cctggtatga gtcagcaaca ccttcttcac gaggcagacc tcagcgcccc    7260 cccccctg caggtcccac ggcggcggtg ctcaacggcc tcaacctact actgggctgc    7320
ttcctaatgc aggagtcgca taaggagag cgtcgagtat ctatgattgg aagtatggga    7380
atggtgatac ccgcattctt cagtgtcttg aggtctccta tcagattatg cccaactaaa    7440
gcaaccggag gaggagattt catggtaaat ttctctgact tttggtcatc agtagactcg    7500
aactgtgaga ctatctcggt tatgacagca gaaatgtcct tcttggagac agtaaatgaa    7560
gtcccaccaa taaagaaatc cttgttatca ggaacaaact tcttgtttcg aacttttcg    7620 gtgccttgaa ctataaaatg tagagtggat atgtcgggta ggaatggagc gggcaaatgc    7680
ttaccttctg gaccttcaag aggtatgtag ggtttgtaga tactgatgcc aacttcagtg    7740
acaacgttgc tatttcgttc aaaccattcc gaatccagag aaatcaaagt tgtttgtcta    7800
ctattgatcc aagccagtgc ggtcttgaaa ctgacaatag tgtgctcgtg ttttgaggtc    7860
atctttgtat gaataaatct agtctttgat ctaaataatc ttgacgagcc aaggcgataa    7920
atacccaaat ctaaaactct tttaaaacgt taaaaggaca agtatgtctg cctgtattaa    7980
accccaaatc agctcgtagt ctgatcctca tcaacttgag gggcactatc ttgttttaga    8040
```

```
gaaatttgcg gagatgcgat atcgagaaaa aggtacgctg attttaaacg tgaaatttat    8100
ctcaagatct ctgcctcgcg cgtttcggtg atgacggtga aaacctctga cacatgcagc    8160
tcccggagac ggtcacagct tgtctgtaag cggatgccgg gagcagacaa gcccgtcagg    8220
gcgcgtcagc gggtgttggc gggtgtcggg gcgcagccat gacccagtca cgtagcgata    8280
gcggagtgta tactggctta actatgcggc atcagagcag attgtactga gagtgcacca    8340
tatgcggtgt gaaataccgc acagatgcgt aaggagaaaa taccgcatca ggcgctcttc    8400
cgcttcctcg ctcactgact cgctgcgctc ggtcgttcgg ctgcggcgag cggtatcagc    8460
tcactcaaag gcggtaatac ggttatccac agaatcaggg gataacgcag gaaagaacat    8520
gtgagcaaaa ggccagcaaa aggccaggaa ccgtaaaaag gccgcgttgc tggcgttttt    8580
ccataggctc cgcccccctg acgagcatca caaaaatcga cgctcaagtc agaggtggcg    8640
aaacccgaca ggactataaa gataccaggc gtttccccct ggaagctccc tcgtgcgctc    8700
tcctgttccg accctgccgc ttaccggata cctgtccgcc tttctccctt cgggaagcgt    8760
ggcgctttct caatgctcac gctgtaggta tctcagttcg gtgtaggtcg ttcgctccaa    8820
gctgggctgt gtgcacgaac ccccccgttca gcccgaccgc tgcgccttat ccggtaacta    8880
tcgtcttgag tccaacccgg taagacacga cttatcgcca ctggcagcag ccactggtaa    8940
caggattagc agagcgaggt atgtaggcgg tgctacagag ttcttgaagt ggtggcctaa    9000
ctacggctac actagaagga cagtatttgg tatctgcgct ctgctgaagc cagttacctt    9060
cggaaaaaga gttggtagct cttgatccgg caaacaaacc accgctggta gcggtggttt    9120
ttttgtttgc aagcagcaga ttacgcgcag aaaaaaagga tctcaagaag atcctttgat    9180
cttttctacg gggtctgacg ctcagtggaa cgaaaactca cgttaaggga ttttggtcat    9240
gagattatca aaaaggatct tcacctagat ccttttaaat taaaaatgaa gttttaaatc    9300
aatctaaagt atatatgagt aaacttggtc tgacagttac caatgcttaa tcagtgaggc    9360
acctatctca gcgatctgtc tatttcgttc atccatagtt gcctgactcc ccgtcgtgta    9420
gataactacg atacgggagg gcttaccatc tggccccagt gctgcaatga taccgcgaga    9480
cccacgctca ccggctccag atttatcagc aataaaccag ccagccggaa gggccgagcg    9540
cagaagtggt cctgcaactt tatccgcctc catccagtct attaattgtt gccgggaagc    9600
tagagtaagt agttcgccag ttaatagttt gcgcaacgtt gttgccattg ctgcaggcat    9660
cgtggtgtca cgctcgtcgt ttggtatggc ttcattcagc tccggttccc aacgatcaag    9720
gcgagttaca tgatccccca tgttgtgcaa aaaagcggtt agctccttcg gtcctccgat    9780
cgttgtcaga agtaagttgg ccgcagtgtt atcactcatg gttatggcag cactgcataa    9840
ttctcttact gtcatgccat ccgtaagatg cttttctgtg actggtgagt actcaaccaa    9900
gtcattctga gaatagtgta tgcggcgacc gagttgctct tgcccggcgt caacacggga    9960
taataccgcg ccacatagca gaactttaaa agtgctcatc attggaaaac gttcttcggg   10020
gcgaaaactc tcaaggatct taccgctgtt gagatccagt tcgatgtaac ccactcgtgc   10080
acccaactga tcttcagcat cttttacttt caccagcgtt tctgggtgag caaaaacagg   10140
aaggcaaaat gccgcaaaaa agggaataag ggcgacacgg aaatgttgaa tactcatact   10200 cttcctttttt caatattatt gaagcattta tcagggttat tgtctcatga gcggatacat   10260
atttgaatgt atttagaaaa ataaacaaat aggggttccg cgcacatttc cccgaaaagt   10320
gccacctgac gtctaagaaa ccattattat catgacatta acctataaaa ataggcgtat   10380
```

```
cacgaggccc tttcgtcttc aagaattaat tctcatgttt gacagcttat catcgataag    10440
ctgactcatg ttggtattgt gaaatagacg cagatcggga acactgaaaa ataacagtta    10500
ttattcgaga tc                                                        10512
```

<210> SEQ ID NO 34
<211> LENGTH: 10462
<212> TYPE: DNA
<213> ORGANISM: Plasmid pUB116

<400> SEQUENCE: 34

```
gatctaacat ccaaagacga aaggttgaat gaaacctttt tgccatccga catccacagg      60
tccattctca cacataagtg ccaaacgcaa caggagggga tacactagca gcagaccgtt     120
gcaaacgcag gacctccact cctcttctcc tcaacaccca cttttgccat cgaaaaacca     180
gcccagttat tgggcttgat tggagctcgc tcattccaat tccttctatt aggctactaa     240
caccatgact ttattagcct gtctatcctg gcccccctgg cgaggttcat gtttgtttat     300
ttccgaatgc aacaagctcc gcattacacc cgaacatcac tccagatgag ggctttctga     360
gtgtggggtc aaatagtttc atgttcccca aatgggccaa aactgacagt ttaaacgctg     420
tcttggaacc taatatgaca aaagcgtgat ctcatccaag atgaactaag tttggttcgt     480
tgaaatgcta acggccagtt ggtcaaaaag aaacttccaa aagtcgccat accgtttgtc     540
ttgtttggta ttgattgacg aatgctcaaa aataatctca ttaatgctta gcgcagtctc     600
tctatcgctt ctgaaccccg gtgcacctgt gccgaaacgc aaatggggaa cacccgctt      660 tttggatgat tatgcattgt ctccacattg tatgcttcca agattctggt gggaatactg     720
ctgatagcct aacgttcatg atcaaaattt aactgttcta accccctactt gacagcaata     780 tataaacaga aggaagctgc cctgtcttaa acctttttt ttatcatcat tattagctta      840 cttttcataat tgcgactggt tccaattgac aagcttttga ttttaacgac ttttaacgac     900
aacttgagaa gatcaaaaaa caactaatta ttcgaaggat ccaaacgatg agatttcctt     960
caatttttac tgcagtttta ttcgcagcat cctccgcatt agctgctcca gtcaacacta    1020
caacagaaga tgaaacggca caaattccgg ctgaagctgt catcggttac tcagatttag    1080
aaggggattt cgatgttgct gttttgccat tttccaacag cacaaataac gggttattgt    1140
ttataaatac tactattgcc agcattgctg ctaaagaaga aggggtatct ctcgagaaaa    1200
gatgcggacc gggcagggg ttcgggaaga ggaggcaccc caaaaagctg accccttag       1260 cctacaagca gtttatcccc aatgtggccg agaagaccct aggcgccagc ggaaggtatg    1320
aagggaagat ctccagaaac tccgagcgat ttaaggaact caccccccaat tacaaccccg    1380 acatcatatt taaggatgaa gaaaacaccg gagcggacag gctgatgact cagaggtgta    1440
aggacaagtt gaacgctttg gccatctcgg tgatgaacca gtggccagga gtgaaactgc    1500
gggtgaccga gggctgggac gaagatgcc accactcaga ggagtctctg cactacgagg    1560
gccgcgcagt ggacatcacc acgtctgacc gcgaccgcag caagtacggc atgctggccc    1620
gcctggcggt ggaggccggc ttcgactggg tgtactacga gtccaaggca catatccact    1680
gctcggtgaa agcagagaac tcggtggcgg ccaaatcggg aggcgtcgac aaaactcaca    1740
catgcccacc gtgcccagca cctgaactcc tgggggacc gtcagtcttc ctcttccccc     1800
caaaacccaa ggacaccctc atgatctccc ggacccctga ggtcacatgc gtggtggtgg    1860
acgtgagcca cgaagaccct gaggtcaagt tcaactggta cgtggacggc gtggaggtgc    1920
ataatgccaa gacaaagccg cgggaggagc agtaccagag cacgtaccgt gtggtcagcg    1980
```

```
tcctcaccgt cctgcaccag gactggctga atggcaagga gtacaagtgc aaggtctcca    2040
acaaagccct cccagccccc atcgagaaaa ccatctccaa agccaaaggg cagccccgag    2100
aaccacaggt gtacaccctg cccccatccc gggatgagct gaccaagaac caggtcagcc    2160
tgacctgcct ggtcaaaggc ttctatccca gcgacatcgc cgtggagtgg gagagcaatg    2220
ggcagccgga gaacaactac aagaccacgc ctcccgtgtt ggactccgac ggctccttct    2280
tcctctacag caagctcacc gtggacaaga gcaggtggca gcaggggaac gtcttctcat    2340
gctccgtgat gcatgaggct ctgcacaacc actacacgca gaagagcctc tccctgtctc    2400
ccgggaaatg agtgcggcgg ccgcgaatta attcgcctta gacatgactg ttcctcagtt    2460
caagttgggc acttacgaga agaccggtct tgctagattc taatcaagag gatgtcagaa    2520
tgccatttgc ctgagagatg caggcttcat ttttgatact tttttatttg taacctatat    2580
agtataggat tttttttgtc attttgtttc ttctcgtacg agcttgctcc tgatcagcct    2640
atctcgcagc tgatgaatat cttgtggtag gggtttggga aaatcattcg agtttgatgt    2700
ttttcttggt atttcccact cctcttcaga gtacagaaga ttaagtgaga agttcgtttg    2760
tgcaagctta tcgataagct ttaatgcggt agtttatcac agttaaattg ctaacgcagt    2820
caggcaccgt gtatgaaatc taacaatgcg ctcatcgtca tcctcggcac cgtcaccctg    2880
gatgctgtag gcataggctt ggttatgccg gtactgccgg cctcttgcg  ggatatcgtc    2940 cattccgaca gcatcgccag tcactatggc gtgctgctag cgctatatgc gttgatgcaa    3000
tttctatgcg cacccgttct cggagcactg tccgaccgct ttggccgccg cccagtcctg    3060
ctcgcttcgc tacttggagc cactatcgac tacgcgatca tggcgaccac acccgtcctg    3120
tggatctatc gaatctaaat gtaagttaaa atctctaaat aattaaataa gtcccagttt    3180
ctccatacga accttaacag cattgcggtg agcatctaga ccttcaacag cagccagatc    3240
catcactgct tggccaatat gtttcagtcc ctcaggagtt acgtcttgtg aagtgatgaa    3300
cttctggaag gttgcagtgt taactccgct gtattgacgg gcatatccgt acgttggcaa    3360
agtgtggttg gtaccggagg agtaatctcc acaactctct ggagagtagg caccaacaaa    3420
cacagatcca gcgtgttgta cttgatcaac ataagaagaa gcattctcga tttgcaggat    3480
caagtgttca ggagcgtact gattggacat ttccaaagcc tgctcgtagg ttgcaaccga    3540
tagggttgta gagtgtgcaa tacacttgcg tacaatttca acccttggca actgcacagc    3600
ttggttgtga acagcatctt caattctggc aagctccttg tctgtcatat cgacagccaa    3660
cagaatcacc tgggaatcaa taccatgttc agcttgagca gaaggtctga ggcaacgaaa    3720
tctggatcag cgtatttatc agcaataact agaacttcag aaggcccagc aggcatgtca    3780
atactacaca gggctgatgt gtcattttga accatcatct tggcagcagt aacgaactgg    3840
tttcctggac caaatatttt gtcacactta ggaacagttt ctgttccgta agccatagca    3900
gctactgcct gggcgcctcc tgctagcacg atacacttag caccaacctt gtgggcaacg    3960
tagatgactt ctggggtaag ggtaccatcc ttcttaggtg gagatgcaaa acaatttct     4020 ttgcaaccag caactttggc aggaacaccc agcatcaggg aagtggaagg cagaattgcg    4080
gttccaccag gaatatagag gccaactttc tcaataggtc ttgcaaaacg agagcagact    4140
acaccagggc aagtctcaac ttgcaacgtc tccgttagtt gagcttcatg gaatttcctg    4200
acgttatcta tagagagatc aatggctctc ttaacgttat ctggcaattg cataagttcc    4260
tctgggaaag gagcttctaa cacaggtgtc ttcaaagcga ctccatcaaa cttggcagtt    4320
```

```
agttctaaaa gggctttgtc accattttga cgaacattgt cgacaattgg tttgactaat    4380
tccataatct gttccgtttt ctggatagga cgacgaaggg catcttcaat ttcttgtgag    4440
gaggccttag aaacgtcaat tttgcacaat tcaatacgac cttcagaagg gacttcttta    4500
ggtttggatt cttctttagg ttgttccttg gtgtatcctg gcttggcatc tcctttcctt    4560
ctagtgacct ttagggactt catatccagg tttctctcca cctcgtccaa cgtcacaccg    4620
tacttggcac atctaactaa tgcaaaataa aataagtcag cacattccca ggctatatct    4680
tccttggatt tagcttctgc aagttcatca gcttcctccc taattttagc gttcaaacaa    4740
aacttcgtcg tcaaataacc gtttggtata agaaccttct ggagcattgc tcttacgatc    4800
ccacaaggtg cttccatggc tctaagaccc tttgattggc caaaacagga agtgcgttcc    4860
aagtgacaga aaccaacacc tgtttgttca accacaaatt tcaagcagtc tccatcacaa    4920
tccaattcga tacccagcaa cttttgagtt cgtccagatg tagcacccttt ataccacaaa    4980
ccgtgacgac gagattggta gactccagtt tgtgtcctta tagcctccgg aatagacttt    5040
ttggacgagt acaccaggcc caacgagtaa ttagaagagt cagccaccaa agtagtgaat    5100
agaccatcgg ggcggtcagt agtcaaagac gccaacaaaa tttcactgac agggaacttt    5160
ttgacatctt cagaaagttc gtattcagta gtcaattgcc gagcatcaat aatggggatt    5220
ataccagaag caacagtgga agtcacatct accaactttg cggtctcaga aaaagcataa    5280
acagttctac taccgccatt agtgaaactt ttcaaatcgc ccagtggaga agaaaaaggc    5340
acagcgatac tagcattagc gggcaaggat gcaactttat caaccagggt cctatagata    5400
accctagcgc ctgggatcat cctttggaca actctttctg ccaaatctag gtccaaaatc    5460
acttcattga taccattatt gtacaacttg agcaagttgt cgatcagctc ctcaaattgg    5520
tcctctgtaa cggatgactc aacttgcaca ttaacttgaa gctcagtcga ttgagtgaac    5580
ttgatcaggt tgtgcagctg gtcagcagca tagggaaaca cggcttttcc taccaaactc    5640
aaggaattat caaactctgc aacacttgcg tatgcaggta gcaagggaaa tgtcatactt    5700
gaagtcggac agtgagtgta gtcttgagaa attctgaagc cgtattttta ttatcagtga    5760
gtcagtcatc aggagatcct ctacgccgga cgcatcgtgg ccgacctgca ggtcggcatc    5820
accggcgcca caggtgcggt tgctggcgcc tatatcgccg acatcaccga tggggaagat    5880
cgggctcgcc acttcgggct catgagcgct tgtttcggcg tgggtatggt ggcaggcccc    5940
gtggccgggg gactgttggg cgccatctcc ttggacctgc aggggggggg ggggaaagcc    6000
acgttgtgtc tcaaaatctc tgatgttaca ttgcacaaga taaaaatata tcatcatgaa    6060
caataaaact gtctgcttac ataaacagta atacaagggg tgttatgagc catattcaac    6120
gggaaacgtc ttgctcaagg ccgcgattaa attccaacat ggatgctgat ttatatgggt    6180
ataaatgggc tcgcgataat gtcgggcaat caggtgcgac aatctatcga ttgtatggga    6240
agcccgatgc gccagagttg tttctgaaac atggcaaagg tagcgttgcc aatgatgtta    6300
cagatgagat ggtcagacta aactggctga cggaatttat gcctcttccg accatcaagc    6360
attttatccg tactcctgat gatgcatggt tactcaccac tgcgatcccc gggaaaacag    6420
cattccaggt attagaagaa tatcctgatt caggtgaaaa tattgttgat gcgctggcag    6480
tgttcctgcg ccggttgcat tcgattcctg tttgtaattg tccttttaac agcgatcgcg    6540
tatttcgtct cgctcaggcg caatcacgaa tgaataacgg tttggttgat gcgagtgatt    6600
ttgatgacga gcgtaatggc tggcctgttg aacaagtctg gaaagaaatg cataagcttt    6660
tgccattctc accggattca gtcgtcactc atggtgattt ctcacttgat aaccttattt    6720
```

```
ttgacgaggg gaaattaata ggttgtattg atgttggacg agtcggaatc gcagaccgat    6780
accaggatct tgccatccta tggaactgcc tcggtgagtt ttctccttca ttacagaaac    6840
ggctttttca aaaatatggt attgataatc ctgatatgaa taaattgcag tttcatttga    6900
tgctcgatga gttttttctaa tcagaattgg ttaattggtt gtaacactgg cagagcatta   6960
cgctgacttg acgggacggc ggctttgttg aataaatcga acttttgctg agttgaagga    7020
tcagatcacg catcttcccg acaacgcaga ccgttccgtg gcaaagcaaa agttcaaaat    7080
caccaactgg tccacctaca acaaagctct catcaaccgt ggctccctca ctttctggct    7140
ggatgatggg gcgattcagg cctggtatga gtcagcaaca ccttcttcac gaggcagacc    7200
tcagcgcccc cccccccctg caggtcccac ggcggcggtg ctcaacggcc tcaacctact    7260
actgggctgc ttcctaatgc aggagtcgca taagggagag cgtcgagtat ctatgattgg    7320
aagtatggga atggtgatac ccgcattctt cagtgtcttg aggtctccta tcagattatg    7380
cccaactaaa gcaaccggag gaggagattt catggtaaat ttctctgact tttggtcatc    7440
agtagactcg aactgtgaga ctatctcggt tatgacagca gaaatgtcct tcttggagac    7500
agtaaatgaa gtcccaccaa taaagaaatc cttgttatca ggaacaaact tcttgtttcg    7560
aacttttttcg gtgccttgaa ctataaaatg tagagtggat atgtcgggta ggaatggagc    7620
gggcaaatgc ttaccttctg gaccttcaag aggtatgtag ggtttgtaga tactgatgcc    7680
aacttcagtg acaacgttgc tatttcgttc aaaccattcc gaatccagag aaatcaaagt    7740
tgtttgtcta ctattgatcc aagccagtgc ggtcttgaaa ctgacaatag tgtgctcgtg    7800
ttttgaggtc atctttgtat gaataaatct agtctttgat ctaaataatc ttgacgagcc    7860
aaggcgataa atacccaaat ctaaaactct tttaaaacgt taaaaggaca agtatgtctg    7920
cctgtattaa accccaaatc agctcgtagt ctgatcctca tcaacttgag gggcactatc    7980
ttgttttaga gaaatttgcg gagatgcgat atcgagaaaa aggtacgctg attttaaacg    8040
tgaaatttat ctcaagatct ctgcctcgcg cgtttcggtg atgacggtga aaacctctga    8100
cacatgcagc tcccggagac ggtcacagct tgtctgtaag cggatgccgg gagcagacaa    8160
gcccgtcagg gcgcgtcagc gggtgttggc gggtgtcggg gcgcagccat gacccagtca    8220
cgtagcgata gcggagtgta tactggctta actatgcggc atcagagcag attgtactga    8280
gagtgcacca tatgcggtgt gaaataccgc acagatgcgt aaggagaaaa taccgcatca    8340
ggcgctcttc cgcttcctcg ctcactgact cgctgcgctc ggtcgttcgg ctgcggcgag    8400
cggtatcagc tcactcaaag gcggtaatac ggttatccac agaatcaggg gataacgcag    8460
gaaagaacat gtgagcaaaa ggccagcaaa aggccaggaa ccgtaaaaag gccgcgttgc    8520
tggcgttttt ccataggctc cgcccccctg acgagcatca caaaaatcga cgctcaagtc    8580
agaggtggcg aaacccgaca ggactataaa gataccaggc gtttccccct ggaagctccc    8640
tcgtgcgctc tcctgttccg accctgccgc ttaccggata cctgtccgcc tttctccctt    8700
cgggaagcgt ggcgctttct caatgctcac gctgtaggta tctcagttcg gtgtaggtcg    8760
ttcgctccaa gctgggctgt gtgcacgaac cccccgttca gcccgaccgc tgcgccttat    8820
ccggtaacta tcgtcttgag tccaacccgg taagacacga cttatcgcca ctggcagcag    8880
ccactggtaa caggattagc agagcgaggt atgtaggcgg tgctacagag ttcttgaagt    8940
ggtggcctaa ctacggctac actagaagga cagtatttgg tatctgcgct ctgctgaagc    9000
cagttacctt cggaaaaaga gttggtagct cttgatccgg caaacaaacc accgctggta    9060
```

```
gcggtggttt ttttgtttgc aagcagcaga ttacgcgcag aaaaaaagga tctcaagaag    9120
atcctttgat cttttctacg gggtctgacg ctcagtggaa cgaaaactca cgttaaggga    9180
ttttggtcat gagattatca aaaggatctt caccttagat cctttttaaat taaaaatgaa   9240 gttttaaatc aatctaaagt atatatgagt aaacttggtc tgacagttac caatgcttaa    9300
tcagtgaggc acctatctca gcgatctgtc tatttcgttc atccatagtt gcctgactcc    9360
ccgtcgtgta gataactacg atacgggagg gcttaccatc tggccccagt gctgcaatga    9420
taccgcgaga cccacgctca ccggctccag atttatcagc aataaaccag ccagccggaa    9480
gggccgagcg cagaagtggt cctgcaactt tatccgcctc catccagtct attaattgtt    9540
gccgggaagc tagagtaagt agttcgccag ttaatagttt gcgcaacgtt gttgccattg    9600
ctgcaggcat cgtggtgtca cgctcgtcgt ttggtatggc ttcattcagc tccgttccc     9660 aacgatcaag gcgagttaca tgatccccca tgttgtgcaa aaaagcggtt agctccttcg    9720
gtcctccgat cgttgtcaga agtaagttgg ccgcagtgtt atcactcatg gttatggcag    9780
cactgcataa ttctcttact gtcatgccat ccgtaagatg cttttctgtg actggtgagt    9840
actcaaccaa gtcattctga gaatagtgta tgcggcgacc gagttgctct tgcccggcgt    9900
caacacggga taataccgcg ccacatagca gaactttaaa agtgctcatc attggaaaac    9960
gttcttcggg gcgaaaactc tcaaggatct taccgctgtt gagatccagt tcgatgtaac   10020
ccactcgtgc acccaactga tcttcagcat cttttacttt caccagcgtt tctgggtgag   10080
caaaaacagg aaggcaaaat gccgcaaaaa agggaataag ggcgacacgg aaatgttgaa   10140
tactcatact cttccttttt caatattatt gaagcattta tcagggttat tgtctcatga   10200
gcggatacat atttgaatgt atttagaaaa ataaacaaat aggggttccg cgcacatttc   10260
cccgaaaagt gccacctgac gtctaagaaa ccattattat catgacatta acctataaaa   10320
ataggcgtat cacgaggccc tttcgtcttc aagaattaat tctcatgttt gacagcttat   10380
catcgataag ctgactcatg ttggtattgt gaaatagacg cagatcggga acactgaaaa   10440
ataacagtta ttattcgaga tc                                            10462
```

<210> SEQ ID NO 35
<211> LENGTH: 4205
<212> TYPE: DNA
<213> ORGANISM: Plasmid pEAG657

<400> SEQUENCE: 35

```
ctaaattgta agcgttaata ttttgttaaa attcgcgtta aatttttgtt aaatcagctc      60
attttttaac caataggccg aaatcggcaa aatcccttat aaatcaaaag aatagaccga     120
gatagggttg agtgttgttc cagtttggaa caagagtcca ctattaaaga acgtggactc     180
caacgtcaaa gggcgaaaaa ccgtctatca gggcgatggc ccactacgtg aaccatcacc     240
ctaatcaagt ttttttgggt cgaggtgccg taaagcacta atcggaacc ctaaagggag      300 cccccgattt agagcttgac ggggaaagcc ggcgaacgtg gcgagaaagg aagggaagaa     360
agcgaaagga gcgggcgcta gggcgctggc aagtgtagcg gtcacgctgc gcgtaaccac     420
cacacccgcc gcgcttaatg cgccgctaca gggcgcgtcc cattcgccat tcaggctgcg     480
caactgttgg gaagggcgat cggtgcgggc ctcttcgcta ttacgccagc tggcgaaagg     540
gggatgtgct gcaaggcgat taagttgggt aacgccaggg ttttcccagt cacgacgttg     600
taaaacgacg gccagtgagc gcgcgtaata cgactcacta tagggcgaat tgggtaccgg    660
gccctctaga tccttcagc tccctgcccc ggacatgccc agtgggtgga agctgccctc      720
```

```
ttctagcagg agacgcccca ggcggtagag cagctggggg taccaatgca caccctcccc    780
cggagtccag ctgccccatg ccaagctgtg aaagagtctc aggggccaga aggccaactg    840
agccaggtgg tggtcagcca cggccgcgaa gcaggatgcc accacatcct ccaccaccag    900
tgtcccatgc tttgtgagcg gggcgtaggc cccgagggcc acgtgtgtag agacagctgc    960
cacgcgggca ggctgcaggc ctggcacccc agccaccagc acgtactggc caggctgcac   1020
gtggctggca aatgtggccc ggaagcgggc tgccggctcc gtgtgattgt cagccgtaaa   1080
gagcaggtga gcgggtgtga gtgccaggcg cgtgggggg tcctgagtct cgatgacctg    1140
gaaggctctc agcctgtggg gctcgcggtc caggaaaatg agcacatcgc tgaaggtggg   1200
gctcccatcc tcccccatgg ccagcacacg gtctcccggc ctcacggctg acaaggccac   1260
acgcgcccca ctctccaggc gtacctgggc tgcggccgcg aatcagccgc ccgtcttggc   1320
tgcggccgag tgctcggact tgacggagca atgcacgtgg gcctttgact cgtaatacac   1380
ccagtcaaag ccggcctcca ctgccaagcg cgccagcagt ccatacttat tgcggtcgcg   1440
gtctgatgtg gtgatgtcca ccgcgcggcc ctcataatgc agggactcct ctgagtggtg   1500
gccgtcctcg tcccagccct cggtcacccg cagcttcaca ccgggccact ggttcatcac   1560
cgagatagcc agcgagttca ggcggtcctt gcagcgctgg gtcatgaggc ggtcggcgcc   1620
tgtgttctcc tcgtccttga agatgatgtc tggattgtaa ttgggggtga gctccttgaa   1680
gcgctcggag ctgcgagcga tcttgccttc atagcgtccg ctggcgccca gggtcttctc   1740
gggcacattg ggctgaact gcttgtaggc gagcggcacg agtttgcgtg gcggtcgccg    1800
gcggctgccc accacccgac ccggcccgca gccccatgcc gccggcacca ccagcagcag   1860
caacaggacc aggcagaagt gcagtcgggg ccggagccgg gcgggagaca tggcggccgc   1920
gacggtatcg ataagcttga tatcgaattc ctgcagcccg ggggatccac tagttctaga   1980
gcggccgcca ccgcggtgga gctccagctt ttgttccctt tagtgagggt taattgcgcg   2040
cttggcgtaa tcatggtcat agctgttttc tgtgtgaaat tgttatccgc tcacaattcc   2100
acacaacata cgagccggaa gcataaagtg taaagcctgg ggtgcctaat gagtgagcta   2160
actcacatta attgcgttgc gctcactgcc cgctttccag tcgggaaacc tgtcgtgcca   2220
gctgcattaa tgaatcggcc aacgcgcggg gagaggcggt ttgcgtattg ggcgctcttc   2280
cgcttcctcg ctcactgact cgctgcgctc ggtcgttcgg ctgcggcgag cggtatcagc   2340
tcactcaaag gcggtaatac ggttatccac agaatcaggg gataacgcag gaaagaacat   2400
gtgagcaaaa ggccagcaaa aggccaggaa ccgtaaaaag gccgcgttgc tggcgttttt   2460
ccataggctc cgcccccctg acgagcatca caaaaatcga cgctcaagtc agaggtggcg   2520
aaacccgaca ggactataaa gataccaggc gtttccccct ggaagctccc tcgtgcgctc   2580
tcctgttccg accctgccgc ttaccggata cctgtccgcc tttctccctt cgggaagcgt   2640
ggcgctttct catagctcac gctgtaggta tctcagttcg gtgtaggtcg ttcgctccaa   2700
gctgggctgt gtgcacgaac cccccgttca gcccgaccgc tgcgccttat ccggtaacta   2760
tcgtcttgag tccaacccgg taagacacga cttatcgcca ctggcagcag ccactggtaa   2820
caggattagc agagcgaggt atgtaggcgg tgctacagag ttcttgaagt ggtggcctaa   2880
ctacggctac actagaagga cagtatttgg tatctgcgct ctgctgaagc cagttacctt   2940
cggaaaaaga gttggtagct cttgatccgg caaacaaacc accgctggta gcggtggttt   3000
ttttgtttgc aagcagcaga ttacgcgcag aaaaaaagga tctcaagaag atcctttgat   3060
```

-continued

```
cttttctacg gggtctgacg ctcagtggaa cgaaaactca cgttaaggga ttttggtcat   3120

gagattatca aaaaggatct tcacctagat ccttttaaat taaaaatgaa gttttaaatc   3180
aatctaaagt atatatgagt aaacttggtc tgacagttac caatgcttaa tcagtgaggc   3240
acctatctca gcgatctgtc tatttcgttc atccatagtt gcctgactcc ccgtcgtgta   3300
gataactacg atacgggagg gcttaccatc tggccccagt gctgcaatga taccgcgaga   3360
cccacgctca ccggctccag atttatcagc aataaaccag ccagccggaa gggccgagcg   3420
cagaagtggt cctgcaactt tatccgcctc catccagtct attaattgtt gccgggaagc   3480
tagagtaagt agttcgccag ttaatagttt gcgcaacgtt gttgccattg ctacaggcat   3540
cgtggtgtca cgctcgtcgt ttggtatggc ttcattcagc tccggttccc aacgatcaag   3600
gcgagttaca tgatccccca tgttgtgcaa aaaagcggtt agctccttcg gtcctccgat   3660
cgttgtcaga agtaagttgg ccgcagtgtt atcactcatg gttatggcag cactgcataa   3720
ttctcttact gtcatgccat ccgtaagatg cttttctgtg actggtgacg cgtcaaccaa   3780
gtcattctga gaatagtgta tgcggcgacc gagttgctct tgcccggcgt caatacggga   3840
taataccgcg ccacatagca gaactttaaa agtgctcatc attggaaaac gttcttcggg   3900
gcgaaaactc tcaaggatct taccgctgtt gagatccagt tcgatgtaac ccactcgtgc   3960
acccaactga tcttcagcat cttttacttt caccagcgtt tctgggtgag caaaaacagg   4020
aaggcaaaat gccgcaaaaa agggaataag ggcgacacgg aaatgttgaa tactcatact   4080
cttccttttt caatattatt gaagcattta tcagggttat tgtctcatga gcggatacat   4140
atttgaatgt atttagaaaa ataaacaaat aggggttccg cgcacatttc cccgaaaagt   4200
gccac                                                               4205

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide
<400> SEQUENCE: 36
tcgagaaaag atgcggaccg ggcagggggt                                      30

<210> SEQ ID NO 37
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide
<400> SEQUENCE: 37
cgaacccccct gcccggtccg catcttttc                                      29

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 38
tcaggatgca tttgacagtg actgg                                           25
```

```
<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 39
actccgagtc ggaggaatca gaccc                                       25

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 40
cgaagtggtg aagttcatgg atg                                         23

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 41
ttctgtatca gtctttcctg gtgag                                       25

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 42
tacaacttca agcagaagag                                             20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 43
cagctcttag cagacattgg                                             20

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 44
caacacaaac gctctgcaga gaga                                        24

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Primer
```

```
<400> SEQUENCE: 45
ctccagttgc tgcttctgaa ggac                                              24

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 46
agcgacgtga ggatggcagc gtt                                               23

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 47
atttcctggt tggctgatgc tgctt                                             25

<210> SEQ ID NO 48
<211> LENGTH: 4205
<212> TYPE: DNA
<213> ORGANISM: Plasmid pEAG658

<400> SEQUENCE: 48
ctaaattgta agcgttaata ttttgttaaa attcgcgtta aattttttgtt aaatcagctc        60 attttttaac caataggccg aaatcggcaa aatcccttat aaatcaaaag aatagaccga       120
gatagggttg agtgttgttc cagtttggaa caagagtcca ctattaaaga acgtggactc       180
caacgtcaaa gggcgaaaaa ccgtctatca gggcgatggc ccactacgtg aaccatcacc       240
ctaatcaagt ttttttgggt cgaggtgccg taaagcacta aatcggaacc ctaaagggag       300
cccccgattt agagcttgac ggggaaagcc ggcgaacgtg gcgagaaagg aagggaagaa       360
agcgaaagga gcgggcgcta gggcgctggc aagtgtagcg gtcacgctgc gcgtaaccac       420
cacacccgcc gcgcttaatg cgccgctaca gggcgcgtcc cattcgccat tcaggctgcg       480
caactgttgg gaagggcgat cggtgcgggc ctcttcgcta ttacgccagc tggcgaaagg       540
gggatgtgct gcaaggcgat taagttgggt aacgccaggg ttttcccagt cacgacgttg       600
taaaacgacg gccagtgagc gcgcgtaata cgactcacta tagggcgaat tgggtaccgg       660 gcccctctaga tcctttcagc tccctgcccc ggacatgccc agtgggtgga agctgccctc       720
ttctagcagg agacgcccca ggcggtagag cagctggggg taccaatgca cccctcccc       780 cggagtccag ctgccccatg ccaagctgtg aaagagtctc aggggccaga aggccaactg       840
agccaggtgg tggtcagcca cggccgcgaa gcaggatgcc accacatcct ccaccaccag       900
tgtcccatgc tttgtgagcg gggcgtaggc cccgagggcc acgtgtgtag agacagctgc       960
cacgcgggca ggctgcaggc ctggcacccc agccaccagc acgtactggc caggctgcac      1020
gtggctggca aatgtggccc ggaagcgggc tgccggctcc gtgtgattgt cagccgtaaa      1080
gagcaggtga gcgggtgtga gtgccaggcg gcgtggggggg tcctgagtct cgatgacctg      1140
gaaggctctc agcctgtggg gctcgcggtc caggaaaatg agcacatcgc tgaaggtggg      1200
gctcccatcc tcccccatgg ccagcacacg gtctcccggc ctcacggctg acaaggccac      1260
acgcgcccca ctctccaggc gtacctgggc tccggcaggg tcgacgccgc ccgtcttggc      1320
```

```
tgcggccgag tgctcggact tgacggagca atgcacgtgg gcctttgact cgtaatacac   1380
ccagtcaaag ccggcctcca ctgccaagcg cgccagcagt ccatacttat tgcggtcgcg   1440
gtctgatgtg gtgatgtcca ccgcgcggcc ctcataatgc agggactcct ctgagtggtg   1500
gccgtcctcg tcccagccct cggtcacccg cagcttcaca ccgggccact ggttcatcac   1560
cgagatagcc agcgagttca gcggtccttt gcagcgctgg gtcatgaggc ggtcggcgcc   1620
tgtgttctcc tcgtccttga agatgatgtc tggattgtaa ttggggggtga gctccttgaa   1680 gcgctcggag ctgcgagcga tcttgccttc atagcgtccg ctggcgccca gggtcttctc   1740
gggcacattg gggctgaact gcttgtaggc gagcggcacg agtttgcgtg gcggtcgccg   1800
gcggctgccc accacccgac ccggcccgca gccccatgcc gccggcacca ccagcagcag   1860
caacaggacc aggcagaagt gcagtcgggg ccggagccgg gcgggagaca tggcggccgc   1920
gacggtatcg ataagcttga tatcgaattc ctgcagcccg ggggatccac tagttctaga   1980
gcggccgcca ccgcggtgga gctccagctt ttgttccctt tagtgagggt taattgcgcg   2040
cttggcgtaa tcatggtcat agctgttttc tgtgtgaaat tgttatccgc tcacaattcc   2100
acacaacata cgagccggaa gcataaagtg taaagcctgg ggtgcctaat gagtgagcta   2160
actcacatta attgcgttgc gctcactgcc cgctttccag tcgggaaacc tgtcgtgcca   2220
gctgcattaa tgaatcggcc aacgcgcggg gagaggcggt ttgcgtattg ggcgctcttc   2280
cgcttcctcg ctcactgact cgctgcgctc ggtcgttcgg ctgcggcgag cggtatcagc   2340
tcactcaaag gcggtaatac ggttatccac agaatcaggg gataacgcag gaaagaacat   2400
gtgagcaaaa ggccagcaaa aggccaggaa ccgtaaaaag gccgcgttgc tggcgttttt   2460
ccataggctc cgcccccctg acgagcatca aaaaatcga cgctcaagtc agaggtggcg   2520
aaacccgaca ggactataaa gataccaggc gtttccccct ggaagctccc tcgtgcgctc   2580
tcctgttccg accctgccgc ttaccggata cctgtccgcc tttctccctt cgggaagcgt   2640
ggcgctttct catagctcac gctgtaggta tctcagttcg gtgtaggtcg ttcgctccaa   2700
gctgggctgt gtgcacgaac cccccgttca gcccgaccgc tgcgccttat ccggtaacta   2760
tcgtcttgag tccaacccgg taagacacga cttatcgcca ctggcagcag ccactggtaa   2820
caggattagc agagcgaggt atgtaggcgg tgctacagag ttcttgaagt ggtggcctaa   2880
ctacggctac actagaagga cagtatttgg tatctgcgct ctgctgaagc cagttacctt   2940
cggaaaaaga gttggtagct cttgatccgg caaacaaacc accgctggta gcggtggttt   3000
ttttgtttgc aagcagcaga ttacgcgcag aaaaaaagga tctcaagaag atcctttgat   3060
cttttctacg gggtctgacg ctcagtggaa cgaaaactca cgttaaggga ttttggtcat   3120
gagattatca aaaaggatct tcacctagat ccttttaaat taaaaatgaa gttttaaatc   3180
aatctaaagt atatatgagt aaacttggtc tgacagttac caatgcttaa tcagtgaggc   3240
acctatctca gcgatctgtc tatttcgttc atccatagtt gcctgactcc ccgtcgtgta   3300
gataactacg atacgggagg gcttaccatc tggccccagt gctgcaatga taccgcgaga   3360
cccacgctca ccggctccag atttatcagc aataaaccag ccagccggaa gggccgagcg   3420
cagaagtggt cctgcaactt tatccgcctc catccagtct attaattgtt gccgggaagc   3480
tagagtaagt agttcgccag ttaatagttt gcgcaacgtt gttgccattg ctacaggcat   3540
cgtggtgtca cgctcgtcgt ttggtatggc ttcattcagc tccggttccc aacgatcaag   3600
gcgagttaca tgatccccca tgttgtgcaa aaaagcggtt agctccttcg gtcctccgat   3660
```

-continued

```
cgttgtcaga agtaagttgg ccgcagtgtt atcactcatg gttatggcag cactgcataa    3720
ttctcttact gtcatgccat ccgtaagatg cttttctgtg actggtgacg cgtcaaccaa    3780
gtcattctga gaatagtgta tgcggcgacc gagttgctct tgcccggcgt caatacggga    3840
taataccgcg ccacatagca gaactttaaa agtgctcatc attggaaaac gttcttcggg    3900
gcgaaaactc tcaaggatct taccgctgtt gagatccagt tcgatgtaac ccactcgtgc    3960
acccaactga tcttcagcat cttttacttt caccagcgtt tctgggtgag caaaaacagg    4020
aaggcaaaat gccgcaaaaa agggaataag ggcgacacgg aaatgttgaa tactcatact    4080
cttccttttt caatattatt gaagcattta tcagggttat tgtctcatga gcggatacat    4140
atttgaatgt atttagaaaa ataaacaaat aggggttccg cgcacatttc cccgaaaagt    4200
gccac                                                                4205
```